US011786531B1

(12) United States Patent
Paik et al.

(10) Patent No.: US 11,786,531 B1
(45) Date of Patent: Oct. 17, 2023

(54) METHODS OF TREATING B-CELL PROLIFERATIVE DISORDER

(71) Applicant: BeiGene Switzerland GmbH, Basel (CH)

(72) Inventors: Jason Paik, Cambridge, MA (US); Tommi Salmi, Cambridge, MA (US); Ying Ou, Cambridge, MA (US)

(73) Assignee: BeiGene Switzerland GmbH, Basel (CH)

( * ) Notice: Subject to any disclaimer, the term of this patent is extended or adjusted under 35 U.S.C. 154(b) by 0 days.

(21) Appl. No.: 18/098,938

(22) Filed: Jan. 19, 2023

Related U.S. Application Data

(60) Provisional application No. 63/366,053, filed on Jun. 8, 2022, provisional application No. 63/383,503, filed on Nov. 13, 2022, provisional application No. 63/383,504, filed on Nov. 13, 2022, provisional application No. 63/384,864, filed on Nov. 23, 2022, provisional application No. 63/387,796, filed on Dec. 16, 2022.

(51) Int. Cl.
　　*A61K 31/52* (2006.01)
　　*A61K 45/06* (2006.01)
　　*A61P 35/00* (2006.01)

(52) U.S. Cl.
　　CPC .............. *A61K 31/52* (2013.01); *A61K 45/06* (2013.01); *A61P 35/00* (2018.01)

(58) Field of Classification Search
　　CPC .......... A61K 31/52; A61K 45/06; A61P 35/00
　　See application file for complete search history.

(56) References Cited

U.S. PATENT DOCUMENTS

| 7,393,848 | B2 | 7/2008 | Currie |
| 7,514,444 | B2 | 4/2009 | Honigberg |
| 7,718,662 | B1 | 5/2010 | Chen |
| 8,084,620 | B2 | 12/2011 | Liu |
| 9,447,106 | B2 | 9/2016 | Wang |
| 9,556,188 | B2 | 1/2017 | Wang |
| 10,005,782 | B2 | 6/2018 | Wang |
| 10,570,139 | B2 | 2/2020 | Wang |
| 2006/0178367 | A1 | 8/2006 | Currie |
| 2006/0183746 | A1 | 8/2006 | Currie |
| 2008/0076921 | A1 | 3/2008 | Honigberg |

(Continued)

FOREIGN PATENT DOCUMENTS

| GB | 1412017 | 10/1975 |
| JP | H07278148 | 10/1995 |

(Continued)

OTHER PUBLICATIONS

Barr, Paul M., "Impact of ibrutinib dose adherence on therapeutic efficacy in patients with previously treated CLL/SLL," Blood, vol. 129, No. 19, May 11, 2017, 5 pages.

(Continued)

*Primary Examiner* — David Browe
(74) *Attorney, Agent, or Firm* — Ice Miller LLP

(57) ABSTRACT

Provided herein is a method of treating a patient having a B-cell proliferative disorder, the method comprising administering to the patient zanubrutinib, or a pharmaceutically acceptable salt thereof, wherein the patient is characterized by being administered with a moderate CYP3A inducer. In one embodiment, zanubrutinib is administered at a dose of about 320 mg twice a day, or at a total daily dose of about 640 mg.

30 Claims, 23 Drawing Sheets

(56) References Cited

U.S. PATENT DOCUMENTS

| | | |
|---|---|---|
| 2008/0139582 A1 | 6/2008 | Honigberg |
| 2009/0105209 A1 | 4/2009 | Dewdney |
| 2009/0318441 A1 | 12/2009 | Brain |
| 2010/0004231 A1 | 1/2010 | Dewdney |
| 2010/0016296 A1 | 1/2010 | Singh |
| 2010/0016301 A1 | 1/2010 | Dewdney |
| 2010/0029610 A1 | 2/2010 | Singh |
| 2010/0035841 A1 | 2/2010 | Jankowski |
| 2010/0087464 A1 | 4/2010 | Mi |
| 2010/0105676 A1 | 4/2010 | Liu |
| 2010/0144705 A1 | 6/2010 | Miller |
| 2010/0160292 A1 | 6/2010 | Whitney |
| 2010/0160303 A1 | 6/2010 | Liu |
| 2010/0222325 A1 | 9/2010 | Berthel |
| 2010/0249092 A1 | 9/2010 | Singh |
| 2010/0254905 A1 | 10/2010 | Honigberg |
| 2011/0118233 A1 | 5/2011 | Blomgren |
| 2011/0124640 A1 | 5/2011 | Liu |
| 2011/0224235 A1 | 9/2011 | Honigberg |
| 2011/0301145 A1 | 12/2011 | Barbosa Jr. |
| 2012/0028981 A1 | 2/2012 | Miller |
| 2012/0040961 A1 | 2/2012 | Gray |
| 2012/0053189 A1 | 3/2012 | Loury |
| 2012/0058996 A1 | 3/2012 | Liu |
| 2012/0077832 A1 | 3/2012 | Witowski |
| 2012/0082702 A1 | 4/2012 | Delucca |
| 2012/0129852 A1 | 5/2012 | Duan |
| 2012/0157442 A1 | 6/2012 | Bui |
| 2012/0157443 A1 | 6/2012 | Bui |
| 2012/0232054 A1 | 9/2012 | Moriarty |
| 2013/0079327 A1 | 3/2013 | Yamamoto |
| 2013/0096118 A1 | 4/2013 | Liu |
| 2013/0116213 A1 | 5/2013 | Cha |
| 2013/0261103 A1 | 10/2013 | Currie |
| 2013/0281432 A1 | 10/2013 | Currie |
| 2014/0045833 A1 | 2/2014 | Laurent |
| 2014/0094459 A1 | 4/2014 | Goldstein |
| 2014/0107151 A1 | 4/2014 | Goldstein |
| 2014/0162983 A1 | 6/2014 | Hodous |
| 2014/0221398 A1 | 8/2014 | Goldstein |
| 2014/0243306 A1 | 8/2014 | Heng |
| 2015/0079109 A1 | 3/2015 | Li |
| 2015/0259354 A1 | 9/2015 | Wang |
| 2016/0083392 A1 | 3/2016 | Wang |
| 2017/0073349 A1 | 3/2017 | Wang |
| 2018/0251466 A1 | 9/2018 | Wang |
| 2020/0148690 A1 | 5/2020 | Wang |
| 2020/0181150 A1 | 6/2020 | Wang |

FOREIGN PATENT DOCUMENTS

| | | |
|---|---|---|
| WO | 0119829 | 3/2001 |
| WO | 2001016138 | 3/2001 |
| WO | 0250071 | 6/2002 |
| WO | 2002072576 | 9/2002 |
| WO | 03004497 | 1/2003 |
| WO | 2004017908 | 3/2004 |
| WO | 2005005429 | 1/2005 |
| WO | 2005011597 | 2/2005 |
| WO | 2005014599 | 2/2005 |
| WO | 2005047290 | 5/2005 |
| WO | 2006053121 | 5/2006 |
| WO | 2006065946 | 6/2006 |
| WO | 2006099075 | 9/2006 |
| WO | 2007026720 | 3/2007 |
| WO | 2007026950 | 3/2007 |
| WO | 2007027594 | 3/2007 |
| WO | 2007027729 | 3/2007 |
| WO | 2007087068 | 8/2007 |
| WO | 2007136790 | 11/2007 |
| WO | 2008033834 | 3/2008 |
| WO | 2008033854 | 3/2008 |
| WO | 2008033857 | 3/2008 |
| WO | 2008039218 | 4/2008 |
| WO | 2008054827 | 5/2008 |
| WO | 2008144253 | 11/2008 |
| WO | 2009039397 | 3/2009 |
| WO | 2009051822 | 4/2009 |
| WO | 2009077334 | 6/2009 |
| WO | 2009098144 | 8/2009 |
| WO | 2009158571 | 12/2009 |
| WO | 2010000633 | 1/2010 |
| WO | 2010006947 | 1/2010 |
| WO | 2010006970 | 1/2010 |
| WO | 2010028236 | 3/2010 |
| WO | 2010051549 | 5/2010 |
| WO | 2010065898 | 6/2010 |
| WO | 2010068788 | 6/2010 |
| WO | 2010068806 | 6/2010 |
| WO | 2010068810 | 6/2010 |
| WO | 2010122038 | 10/2010 |
| WO | 2011006074 | 1/2011 |
| WO | 2011140488 | 11/2011 |
| WO | 2011153514 | 12/2011 |
| WO | 2012020008 | 2/2012 |
| WO | 2012135801 | 10/2012 |
| WO | 2012143522 | 10/2012 |
| WO | 2012156334 | 11/2012 |
| WO | 2012158795 | 11/2012 |
| WO | 2014173289 | 10/2014 |
| WO | 2015061752 | 4/2015 |
| WO | 2016087994 | 6/2016 |
| WO | 2016100914 | 6/2016 |
| WO | 2016105582 | 6/2016 |
| WO | 2017046746 | 3/2017 |
| WO | 2017059224 | 4/2017 |
| WO | 2018033135 | 2/2018 |
| WO | 2018137681 | 8/2018 |
| WO | 2018193105 | 10/2018 |
| WO | 2019034009 | 2/2019 |
| WO | 2019108795 | 6/2019 |

OTHER PUBLICATIONS

Bradshaw, J. M., "The Src, Syk, and Tec family kinases: Distinct types of molecular switches," Cell Signalling, 22:1175-1184(2010).

Brukinsa: EPAR—Product Information Published Dec. 15, 2021, 31 pages.

Caira, E. D. et al., "Crystalline polymorphism of organic compounds," Topics in Current Chemistry, vol. 198, 1998, pp. 163-208.

Donley, M. E. et al., "Primary B Cell Immunodeficiencies: Comparisons and Contrasts," Annu. Rev. Immunol., 27:199-227 (2009).

Davis, R. E. et al., "Chronic active B-cell-receptor signalling in diffuse large B-cell lymphoma," Nature, 463:88-92 (2010).

Extended European Search Report for European Application No. 14787642.9, dated Jan. 26, 2016, 5 pages.

Extended European Search Report for European Application No. 17841107.0, dated Feb. 21, 2020, 12 pages.

Extended European Search Report for European Application No. 17841172.4, dated Mar. 5, 2020, 6 pages.

Gurcan, H. M. et al., "A review of the current use of rituximab in autoimmune diseases," Int. Immunopharmacol., 9:10-25 (2009).

Hackam, D. G. et al., "Translation of research evidence from animals to humans," JAMA, 296(14):1731-1732 (2006).

Humphries, L. A. et al., "Tec Kinases Mediate Sustained Calcium Influx via Site-specific Tyrosine Phosphorylation of the Phospholipase Cy Src Homology 2-Src Homology 3 Linker," J. Biol.Chem. 279(36):37651-37661 (2004).

International Search Report and Written Opinion for International Application No. PCT/CN2014/075943, dated Jul. 18, 2014, 10 pages.

International Search Report and Written Opinion for International Application No. PCT/CN2017/098023, dated Nov. 16, 2017, 10 pages.

International Search Report and Written Opinion for International Application No. PCT/CN2018/074108, dated Apr. 23, 2018, 12 pages.

International Search Report and Written Opinion for International Application No. PCT/CN2018/100145, dated Nov. 14, 2018, 8 pages.

(56) References Cited

OTHER PUBLICATIONS

International Search Report and Written Opinion for International Application No. PCT/IB2017/054955, dated Sep. 10, 2018, 16 pages.
International Search Report and Written Opinion for International Application No. PCT/US2018/063068, dated Feb. 27, 2019, 8 pages.
Jenkins, S. M. et al., "Substituent variation in azabicyclic triazole- and tetrazole-based muscarinic receptor ligands," J. Med. Chem., 35(13):2392-2406 (1992).
Jordan, V. C., "Tamoxifen: A most unlikely pioneering medicine," Nature Reviews: Drug Discovery, 2:205-213 (2003).
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Luo, J. et al., "Modem Physical Pharmaceutics Theory and Practice," Shang Hai Science and Technology Literature Publishing House, Apr. 2005, pp. 293-295.
Mohamed, A. J. et al., "Bruton's tyrosine kinase (Btk): function, regulation, and transformation with special emphasis on the PH domain," Immunol. Rev., 228:58-73 (2009).
Pan, Z, "Bruton's tyrosine kinase as a drug discovery target," Drug News Perspect, 21(7):357-362 (2008).
Rokosz, L. L. et al., "Kinase inhibitors as drugs for chronic inflammatory and immunological diseases: progress and challenges," Expert Opin. Ther. Targets, 12(7):883-903 (2008).
Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Uckun, F. M. et al., "Bruton's tyrosine kinase as a new therapeutic target," Anti-Cancer Agents in Medicinal Chemistry, 7(6):624-632 (2007).
Vetrie, D. et al., "The gene involved in X-linked agammaglobulinaemia is a member of the src family of protein-tyrosine kinases," Nature, 361:226-233 (1993).
Wilson, W. H et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012). 3 pages.
Wang, Kun, et al., "Comprehensive PBPK model to predict drug interaction potential of Zanubrutinib as a victim or perpetrator," CPT Pharmacometrics Syst. Pharmacol., vol. 00, pp. 1-14 (2021).
CYP3A4 Inhibitor/Inducer Drug-drug Interactions—All Kinase Inhibitors, Oncology/Pro, (2015).
Rddad, Youssef, "Concomitant CYP3A Inducers Taken with Ibrutinib Tied to Worse Outcomes in CLL," Chronic Lymphocytic Leukemia (CLL), OBROncology, downloaded from the Internet: https://www.obronocology.com/article/concomitant-cyp3a-inducers-taken-with-ibrutinib-tied-to-worse-outcomes-in-cll.
Hoang, Tuan, et al.,"The Impact of Drug Interactions on Outcomes in Ibrutinib-Treated Patients with Chronic Lymphocytic Leukemia in Routine Clinical Care: A population-Based Cohort Study," Blood, vol. 140, Supplement 1, pp. 2159-2160 (2022).
Drug Development and Drug Interactions, Table of Substrates, Inhibitors and Inducers, downloaded from the Internet: https://222.fda.gov/drugs/drug-interactions-labeling/drug-development-and-drug-interactions-table-substrates-inhibitors-and-inducers.
Molenaar-Kuijsten, Laura, et al., "A Review of CYP3A Drug-Drug Interaction Studies: Practical Guidelines for Patients Using Targeted Oral Anticancer Drugs," Frontiers in Pharmacology, vol. 12, Article 670862, Aug. 2021.
US Food & Drug Administration. Guidance for industry: drug interaction studies-study design, data analysis, implications for dosing, and labeling recommendations. Draft Guidance Dec. 2, 2012. Accessed Oct. 29, 2022. https://www.federalregistergov/documents/2012/02/21/2012-3958/draft-guidance-for-industry-on-drug-interaction-studies-study-design-data-analysis-implications-for.
Brukinsa (zanubrutinib) Capsules—US Food & Drug Administration Accelerated Approval Letter No. NDA 213217, Reference ID: 4520008 (2019).
Greenblatt DJ. In vitro prediction of clinical drug interactions with CYP3A substrates: we are not there yet. Clin Pharmacol Ther Feb. 2014;95(2):133-5. doi: 10.1038/clpt.2013.230. PMID: 24448459.
Palatini, Pietro, et al., "Pharmacokinetic drug interactions in liver disease: An update," World Journal of Gastroenterology, vol. 22(3), pp. 1260-1278, Jan. 21, 2016.
Kim, Wonseog, et al., "First Interim Analysis Results of ALPINE Phase 3 Study of Zanubrutinib vs. Ibrutinib in R/R Chronic Lymphocytic Leukemia/Small Lymphocytic Lymphoma," 2022 Korean Society of Hematology International Conference & 63rd Annual Metting, Mar. 31, 2022.
Tam et al., "Phase 1 study of the selective BTK inhibitor zanubrutinib in B-cell malignancies and safety and efficacy evaluation in CLL," Clinical Trials and Observations, Sep. 12, 2019. (Year: 2019).
Ou et al., "Evaluation of drug interaction potential of zanubrutinib with cocktail probes representative of CYP3A4, CYP2C9, CYP2C19, P-gp and BCRP," British Pharmacological Society Aug. 14, 2020. (Year: 2020).
NCT04470908 (posted Jul. 14, 2020). (Year: 2020).
Tuloup et al., Model-Based Comparative Analysis of Rifampicin and Rifabutin Drug-Drug Interaction Profile, Antimicrobial Agents and Chemotherapy Sep. 2021 vol. 65, Issue 9. (Year: 2021).
Paccoud et al., "A Woman with Relapsed Chronic Lymphocytic Leukemia and Upper Lobe Consolidation," The Expert Clinician Nov. 2021. (Year: 2021).
Corresponding U.S. Appl. No. 18/098,917.
Pirmohamed, Munir, et al., "The Role of Active Metabolites in Drug Toxocity," Drug Safety Concepts, vol. 11, No. 2, pp. 114-144 (1994).
Park, B. Kevin, et al., "The Role of Cytochrome P450 Enzymes in Hepatic and Extrahepatic Human Drug Toxicity," Pharmac. Ther. vol. 68, No. 3, pp. 385-424 (1995).
Tam, Constantine S., et al., "clinical pharmacology and PK/PD translation of the second-generation Bruton's tyrosine kinase inhibitor, zanubrutinib," Expert Review of Clinical Pharmacology, vol. 14, No. 11, pp. 1329-1344 (2021).

$$EAIR_{event} = \frac{\sum_{i=1}^{n} TEAE_{event,i}}{\sum_{i=1}^{n} t_{event,i}}$$

FIG. 23

METHODS OF TREATING B-CELL PROLIFERATIVE DISORDER

CROSS-REFERENCE TO RELATED APPLICATIONS

This application claims the benefit of priority to U.S. Provisional Application Ser. No. 63/366,053, filed Jun. 8, 2022; U.S. Provisional Application Ser. No. 63/383,504, filed Nov. 13, 2022; U.S. Provisional Application Ser. No. 63/383,503, filed Nov. 13, 2022; U.S. Provisional Application Ser. No. 63/384,864, filed Nov. 23, 2022; and U.S. Provisional Application Ser. No. 63/387,796, filed Dec. 16, 2022, each of which is incorporated herein by reference in its entirety and for all purposes.

FIELD

Provided herein are methods of treating a patient having a B-cell proliferative disorder, particularly methods of prolonging progression-free survival time of a patient having chronic lymphocytic leukemia/small lymphocytic lymphoma (CLL/SLL), comprising administering to the patient an effective amount of zanubrutinib.

BACKGROUND

The B-cell receptor signaling pathway is not only essential for normal B-cell development but is also implicated in the survival and proliferation of malignant B cells. Inhibition of B-cell receptor signaling has recently been established as an effective approach for management of B-cell malignancies. Bruton tyrosine kinase (BTK) is a key component of the B-cell receptor signaling pathway, and the first-generation BTK inhibitor, ibrutinib, has become a standard of care in frontline and previously treated chronic lymphocytic leukemia/small lymphocytic lymphoma (CLL/SLL), previously treated mantle cell lymphoma (MCL), and Waldenström macroglobulinemia (WM).

Zanubrutinib is a highly specific next-generation BTK inhibitor with favorable oral bioavailability, as shown in preclinical studies. Compared with ibrutinib, zanubrutinib has shown greater selectivity for BTK and fewer off-target effects in multiple in vitro enzymatic and cell-based assays. zanubrutinib, ibrutinib, and other active BTK inhibitors covalently bind cysteine 481 in the adenosine triphosphate—binding pocket of BTK, and display varying affinities (depending on specificity of the individual drug) for related and unrelated adenosine triphosphate—binding kinases that contain a sterically available cysteine at this position, including epidermal growth factor receptor (EGFR), human EGFR-2 (HER2), human EGFR-4 (HER4), interleukin-2-inducible T-cell kinase (ITK), bone marrow tyrosine kinase gene in chromosome X (BMX), JAK2, TEC, and B-lymphocyte kinase (BLK). Off-target inhibition likely contributes to the toxicities reported in patients treated with ibrutinib, such as diarrhea and rash (toxicities associated with EGFR inhibition), bleeding or bruising, and atrial fibrillation, and those that are not seen in patients with congenital X-linked agammaglobulinemia due to germline mutations in the BTK gene; a more specific BTK inhibitor may have fewer toxicities.

Though there have been many recent advances in the methods of extending progression-free survival (PFS) of a patient having a B-cell proliferative disorder for the treatment of B-cell proliferative disorder, there remains a need for more effective and/or enhanced methods of extending PFS, in particular, in the treatment with BTK inhibitors.

Oxidative metabolism by the CYP3A4 and CYP3A5 members of the CYP3A enzyme subfamily plays a dominant role in the elimination of a large number of drugs, and it can be difficult to maintain therapeutically effective blood plasma levels of drugs which are metabolized by these enzymes, e.g., zanubrutinib. Also, for some drugs, the metabolic by-products of CYP3A-mediated metabolism are highly toxic and can result in severe side effects.

Thus, a need exists to identify whether and how CYP3A inducers can be used to improve the therapeutic efficacy of drugs, e.g., zanubrutinib, metabolized by CYP3A.

Citation or identification of any reference in this section is not to be construed as an admission that the reference is prior art to the present application.

SUMMARY

Provided herein is a method of treating a patient having a B-cell proliferative disorder, the method comprising administering to the patient zanubrutinib, or a pharmaceutically acceptable salt thereof, wherein the patient is characterized by being administered with a moderate CYP3A inducer. In one embodiment, zanubrutinib is administered at a dose of about 320 mg twice a day, or at a total daily dose of 640 mg. In one embodiment, the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL). In one embodiment, the zanubrutinib is administered at a dose of about 320 mg twice a day, which has a total daily dose of about 640 mg. In one embodiment, the B-cell proliferative disorder is chronic lymphocytic leukemia (CLL). In one embodiment, the B-cell proliferative disorder is small lymphocytic lymphoma (SLL). In one embodiment, the B-cell proliferative disorder is Waldenström macroglobulinemia (WM). In one embodiment, the B-cell proliferative disorder is mantle cell lymphoma (MCL). In one embodiment, the B-cell proliferative disorder is marginal zone lymphoma (MZL). In one embodiment, the B-cell proliferative disorder is follicular lymphoma (FL). In one embodiment, the moderate CYP3A inducer is rifabutin, bosentan, phenobarbital, efavirenz, etravirine, modafinil, or nafcillin. In one embodiment, the patient is characterized by a 17p deletion (del(17p)) mutation or TP53 mutation. In one embodiment, the administration prolongs the progression-free survival (PFS) time of the patient as compared to the PFS time of a comparable patient orally administered with ibrutinib at a dose of 420 mg once daily. In one embodiment, the administration causes lower rate of atrial fibrillation and/or flutter as compared to the rate of atrial fibrillation and/or flutter of a comparable patient orally administered with ibrutinib at a dose of 420 mg once daily.

BRIEF DESCRIPTION OF DRAWINGS

FIG. 7 is for Investigator-assessed ORR and FIG. 8 is for IRC-assessed ORR. All subgroups, with the exception of complex karyotype were prespecified. Rate difference (zanubrutinib minus ibrutinib) and 95% CI were unstratified for subgroups. Bulky disease is derived from any target lesion longest diameter ≥5 cm. ECOG—Eastern Cooperative Oncology Group; IGHV—immunoglobulin heavy chain variable region; ORR—overall response rate.

FIG. 23 depicts Formula (EAIR).

DETAILED DESCRIPTION

Definitions

Figure 1:
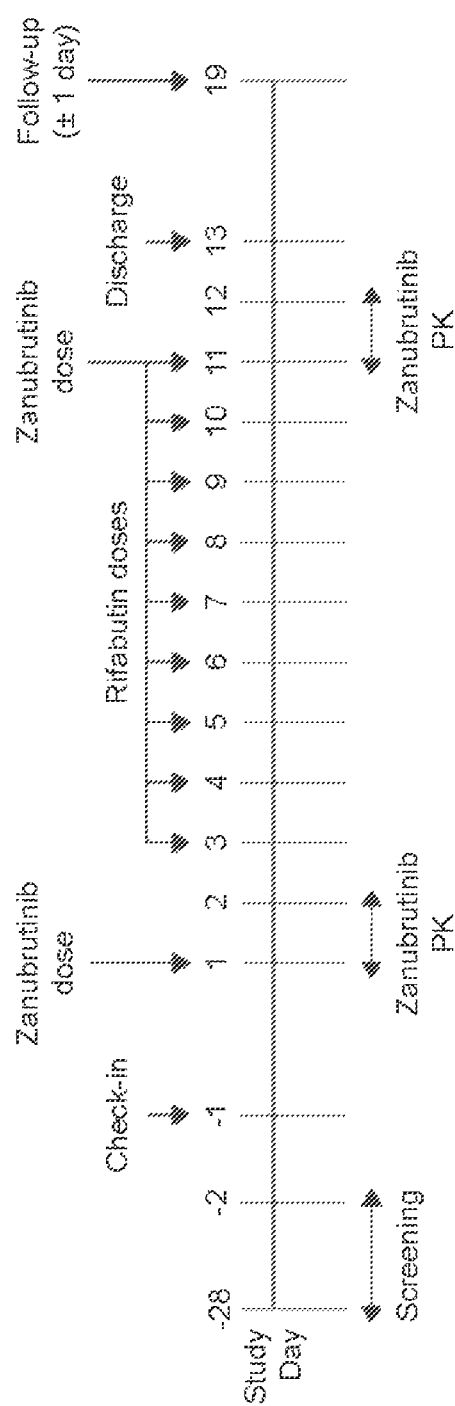
FIG. 1 depicts the pharmacokinetics (PK) study design of Example 1.

As used herein, "Zanubrutinib" or "zanubrutinib" refers to the compound having the name of (S)-7-(1-acryloylpiperidin-4-yl)-2-(4-phenoxyphenyl)-4,5,6,7-tetrahydropyrazolo[1,5-a]pyrimidine-3-carboxamide, or the structure of formula (I):

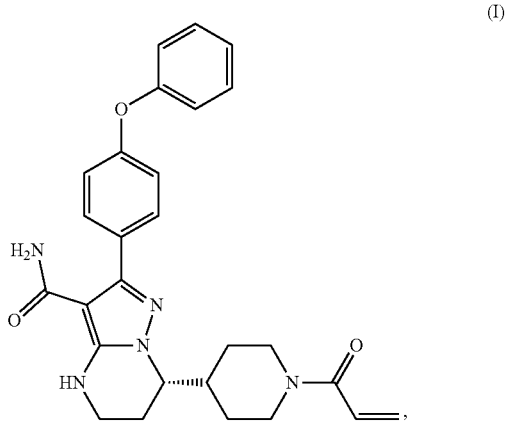 [SMILES: C=CC(=O)N1CCC([C@@H]2CCNc3c(C(N)=O)c(-c4ccc(Oc5ccccc5)cc4)nn32)CC1]

or a pharmaceutically acceptable salt, tautomer, stereoisomer, enantiomer, isotopologue, solvate, or prodrug thereof. Zanubrutinib is disclosed and claimed, along with pharmaceutically acceptable salts thereof, and also as solvates thereof, as being useful as an inhibitor of BTK activity, particularly in treatment of cancer, in WO2014173289, the entire disclosure of which is incorporated herein by reference. Zanubrutinib is compound 27b in WO2014173289 and Compound 1 in WO2018033853, the entire disclosure of which is incorporated herein by reference. Zanubrutinib can be prepared as described in WO2014173289 and WO2018033853. In one embodiment, zanubrutinib is a hydrate.

In one embodiment, a solid form of zanubrutinib is used for the treatment provided herein. In one embodiment, a crystal form of zanubrutinib is used for the treatment provided herein. In one embodiment, an amorphous form of zanubrutinib is used for the treatment provided herein. In one embodiment, a freebase of zanubrutinib is used for the treatment provided herein. In one embodiment, an oxalate form of zanubrutinib is used for the treatment provided herein. In one embodiment, Form A of zanubrutinib described in WO2018033853 is used for the treatment provided herein.

The term "CYP3A inducer" refers to any chemical entity that increases the normal function of the Cytochrome P450 3A (CYP3A) subfamily of genes and proteins. The CYP3A inducer can increase the action of the CYP3A gene or the CYP3A protein/enzyme. Examples of CYP3A inducers include, but are not limited to, armodafinil, apalutamide, bexarotene, bosentan, carbamazepine, cenobamate, dabrafenib, dexamethasone, dipyrone, efavirenz, elagolix, enzalutamide, eslicarbazepine, estradiol, Etravirine, ivosidenib, lumacaftor, lorlatinib, mitapivat, mitotane, mobocertinib, modafinil, nafcillin, pexidartinib, phenobarbital, phenytoin, primidone, rifabutin, rifampin, rifapentine, rufinamide, sotorasib, St. John's Wort or vemurafenib. In one embodiment, the CYP3A inducer is a moderate CYP3A inducer, examples of which include, but are not limited to rifabutin, bexarotene, bosentan, cenobamate, dabrafenib, dexamethasone, dipyrone, efavirenz, a combination of elagolix, estradiol, and norethindrone, eslicarbazepine, etravirine, lorlatinib, mitapivat, modafinil, or nafcillin, pexidartinib, phenobarbital, primidone, rifapentine, sotorasib. and St. John's Wort. In one embodiment, the moderate CYP3A inducer is rifabutin, bosentan, cenobamate, dabrafenib, efavirenz, etravirine, lorlatinib, pexidartinib, phenobarbital, primidone, or sotorasib. In one embodiment, a moderate CYP3A inducer is phenobarbital.

The term "BTK inhibitor," as used herein, refers to compounds having inhibitory activity against Bruton's Tyrosine Kinase (BTK). Exemplary BTK inhibitors include, but are not limited to, those described above: ibrutinib, acalabrutinib, evobrutinib, fenebrutinib, poseltinib, vecabrutinib, tirabrutinib, spebrutinib, and zanubrutinib.

The term "progression-free survival" or "PFS" as used herein, refers to the length of time from the beginning of the treatment to the first disease progression or death, whichever occurs first. The PFS can be during or after the treatment of a disease, such as cancer, during which a patient can live with the disease, but the disease does not get worse. A "PFS event" refers to the first disease progression or death observed in a patient under treatment of a disease. PFS can be measured using methods known in the art in view of the present disclosure.

The terms "progression-free survival probability" and "progression-free survival rate" are interchangeable. They refer to the probability of a patient stays PFS event free during or after a treatment, or the PFS event-free rate in a patient population that are receiving or have received a treatment.

As used herein, "ibrutinib" refers to the compound having the name of 1-[(3R)-3-[4-amino-3-(4-phenoxyphenyl)-1H-pyrazolo[3,4-d]pyrimidin-1-yl]-1-piperidinyl]-2-propen-1-one, and the following structure:

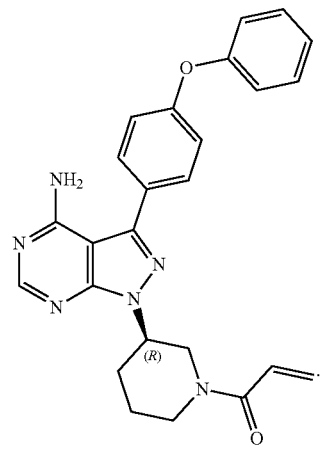

As used herein, "acalabrutinib" refers to the compound having the name of 4-{8-amino-3-[(2 S)-1-(but-2-ynoyl) pyrrolidin-2-yl]imidazo[1,5-a]pyrazin-1-yl)}-N-(pyridine-2-yl)benzamide, and the following structure:

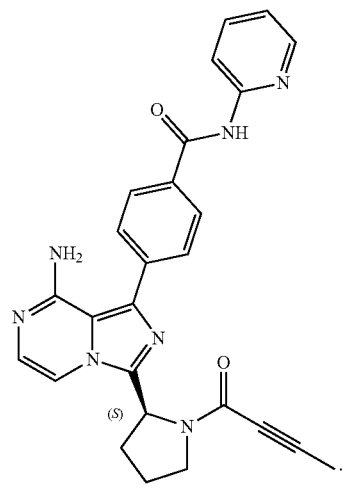

The term "treating" or derivatives thereof as used herein refers to therapeutic therapy. In reference to a particular condition, treating means: (1) to ameliorate the condition or one or more of the biological manifestations of the condition, (2) to interfere with (a) one or more points in the biological cascade that leads to or is responsible for the condition or (b) one or more of the biological manifestations of the condition (3) to alleviate one or more of the symptoms, effects or side effects associated with the condition or one or more of the symptoms, effects or side effects associated with the condition or treatment thereof, or (4) to slow the progression of the condition or one or more of the biological manifestations of the condition.

As used herein, "prevention" is understood to refer to the prophylactic administration of a drug to substantially diminish the likelihood or severity of a condition or biological manifestation thereof, or to delay the onset of such condition or biological manifestation thereof. The skilled artisan would appreciate that "prevention" is not an absolute term. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Zanubrutinib disclosed herein may contain one or more chiral atoms, or may otherwise be capable of existing as enantiomers. Accordingly, the compounds of this invention include mixtures of enantiomers as well as purified enantiomers or enantiomerically enriched mixtures. Also, it is understood that all tautomers and mixtures of tautomers are included within the scope of zanubrutinib.

As used herein, the term "solvate" refers to a complex of variable stoichiometry formed by a solute (in this invention, compounds of formula (I) or a salt thereof and a solvent. Also, it is understood that zanubrutinib may be presented, separately or both, as solvates. Such solvents for the purpose of the invention may not interfere with the biological activity of the solute. Examples of suitable solvents include, but are not limited to, water, methanol, dimethylsulforide. ethanol and acetic acid. In one embodiment, the solvent used is a pharmaceutically acceptable solvent. Examples of suitable pharmaceutically acceptable solvents include, without limitation, water, ethanol and acetic acid. In another embodiment, the solvent used is water (i.e., a hydrate).

Zanubrutinib may have the ability to crystallize in more than one form, a characteristic, which is known polymorphism, and it is understood that such polymorphic forms ("polymorphs") are within the scope of zanubrutinib. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percentages of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous solids include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to $\pm 0.2°$ $2\theta$ (or $\pm 0.2$ degrees $2\theta$) while still describing the particular XRPD peak.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds provided herein include, but are not limited to, those well-known in the art, see for example, *Remington's Pharmaceutical Sciences,* $18^{th}$ eds., Mack Publishing, Easton Pa. (1990) or *Remington: The Science and Practice of Pharmacy,* $19^{th}$ eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center is substantially free of the opposite enantiomer of the compound. A stereomerically pure compound having two chiral centers is substantially free of other diastereomers of the compound. A typical stereomerically pure compound comprises greater than about 80% by weight of one stereoisomer of the zanubrutinib and less than about 20% by weight of other stereoisomers of the compound, greater than about 90% by weight of one stereoisomer of the zanubrutinib and less than about 10% by weight of the other stereoisomers of the compound, greater than about 95% by weight of one stereoisomer of the zanubrutinib and less than about 5% by weight of the other stereoisomers of the compound, or greater than about 97% by weight of one stereoisomer of the zanubrutinib and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

The use of stereomerically pure forms of such compounds, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates*

*and Resolutions* (Wiley-Interscience, New York, 1981); Wilen, S. H., et al., Tetrahedron 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds can include E and Z isomers, or a mixture thereof, and cis and trans isomers or a mixture thereof. In certain embodiments, the compounds are isolated as either the E or Z isomer. In other embodiments, the compounds are a mixture of the E and Z isomers.

"Tautomers" refers to isomeric forms of a compound that are in equilibrium with each other. The concentrations of the isomeric forms depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

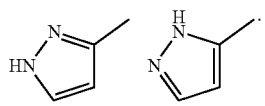

As readily understood by one skilled in the art, a wide variety of functional groups and other structures may exhibit tautomerism and all tautomers of the compounds provided herein are within the scope of the present invention.

The term "subject" includes an animal, including, but not limited to, an animal such as a cow, monkey, horse, sheep, pig, chicken, turkey, quail, cat, dog, mouse, rat, rabbit, or guinea pig, in one embodiment a mammal, in another embodiment a human.

While it is possible that, for use in therapy, zanubrutinib, may be administered as the raw chemical, it is possible to present the active ingredient as a pharmaceutical composition. Accordingly, the invention further provides pharmaceutical compositions, which include zanubrutinib, and one or more pharmaceutically acceptable carriers, diluents, or excipients. Zanubrutinib is as described above. The carrier(s), diluent(s) or excipient(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical composition including admixing a zanubrutinib with one or more pharmaceutically acceptable carriers, diluents, or excipients. Such elements of the pharmaceutical compositions utilized may be presented in separate pharmaceutical combinations or formulated together in one pharmaceutical composition. Accordingly, the invention further provides a pharmaceutical composition containing zanubrutinib and one or more pharmaceutically acceptable carriers, diluents, or excipients. Zanubrutinib described above may be utilized in any of the compositions described above.

Pharmaceutical compositions may be presented in unit dose forms containing a predetermined amount of active ingredient per unit dose. As is known to those skilled in the art, the amount of active ingredient per dose depends on the condition being treated, the route of administration and the age, weight, and condition of the patient. Preferred unit dosage compositions are those containing a daily dose or sub-dose, or an appropriate fraction thereof, of an active ingredient. Furthermore, such pharmaceutical compositions may be prepared by any of the methods well known in the pharmacy art.

Zanubrutinib may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It is appreciated that the preferred route may vary with, for example, the condition of the recipient of the combination and the cancer to be treated. It will also be appreciated that each of the agents administered may be administered by the same or different routes and that zanubrutinib may be compounded together in a pharmaceutical composition.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

The term "kit" or "kit of parts" as used herein refers to a pharmaceutical composition or a composition that is used to administer zanubrutinib according to the disclosure. In one embodiment, the kit can contain zanubrutinib in a single pharmaceutical composition, such as a tablet, or in separate pharmaceutical compositions. In one aspect, there is provided a kit of parts comprising components: zanubrutinib in association with a pharmaceutically acceptable excipients, diluents, or carrier. The kit can also be provided with instruction, such as dosage and administration instructions. Such dosage and administration instructions can be of the kind that are provided to a doctor, for example by a drug product label, or they can be of the kind that are provided by a doctor, such as instructions to a patient.

The term "dose" as used herein is understood to mean a dose that is intended to either slowly raise plasma or blood concentration levels of the compound to a therapeutically effective level, or to maintain such a therapeutically effective level.

In one embodiment, zanubrutinib and a moderate CYP3A inducer can be used in coordinated fashion but such a use does not necessarily mean that zanubrutinib is used in the combination or coadministration with the moderate CYP3A inducer. In one embodiment, zanubrutinib and the moderate CYP3A inducer can be administered simultaneously, consecutively, or sequentially. In one embodiment, the concomitant administration of zanubrutinib and the moderate CYP3A inducer refers to that zanubrutinib and the moderate CYP3A inducer can be administered simultaneously, consecutively, or sequentially. In some embodiments, zanubrutinib and the moderate CYP3A inducer have separate dosing regimens, such as, one therapeutically active agent can be administered once a day while the other therapeutically active agent can be administered multiple times a day, or the different therapeutic agents can be dosed on different days. In one embodiment, the use of a moderate CYP3A inducer is used to identify a patient population.

In one embodiment, "assessing a patient receiving a moderate CYP3A inducer as to whether administration of the moderate CYP3A inducer can be avoided" refers to a step of determining if the patient has an alternative option to replace the moderate CYP3A inducer or a method by which the patient may stop receiving the moderate CYP3A inducer. Such an alternative option or method would not lead to the deterioration of the patient condition. If such an alternative option or method is not available to the patient, it is determined that the administration of the moderate CYP3A inducer cannot be avoided.

As used herein, all amounts specified for zanubrutinib are indicated as the amount of free or unsalted compound.

Method of Treatment

Provided herein is a method of treating a patient having a B-cell proliferative disorder, the method comprising administering to the patient zanubrutinib, or a pharmaceutically acceptable salt thereof, wherein the patient is characterized by being administered with a moderate CYP3A inducer.

Also provided herein is a method of treating or delaying progression of a B-cell proliferative disorder in a patient, the method comprising administering to the patient zanubrutinib, or a pharmaceutically acceptable salt thereof, at a dose of about 320 mg twice a day, or at a total daily dose of about 640 mg.

wherein the patient is characterized by being administered with a moderate CYP3A inducer; and the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Also provided herein is a method of treating or delaying progression of a B-cell proliferative disorder in a patient, the method comprising determining whether the patient is being treated with a moderate CYP3A inducer; and if the patient is being treated with a moderate CYP3A inducer, administering to the patient zanubrutinib, or a pharmaceutically acceptable salt thereof, at a dose of about 320 mg twice a day, or at a total daily dose of about 640 mg;

wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Provided herein is a method of treating or delaying progression of a B-cell proliferative disorder in a patient receiving a moderate CYP3A inducer, the method comprising assessing the patient as to whether administration of the moderate CYP3A inducer can be avoided; and if the administration of the moderate CYP3A inducer cannot be avoided, administering to the patient zanubrutinib, or a pharmaceutically acceptable salt thereof, at a dose of about 320 mg twice a day, or at a total daily dose of about 640 mg;

wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Also provided herein is a method of treating or delaying progression of a B-cell proliferative disorder in a patient receiving a moderate CYP3A inducer, the method comprising concomitantly administering to the patient zanubrutinib, or a pharmaceutically acceptable salt thereof, at a dose of about 320 mg twice a day, or at a total daily dose of about 640 mg, and the moderate CYP3A inducer;

wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Also provided herein is a method of treating or delaying progression of a B-cell proliferative disorder in a patient, the method comprising determining whether the patient is being treated with a moderate CYP3A inducer; and if the patient is being treated with a moderate CYP3A inducer, concomitantly administering to the patient zanubrutinib, or a pharmaceutically acceptable salt thereof, at a dose of about 320 mg twice a day, or at a total daily dose of about 640 mg; and the moderate CYP3A inducer;

wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Also provided herein is a method of treating or delaying progression of a B-cell proliferative disorder in a patient receiving a moderate CYP3A inducer, the method comprising assessing the patient as to whether administration of the moderate CYP3A inducer can be avoided; and if the administration of the moderate CYP3A inducer cannot be avoided, concomitantly administering to the patient zanubrutinib, or a pharmaceutically acceptable salt thereof, at a dose of about 320 mg twice a day, or at a total daily dose of about 640 mg, and the moderate CYP3A inducer;

wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

Also provided herein is a method of treating or delaying progression of a B-cell proliferative disorder in a patient, the method comprising administering to the patient zanubrutinib, or a pharmaceutically acceptable salt thereof, wherein the patient is characterized by being administered with a moderate CYP3A inducer.

Also provided herein is zanubrutinib, or a pharmaceutically acceptable salt thereof, for use in treating or preventing a B-cell proliferative disorder. Provided here is zanubrutinib, or a pharmaceutically acceptable salt thereof, for use as a medicament in the treatment of a B-cell proliferative disorder.

In one embodiment, zanubrutinib is administered at a dose of about 320 mg twice a day (BID), or at a total daily dose of about 640 mg. In one embodiment, zanubrutinib is administered at a dose of about 320 mg twice a day (BID).

In one embodiment, zanubrutinib is administered at a dose of about 80 mg BID, about 90 mg BID, about 100 mg BID, about 110 mg BID, about 120 mg BID, about 130 mg BID, about 140 mg BID, about 150 mg BID, about 160 mg BID, 170 mg BID, about 180 mg BID, about 190 mg BID, about 200 mg BID, about 210 mg BID, about 220 mg BID, about 230 mg BID, about 240 mg BID, about 250 mg BID, about 260 mg BID, about 270 mg BID, about 280 mg BID, about 290 mg BID, about 300 mg BID, about 310 mg BID, about 320 mg BID, about 330 mg BID, about 340 mg BID, about 350 mg BID, about 360 mg BID, about 370 mg BID, about 380 mg BID, about 390 mg BID, about 400 mg BID, about 410 mg BID, about 420 mg BID, about 430 mg BID, about 440 mg BID, about 450 mg BID, about 460 mg BID, about 470 mg BID, about 480 mg BID, about 490 mg BID, about 500 mg BID, about 510 mg BID, about 520 mg BID, about 530 mg BID, about 540 mg BID, about 550 mg BID, about 560 mg BID, about 570 mg BID, about 580 mg BID, about 590 mg BID, about 600 mg BID, about 610 mg BID, about 620 mg BID, about 630 mg BID, or about 640 mg BID, or any dose in between thereof.

In one embodiment, zanubrutinib is administered at a dose of about 540 mg QD, about 550 mg QD, about 560 mg QD, about 570 mg QD, about 580 mg QD, about 590 mg QD, about 600 mg QD, about 610 mg QD, about 620 mg QD, about 630 mg QD, about 640 mg QD, about 650 mg QD, about 660 mg QD, about 670 mg QD, about 680 mg QD, about 690 mg QD, about 700 mg QD, about 710 mg QD, about 720 mg QD, about 730 mg QD, or about 740 mg QD, or any dose in between thereof.

In one embodiment, the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

In one embodiment, the zanubrutinib is administered at a dose of about 320 mg twice a day.

In one embodiment, the zanubrutinib is administered at a total daily dose of about 640 mg.

In one embodiment, the B-cell proliferative disorder is chronic lymphocytic leukemia (CLL).

In one embodiment, the B-cell proliferative disorder is small lymphocytic lymphoma (SLL).

In one embodiment, the B-cell proliferative disorder is Waldenström macroglobulinemia (WM).

In one embodiment, the B-cell proliferative disorder is mantle cell lymphoma (MCL).

In one embodiment, the B-cell proliferative disorder is marginal zone lymphoma (MZL).

In one embodiment, the B-cell proliferative disorder is follicular lymphoma (FL).

In one embodiment, the B-cell proliferative disorder is Diffuse Large B-Cell Lymphoma (DLBCL).

In one embodiment, the B-cell proliferative disorder is Diffuse Large B-Cell Lymphoma (DLBCL) with CD79B mutation. In one embodiment, the B-cell proliferative disorder is Diffuse Large B-Cell Lymphoma (DLBCL) characterized by CD79B mutation.

In one embodiment, the patient is assessed as to whether administration of the moderate CYP3A inducer should be avoided, and if the administration of the moderate CYP3A inducer should not be avoided, the patient is administered with the moderate CYP3A inducer and zanubrutinib.

In one embodiment, the patient is assessed as to whether administration of the moderate CYP3A inducer can be avoided, and if the administration of the moderate CYP3A inducer cannot be avoided, the patient is administered with the moderate CYP3A inducer and zanubrutinib.

In one embodiment, the moderate CYP3A inducer is rifabutin, bosentan, efavirenz, etravirine, modafinil, or nafcillin. In one embodiment, the moderate CYP3A inducer is rifabutin, bosentan, efavirenz, etravirine, modafinil, phenobarbital, or nafcillin.

In one embodiment, the moderate CYP3A inducer is rifabutin, or efavirenz.

In one embodiment, the moderate CYP3A inducer is rifabutin.

In one embodiment, the patient is characterized by being administered with rifabutin at 300 mg per day.

In one embodiment, the moderate CYP3A inducer is Bexarotene, Bosentan, Cenobamate, Dabrafenib, Dexamethasone, Dipyrone, Efavirenz, Elagolix, estradiol, Eslicarbazepine, Etravirine, Lorlatinib, Mitapivat, Modafinil, Nafcillin, Pexidartinib, Rifabutin, Rifapentine, or Sotorasib. In one embodiment, a moderate CYP3A inducer is phenobarbital.

In one embodiment, the patient is characterized by a 17p deletion (del(17p)) mutation. In one embodiment, the patient is characterized by a TP53 mutation.

In one embodiment, the administration prolongs the progression-free survival (PFS) time of the patient as compared to the PFS time of a comparable patient orally administered with ibrutinib at a dose of 420 mg once daily. In one embodiment, the progression-free survival (PFS) time of the patient is longer compared to the PFS time of a comparable patient orally administered with ibrutinib at a dose of 420 mg once daily In one embodiment, the administration causes lower rate of atrial fibrillation and/or flutter as compared to the rate of atrial fibrillation and/or flutter of a comparable patient orally administered with ibrutinib at a dose of 420 mg once daily.

In one embodiment, the administration prolongs the progression-free survival (PFS) time of the patient as compared to the PFS time of a comparable patient orally administered with ibrutinib at a dose of 420 mg once daily;
wherein the patient meets all of the following criteria prior to the initial administration of zanubrutinib or the pharmaceutically acceptable salt thereof:
(i) an age greater than or equal to 18;
(ii) relapsed or refractory to at least 1 prior therapy for CLL or SLL; and
(iii) measurable disease by CT or magnetic resonance imaging (MM);
wherein the patient does not have any one of the medical conditions:
(iv) prior treatment with a BTK inhibitor;
(v) prior malignancy within the past 3 years, except for curatively treated basal or squamous cell skin cancer, non-muscle-invasive bladder cancer, carcinoma in situ of the cervix or breast;
(vi) history of severe bleeding disorder;
(vii) history of stroke or intracranial hemorrhage within 180 days;
(viii) active fungal, bacterial, or viral infection requiring systemic therapy; and
(ix) major surgery within 4 weeks.

In one embodiment, the progression-free survival (PFS) time of the patient is longer compared to the PFS time of a comparable patient orally administered with ibrutinib at a dose of 420 mg once daily.

In one embodiment, the patient was treated with ibrutinib or acalabrutinib but discontinued the treatment prior to the initial administration of zanubrutinib or the pharmaceutically acceptable salt thereof.

In one embodiment, the patient is intolerant to ibrutinib or acalabrutinib.

In one embodiment, the patient has all of the factors:
(i) an age greater than or equal to 18; and
(ii) received ibrutinib or acalabrutinib treatment at least 4 weeks prior to the treatment;
wherein the patient does not have any one of the medical conditions:
(iii) progressive disease during the prior ibrutinib or acalabrutinib treatment;
(iv) pregnancy; and
(v) lactating.

In one embodiment, the PFS of the patient is prolonged to more than about 1 month, more than about 6 months, more than about 1 year, more than about 2 years, more than about 3 years, more than about 4 years, or more than about 5 years.

In one embodiment, the PFS of the patient is prolonged to more than about 6 months, more than about 1 year, or more than about 2 years. In one embodiment, the PFS of the patient is prolonged to more than about 1 year, or more than about 2 years. In one embodiment, the PFS of the patient is prolonged for more than about 1 month, more than about 6 months, more than about 1 year, more than about 2 years, more than about 3 years, more than about 4 years, or more than about 5 years. In one embodiment, the PFS of the patient is prolonged for more than about 6 months, more than about 1 year, or more than about 2 years. In one embodiment, the PFS of the patient is prolonged for more than about 1 year, or more than about 2 years.

In one embodiment, the PFS of the patient is prolonged for more than about 1 month, more than about 6 months, more than about 1 year, more than about 2 years, more than about 3 years, more than about 4 years, or more than about 5 years longer compared to the PFS time of a comparable patient orally administered with ibrutinib at a dose of 420 mg once daily. In one embodiment, the PFS of the patient is prolonged for more than about 6 months, more than about 1 year, or more than about 2 years longer compared to the PFS time of a comparable patient orally administered with ibrutinib at a dose of 420 mg once daily. In one embodiment, the PFS of the patient is prolonged for more than about 1 year, or more than about 2 years longer compared to the PFS time of a comparable patient orally administered with ibrutinib at a dose of 420 mg once daily. In one embodiment, the PFS of the patient is prolonged for more than about 2 years longer compared to the PFS time of a comparable patient orally administered with ibrutinib at a dose of 420 mg once daily.

In one embodiment, the PFS of the patient is extended to more than about 20 months, more than about 25 months, more than about 30 months, more than about 35 months, more than about 40 months, more than about 45 months, more than about 50 months, more than about 55 months, more than about 60 months, more than about 65 months, more than about 70 months, more than about 75 months, more than about 80 months, or more than about 85 months.

In one embodiment, the patient further does not have Hemorrhage, infection, Cytopenia, Second Primary Malignancies, Cardiac Arrhythmias, or Embryo-Fetal Toxicity.

In one embodiment, the patient further does not have Hemorrhage, opportunistic infection, Cytopenia, skin cancer, atrial fibrillation, atrial flutter, or pregnancy.

Also provided here is a method of treating a patient having a B-cell proliferative disorder, the method comprising concomitantly administering to the patient zanubrutinib, or a pharmaceutically acceptable salt thereof, and a CYP3A inducer.

In one embodiment, the dose of zanubrutinib is increased by 2-fold in the presence of a moderate CYP3A inducer.

In one embodiment, the patient is assessed as to whether administration of the moderate CYP3A inducer can be avoided, and if the administration of the moderate CYP3A inducer cannot be avoided, the patient is administered the moderate CYP3A inducer and zanubrutinib.

In one embodiment, provided herein is a method of determining a therapeutic dosage of zanubrutinib, or a pharmaceutically acceptable salt thereof, in the treatment of a patient with a B-cell proliferative disorder, comprising:
a) obtaining a suitable cell or tissue sample from the patient;
b) identifying the cytochrome P450 enzymatic genotype of the patient;
c) assessing the patient's medical history for a history of smoking or use of medications that act as inducers of CYP3A; and
d) administering 320 mg of zanubrutinib twice daily to a patient determined to require a moderate CYP3A inducer.

In one embodiment, provided herein is a method of treating a B-cell proliferative disorder in a patient receiving a moderate CYP3A inducer, the method comprising administering 320 mg of zanubrutinib, or a pharmaceutically acceptable salt thereof, twice daily to the patient.

In one embodiment, the moderate CYP3A inducer is administered before, concurrently with, or after zanubrutinib, or a pharmaceutically acceptable salt thereof.

In one embodiment, provided herein is a method of treating a patient with a B-cell proliferative disorder comprising administering an adjusted dose of zanubrutinib, or a pharmaceutically acceptable salt thereof, wherein the adjusted dose is 320 mg of zanubrutinib twice daily when the patient is receiving a moderate CYP3A inducer.

Also provided herein is a method of treating or delaying progression of a B-cell proliferative disorder in a patient, wherein the patient is characterized by being administered with a moderate CYP3A inducer,
the method comprising
assessing the patient as to whether administration of the moderate CYP3A inducer can be avoided; and
if the administration of the moderate CYP3A inducer cannot be avoided, administering to the patient zanubrutinib, or a pharmaceutically acceptable salt thereof, at a dose of about 320 mg twice a day, or at a total daily dose of about 640 mg;
wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL); and
the moderate CYP3A inducer is rifabutin, bosentan, efavirenz, etravirine, modafinil, or nafcillin.

Also provided herein is a method of treating or delaying progression of a B-cell proliferative disorder in a patient receiving a moderate CYP3A inducer, the method comprising
assessing the patient as to whether administration of the moderate CYP3A inducer can be avoided; and
if the administration of the moderate CYP3A inducer cannot be avoided, concomitantly administering to the patient zanubrutinib, or a pharmaceutically acceptable salt thereof, at a dose of about 320 mg twice a day, and a moderate CYP3A inducer;
wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL); and the moderate CYP3A inducer is rifabutin, bosentan, efavirenz, etravirine, modafinil, or nafcillin.

Treatment of CLL/SLL with Improvement of PFS

Provided herein is a method of prolonging progression-free survival (PFS) time of a patient having chronic lymphocytic leukemia (CLL) or small lymphocytic lymphoma (SLL), the method comprising orally administering to the patient zanubrutinib or a pharmaceutically acceptable salt thereof at a dose of 160 mg of zanubrutinib twice a day or 320 mg of zanubrutinib once a day, wherein the administration prolongs the PFS time of the patient as compared to the PFS time of a comparable patient orally administered with ibrutinib at a dose of 420 mg once daily.

In one embodiment, the patient meets all of the following criteria prior to the initial administration of zanubrutinib or the pharmaceutically acceptable salt thereof:
(i) an age greater than or equal to 18;
(ii) relapsed or refractory to at least 1 prior therapy for CLL or SLL; and
(iii) measurable disease by CT or magnetic resonance imaging (MM);
wherein the patient does not have any one of the medical conditions:
(i) prior treatment with a BTK inhibitor;
(ii) prior malignancy within the past 3 years, except for curatively treated basal or squamous cell skin cancer, non-muscle-invasive bladder cancer, carcinoma in situ of the cervix or breast;
(iii) history of severe bleeding disorder;
(iv) history of stroke or intracranial hemorrhage within 180 days;
(v) active fungal, bacterial, or viral infection requiring systemic therapy; and
(vi) major surgery within 4 weeks.

In one embodiment, the patient meets all of the following criteria prior to the initial administration of zanubrutinib or the pharmaceutically acceptable salt thereof:
(i) an age greater than or equal to 18;
(ii) Eastern Cooperative Oncology Group (ECOG) performance status of 0, 1, or 2;
(iii) adequate bone marrow function as defined by:
(a) absolute neutrophil count (ANC) at least 1000/mm$^3$; and
(b) platelet at least 75,000/mm$^3$; and
(iv) adequate organ function defined as:
(a) creatinine clearance at least 30 mL/min;
(b) aspartate aminotransferase/serum glutamic oxaloacetic transaminase, and alanine aminotransferase (ALT)/serum glutamic pyruvic transaminase no more than 2.5 times of upper limit of normal; and
(c) serum total bilirubin less than 2.0 times of upper limit of normal;
wherein the patient does not have any one of the medical conditions:
(i) prolymphocytic leukemia;
(ii) Richter's transformation, or history of, or risk of, Richter's transformation;
(iii) clinically significant cardiovascular condition;
(iv) prior malignancy within the past 3 years, except for curatively treated basal or squamous cell skin cancer, non-muscle-invasive bladder cancer, carcinoma in situ of the cervix or breast;
(v) history of severe bleeding disorder;
(vi) history of spontaneous bleeding requiring blood transfusion;
(vii) history of stroke or intracranial hemorrhage within 180 days;
(viii) severe or debilitating pulmonary disease;
(ix) active fungal, bacterial, or viral infection requiring systemic therapy;
(x) central nervous system involvement by leukemia or lymphoma;
(xi) infection with HIV or serologic status reflecting active viral hepatitis B or C infection selected from the group consisting of:
(a) presence of hepatitis B surface antigen (HBsAg) or hepatitis B core antibody (HBcAb); and
(b) presence of hepatitis C virus (HCV) antibody;
(xii) moderate or severe hepatic impairment.
(xiii) major surgery within 4 weeks; and
(xiv) vaccination with a live vaccine within 35 days.

In one embodiment, the administration causes lower rate of atrial fibrillation and/or flutter as compared to the rate of atrial fibrillation and/or flutter of a comparable patient orally administered with ibrutinib at a dose of 420 mg once daily.

In one embodiment, the patient has relapsed or refractory CLL or SLL.

In one embodiment, the patient was treated with ibrutinib or acalabrutinib but discontinued the treatment prior to the initial administration of zanubrutinib or the pharmaceutically acceptable salt thereof.

In one embodiment, the patient has a 17p deletion (del (17p)).

In one embodiment, the administration prolongs the PFS time of the patient to be more than about 1 month, more than about 6 months, more than about 1 year, more than about 2 years, more than about 3 years, more than about 4 years, or more than about 5 years.

In one embodiment, the administration prolongs the PFS time of the patient to be more than about 20 months, more than about 25 months, more than about 30 months, more than about 35 months, more than about 40 months, more than about 45 months, more than about 50 months, more than about 55 months, more than about 60 months, more than about 65 months, more than about 70 months, more than about 75 months, more than about 80 months, or more than about 85 months.

In one embodiment, the zanubrutinib or the pharmaceutically acceptable salt thereof is administered at a dose of 160 mg of zanubrutinib twice a day.

In one embodiment, the zanubrutinib or the pharmaceutically acceptable salt thereof is administered at a dose of 320 mg of zanubrutinib once a day.

In one embodiment, the method further comprises assessing baseline risk of tumor lysis syndrome (TLS) in the patient, monitoring TLS during the PFS time, and treating TLS when it occurs.

In one embodiment, the patient is administered with a moderate CYP3A inducer.

In one embodiment, the severe bleeding disorder is hemophilia A, hemophilia B, or von Willebrand disease.

In one embodiment, the patient further does not have Hemorrhage, opportunistic infection, Cytopenia, skin cancer, atrial fibrillation, atrial flutter, Tumor Lysis Syndrome, or pregnancy.

In one embodiment, the patient further does not have Tumor Lysis Syndrome.

In one embodiment, the clinically significant cardiovascular condition is selected from the group consisting of:
(a) myocardial infarction within 6 months;
(b) unstable angina within 3 months;
(c) New York Heart Association class III or IV congestive heart failure;
(d) history of clinically significant arrhythmias selected from the group consisting of: sustained ventricular tachycardia, ventricular fibrillation, and Torsades de Pointes;
(e) QTc-Fridericia (QTcF)>480 milliseconds based on Fridericia's formula;
(f) history of Mobitz II second-degree or third-degree heart block without a permanent pacemaker in place; and
(g) uncontrolled hypertension as indicated by a minimum of 2 consecutive blood pressure measurements showing systolic blood pressure >170 mmHg and diastolic blood pressure >105 mmHg.

In one embodiment, the moderate or severe hepatic impairment is Child-Pugh class B or C.

Also provided herein is a method of treating a patient having chronic lymphocytic leukemia (CLL) or small lymphocytic lymphoma (SLL), the method comprising:
 (a) assessing baseline risk of tumor lysis syndrome (TLS) in the patient;
 (b) orally administering to the patient zanubrutinib or a pharmaceutically acceptable salt thereof at a dose of 160 mg of zanubrutinib twice a day or 320 mg of zanubrutinib once a day; and
 (c) monitoring TLS and treating TLS when it occurs, wherein the administration results in a progression-free survival (PFS) rate of at least 75% as measured at 24 months.

In one embodiment, the administration results in a progression-free survival (PFS) rate of at least 75%, such as 75%, 76%, 77%, 78%, 79%, 80%, 81%, 82%, 83%, 84%, 85%, 86%, 87%, 88%, 89%, 90%, 91%, 92%, 93%, 94%, 95%, or any number in between thereof, as measured at 24 months.

In one embodiment, the patient meets all of the following criteria prior to the initial administration of zanubrutinib or the pharmaceutically acceptable salt thereof:
 (i) an age greater than or equal to 18;
 (ii) relapsed or refractory to at least 1 prior therapy for CLL or SLL; and
 (iii) measurable disease by CT or magnetic resonance imaging (MM);
wherein the patient does not have any one of the medical conditions:
 (i) prior treatment with a BTK inhibitor;
 (ii) prior malignancy within the past 3 years, except for curatively treated basal or squamous cell skin cancer, non-muscle-invasive bladder cancer, carcinoma in situ of the cervix or breast;
 (iii) history of severe bleeding disorder;
 (iv) history of stroke or intracranial hemorrhage within 180 days;
 (v) active fungal, bacterial, or viral infection requiring systemic therapy; and
 (vi) major surgery within 4 weeks.

In one embodiment, the patient meets all of the following criteria prior to the initial administration of zanubrutinib or the pharmaceutically acceptable salt thereof:
 (i) an age greater than or equal to 18;
 (ii) Eastern Cooperative Oncology Group (ECOG) performance status of 0, 1, or 2;
 (iii) adequate bone marrow function as defined by:
  (a) absolute neutrophil count (ANC) at least 1000/mm$^3$; and
  (b) platelet at least 75,000/mm$^3$; and
 (iv) adequate organ function defined as:
  (a) creatinine clearance at least 30 mL/min;
  (b) aspartate aminotransferase/serum glutamic oxaloacetic transaminase, and alanine aminotransferase (ALT)/serum glutamic pyruvic transaminase no more than 2.5 times of upper limit of normal; and
  (c) serum total bilirubin less than 2.0 times of upper limit of normal;
wherein the patient does not have any one of the medical conditions: prolymphocytic leukemia;
 (ii) Richter's transformation, or history of, or risk of, Richter's transformation;
 (iii) clinically significant cardiovascular condition;
 (iv) prior malignancy within the past 3 years, except for curatively treated basal or squamous cell skin cancer, non-muscle-invasive bladder cancer, carcinoma in situ of the cervix or breast;
 (v) history of severe bleeding disorder;
 (vi) history of spontaneous bleeding requiring blood transfusion;
 (vii) history of stroke or intracranial hemorrhage within 180 days;
 (viii) severe or debilitating pulmonary disease;
 (ix) active fungal, bacterial, or viral infection requiring systemic therapy;
 (x) central nervous system involvement by leukemia or lymphoma;
 (xi) infection with HIV or serologic status reflecting active viral hepatitis B or C infection selected from the group consisting of:
  (a) presence of hepatitis B surface antigen (HBsAg) or hepatitis B core antibody (HBcAb); and
  (b) presence of hepatitis C virus (HCV) antibody;
 (xii) moderate or severe hepatic impairment.
 (xiii) major surgery within 4 weeks; and
 (xiv) vaccination with a live vaccine within 35 days.

In one embodiment, the administration prolongs the PFS time as compared to the PFS time of a comparable patient orally administered with ibrutinib at a dose of 420 mg once daily.

In one embodiment, the administration causes lower rate of atrial fibrillation and/or flutter as compared to the rate of atrial fibrillation and/or flutter of a comparable patient orally administered with ibrutinib at a dose of 420 mg once daily.

In one embodiment, the patient has relapsed or refractory CLL or SLL.

In one embodiment, the patient was treated with ibrutinib or acalabrutinib but discontinued the treatment prior to the initial administration of zanubrutinib or the pharmaceutically acceptable salt thereof.

In one embodiment, the patient has a 17p deletion (del (17p)).

In one embodiment, the administration prolongs the PFS time of the patient to be more than about 1 month, more than about 6 months, more than about 1 year, more than about 2 years, more than about 3 years, more than about 4 years, or more than about 5 years.

In one embodiment, the administration prolongs the PFS time of the patient to be more than about 20 months, more than about 25 months, more than about 30 months, more than about 35 months, more than about 40 months, more than about 45 months, more than about 50 months, more than about 55 months, more than about 60 months, more than about 65 months, more than about 70 months, more than about 75 months, more than about 80 months, or more than about 85 months.

In one embodiment, the zanubrutinib or the pharmaceutically acceptable salt thereof is administered at a dose of 160 mg of zanubrutinib twice a day.

In one embodiment, the zanubrutinib or the pharmaceutically acceptable salt thereof is administered at a dose of 320 mg of zanubrutinib once a day.

In one embodiment, the patient is administered with a moderate CYP3A inducer.

In one embodiment, the severe bleeding disorder is hemophilia A, hemophilia B, or von Willebrand disease.

In one embodiment, the clinically significant cardiovascular condition is selected from the group consisting of:
 (a) myocardial infarction within 6 months;
 (b) unstable angina within 3 months;

(c) New York Heart Association class III or IV congestive heart failure;
(d) history of clinically significant arrhythmias selected from the group consisting of: sustained ventricular tachycardia, ventricular fibrillation, and Torsades de Pointes;
(e) QTc-Fridericia (QTcF)>480 milliseconds based on Fridericia's formula;
(f) history of Mobitz II second-degree or third-degree heart block without a permanent pacemaker in place; and
(g) uncontrolled hypertension as indicated by a minimum of 2 consecutive blood pressure measurements showing systolic blood pressure >170 mmHg and diastolic blood pressure >105 mmHg.

In one embodiment, the moderate or severe hepatic impairment is Child-Pugh class B or C.

Also provided herein is a method of treating a patient having relapsed or refractory chronic lymphocytic leukemia (CLL) or small lymphocytic lymphoma (SLL), the method comprising:
(a) assessing baseline risk of tumor lysis syndrome (TLS) in the patient;
(b) orally administering to the patient zanubrutinib or a pharmaceutically acceptable salt thereof at a dose of 160 mg of zanubrutinib twice a day or 320 mg of zanubrutinib once a day; and
(c) monitoring TLS and treating TLS when it occurs,
wherein the administration results in a progression-free survival (PFS) rate of at least 75% as measured at 24 months, and the administration prolongs the PFS time and causes lower rate of atrial fibrillation and/or flutter as compared to the PFS time and rate of atrial fibrillation and/or flutter, respectively, of a comparable patient orally administered with ibrutinib at a dose of 420 mg once daily, wherein the patient is optionally administered with a moderate CYP3A inducer.

In one embodiment, the administration results in a progression-free survival (PFS) rate of at least 75%, such as 75%, 76%, 77%, 78%, 79%, 80%, 81%, 82%, 83%, 84%, 85%, 86%, 87%, 88%, 89%, 90%, 91%, 92%, 93%, 94%, 95%, or any number in between thereof, as measured at 24 months.

In one embodiment, the patient meets all of the following criteria prior to the initial administration of zanubrutinib or the pharmaceutically acceptable salt thereof:
(i) an age greater than or equal to 18;
(ii) relapsed or refractory to at least 1 prior therapy for CLL or SLL; and
(iii) measurable disease by CT or magnetic resonance imaging (MM);
wherein the patient does not have any one of the medical conditions:
(i) prior treatment with a BTK inhibitor;
(ii) prior malignancy within the past 3 years, except for curatively treated basal or squamous cell skin cancer, non-muscle-invasive bladder cancer, carcinoma in situ of the cervix or breast;
(iii) history of severe bleeding disorder;
(iv) history of stroke or intracranial hemorrhage within 180 days;
(v) active fungal, bacterial, or viral infection requiring systemic therapy; and
(vi) major surgery within 4 weeks.

In one embodiment, the patient meets all of the following criteria prior to the initial administration of zanubrutinib or the pharmaceutically acceptable salt thereof:
(i) an age greater than or equal to 18;
(ii) Eastern Cooperative Oncology Group (ECOG) performance status of 0, 1, or 2;
(iii) adequate bone marrow function as defined by:
(a) absolute neutrophil count (ANC) at least 1000/mm$^3$; and
(b) platelet at least 75,000/mm$^3$; and
(iv) adequate organ function defined as:
(a) creatinine clearance at least 30 mL/min;
(b) aspartate aminotransferase/serum glutamic oxaloacetic transaminase, and alanine aminotransferase (ALT)/serum glutamic pyruvic transaminase no more than 2.5 times of upper limit of normal; and
(c) serum total bilirubin less than 2.0 times of upper limit of normal;
wherein the patient does not have any one of the medical conditions:
(i) prolymphocytic leukemia;
(ii) Richter's transformation, or history of, or risk of, Richter's transformation;
(iii) clinically significant cardiovascular condition;
(iv) prior malignancy within the past 3 years, except for curatively treated basal or squamous cell skin cancer, non-muscle-invasive bladder cancer, carcinoma in situ of the cervix or breast;
(v) history of severe bleeding disorder;
(vi) history of spontaneous bleeding requiring blood transfusion;
(vii) history of stroke or intracranial hemorrhage within 180 days;
(viii) severe or debilitating pulmonary disease;
(ix) active fungal, bacterial, or viral infection requiring systemic therapy;
(x) central nervous system involvement by leukemia or lymphoma;
(xi) infection with HIV or serologic status reflecting active viral hepatitis B or C infection selected from the group consisting of:
(a) presence of hepatitis B surface antigen (HBsAg) or hepatitis B core antibody (HBcAb); and
(b) presence of hepatitis C virus (HCV) antibody;
(xii) moderate or severe hepatic impairment.
(xiii) major surgery within 4 weeks; and
(xiv) vaccination with a live vaccine within 35 days.

In one embodiment, the patient was treated with ibrutinib or acalabrutinib but discontinued the treatment prior to the initial administration of zanubrutinib or the pharmaceutically acceptable salt thereof.

In one embodiment, the patient has a 17p deletion (del (17p)).

In one embodiment, the administration prolongs the PFS time of the patient to be more than about 1 month, more than about 6 months, more than about 1 year, more than about 2 years, more than about 3 years, more than about 4 years, or more than about 5 years.

In one embodiment, the administration prolongs the PFS time of the patient to be more than about 20 months, more than about 25 months, more than about 30 months, more than about 35 months, more than about 40 months, more than about 45 months, more than about 50 months, more than about 55 months, more than about 60 months, more than about 65 months, more than about 70 months, more than about 75 months, more than about 80 months, or more than about 85 months.

In one embodiment, the zanubrutinib or the pharmaceutically acceptable salt thereof is administered at a dose of 160 mg of zanubrutinib twice a day.

In one embodiment, the zanubrutinib or the pharmaceutically acceptable salt thereof is administered at a dose of 320 mg of zanubrutinib once a day.

In one embodiment, the patient is administered with a moderate CYP3A inducer.

In one embodiment, the severe bleeding disorder is hemophilia A, hemophilia B, or von Willebrand disease.

In one embodiment, the clinically significant cardiovascular condition is selected from the group consisting of:
  (a) myocardial infarction within 6 months;
  (b) unstable angina within 3 months;
  (c) New York Heart Association class III or IV congestive heart failure;
  (d) history of clinically significant arrhythmias selected from the group consisting of: sustained ventricular tachycardia, ventricular fibrillation, and Torsades de Pointes;
  (e) QTc-Fridericia (QTcF)>480 milliseconds based on Fridericia's formula;
  (f) history of Mobitz II second-degree or third-degree heart block without a permanent pacemaker in place; and
  (g) uncontrolled hypertension as indicated by a minimum of 2 consecutive blood pressure measurements showing systolic blood pressure >170 mmHg and diastolic blood pressure >105 mmHg.

In one embodiment, the moderate or severe hepatic impairment is Child-Pugh class B or C.

Also provided herein is a method of treating a patient having chronic lymphocytic leukemia (CLL) or small lymphocytic lymphoma (SLL), comprising orally administering to the patient zanubrutinib or a pharmaceutically acceptable salt thereof at a dose of 160 mg of zanubrutinib twice a day or 320 mg of zanubrutinib once a day, wherein the patient is further administered with a moderate CYP3A inducer.

In one embodiment, the patient has a 17p deletion (del (17p)), and the patient meets all of the following criteria prior to the initial administration of zanubrutinib or the pharmaceutically acceptable salt thereof:
  (i) an age greater than or equal to 18;
  (ii) relapsed or refractory to at least 1 prior therapy for CLL or SLL; and
  (iii) measurable disease by CT or magnetic resonance imaging (MM);
wherein the patient does not have any one of the medical conditions:
  prior treatment with a BTK inhibitor;
  (ii) prior malignancy within the past 3 years, except for curatively treated basal or squamous cell skin cancer, non-muscle-invasive bladder cancer, carcinoma in situ of the cervix or breast;
  (iii) history of severe bleeding disorder;
  (iv) history of stroke or intracranial hemorrhage within 180 days;
  (v) active fungal, bacterial, or viral infection requiring systemic therapy; and
  (vi) major surgery within 4 weeks.

In one embodiment, the patient has a 17p deletion (del (17p)), and the patient meets all of the following criteria prior to the initial administration of zanubrutinib or the pharmaceutically acceptable salt thereof:
  an age greater than or equal to 18;
  (ii) Eastern Cooperative Oncology Group (ECOG) performance status of 0, 1, or 2;
  (iii) adequate bone marrow function as defined by:
    (a) absolute neutrophil count (ANC) at least 1000/mm$^3$; and
    (b) platelet at least 75,000/mm$^3$; and
  (iv) adequate organ function defined as:
    (a) creatinine clearance at least 30 mL/min;
    (b) aspartate aminotransferase/serum glutamic oxaloacetic transaminase, and alanine aminotransferase (ALT)/serum glutamic pyruvic transaminase no more than 2.5 times of upper limit of normal; and
    (c) serum total bilirubin less than 2.0 times of upper limit of normal;
wherein the patient does not have any one of the medical conditions:
  (i) prolymphocytic leukemia;
  (ii) Richter's transformation, or history of, or risk of, Richter's transformation;
  (iii) clinically significant cardiovascular condition;
  (iv) prior malignancy within the past 3 years, except for curatively treated basal or squamous cell skin cancer, non-muscle-invasive bladder cancer, carcinoma in situ of the cervix or breast;
  (v) history of severe bleeding disorder;
  (vi) history of spontaneous bleeding requiring blood transfusion;
  (vii) history of stroke or intracranial hemorrhage within 180 days;
  (viii) severe or debilitating pulmonary disease;
  (ix) active fungal, bacterial, or viral infection requiring systemic therapy;
  (x) central nervous system involvement by leukemia or lymphoma;
  (xi) infection with HIV or serologic status reflecting active viral hepatitis B or C infection selected from the group consisting of:
    (a) presence of hepatitis B surface antigen (HBsAg) or hepatitis B core antibody (HBcAb); and
    (b) presence of hepatitis C virus (HCV) antibody;
  (xii) moderate or severe hepatic impairment.
  (xiii) major surgery within 4 weeks; and
  (xiv) vaccination with a live vaccine within 35 days.

In one embodiment, the administration causes lower rate of atrial fibrillation and/or flutter as compared to the rate of atrial fibrillation and/or flutter of a comparable patient orally administered with ibrutinib at a dose of 420 mg once daily.

In one embodiment, the patient has relapsed or refractory CLL or SLL.

In one embodiment, the zanubrutinib or the pharmaceutically acceptable salt thereof is administered at a dose of 160 mg of zanubrutinib twice a day.

In one embodiment, the zanubrutinib or the pharmaceutically acceptable salt thereof is administered at a dose of 320 mg of zanubrutinib once a day.

In one embodiment, the severe bleeding disorder is hemophilia A, hemophilia B, or von Willebrand disease.

In one embodiment, the patient further does not have Hemorrhage, opportunistic infection, Cytopenia, skin cancer, atrial fibrillation, atrial flutter, Tumor Lysis Syndrome, or pregnancy.

In one embodiment, the patient further does not have Tumor Lysis Syndrome.

In one embodiment, the clinically significant cardiovascular condition is selected from the group consisting of:
  (a) myocardial infarction within 6 months;
  (b) unstable angina within 3 months;
  (c) New York Heart Association class III or IV congestive heart failure;

(d) history of clinically significant arrhythmias selected from the group consisting of: sustained ventricular tachycardia, ventricular fibrillation, and Torsades de Pointes;
(e) QTc-Fridericia (QTcF)>480 milliseconds based on Fridericia's formula;
(f) history of Mobitz II second-degree or third-degree heart block without a permanent pacemaker in place; and
(g) uncontrolled hypertension as indicated by a minimum of 2 consecutive blood pressure measurements showing systolic blood pressure >170 mmHg and diastolic blood pressure >105 mmHg.

In one embodiment, the moderate or severe hepatic impairment is Child-Pugh class B or C.

Also provided herein is a kit comprising zanubrutinib and means for improving progression-free survival (PFS) probability of a patient having chronic lymphocytic leukemia or small lymphocytic lymphoma (CLL/SLL), wherein said patient is relapsed or refractory to at least 1 prior therapy for CLL or SLL.

Treatment of a Patient Intolerant to a BTK Inhibitor Other than Zanubrutinib

Provided herein is a method of treating a patient having B-cell malignancy, the method comprising administering to the patient zanubrutinib, or a pharmaceutically acceptable salt thereof, at a dose of about 160 mg twice a day or about 320 mg once a day, wherein the patient is intolerant to a BTK inhibitor other than zanubrutinib.

Provided herein is a method of treating a patient having B-cell malignancy, the method comprising administering to the patient zanubrutinib, or a pharmaceutically acceptable salt thereof, at a dose of about 160 mg twice a day or about 320 mg once a day, wherein the patient is intolerant to ibrutinib or acalabrutinib.

In one embodiment, the patient has all of the factors:
(i) an age greater than or equal to 18; and
(ii) received ibrutinib or acalabrutinib treatment at least 4 weeks prior to the treatment.

In one embodiment, the patient does not have any one of the medical conditions:
(i) progressive disease during the prior ibrutinib or acalabrutinib treatment;
(ii) pregnancy; and
(iii) lactating.

In one embodiment, the PFS probability of the patient is about 83.8% after about 18-month treatment.

In one embodiment, the patient does not have del(17p)/TP53 mutation.

In one embodiment, the patient has del(17p)/TP53 mutation.

In one embodiment, the zanubrutinib is administered at a dose of about 160 mg twice a day.

In one embodiment, the zanubrutinib is administered at a dose of about 320 mg once a day.

In one embodiment, the patient further does not have Hemorrhage, opportunistic infection, Cytopenia, skin cancer, atrial fibrillation, atrial flutter, Tumor Lysis Syndrome, or pregnancy.

In one embodiment, the patient further does not have Tumor Lysis Syndrome.

In one embodiment, the PFS of the patient is extended to more than about 1 month, more than about 6 months, more than about 1 year, more than about 2 years, more than about 3 years, more than about 4 years, or more than about 5 years.

In one embodiment, the PFS of the patient is extended is more than about 20 months, more than about 25 months, more than about 30 months, more than about 35 months, more than about 40 months, more than about 45 months, more than about 50 months, more than about 55 months, more than about 60 months, more than about 65 months, more than about 70 months, more than about 75 months, more than about 80 months, or more than about 85 months.

In one embodiment, the B-cell malignancy is chronic lymphocytic leukemia (CLL), small lymphocytic lymphoma (SLL), Waldenström macroglobulinemia (WM), mantle cell lymphoma (MCL), or marginal zone lymphoma (MZL).

In one embodiment, the B-cell malignancy is chronic lymphocytic leukemia (CLL).

In one embodiment, the B-cell malignancy is small lymphocytic lymphoma (SLL).

In one embodiment, the B-cell malignancy is Waldenström macroglobulinemia (WM).

In one embodiment, the B-cell malignancy is mantle cell lymphoma (MCL).

In one embodiment, the B-cell malignancy is marginal zone lymphoma (MZL).

The present embodiments can be understood more fully by reference to the detailed description and examples, which are intended to exemplify non-limiting embodiments.

EXAMPLES

The examples below were intended to be purely exemplary and should not be considered to be limiting in any way. Unless otherwise specified, the experimental methods in the Examples described below were conventional methods.

| LIST OF ABBREVIATIONS AND TERMS | |
|---|---|
| Abbreviation | Definition |
| AE | adverse event |
| ALT | alanine aminotransferase |
| ANC | absolute neutrophil count |
| AST | aspartate aminotransferase |
| BTK | Bruton tyrosine kinase |
| CBC | complete blood count |
| CI | confidence interval |
| CLL | chronic lymphocytic leukemia |
| CR | complete response |
| CRi | complete response with incomplete bone marrow recovery |
| CT | computed tomography |
| CYP | cytochrome P450 |
| DMC | Data Monitoring Committee |
| DOR | duration of response |
| ECG | electrocardiogram |
| ECOG | Eastern Cooperative Oncology Group |
| eCRF | electronic case report form |
| EDC | electronic data capture system |
| EORTC QLQ-C30 | European Organisation for Research and Treatment of Cancer quality of life cancer core questionnaire |
| EQ-5D-5L | European quality of life 5-dimensions 5-levels health questionnaire |
| FDA | Food and Drug Administration |
| GCP | Good Clinical Practice |
| HBcAb | hepatitis B core antibody |
| HBsAb | hepatitis B surface antibody |
| HBsAg | hepatitis B surface antigen |
| HBV | hepatitis B virus |
| HCV | hepatitis C virus |
| HR | hazard ratio |
| IC50 | inhibitory concentration |
| ICF | informed consent form |
| IEC | Independent Ethics Committee |
| IGHV | immunoglobulin variable region heavy chain |
| IRB | Institutional Review Board |
| IWCLL | International Workshop on Chronic Lymphocytic Leukemia |

| LIST OF ABBREVIATIONS AND TERMS | |
|---|---|
| Abbreviation | Definition |
| MedDRA | Medical Dictionary for Regulatory Activities |
| MRD | minimal residual disease |
| MRI | magnetic resonance imaging |
| NCI-CTCAE | National Cancer Institute Common Terminology Criteria for Adverse Events |
| NHL | non-Hodgkin lymphoma |
| ORR | overall response rate |
| OS | overall survival |
| PD | progressive disease |
| PFS | progression-free survival |
| Pi3K | phosphatidyl inositol 3-kinase |
| PK | pharmacokinetics |
| PR | partial response |
| PR-L | partial response with lymphocytosis |
| PRO | patient-reported outcome |
| R/R | relapsed/refractory |
| SAE | serious adverse event |
| SLL | small lymphocytic lymphoma |
| zanubrutinib | BGB-3111 |

Example 1

The entire disclosure of NCT04470908 on ClinicalTrials.gov is incorporated herein by reference.

Introduction

Activation of Bruton tyrosine kinase (BTK) in B-cells triggers a cascade of signaling events that impact cell proliferation and survival. Although the exact mechanism underlying B-cell malignancies is unknown, aberrant BTK activation may drive hallmarks of these malignancies and play a key role in its pathogenesis. To date, BTK inhibitors remain at the forefront of the treatment portfolio for various B-cell malignancies.

Zanubrutinib, a second-generation covalent BTK inhibitor, was designed to maximize BTK receptor occupancy and minimize off-target kinase inhibition. Prior pharmacokinetic (PK), safety, efficacy, and exposure-response analyses support the recommended 320 mg total daily dose of zanubrutinib (160 mg twice daily BID or 320 mg once daily QD with or without food) for the approved indications. Previous PK data demonstrate that zanubrutinib is rapidly absorbed and eliminated after oral administration with a median time to peak plasma concentration (Tmax) of 2 hours and a mean terminal elimination half-life (t½) of 2-4 hours. Hepatically, enzymatic metabolism via cytochrome P450, family 3, subfamily A (CYP3A) is considered the primary route of zanubrutinib metabolism.

After multiple-dose administrations of zanubrutinib at doses ranging from 40 mg to 320 mg QD and 160 mg BID, there is a dose proportional increase in the maximum concentration (Cmax) and the area under the plasma concentration-time curve (AUC) from time 0 extrapolated to infinity (AUC0-∞); additionally, limited systemic accumulation is observed, which is consistent with the observed t½ of zanubrutinib.

Given the involvement of CYP3A enzymes in zanubrutinib metabolism, studies have been conducted to explore the interactions between zanubrutinib and various CYP3A modulators. A drug-drug interaction (DDI) study in healthy volunteers assessed the effect of coadministering zanubrutinib with the strong CYP3A inducer rifampin and the strong CYP3A inhibitor itraconazole. Therein, rifampin significantly impacted the bioavailability and apparent clearance of zanubrutinib, as demonstrated by a 12.6-fold and 13.5-fold decrease in zanubrutinib Cmax and AUC0-∞, respectively. Coadministration of zanubrutinib with the strong CYP3A inhibitor itraconazole resulted in a 2.6-fold and 3.8-fold increase in zanubrutinib Cmax and AUC0-∞, respectively. Although the reduction of zanubrutinib exposures with the coadministration of a strong CYP3A inducer such as rifampin has been evaluated, the magnitude and extent of reduction with the coadministration of moderate CYP3A inducers is largely unknown.

Previous recommendations state that coadministration of zanubrutinib with moderate or strong CYP3A inducers should be avoided. However, multiple treatments, including, but not limited to, antibacterial and/or antifungal agents, may often be administered in conjunction with zanubrutinib to manage opportunistic infections in patients with B-cell malignancies. Some of these agents may be CYP3A inducers, and thus it is essential to further elucidate the PK profile of zanubrutinib when coadministered with CYP3A inducers. Rifabutin, a moderate CYP3A inducer, is a first-line therapeutic alternative to the strong CYP3A inducer rifampin and is a clinically relevant anti-infective agent used in patients with B-cell malignancies. Other known moderate CYP3A inducers, including, but not limited to, efavirenz and etravirine, are indicated for the treatment of HIV infection. In another patient population, patients are on chronic usage of anti-seizure medications, which are often moderate inducers. For example, phenobarbital (a moderate CYP inducer) has been used to treat epilepsy since the early decades of the 20th century. It is still commonly used throughout the world because it is both effective and low in cost. In the patient population in which usage of CYP3A inducers can't be stopped, stopping zanubrutinib treatment may not be a viable option. For example, zanubrutinib can be the optimal cancer treatment for those patients, and/or stopping zanubrutinib treatment may encourage development of drug resistance or relapse.

Rifabutin is primarily metabolized by CYP3A enzymes, and multiple doses of rifabutin were associated with induction of enzymes of the CYP3A subfamily. Following a single oral dose of 300 mg, rifabutin was readily absorbed with a Tmax ranging from 2-4 hours and was slowly eliminated from plasma with a mean t½ of 45 (standard deviation, 17) hours (range: 16-69 hours). Although the systemic levels of rifabutin after multiple doses decreased by 38% due to auto-induction, its t½ remained unchanged. To achieve maximal induction of CYP3A, 300 mg rifabutin QD was administered for 8 days to reach steady-state.

Various studies have established rifabutin as a moderate CYP3A inducer. It was reported the AUC0-∞ geometric mean ratio (GMR) after coadministration of rifabutin with the index CYP3A substrate midazolam as 0.31 (3.2-fold reduction in exposure).

This open-label, fixed-sequence phase 1 study was conducted to determine the effect of CYP3A induction by rifabutin on zanubrutinib PK when coadministered in healthy male volunteers. The results of this study were taken into consideration with safety and efficacy data from other clinical studies to determine the appropriate dose recommendation of zanubrutinib when coadministered with moderate CYP3A inducers.

Materials and Methods

Study Design and Volunteers

This was a single-center, phase 1, open-label, fixed-sequence clinical DDI study to investigate the effect of CYP3A induction by steady-state rifabutin on the single-dose PK of zanubrutinib in healthy volunteers (NCT04470908). This study was designed, conducted, and monitored according to sponsor procedures, and complied with the ethical principles of Good Clinical Practice, International Council for Harmonisation of Technical Requirements for Pharmaceuticals for Human Use, the Declaration of Helsinki, and local regulatory requirements. All volunteers provided written, informed consent before study entry. Midlands Independent Review Board (MLIRB (now WCG IRB), Overland Park, Kans.) reviewed and approved the protocol at the respective study center.

Volunteers were screened for eligibility during the screening period (from day −28 through day −2). Those who met all the inclusion criteria and none of the exclusion criteria were admitted into the clinical research unit (CRU) on day −1 and confined to the CRU until discharge on day 13. All volunteers received study drugs in a fixed sequence as shown in FIG. 1. On day 1, volunteers received a single oral dose of 320 mg zanubrutinib after an overnight fast of 8-10 hours. On days 3-10, volunteers were administered an oral dose of 300 mg rifabutin QD with food, and on day 11, volunteers were administered a single oral dose of 320 mg zanubrutinib and 300 mg rifabutin QD after an overnight fast of 8-10 hours. Volunteers were discharged on day 13 after satisfactory completion of study-related procedures.

Key inclusion criteria included healthy men of any race, between ages 18-65 years, with a body mass index (BMI) between 18.0-32.0 kg/m2, and good health determined by investigator's assessment of medical history, physical examination, vital signs, electrocardiograms (ECGs), and laboratory tests at screening.

Key exclusion criteria included considerable history or clinical manifestation of any metabolic, allergic, dermatological, hepatic, renal, hematological, pulmonary, cardiovascular, gastrointestinal, neurological, respiratory, endocrine, or psychiatric disorder; evidence of any infections (e.g., bacterial, viral, fungal, and parasitic) within 4 weeks before the first dose of study drug; history of significant hypersensitivity, intolerance, or allergy to any drug compound, food, or other substance; history of stomach or intestinal surgery or resection that would potentially alter absorption and/or excretion of orally administered drugs; and use or intended use of any medications/products known to alter drug absorption, metabolism, or elimination processes, including St. John's Wort, within 30 days before check-in.

Treatments

Volunteers received a single oral dose of zanubrutinib (320 mg) as 4×80 mg capsules in the fasted state on days 1 and 11. A single dose of rifabutin (300 mg) was given orally as 2×150 mg capsules with food on days 3-10 and in the fasted state on day 11.

On PK sampling days (days 1 and 11), zanubrutinib and rifabutin were administered after an overnight fast of 8-10 hours. Each dose of zanubrutinib and rifabutin was administered orally with approximately 240 mL of room temperature water. When zanubrutinib and rifabutin were administered concurrently (on day 11), an additional amount (up to 240 mL) of room temperature water was allowed to be administered.

Pharmacokinetic Analyses

Noncompartmental analysis was conducted using Phoenix® WinNonlin™ version 8.1 (Certara USA, Inc., Princeton, N.J., USA). PK parameters were derived for zanubrutinib alone and in combination with rifabutin, including AUC, Cmax, Tmax, t½, apparent total oral clearance (CL/F), and apparent volume of distribution during the terminal elimination phase (Vd/F).

Plasma samples were collected to assess single-dose zanubrutinib PK on day 1 and after coadministration with rifabutin on day 11 at the following timepoints: 0.5, 1, 1.5, 2, 3, 4, 6, 8, 12, 24, and 36 hours postdose.

Plasma concentrations of zanubrutinib were determined using a validated liquid chromatography coupled to tandem mass spectrometry (LC-MS/MS) method by XenoBiotic Laboratories, Inc. (Plainsboro, N.J., United States). Protein precipitation was utilized to extract the analyte and internal standard from human plasma containing dipotassium ethylenediaminetetraacetic acid (K2EDTA) as an anticoagulant. The calibration range was 1.00-1000 ng/mL for the plasma zanubrutinib concentration, with a lower limit of quantification of 1.00 ng/mL.

Safety Assessments

Safety was assessed by monitoring and recording of adverse events (AEs), serious adverse events (SAEs), clinical laboratory tests, physical examinations, and vital signs. Safety was measured by the incidence, timing, and severity of treatment-emergent adverse events (TEAEs), according to the National Cancer Institute Common Terminology Criteria for Adverse Events Version 5.0 (NCI CTCAE v5.0). A TEAE was defined as an AE that started during or after the first dose or started before the first dose and increased in severity after the first dose. AEs were classified based on MedDRA Version 24.0.

Statistical Analyses

The study sample size was based on precedent set by other PK studies of a similar nature and was not based on power calculations. It was aimed to enroll 15 volunteers to ensure that at least 12 volunteers completed the study.

The safety analysis set included all patients who received ≥1 dose of zanubrutinib. Safety and tolerability were assessed, when applicable, by incidence, severity, change from baseline values, and abnormal values for all relevant parameters such as AEs, laboratory parameters, vital signs, and physical examination.

The GMRs of PK parameters of zanubrutinib with and without coadministration of rifabutin and the associated 90% confidence interval (CI) was constructed based on the least squares mean (LSM) and intra-subject coefficient of variation (CV) from a mixed effects model of log-transformed PK parameters. The geometric least squares mean (GLSM) and their ratios were obtained by taking the exponential of the corresponding estimates of LSM and their differences on the natural logarithm scale, where ratio=test/reference. Within-subject CV was calculated as 100×square root[exp(mean square error from the analysis model)−1]. Estimates of GMRs and the corresponding 90% CIs were derived for the comparisons of area under the concentration-time curve from time zero to the time of the last quantifiable concentration (AUC0-t), AUC0-∞, and Cmax for zanubrutinib coadministration with rifabutin (test) versus zanubrutinib alone (reference).

Results

Demographics and Baseline Characteristics

A total of 13 volunteers were enrolled, and 12 completed the study. One volunteer was unable to return for the follow-up visit and was, therefore, noted as lost to follow-up. All 13 volunteers completed the study through day 13. Baseline demographics are shown in Table 1.

TABLE 1

Volunteer Demographics

| Demographic | N = 13 |
|---|---|
| Age (years), mean (SD) | 48.8 (11.0) |
| Male sex, n, (%) | 13 (100%) |
| Race, n (%) | |
| White | 12 (92.3%) |
| American Indian or Alaska Native | 1 (7.7%) |
| Ethnicity, n (%) | |
| Hispanic or Latino | 8 (61.5%) |
| Not Hispanic or Latino | 5 (38.5%) |
| Height (cm), mean (SD) | 174.5 (3.7) |
| Body weight (kg), mean (SD) | 83.0 (9.0) |
| Body mass index (kg/m$^2$), mean (SD) | 27.3 (2.7) |

N, number of volunteers; n, number of volunteers with valid observation; SD, standard deviation.

Volunteers were men aged between 28-63 years with BMI values ranging from 23.5-31.3 kg/m2. Twelve of the volunteers were White and 1 volunteer was an American Indian or Alaska Native.

Pharmacokinetics

Figure 2A:
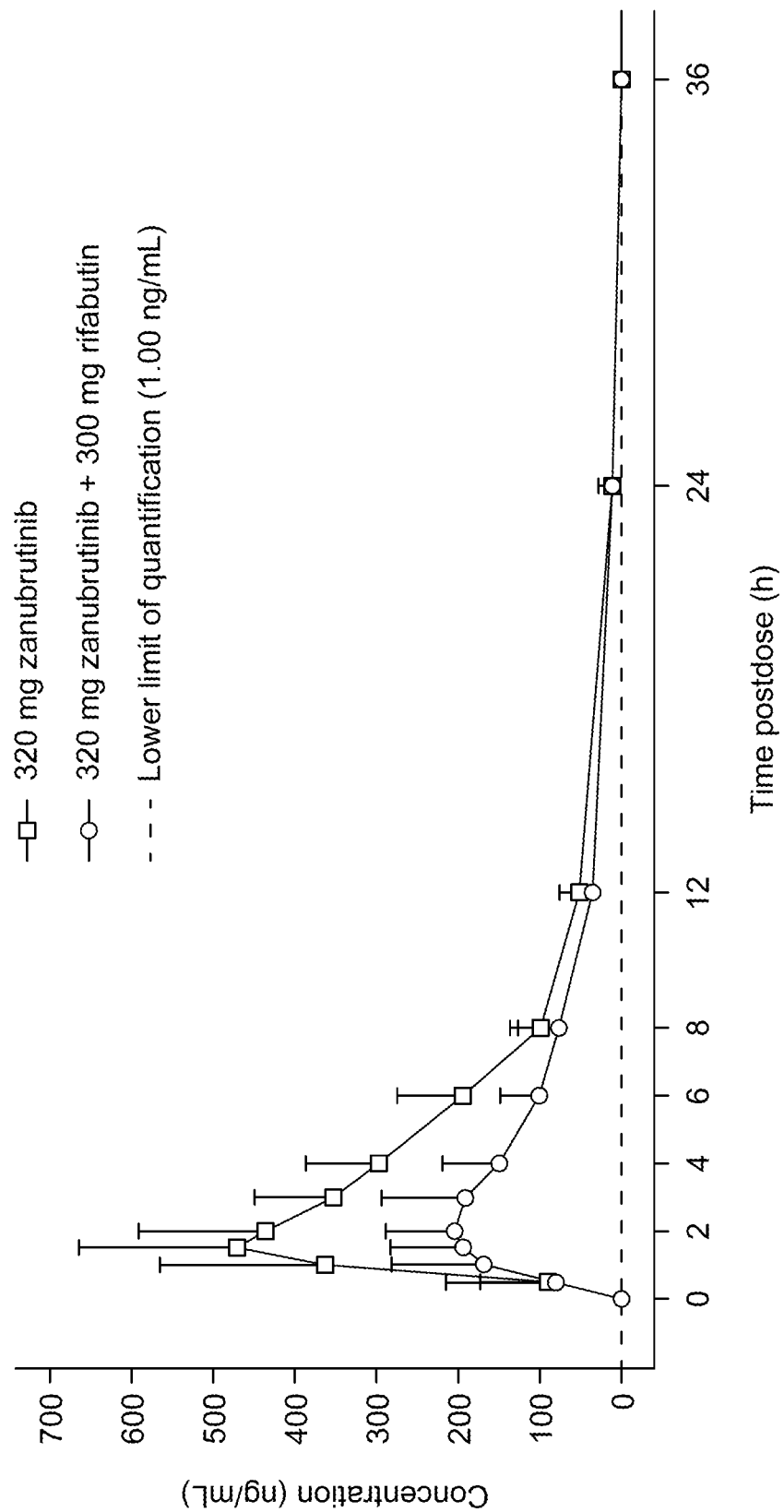
FIGS. 2A-2B depict arithmetic mean (+SD) plasma concentrations of zanubrutinib after administration of zanubrutinib alone and after coadministration of zanubrutinib with rifabutin on a (FIG. 2A) linear and (FIG. 2B) semi-logarithmic scale. SD, standard deviation.
Figure 2B:
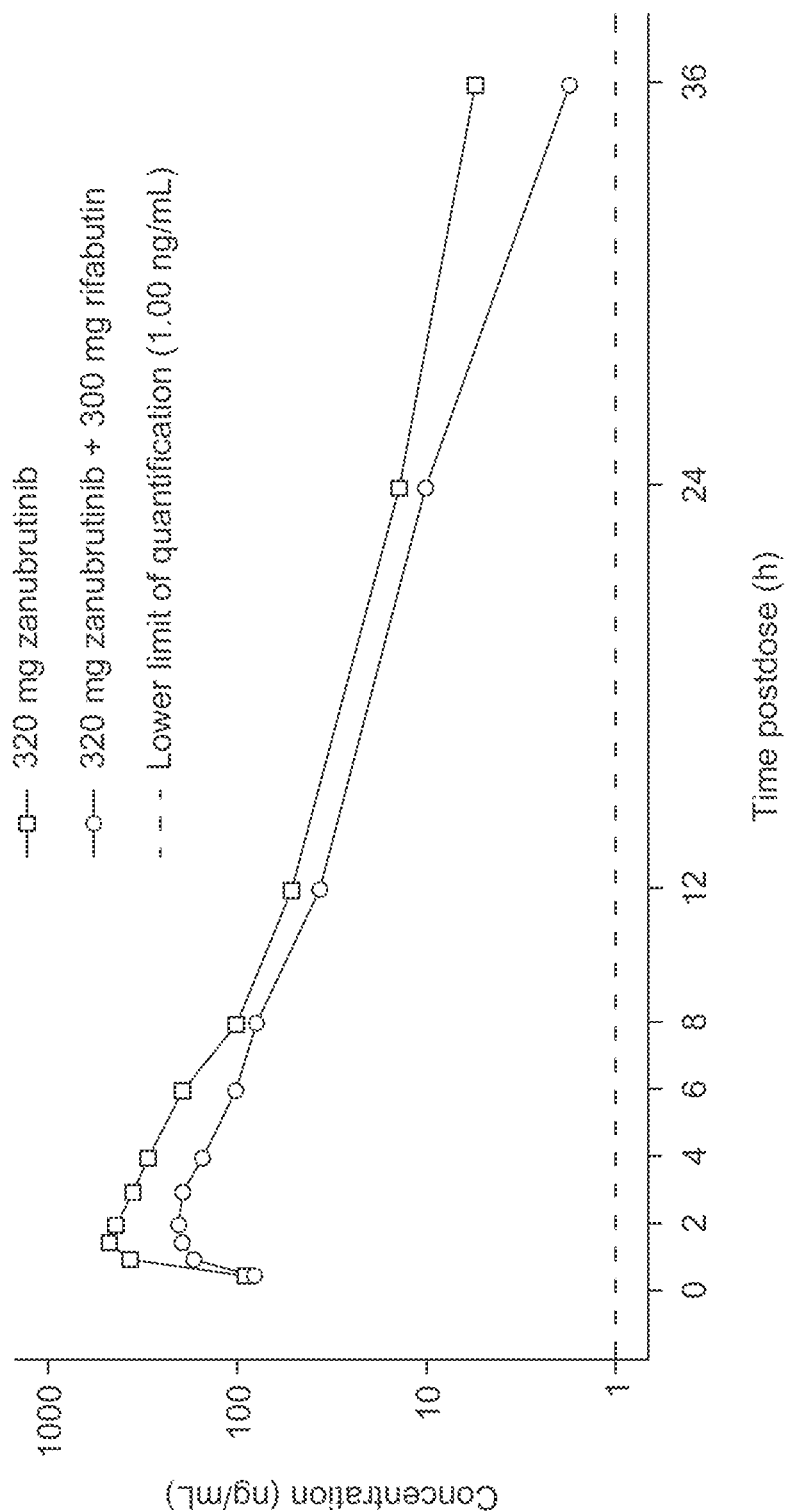

After administration of zanubrutinib alone (day 1) and coadministration with 300 mg rifabutin (day 11), zanubrutinib was rapidly absorbed with a median Tmax of 1.5 and 2.0 hours postdose, respectively (FIGS. 2A-2B). The zanubrutinib arithmetic mean t½ was similar when zanubrutinib was administered alone (7.2 hours) compared to when zanubrutinib was coadministered with rifabutin (7.0 hours; Table 2).

The arithmetic mean plasma concentration-time profiles and PK parameters of zanubrutinib in the absence and presence of rifabutin are presented in FIGS. 2A-2B and Table 2, respectively. The results of statistical analyses of AUCs and Cmax are summarized in Table 3. Plasma concentrations of zanubrutinib were significantly lower after coadministration of 320 mg zanubrutinib with 300 mg rifabutin compared with the administration of 320 mg zanubrutinib alone. The GLSM for AUC0-t, AUC0-∞, and Cmax values were lower when zanubrutinib was coadministered with rifabutin than when zanubrutinib was administered alone, with GLSM ratios of 0.57 (90% CI: 0.53-0.61), 0.56 (90% CI: 0.53-0.59), and 0.52 (90% CI: 0.44-0.61) for AUC0-t, AUC0-∞, and Cmax, respectively (Table 3). Additionally, as assessed from the geometric CV, within-subject variability was low for zanubrutinib, with values of 10.7%, 7.0%, and 23.2% for AUC0-t, AUC0-∞, and Cmax, respectively (Table 3).

TABLE 2

Summary of the Pharmacokinetic Parameters of zanubrutinib After Administration of zanubrutinib Alone and After Coadministration of zanubrutinib With Rifabutin

| Parameter | 320 mg zanubrutinib (N = 13) | 320 mg zanubrutinib + 300 mg rifabutin (N = 13) |
|---|---|---|
| AUC$_{0-t}$ (h * ng/mL)$^a$ | 2700 (24.8) [13] | 1530 (21.4) [13] |
| AUC$_{0-\infty}$ (h * ng/mL)$^a$ | 2780 (23.3) [13] | 1590 (22.2) [12] |
| C$_{max}$ (ng/mL)$^a$ | 489 (38.1) [13] | 253 (33.7) [13] |
| T$_{max}$ (h)$^b$ | 1.5 (1.0-4.0) [13] | 2.0 (1.0-8.0) [13] |
| T$_{last}$ (h)$^b$ | 36.0 (24.0-36.0) [13] | 36.0 (24.0-36.0) [13] |
| t$_{1/2}$ (h)$^c$ | 7.2 (3.10) [13] | 7.0 (4.5) [12] |
| CL/F (L/h)$^a$ | 115 (23.3) [13] | 201 (22.2) [12] |
| V$_d$/F (L)$^a$ | 1080 (68.4) [13] | 1750 (70.9) [12] |

AUC$_{0-\infty}$, area under the concentration-time curve from time zero to infinity; AUC$_{0-t}$, area under the concentration-time curve from time zero to the time of the last quantifiable concentration (T$_{last}$); CL/F, apparent oral clearance; C$_{max}$, maximum observed concentration; CV, coefficient of variation (%); n, number of volunteers with valid observations; N, number of volunteers; t$_{1/2}$, apparent terminal elimination half-life; T$_{last}$, time of the last quantifiable concentration; T$_{max}$, time of the maximum observed concentration; V$_d$/F, apparent volume of distribution.

$^a$Geometric mean (CV) [n] statistics are presented.

$^b$Median (min-max) [n] data are presented.

$^c$Arithmetic mean (SD) [n] data are presented.

TABLE 3

Statistical Analysis of the Pharmacokinetic Parameters of zanubrutinib After Administration of zanubrutinib Alone and After Coadministration of zanubrutinib With Rifabutin

| Parameter | Treatment | N | GLSM | Test versus reference Ratios of GLSM (90% CI) | Within-subject CV |
|---|---|---|---|---|---|
| AUC$_{0-t}$ (h * ng/ml) | 320 mg zanubrutinib (reference) | 13 | 2700 | 0.57 (0.53, 0.61) | 10.7 |
| | 320 mg zanubrutinib + 300 mg rifabutin (test) | 13 | 1530 | | |
| AUC$_{0-\infty}$ (h * ng/ml) | 320 mg zanubrutinib (reference) | 13 | 2780 | 0.56 (0.53, 0.59) | 7.0 |
| | 320 mg zanubrutinib + 300 mg rifabutin (test) | 12 | 1560 | | |
| C$_{max}$ (ng/ml) | 320 mg zanubrutinib (reference) | 13 | 489 | 0.52 (0.44, 0.61) | 23.2 |
| | 320 mg zanubrutinib + 300 mg rifabutin (test) | 13 | 253 | | |

AUC$_{0-\infty}$, area under the concentration-time curve from time zero to infinity; AUC$_{0-t}$, area under the concentration-time curve from time zero to the time of the last quantifiable concentration (T$_{last}$); C$_{max}$, maximum observed concentration, CI, confidence interval; CV, coefficient of variation (%); GLSM, geometric least squares mean; n, number of volunteers with valid observations; N, number of volunteers.

Model: natural logarithm(parameter) = treatment + subject + random error, with volunteer fitted as a random effect Safety Zanubrutinib monotherapy and in combination with the moderate CYP3A inducer rifabutin demonstrated a favorable safety and tolerability profile in all volunteers.

Overall, 6 of 13 volunteers (46.2%) experienced 7 TEAEs, all of which were grade 1 in severity; 1 TEAE was related to zanubrutinib on day 1 (Table 4). All TEAEs resolved by the end of the study, no volunteers discontinued study treatment because of a TEAE, and no deaths or SAEs were reported.

TABLE 4

Frequency of Treatment-Emergent Adverse Events by System Organ Class and Preferred Term

| System organ class Preferred term | 320 mg zanubrutinib on Day 1 (N = 13), n (%) | 300 mg rifabutin on Days 3-10 (N = 13), n (%) | 320 mg zanubrutinib + 300 mg rifabutin on Day 11 (N = 13), n (%) | N = 13, n (%) |
|---|---|---|---|---|
| Overall | 1 (7.7) | 6 (46.2) | — | 6 (46.2) |
| Renal and urinary disorders | — | 6 (46.2) | — | 6 (46.2) |
| Chromaturia | — | 6 (46.2) | — | 6 (46.2) |
| General disorders and administration siteconditions | 1 (7.7) | — | — | 1 (7.7) |
| Vessel puncture site hematoma | 1 (7.7) | — | — | 1 (7.7) | n, number of volunteers with an adverse event; N, number of volunteers; %, percentage of volunteers with an adverse event (n/N × 100).

Discussion

This was a single-center, phase 1, open-label, fixed-sequence clinical DDI study to investigate the effect of CYP3A induction by steady-state rifabutin on the single-dose PK of zanubrutinib in healthy volunteers and to evaluate dose-adjustment recommendations. Overall, coadministration of zanubrutinib with rifabutin resulted in a decrease in zanubrutinib exposures by approximately 44% for AUC0-t and AUC0-∞, and 48% for Cmax, respectively, compared with administration of zanubrutinib alone. This represented approximately or less than 2-fold reduction in zanubrutinib AUC and Cmax (a 1.8-fold decrease in exposure for AUC0-t and AUC0-∞, and 1.9-fold for Cmax) when zanubrutinib was coadministered with rifabutin. The extent of exposure changes herein is significantly lower than the 13-fold observed for rifampin, a strong CYP3A inducer, in a previous DDI study.

A GMR of 57% for zanubrutinib was observed in the results in this study (~=<2-fold reduction in exposure). Patients with B-cell malignancies are at an increased risk of infection due to immune defects associated with disease. The current therapies to treat opportunistic infections, such as mycobacterial infections, include rifampin and rifabutin. An exemplary moderate CYP3A inducer is rifabutin, bosentan, efavirenz, etravirine, modafinil, or nafcillin. Rifabutin coadministration with the index CYP3A substrate midazolam demonstrated moderate induction potential, resulting in AUC0-∞ and Cmax GMRs of 0.31 (90% CI: 0.27, 0.35) and 0.47 (90% CI: 0.42, 0.51), respectively. Since many anti-cancer agents are metabolized by CYP3A and rifabutin is a moderate CYP3A inducer, rifabutin may be considered a clinically relevant anti-infective agent in patients with B-cell malignancies. This study was conducted to elucidate the DDI potential of zanubrutinib when coadministered with rifabutin specifically. Additionally, these study results could aid in the development and validation of a PBPK model for rifabutin, which would be a useful development tool to predict the clinical DDI potential of rifabutin when used with other anticancer agents that are CYP3A substrates.

The t½ of zanubrutinib in our study (~7 hours) was longer than the reported t½ of 2-4 hours for a single oral dose of 160 mg or 320 mg zanubrutinib in patients with B-cell malignancies. In a previous clinical DDI study in healthy volunteers, the reported mean t½ was 6.8 hours and the PK samples were collected up to 48 hours post dose. The reported t½ of zanubrutinib was estimated after repeated dosing where blood samples were collected up to 8 hours postdose on day 1 of weeks 1 or week 2.

All TEAEs resolved by the end of the study, no volunteers discontinued because of a TEAE, and no deaths or SAEs were reported during the study. Clinical laboratory evaluations, vital signs, 12-lead ECGs, and physical examinations were unremarkable and showed no apparent association with plasma drug concentrations of zanubrutinib.

The results of this study provided useful information for the evaluation of clinical DDI between rifabutin and zanubrutinib and management of clinical DDIs for zanubrutinib when a moderate CYP3A inducer is coadministered. In conjunction with safety and efficacy data from other clinical studies, results from this study help determine the appropriate dose recommendation of zanubrutinib when coadministered with moderate CYP3A inducers. In addition, this study is one of the few reported clinical studies that could be used to aid the development and validation of a PBPK model for rifabutin, which would be a useful tool to predict the impact of moderate CYP3A inducers on CYP3A substrates, especially in patients with B-cell malignancies.

Conclusions

Results of the current study showed less than a two-fold reduction of systemic exposures of zanubrutinib after coadministration of zanubrutinib with rifabutin, a moderate CYP3A inducer, compared with administration of zanubrutinib alone. No new safety signals were identified. Single doses of 320 mg zanubrutinib administered alone or coadministered with 300 mg rifabutin were well tolerated in healthy volunteers in this study.

Overall, coadministration of zanubrutinib with a moderate CYP3A inducer, e.g., rifabutin, resulted in a decrease in zanubrutinib exposures by approximately 44% for AUC0-t and AUC0-∞, and 48% for Cmax, respectively, compared with administration of zanubrutinib alone. This represented a 1.8-fold decrease in exposure for AUC0-t and AUC0-∞, and 1.9-fold for Cmax when zanubrutinib was coadministered with a moderate CYP3A inducer, e.g., rifabutin.

It is unexpected that the extent of exposure changes herein are significantly lower than the 13-fold observed for rifampin, a strong CYP3A inducer, in a previous DDI study.

Zanubrutinib, under the brand name Brukinsa, was approved by FDA for treating Mantle cell lymphoma (MCL), Waldenström's macroglobulinemia (WM), marginal zone lymphoma (MZL) on Nov. 14, 2019, Aug. 31, 2021, and Sep. 12, 2021, respectively, at 160 mg twice a day or 320 mg once a day. However, zanubrutinib was advised to avoid concomitant use with a moderate CYP3A inducer on the approved FDA label (see section 2.3 Table 1 on the approved FDA label). The FDA approved label can be downloaded from the FDA database, e.g., https://www.accessdata.fda.gov/drugsatfda_docs/label/2021/213217s0051b1.pdf (last visit Dec. 16, 2022).

This study demonstrated an approximately 2-fold reduction in zanubrutinib exposure (i.e., 1.8-fold decrease in exposure for AUC0-t and AUC0-∞, and 1.9-fold for Cmax) when zanubrutinib was coadministered in a patient receiving a moderate CYP3A inducer, e.g., rifabutin. The inventors have found that the use of 320 mg BID of zanubrutinib (a total daily dose of 640 mg) on a patient receiving a moderate CYP3A inducer leads to exposure (e.g., AUC or Cmax) similar to that on a patient receiving 160 mg BID of zanubrutinib (a total daily dose of 320 mg). However, there is a safety concern because patients may not comply with their treatment regimens for a moderate CYP3A inducer, including by not taking the moderate CYP3A inducer or skipping one or more doses of the moderate CYP3A inducer.

Such non-compliance thereby enhances exposure to zanubrutinib compared to existing use. The enhanced exposure may lead to the safety concern.

The study in Example 2 addressed concerns regarding the safety of zanubrutinib when it is administered at a higher dose, e.g., 320 mg twice a day (a total daily dose of 640 mg).

Example 2

A DDI study in healthy patients assessing the coadministration of zanubrutinib with the strong CYP3A inhibitor itraconazole resulted in zanubrutinib Cmax and AUC increasing by 2.6-fold and 3.8-fold, respectively. Mu, Song, et al., Cancer chemotherapy and pharmacology 85.2 (2020): 391-399 (incorporated herein by reference). Physiologically based pharmacokinetic (PBPK) simulations (Wang, K. et al., *CPT: pharmacometrics & systems pharmacology*, 2021 May, 10(5), pages 441-454) and a clinical study in patients with B-cell malignancy showed that when coadministered with multiple doses of a moderate CYP3A inhibitor (e.g. fluconazole, diltiazem, erythromycin), zanubrutinib Cmax and AUC may increase by approximately 2- to 3-fold. Tariq B, et. al., *Leuk Lymphoma*, 2022 Dec. 8:1-10 (incorporated herein by reference).

Surprisingly, this study result demonstrated a non-inferior safety profile of the patients receiving 160 mg twice a day of zanubrutinib with a moderate or stronger CYP3A inhibitor when compared to the patients receiving 160 mg of zanubrutinib twice a day without coadministration of a moderate or stronger CYP3A inhibitor even though there was a 2 to 3-fold increase (AUC and Cmax) over therapeutic exposure range of zanubrutinib when used with strong or moderate CYP3A inhibitors (ie., with zanubrutinib exposure equivalent or higher than 640 mg total daily dose). In particular, 123 patients received a dose of 320 mg zanubrutinib daily with a moderate or stronger CYP3A inhibitor. The percentage of the 123 patients with at least 1 TEAE is non-inferior when compared to that of the patients receiving 160 mg of zanubrutinib twice a day without coadministration of a moderate or stronger CYP3A inhibitor.

Thus, this study result suggested a non-inferior safety profile of the patients receiving 320 mg twice a day of zanubrutinib when compared to the patients receiving 160 mg twice a day of zanubrutinib. Such a study result solved the safety concern in Example 1.

Background

This study summarized the assessment of the integrated safety data in patients receiving zanubrutinib before, during, and after concomitant treatment with moderate or strong cytochrome P450 (CYP)3A inhibitors in these studies.

The assessment includes patients with B-cell malignancies treated with single-agent zanubrutinib studies. The list of studies included in this analysis Studies BGB-3111-AU-003, BGB-3111-1002, BGB-3111-205, BGB-3111-206, BGB-3111-210, BGB-3111-214, and BGB-3111-302. Key design features of these studies are summarized in Table 5.

The endpoint of this assessment is the incidence of treatment-emergent adverse events (TEAEs) (including all adverse events (AEs); AEs leading to dose reductions, interruptions, and discontinuation; and AEs of special interest (AESI)) assessed before, during, and after coadministration of moderate or strong CYP3A inhibitors.

TABLE 5

Key Study Design Features of Integrated Studies

| Study | BGB-3111-AU-003 | BGB-3111-1002 | BGB-3111-205 | BGB-3111-206 | BGB-3111-210 | BGB-3111-214 | BGB-3111-302 |
|---|---|---|---|---|---|---|---|
| Countries | AU, NZ, SK, USA, IT, UK | China | China | China | China | USA, UK, IT, FR, CZ, AU, NZ, SK | AU, USA, UK, EU (CZ, DE, ES, FR, GR, IT, NL, PO, SW) |
| Phase | 1/2 | 1 | 2 | 2 | 2 | 2 | 3 |
| Arm | Single-arm | Single-arm | Single-arm | Single-arm | Single-arm | Single-arm | Randomized (1:1 zanubrutinib to ibrutinib) in Cohort 1, single-arm in Cohort 2 |
| Study Treatment | Zanubrutinib | Zanubrutinib | Zanubrutinib | Zanubrutinib | Zanubrutinib | Zanubrutinib | Zanubrutinib or ibrutinib |
| Blinding | Open-label | Open-label | Open-label | Open-label | Open-label | Open-label | Open-label |
| Disease Type | CLL/SLL, DLBCL, FL, MALT, MCL, HCL, MZL, NHL, RT, WM | CLL/SLL, MCL, WM/LPL, FL, MZL, HCL, nGCB-DLBCL | CLL/SLL | MCL | WM | MZL | WM |
| Previous Treatment | R/R or TN | R/R | R/R | R/R | R/R | R/R | R/R or TN |
| Primary objective | To determine the safety and tolerability and determine the RP2D/regimen in Part 1; to further assess the safety and tolerability in Part 2 | To evaluate the safety and tolerability and determine the RP2D in Part I; to evaluate the preliminary anti-tumor activity in | To evaluate the efficacy of BGB-3111 at 160 mg BID as assessed by the ORR | To evaluate the efficacy of BGB-3111 at 160 mg BID as measured by the ORR | To determine the efficacy of BGB-3111 as measured by the MRR | To evaluate the efficacy of zanubrutinib in R/R MZL as measured by ORR in accordance with the Lugano Classification (Cheson et al | To compare the efficacy of zanubrutinib vs ibrutinib in patients with MYD88$^{MUT}$ WM in Cohort 1 |

TABLE 5-continued

Key Study Design Features of Integrated Studies

| Study | BGB-3111-AU-003 | BGB-3111-1002 | BGB-3111-205 | BGB-3111-206 | BGB-3111-210 | BGB-3111-214 | BGB-3111-302 |
|---|---|---|---|---|---|---|---|
| | | Part II | | | | 2014) determined by the IRC | |
| Dose of zanubrutinib | 40/80/160/320 mg orally QD and 160 mg orally BID | 160 mg orally BID and 320 mg orally QD | 160 mg orally BID | 160 mg orally BID | 160 mg orally BID | 160 mg orally BID | 160 mg orally BID |
| Sample size (planned) | 405 | 40 | 80 | 80 | 40 | 65 | 116 zanubrutinib, 94 ibrutinib |
| End of Treatment | PD, death, intolerance, withdrawal of consent, lost to follow-up, study termination by sponsor | PD, death, unacceptable toxicity, withdrawal of consent, lost to follow-up, study termination by sponsor, maximum 3 years | PD, death, unacceptable toxicity, withdrawal of consent, lost to follow-up, study termination by sponsor, maximum 3 years | PD, death, unacceptable toxicity, withdrawal of consent, lost to follow-up, study termination by sponsor, maximum 3 years | PD, death, unacceptable toxicity, withdrawal of consent, lost to follow-up, study termination by sponsor, maximum 3 years | PD, pregnancy, AE, withdrawal of consent, investigator decision, other | PD, death, unacceptable toxicity, withdrawal of consent, lost to follow-up, study termination by sponsor |
| Safety Follow-up | 28 days after last dose | 30 days after last dose | 30 days after last dose | 30 days after last dose | 30 days after last dose | 30 days after last dose | 30 days after last dose |
| Survival Follow-up | Quarterly after last visit | Quarterly after last visit | Quarterly after last visit | Quarterly after last visit | Quarterly after last visit | Quarterly after last visit | Quarterly after last visit |

Abbreviations: AE, adverse event; AU, Australia; BID, twice a day; CLL/SLL, chronic lymphocytic leukemia/small lymphocytic lymphoma; CZ, Czech Republic; DE, Germany; DLBCL, diffuse large B-cell lymphoma (subdiagnosis of NHL); ES, Spain; EU, European Union; FL, follicular lymphoma (subdiagnosis of NHL); FR, France; GR, Greece; HCL, hairy cell leukemia; IRC, Independent Review Committee; IT, Italy; LPL, lymphoplasmacytic lymphoma; MALT, mucosa-associated lymphoid tissue; MCL, mantle cell lymphoma (subdiagnosis of NHL); MRR, major response rate; MZL, marginal zone lymphoma (subdiagnosis of NHL); nGCB, nongerminal center B-cell (subdiagnosis of DLBCL); NHL, non-Hodgkin's lymphoma; NL, Netherlands; NZ, New Zealand; ORR, overall response rate; PD, disease progression; PO, Poland; QD, once a day; RP2D, recommended Phase 2 dose; R/R, relapsed or refractory; RT, Richter's transformation; SK, South Korea; SW, Sweden; TN, treatment-naive; UK, United Kingdom; USA, United States of America; WM, Waldenstrom's macroglobulinemia.

Statistical Methods

The analyses were performed in patients who had received at least one concomitant treatment with moderate or strong CYP3A inhibitors while on a total daily dose up to 320 mg zanubrutinib, including patients on a reduced dose of zanubrutinib. Patients who did not take any dose of zanubrutinib during the CYP3A inhibitor treatment period were not included in the analyses.

Concomitant medications were defined as medications that (1) started before the first dose of zanubrutinib and were continuing at the first dose date of zanubrutinib, or (2) started on or after the first dose date of zanubrutinib up to 30 days after the patient's last dose of study treatment or initiation of a new anticancer therapy.

Classification of CYP3A inhibitors were coded according to World Health Organization (WHO) Drug Standardized Drug Group, Version September 2018, to provide a standardized and unbiased search strategy for groupings of drugs.

Exposure

The number of patients receiving a total daily dose of 320 mg or a reduced dose of zanubrutinib during coadministration with a moderate or strong CYP3A inhibitor was summarized. The reasons for dose reductions were also to be presented.

Definition of Study Periods

The number (%) of patients experiencing events was compared among 3 study periods, which were defined as follows:

Prior to Coadministration Period: This period extends from the date of the first dose of zanubrutinib to the date of the first coadministration of zanubrutinib and a moderate or strong CYP3A inhibitor. All TEAEs occurring on the first day of coadministration were summarized in this period, since in many cases, the CYP3A inhibitor may have been initiated as treatment for such TEAEs. These events were also to be reviewed and described.

During Coadministration Period: This period extends from the date of the second day of coadministration of zanubrutinib and a moderate or strong CYP3A inhibitor to either 30 days from end of coadministration, end of study date, death date, initiation of a new anticancer therapy, or data cutoff date, whichever came first. The "During" period starts on Day 2 of coadministration to avoid capture of events in which the CYP3A inhibitor was used to treat an AE (e.g., voriconazole was given to treat a fungal infection).

After Coadministration Period: This period begins at 30 days after the end of coadministration of zanubrutinib and a moderate or strong CYP3A inhibitor to either 30 days after last dose of zanubrutinib (permanent discontinuation), end of study date, death date, initiation of a new anticancer therapy, or data cutoff date, whichever came first. For patients treated with multiple concomitant moderate or strong CYP3A inhibitors at different times, time between the coadministration periods was included in this "after" period.

Adverse events occurring in one study period and continuing into the next study period were counted in the period the event first occurred unless the toxicity grade changed. If an AE worsened in a subsequent study period, the toxicity grades in the current study period and in the subsequent study period were both to be summarized.

Treatment-Emergent Adverse Events

A TEAE was defined as an AE with onset date or increase in severity level on or after the first dose of zanubrutinib and within 30 days after the last dose of zanubrutinib (permanent discontinuation) or initiation of a new anticancer therapy (if collected), whichever came first. Only those AEs that were treatment emergent were included in summary tables.

A treatment-related AE is an AE that was noted by the investigator as related, possibly related, probably related to study drug, or with missing causal relationship.

Adverse events were graded by the investigators using National Cancer Institute-Common Terminology Criteria for Adverse Events (NCI-CTCAE) v4.03 and coded to the Medical Dictionary for Regulatory Activities (MedDRA v22.0 or higher) Lowest Level Terms closest to the verbatim term. The linked MedDRA Preferred Term (PT) and primary System Organ Class (SOC) were also to be captured in the database.

Clinically significant abnormal laboratory findings or other abnormal assessments that were detected during the study periods or were present at baseline and significantly worsened following the start of the study were reported as AEs.

An overall summary was presented with the number (%) of patients with any TEAE, any ≥Grade 3, serious, treatment-related, or fatal TEAE, as well as TEAEs leading to zanubrutinib dose reduction, treatment interruption, or treatment discontinuation by the study periods.

TEAEs were also to be summarized by SOC and PT. A patient reporting the same TEAE more than once within the same period was counted only once when calculating incidence 1) within a given SOC, and 2) within a given SOC and PT combination. For such cases, the maximum CTCAE toxicity grade and strongest causal relationship to study drug for the event (ie, definitely, probably, or possibly related to study treatment, or with missing assessment of the causal relationship versus not related) was used in the incidence calculations for each study period.

Summaries of the following TEAEs were provided by SOC, PT, and study period:
All TEAEs
TEAEs of ≥Grade 3
Serious TEAEs
Fatal TEAEs
TEAEs leading to zanubrutinib dose reduction
TEAEs leading to zanubrutinib treatment interruption
TEAEs leading to zanubrutinib discontinuation
   Adverse Events of Special Interest
   The incidence of AESIs, ≥Grade 3 AESIs, serious AESIs, fatal AESIs, AESIs leading to zanubrutinib dose reduction, AESIs leading to zanubrutinib treatment interruption, and AESIs leading to zanubrutinib discontinuation were summarized by category, PT, and study period.

The AESIs are prospectively defined TEAEs that are consistent with the known and theoretical toxicity profile for the class of Bruton tyrosine kinase (BTK) inhibitors. The categories and criteria that define each category of AESI are shown in Table 6.

TABLE 6

Categories of Adverse Events of Special Interest

| AESI category | Search Criteria |
|---|---|
| 1. Hemorrhage (including minor bleeding events such as contusion and petechia) | Haemorrhage terms (excluding laboratory terms) (SMQ) Narrow |
| Major hemorrhage | Major haemorrhage is defined as Subdural haematoma PT, Subdural haemorrhage PT, and all Haemorrhage PTs if the SOC is "Nervous system disorders" or serious or Grade 3 and above Haemorrhage PTs if the SOC is not "Nervous system disorders" |

TABLE 6-continued

Categories of Adverse Events of Special Interest

| AESI category | Search Criteria |
|---|---|
| 2. Atrial fibrillation and flutter | Atrial fibrillation PT, Atrial flutter PT |
| 3. Hypertension | Hypertension (SMQ) Narrow |
| 4. Second primary malignancies | Malignant tumours (SMQ) Narrow |
| Skin cancer | Skin malignant tumours (SMQ) Narrow |
| 5. Tumor lysis syndrome | Tumour lysis syndrome (SMQ) Narrow |
| 6. Infections | Infections and infestations SOC |
| Opportunistic infections | Subcategory - Opportunistic infections (SMQ) Narrow |
| 7. Cytopenias | |
| Neutropenia | Neutropenia PT, Neutrophil count decreased PT, Febrile neutropenia PT, Agranulocytosis PT, Neutropenic infection PT, Neutropenic sepsis PT |
| Thrombocytopenia | Thrombocytopaenia PT, Platelet count decreased PT |
| Anemia | Anemia PT, Haemoglobin decreased PT |

Abbreviations: AESI, adverse event of special interest; MedDRA, Medical Dictionary for Regulatory Activities; PT, Preferred Term; SMQ, Standardized MedDRA Query; SOC, System Organ Class.

The exposure-adjusted incidence rate (EAIR) was also to be calculated for AESIs (all grades), ≥Grade 3 AESIs, and serious AESIs and were presented by AESI category and study period.

In calculating EAIR, the analysis was restricted to the occurrence of the first event for each study period. The incidence rate for a patient was derived from the duration of exposure of that patient. A patient's duration of exposure for each study period was calculated as either 1) time from the first date of the period to the date of the AE first occurring in this period (non-censored), or 2) total duration of the period if the patient did not experience the event in the period (censored). Only the time during the corresponding study period was counted in the above calculations if a patient received multiple CYP3A inhibitors at different times.

Depending on whether a patient had an event or not, the duration of exposure entered the denominator in its non-censored or censored form, respectively. The EAIR per event considered the first event per patient for each study period, and the corresponding exposure time in the denominator for each study period in Formula (EAIR) in FIG. 23.

Whereby $TEAE_{event,i}$ represented if "patient" experienced the event (1) or not (0), and $t_{event,i}$ represented the time when the first TEAE occurred (non-censored data) or total duration of exposure if no event occurred (censored data).

Summary by Dose Modification

Because criteria for dose modification of zanubrutinib when coadministered with moderate or strong CYP3A inhibitors had been added to protocols in 2019, the dataset included both patients receiving full dose zanubrutinib in combination with CYP3A inhibitors as well as those receiving the United States Package Insert (USPI)-recommended dose modifications for coadministration. Incidence of AEs during coadministration of moderate or strong CYP3A inhibitors with or without USPI-specified dose modification of zanubrutinib were also to be described.

Summary of Results

Extent of Exposure

Among the 835 patients overall treated in the studies assessed (BGB-3111-AU-003, BGB-3111-1002, BGB- 3111-205, BGB-3111-206, BGB-3111-210, BGB-3111-214, and BGB-3111-302), 138 patients (16.5%) received CYP3A inhibitors and were included in the safety dataset for the integrated analysis. Of the 138 patients with a During Coadministration Period, 119 patients had a Prior to Coadministration Period defined, and 107 patients had an After Coadministration Period defined. A total of 102 patients had all 3 periods defined.

The median duration was shortest for the During Coadministration Period (56.0 days) compared with the Prior to Coadministration Period (270.0 days) and the After Coadministration Period (620.0 days) (Table 7).

In the During Coadministration Period, most patients (123 (89.1%)) received a full dose of 320 mg zanubrutinib daily (Table 7). Seven (5.1%) patients received a reduced dose of 80 mg twice a day, 8 (5.8%) patients received a reduced dose of 80 mg once a day, and 1 (0.7%) patient received a reduced dose of 120 mg twice daily. The main reason that led to dose reduction was occurrence of an AE.

Among the 138 patients who had coadministration of zanubrutinib and a CYP3A inhibitor, 57 (41.3%) patients received strong CYP3A inhibitors and 94 (68.1%) patients received moderate CYP3A inhibitors. The majority of the CYP3A inhibitors were antibacterials and antimycotics. The most frequently administered strong CYP3A inhibitors (>5% of patients) were clarithromycin (23.9%) and voriconazole (9.4%); the most frequently administered moderate CYP3A inhibitors were ciprofloxacin (37.0%), fluconazole (18.1%), erythromycin (8.7%), and cimetidine (5.1%).

TABLE 7

Duration of Study Periods and Dose in the During Coadministration Period

|  | Prior to Coadministration Period[a] (N = 119) n (%) | During Coadministration Period[b] (N = 138) n (%) | After Coadministration Period[c] (N = 107) n (%) |
| --- | --- | --- | --- |
| Duration (days) |  |  |  |
| n | 119 | 138 | 107 |
| Mean (SD) | 403.4 (376.12) | 134.8 (263.39) | 650.5 (426.12) |
| Median | 270.0 | 56.0 | 620.0 |
| Min, max | 1, 1823 | 4, 1801 | 6, 1721 |
| Full dose of 320 mg daily | NC | 123 (89.1) | NC |
| Reduced dose of 80 mg twice daily | NC | 7 (5.1) | NC |
| Adverse Event | NC | 5 (3.6) | NC |
| PI Decision | NC | 1 (0.7) | NC |
| Other | NC | 1 (0.7) | NC |
| Reduced dose of 80 mg daily | NC | 8 (5.8) | NC |
| Adverse Event | NC | 7 (5.1) | NC |
| Other | NC | 1 (0.7) | NC |
| Other daily doses | NC |  | NC |
| Reduced dose of 120 mg twice daily | NC | 1 (0.7) | NC |
| Adverse Event | NC | 1 (0.7) | NC |

Abbreviations: CYP, cytochrome P450; NC, not calculated; PI, principal investigator
N = number of patients receiving a planned dose of 320 mg daily and having at least 1 coadministration of zanubrutinib and a strong or moderate CYP3A inhibitor.
[a] The Prior to Coadministration Period is defined as the period from the first dose date of zanubrutinib to the first date of the coadministration of zanubrutinib and a moderate or strong CYP3A inhibitor.
[b] The During Coadministration Period is defined as the period from the second day of the coadministration of zanubrutinib and a moderate or strong CYP3A inhibitor to the date of the end of the coadministration +30 days, end of study, death, initiation of a new anticancer therapy, or data cutoff, whichever comes first.
[c] The After Coadministration Period is defined as the period from the end of the coadministration of zanubrutinib and a moderate or strong CYP3A inhibitor +31 days to the last dose of zanubrutinib (end of treatment) +30 days, end of study, death, initiation of a new anticancer therapy, or data cutoff, whichever comes first.

Overview of Adverse Events

The percentages of patients with at least 1 TEAE, ≥Grade 3 TEAE, serious TEAE, TEAE leading to death, TEAE leading to dose reduction, TEAE leading to dose hold, or AESI showed an expected trend across the 3 study periods when considering the different durations of each period (Table 8). The percentages of patients with events were relatively lower in the During Coadministration Period and After Coadministration Period, as compared to the Prior to Coadministration Period, for ≥Grade 3 TEAEs, serious TEAEs, TEAEs leading to dose reduction, and TEAEs leading to dose hold while the percentage of patients experiencing TEAEs leading to treatment discontinuation was relatively lower in the Prior to Coadministration Period compared with the other 2 periods. Of note, the number of patients experiencing TEAEs leading to death and TEAEs leading to discontinuation in each administration period was low; thus, interpretation should be made with caution. In addition, comparison of crude rates of events should be interpreted with caution as the median duration of exposure in each period differed significantly, as summarized herein.

TABLE 8

Overall Summary of Treatment-Emergent Adverse Events

|  | Prior to Coadministration Period[a] (N = 119) n (%) | Coadministration Period[b] (N = 138) n (%) | Coadministration Period[c] (N = 107) n (%) |
| --- | --- | --- | --- |
| Median duration of exposure in period (days) | 270.0 | 56.0 | 620.0 |
| Patients with at least 1 TEAE | 117 (98.3) | 89 (64.5) | 94 (87.9) |
| Grade 3 or higher[d] | 82 (68.9) | 42 (30.4) | 62 (57.9) |
| Serious | 67 (56.3) | 37 (26.8) | 49 (45.8) |
| Leading to death | 1 (0.8) | 8 (5.8) | 5 (4.7) |
| Leading to treatment discontinuation | 3 (2.5) | 10 (7.2) | 11 (10.3) |
| Leading to dose reduction | 15 (12.6) | 3 (2.2) | 6 (5.6) |
| Leading to dose hold | 60 (50.4) | 25 (18.1) | 44 (41.1) |
| Patients with at least 1 AESI | 115 (96.6) | 67 (48.6) | 89 (83.2) |
| Grade 3 or higher AESI | 69 (58.0) | 36 (26.1) | 48 (44.9) |
| Serious AESI | 53 (44.5) | 29 (21.0) | 32 29.9) |

Abbreviation(s): AESI, adverse event of special interest; CYP, cytochrome P450; NCI-CTCAE, National Cancer Institute Common Terminology Criteria for Adverse Events; TEAE, treatment-emergent adverse event.
N = number of patients receiving a planned dose of 320 mg daily and having at least 1 coadministration of zanubrutinib and a strong or moderate CYP3A inhibitor.
[a] The Prior to Coadministration Period is defined as the period from the first dose date of zanubrutinib to the first date of the coadministration of zanubrutinib and a moderate or strong CYP3A inhibitor.
[b] The During Coadministration Period is defined as the period from the second day of the coadministration of zanubrutinib and a moderate or strong CYP3A inhibitor to the date of the end of the coadministration +30 days, end of study, death, initiation of a new anticancer therapy, or data cutoff, whichever comes first.
[c] The After Coadministration Period is defined as the period from the end of the coadministration of zanubrutinib and a moderate or strong CYP3A inhibitor +31 days to the last dose of zanubrutinib (end of treatment) +30 days, end of study, death, initiation of a new anticancer therapy, or data cutoff, whichever comes first.
[d] Adverse event grades are evaluated based on NCI-CTCAE (Version 4.03).

Common Treatment-Emergent Adverse Events

In the Coadministration Period, the most frequently reported TEAEs (>5% of patients) were neutropenia and neutrophil count decreased (8.0%, each), anaemia and constipation (7.2%, each), contusion, pneumonia, and pyrexia (6.5%, each), upper respiratory tract infection (5.8%), and cough and dyspnoea (5.1%, each). Each of these events occurred less frequently in the During Coadministration Period than in the other periods, except for neutrophil count decreased, which occurred in a similar percentage of patients in the During Coadministration Period and After Coadministration Period.

The most frequently reported TEAEs (>20% of patients in any study period) in the Prior to Coadministration, During Coadministration, and After Coadministration Periods were upper respiratory tract infection (40.3%, 5.8%, and 25.2%, respectively), contusion (30.3%, 6.5%, and 9.3%, respectively), diarrhoea (25.2%, 2.9%, 12.1%), and cough (24.4%, 5.1%, and 14.0%, respectively). All of these TEAEs were reported most frequently in the Prior to Coadministration Period.

TABLE 9

Treatment-Emergent Adverse Events by System Organ Class and Preferred Term in >10% of Patients in Any Study Period

| System Organ Class Preferred Term | Prior to Coadministration Period [a] (N = 119) n (%) | During Coadministration Period [b] (N = 138) n (%) | After Coadministration Period [c] (N = 107) n (%) |
|---|---|---|---|
| Patients with at least 1 TEAE | 117 (98.3) | 89 (64.5) | 94 (87.9) |
| Infections and infestations | 105 (88.2) | 47 (34.1) | 78 (72.9) |
| Pneumonia | 19 (16.0) | 9 (6.5) | 15 (14.0) |
| Upper respiratory tract infection | 48 (40.3) | 8 (5.8) | 27 (25.2) |
| Lower respiratory tract infection | 12 (10.1) | 4 (2.9) | 11 (10.3) |
| Cellulitis | 14 (11.8) | 2 (1.4) | 7 (6.5) |
| Urinary tract infection | 23 (19.3) | 2 (1.4) | 14 (13.1) |
| Gastrointestinal disorders | 65 (54.6) | 33 (23.9) | 46 (43.0) |
| Constipation | 20 (16.8) | 10 (7.2) | 15 (14.0) |
| Vomiting | 12 (10.1) | 6 (4.3) | 9 (8.4) |
| Nausea | 17 (14.3) | 5 (3.6) | 13 (12.1) |
| Diarrhoea | 30 (25.2) | 4 (2.9) | 13 (12.1) |
| General disorders and administration site conditions | 57 (47.9) | 25 (18.1) | 30 (28.0) |
| Pyrexia | 16 (13.4) | 9 (6.5) | 10 (9.3) |
| Fatigue | 17 (14.3) | 6 (4.3) | 4 (3.7) |
| Investigations | 30 (25.2) | 22 (15.9) | 25 (23.4) |
| Neutrophil count decreased | 14 (11.8) | 11 (8.0) | 8 (7.5) |
| Respiratory, thoracic and mediastinal disorders | 50 (42.0) | 22 (15.9) | 35 (32.7) |
| Cough | 29 (24.4) | 7 (5.1) | 15 (14.0) |
| Blood and lymphatic system disorders | 42 (35.3) | 20 (14.5) | 25 (23.4) |
| Neutropenia | 21 (17.6) | 11 (8.0) | 10 (9.3) |
| Anaemia | 15 (12.6) | 10 (7.2) | 11 (10.3) |
| Nervous system disorders | 45 (37.8) | 19 (13.8) | 26 (24.3) |
| Headache | 20 (16.8) | 5 (3.6) | 7 (6.5) |
| Metabolism and nutrition disorders | 31 (26.1) | 18 (13.0) | 32 (29.9) |
| Hypokalaemia | 12 (10.1) | 6 (4.3) | 6 (5.6) |
| Musculoskeletal and connective tissue disorders | 46 (38.7) | 17 (12.3) | 36 (33.6) |
| Arthralgia | 12 (10.1) | 4 (2.9) | 13 (12.1) |
| Back pain | 13 (10.9) | 3 (2.2) | 13 (12.1) |
| Muscle spasms | 14 (11.8) | 2 (1.4) | 2 (1.9) |
| Skin and subcutaneous tissue disorders | 59 (49.6) | 17 (12.3) | 30 (28.0) |
| Rash | 18 (15.1) | 3 (2.2) | 7 (6.5) |
| Injury, poisoning and procedural complications | 54 (45.4) | 16 (11.6) | 33 (30.8) |
| Contusion | 36 (30.3) | 9 (6.5) | 10 (9.3) |
| Vascular disorders | 24 (20.2) | 8 (5.8) | 14 (13.1) |
| Hypertension | 14 (11.8) | 4 (2.9) | 8 (7.5) |

Abbreviation(s): CYP, cytochrome P450; MedDRA, Medical Dictionary for Regulatory Activities; TEAE, treatment-emergent adverse event.
N = number of patients receiving a planned dose of 320 mg daily and having at least 1 coadministration of zanubrutinib and a strong or moderate CYP3A inhibitor. Patients with multiple events for a given Preferred Term and System Organ Class are counted only once for each Preferred Term and System Organ Class, respectively. MedDRA Version: 23.0.
[a] The Prior to Coadministration Period is defined as the period from the first dose date of zanubrutinib to the first date of the coadministration of zanubrutinib and a moderate or strong CYP3A inhibitor.
[b] The During Coadministration Period is defined as the period from the second day of the coadministration of zanubrutinib and a moderate or strong CYP3A inhibitor to the date of the end of the coadministration +30 days, end of study, death, initiation of a new anticancer therapy, or data cutoff, whichever comes first.
[c] The After Coadministration Period is defined as the period from the end of the coadministration of zanubrutinib and a moderate or strong CYP3A inhibitor +31 days to the last dose of zanubrutinib (end of treatment) +30 days, end of study, death, initiation of a new anticancer therapy, or data cutoff, whichever comes first.

Grade 3 or Higher Treatment-Emergent Adverse Events

The percentage of patients with at least one ≥Grade 3 TEAE was lower in the During Coadministration Period (30.4%) compared with the Prior to Coadministration Period (68.9%) and the After Coadministration Period (57.9%) (Table 10). During each period, the pattern of reported TEAEs was similar.

In the During Coadministration Period, the most frequently reported ≥Grade 3 TEAEs (>5% of patients) were anaemia (6.5%), neutropenia (6.5%), and pneumonia (5.1%). Each of these events occurred less frequently or at a similar frequency in the During Coadministration Period compared with the other periods.

The most frequently reported ≥Grade 3 TEAEs overall (>5% of patients in any study period) by PT in the Prior to Coadministration, During Coadministration, and After Coadministration Periods were neutrophil count decreased including the terms neutropenia and neutrophil count decrease (20.2%, 10.8%, and 11.2%, respectively), pneumonia (10.1%, 5.1%, and 6.5%, respectively), anaemia (6.7%, 6.5%, and 3.7%, respectively), and urinary tract infection (5.9%, 0.7%, and 4.7%, respectively). Although there were numeric differences noted among these TEAEs, the patterns of TEAEs observed were similar across all three administration periods.

Analysis of cytopenias, combining multiple PTs within the same categories, are described in AESI section.

TABLE 10

Treatment-Emergent Adverse Events of Grade 3 or Higher by System Organ Class and Preferred Term in >2% of Patients

| System Organ Class Preferred Term | Prior to Coadministration Period [a] (N = 119) n (%) | Coadministration Period [b] (N = 138) n (%) | Coadministration Period [c] (N = 107) n (%) |
|---|---|---|---|
| Patients with at least 1 Grade 3 or Higher TEAE | 82 (68.9) | 42 (30.4) | 62 (57.9) |
| Infections and infestations | 47 (39.5) | 24 (17.4) | 28 (26.2) |
| Pneumonia | 12 (10.1) | 7 (5.1) | 7 (6.5) |
| Sepsis | 1 (0.8) | 3 (2.2) | 2 (1.9) |
| Cellulitis | 5 (4.2) | 2 (1.4) | 1 (0.9) |
| Urinary tract infection | 7 (5.9) | 1 (0.7) | 5 (4.7) |
| Skin infection | 3 (2.5) | 0 (0.0) | 0 (0.0) |
| Upper respiratory tract infection | 5 (4.2) | 0 (0.0) | 0 (0.0) |
| Blood and lymphatic system disorders | 24 (20.2) | 15 (10.9) | 13 (12.1) |
| Anaemia | 8 (6.7) | 9 (6.5) | 4 (3.7) |
| Neutropenia | 15 (12.6) | 9 (6.5) | 8 (7.5) |
| Febrile neutropenia | 2 (1.7) | 4 (2.9) | 4 (3.7) |
| Thrombocytopenia | 3 (2.5) | 3 (2.2) | 2 (1.9) |
| Investigations | 12 (10.1) | 8 (5.8) | 9 (8.4) |
| Neutrophil count decreased | 9 (7.6) | 6 (4.3) | 4 (3.7) |
| Respiratory, thoracic and mediastinal disorders | 4 (3.4) | 5 (3.6) | 10 (9.3) |
| Pleural effusion | 1 (0.8) | 1 (0.7) | 3 (2.8) |
| Renal and urinary disorders | 2 (1.7) | 4 (2.9) | 1 (0.9) |
| Acute kidney injury | 0 (0.0) | 3 (2.2) | 0 (0.0) |
| Metabolism and nutrition disorders | 5 (4.2) | 3 (2.2) | 4 (3.7) |
| Hypokalaemia | 4 (3.4) | 0 (0.0) | 0 (0.0) |
| Vascular disorders | 9 (7.6) | 1 (0.7) | 9 (8.4) |
| Hypertension | 8 (6.7) | 1 (0.7) | 4 (3.7) |
| Hypotension | 1 (0.8) | 0 (0.0) | 3 (2.8) |

Abbreviation(s): CYP, cytochrome P450; MedDRA, Medical Dictionary for Regulatory Activities; NCI-CTCAE, National Cancer Institute Common Terminology Criteria for Adverse Events; TEAE, treatment-emergent adverse event.
N = number of patients receiving a planned dose of 320 mg daily and having at least 1 coadministration of zanubrutinib and a strong or moderate CYP3A inhibitor. Patients with multiple events for a given Preferred Term and System Organ Class are counted only once for each Preferred Term and System Organ Class, respectively. MedDRA Version: 23.0. Adverse event grades are evaluated based on NCI-CTCAE (Version 4.03).
[a] The Prior to Coadministration Period is defined as the period from the first dose date of zanubrutinib to the first date of the coadministration of zanubrutinib and a moderate or strong CYP3A inhibitor.
[b] The During Coadministration Period is defined as the period from the second day of the coadministration of zanubrutinib and a moderate or strong CYP3A inhibitor to the date of the end of the coadministration +30 days, end of study, death, initiation of a new anticancer therapy, or data cutoff, whichever comes first.
[c] The After Coadministration Period is defined as the period from the end of the coadministration of zanubrutinib and a moderate or strong CYP3A inhibitor +31 days to the last dose of zanubrutinib (end of treatment) +30 days, end of study, death, initiation of a new anticancer therapy, or data cutoff, whichever comes first.

Deaths

The percentage of patients with a TEAE leading to death was highest in the During Coadministration Period (8 (5.8%) patients), follow by the After Coadministration Period (5 (4.7%) patients), and the Prior to Coadministration Period (1 (0.8%) patient). Of note, the number of patients experiencing TEAEs leading to death in each period was low; comparisons should be interpreted with caution.

The only event by PT that occurred in >1 patient in any study period was pneumonia (1 (0.8%) patients in the Prior to Coadministration, 2 (1.4%) patients in the During Coadministration, and 1 (0.9%) patients in the After Coadministration Periods).

In the Prior to Coadministration Period, only 1 patient (0.8%) died from pneumonia, which was assessed as possibly related to study drug by the investigator.

In the During Coadministration Period, among the patients who died, the majority of the deaths were from infection (7 (5.1%) patients), including 2 (1.4%) patients who died from pneumonia, 1 (0.7%) from bacteraemia, 1 (0.7%) from COVID-19 pneumonia, 1 (0.7%) from *Escherichia* sepsis, 1 (0.7%) from *Scedosporium* infection, and 1 (0.7%) from sepsis. One (0.7%) patient died from acute myocardial infarction. In the During Coadministration Period, all deaths, except for 2 patients who died due to pneumonia and 1 patient who died due to bacteremia, were assessed as not related to study drug according to the investigator. Among the 7 patients who died from infections in the During Coadministration Period, 5 patients received CYP3A inhibitors/antimicrobials including antibiotics (clarithromycin and ciprofloxacin) and antifungals (voriconazole). The antimicrobials in 1 patient were initiated for the treatment of the active infection which was the TEAE leading to death, while in 2 patients, antimicrobials were administered as a prophylaxis for infections due to their underlying conditions such as neutropenia or pancytopenia. In the During Coadministration Period, one patient (BGB-3111-AU-003-S2201-2-224) experienced Grade 4 neutropenia with concurrent fatal infections (defined as infections occurring between the onset date of neutropenia to end date plus 14 days). This patient had ongoing medical history of Grade 4 neutropenia at baseline. Patient BGB-3111-AU-003-S702-2-08 had a Grade 3 bronchopulmonary aspergillosis with concurrent neutropenia and recovered before developing fatal pneumonia after neutropenia was resolved. Taken together, the fatal infections were not likely due to zanubrutinib-induced neutropenia.

Of the 8 patients with TEAEs leading to death in the During Coadministration Period.

For the After Coadministration Period, 2 (1.9%) patients died from infections (pneumonia with septic shock, and COVID-19), 2 (1.9%) died from neoplasms benign, malignant and unspecified (lymphoma transformation and recurrent skin squamous cell carcinoma), and 1 (0.9%) patient died from cerebral infarction. All the deaths in the After Coadministration Period were considered as not related to study drug except for one (lymphoma transformation).

For the patients who died, the CYP3 inhibitors administered included antibiotics (clarithromycin, ciprofloxacin), antifungals (voriconazole), and calcium blockers (diltiazem).

Serious Treatment-Emergent Adverse Events

The percentage of patients with at least 1 serious adverse event (SAE) was lower in the During Coadministration Period (26.8%) compared with the Prior to Coadministration Period (56.3%) and After Coadministration Period (45.8%) (Table 8).

In the During Coadministration Period, the most frequently reported ≥Grade 3 TEAEs by PT (>2% of patients) were pneumonia (5.1%) and febrile neutropenia and sepsis (2.2%, each).

The most frequently reported serious TEAEs by SOC in the Prior to Coadministration, During Coadministration, and After Coadministration Periods were infections and infestations (36.1%, 18.1%, and 21.5%, respectively) with pneumonia being the most frequently reported TEAE for each period (10.1%, 5.1%, and 7.5%, respectively). Other frequently reported infection-related serious TEAEs (>2% of patients in any study period) by PT in the Prior to Coadministration, During Coadministration, and After Coadministration Periods included urinary tract infection (5.0%, 0.0%, 2.8%, respectively), cellulitis (4.2%, 1.4%, and 0.9%, respectively), influenza and lower respiratory tract infection (2.5%, 0.0%, and 0.9% each, respectively), and sepsis (0.8%, 2.2%, and 1.9%, respectively).

Blood and lymphatic system disorders was the second most frequently reported serious TEAEs by SOC in the Prior to Coadministration, During Coadministration, and After Coadministration Periods (4.2%, 3.6%, and 4.7%, respectively), with febrile neutropenia (1.7%, 2.2%, and 2.8%, respectively) and neutropenia (1.7%, 1.4%, and 0.9%, respectively) being the most common. None of the patients reported anaemia during the Coadministration Period, and only one patient from both the Prior and After Coadministration Periods (0.8% and 0.9%, respectively) reported anaemia. All serious TEAEs reported in >1 patient were reported less frequently in the During Coadministration Period compared to the Prior and After Coadministration Periods except for cellulitis (1.4% in the During Coadministration Period), febrile neutropenia (2.2%), neutropenia (1.4%), and sepsis (2.2%), Other Significant Treatment-Emergent Adverse Events Treatment-Emergent Adverse Events Leading to Treatment Discontinuation A higher percentage of patients had TEAEs leading to treatment discontinuation in the During Coadministration Period (7.2%) and After Coadministration Period (10.3%) compared with the Prior to Coadministration Period (2.5%). This difference was not driven by any single PT. In the During Coadministration Period, 11.3% of the patients received moderate CYP3A inhibitors and 6.8% of patients received strong CYP3A inhibitors. Most of the patients with TEAEs leading to treatment discontinuation in the During Coadministration Period received moderate CYP3A inhibitors while 4 of them received strong CYP3A inhibitors (itraconazole in 1 patient, voriconazole and clarithromycin in 1 patient, voriconazole in 2 patients).

Of the patients with TEAEs leading to treatment discontinuation, 4 patients discontinued due to TEAEs that they had also experienced in a prior period.

The only event leading to treatment discontinuation by PT that occurred in >1 patient in any period was pneumonia (1 (0.8%) patients in the Prior to Coadministration Period, 3 (2.2%) patients in the During Coadministration Period, and 0 (0.0%) patients in the After Coadministration Period). For approximately half of the patients who had TEAEs leading to treatment discontinuation, the TEAE was infection related.

Treatment-Emergent Adverse Events Leading to Dose Interruption

The percentage of patients with at least 1 TEAE leading to dose interruption was lower in the During Coadministration Period (18.1%) compared with the Prior to Coadministration Period (50.4%) and After Coadministration Period (41.1%). Events of infections and infestations were the most commonly reported TEAEs by SOC that led to dose interruption in the Prior to Coadministration, During Coadministration, and After Coadministration Periods (27.7%, 8.7%, and 14.0%, respectively).

In the During Coadministration Period, the most frequently reported TEAEs leading to dose interruption (>2% of patients) were pneumonia (4.3%), neutropenia (3.6%), and febrile neutropenia and neutrophil count decreased (2.2%, each).

The most frequently reported TEAEs leading to dose interruption (>2% of patients in any study period) by PT in the Prior to Coadministration, During Coadministration, and After Coadministration Periods were pneumonia (6.7%, 4.3%, and 4.7%, respectively), neutropenia (5.0%, 3.6%, and 5.6%, respectively), cellulitis (4.2%, 0.0%, and 0.9%, respectively), squamous cell carcinoma of skin (2.5%, 0.0%, and 0.9%, respectively), urinary tract infection (2.5%, 0.0%, and 1.9%, respectively), febrile neutropenia (1.7%, 2.2%, and 1.9%, respectively), neutrophil count decreased (1.7%, 2.2%, and 0.0%, respectively), and pleural effusion (0.8%, 0%, and 2.8%, respectively).

Treatment-Emergent Adverse Events Leading to Dose Reductions

The percentage of patients with at least 1 TEAE leading to dose reduction was lower in the During Coadministration Period (3 (2.2%) patients) and After Coadministration Period (6 (5.6%) patients) compared with the Prior to Coadministration Period (15 (12.6%) patients). In the During Coadministration Period, 2 (14.3%) patients reported infections (1 with meningitis cryptococcal and 1 with streptococcal bacteraemia) and 1 (7.1%) patient reported vomiting that led to dose reduction.

The most frequently reported TEAEs leading to dose reductions (>1 patient in any study period) by PT in the Prior to Coadministration, During Coadministration, and After Coadministration Periods were pneumonia (5 (3.4%) patients, 0 (0.0%) patients, 1 (0.9%) patient, respectively), neutropenia (2 (1.7%) patients, 0 (0.0%) patients, 1 (0.9%) patients, respectively), and febrile neutropenia (1 (0.8%) patients, 0 (0.0%) patients, 2 (1.9%) patients, respectively).

Hemorrhage

The percentage of patients with an AESI of hemorrhage was lower in the During Coadministration Period than in the other 2 periods. The percentage of patients with an AESI of hemorrhage and the exposure-adjusted incidence of these events in the Prior to Coadministration, During Coadministration, and After Coadministration Periods were 55.5% (9.70 per 100 person-months), 14.5% (4.04 per 100 person-months) and 23.4% (1.39 per 100 person-months), respectively.

In the During Coadministration Period, the most frequently reported (>1% of patients) hemorrhage AESIs by PT were contusion (6.5%) and epistaxis and haematuria (1.4%, each). None of these events was serious or severe (≥Grade 3).

The most frequently reported (>5% of patients in any study period) hemorrhage AESIs by PT in the Prior to Coadministration, During Coadministration, and After Coadministration Periods were contusion (30.3%, 6.5%, and 9.3%, respectively), haematuria (8.4%, 1.4%, and 4.7%, respectively), petechiae (5.9%, 0.7%, and 0.0%, respectively), and purpura (5.9%, 0.0%, and 0.0%, respectively).

The percentage of patients with a ≥Grade 3 AESI of hemorrhage and the exposure-adjusted incidence of these events were 2.5% (0.19 per 100 person-months), 0.7% (0.16 per 100 person-months), and 1.9% (0.09 per 100 person-months) in the Prior to Coadministration, During Coadministration, and After Coadministration Periods, respectively. The only ≥Grade 3 AESI occurring in >1 patient by PT in any study period was haematuria (2 (1.7%) patients, 0 (0.0%) patients, and 0 (0.0%) patients, respectively).

The percentages of patients with an AESI of hemorrhage leading to dose interruption was lower in the During Coadministration Period (0.7%) than in the Prior to Coadministration and After Coadministration Periods (3.4% and 2.8%, respectively). The only hemorrhage PT leading to dose interruption in >1 patient in any study period was haematuria (2 (1.7%) patients, 0 (0.0%) patients, and 0 patients (0.0%), respectively). No AESI of hemorrhage leading to dose reduction occurred in the During Coadministration Period, while 1.7% and 0.9% of patients had an AESI of hemorrhage leading to dose reduction in the Prior to Coadministration and After Coadministration Periods, respectively. No AESI of hemorrhage leading to dose reduction occurred in >1 patient by PT in any study period.

For serious AESIs of hemorrhage, the percentage of patients who experienced the event and EAIRs in the Prior to Coadministration, During Coadministration, and After Coadministration Periods was 3.4% (0.25 per 100 person-months), 0.0% (0.0 per 100 person-months), and 1.9% (0.09 per 100 person-months), respectively. The only serious hemorrhage event that occurred in >1 patient by PT in any study period was haematuria (2 (1.7%) patients, 0 (0.0%) patients, and 0 (0.0%) patients, respectively).

No AESI of hemorrhage led to treatment discontinuation or death.

Major Hemorrhage

The percentage of patients with an AESI of major hemorrhage was lower in the During Coadministration Period (0.7%) than in the Prior to Coadministration and After Coadministration Periods (3.4% and 1.9%, respectively). The EAIRs of major hemorrhage for Prior to Coadministration, During Coadministration, and After Coadministration Periods were 0.25 per 100 person-months, 0.16 per 100 person-months, and 0.09 per 100 person-months, respectively. The only event by PT that occurred in >1 patient in any study period was haematuria (2 (1.7%) patients, 0 (0.0%) patients, 0 (0.0%) patients, respectively).

In the During Coadministration Period, the only AESI of major hemorrhage reported was haemobilia, which was Grade 3 but not serious; the patient recovered quickly from this AESI.

Similar to the percentage of patients with an AESI of major hemorrhage, patients who had ≥Grade 3 AESI of major hemorrhage in the Prior to Coadministration, During Coadministration, and After Coadministration Periods was 2.5%, 0.7%. and 1.9%, respectively. The EAIR of major hemorrhage for ≥Grade 3 AESIs was 0.19 per 100 person-months, 0.16 per 100 person-months, and 0.09 per 100 person-months, respectively. The only ≥Grade 3 AESI of major hemorrhage occurring in >1 patient by PT in any study period was haematuria (2 (1.7%) patients, 0 (0.0%) patients, and 0 (0.0%) patients, respectively).

The percentage of patients with an AESI of major hemorrhage leading to dose interruption was similar in the Prior to Coadministration, During Coadministration, and After Coadministration Periods (1.7%, 0.7%, and 0.9%, respectively). No major hemorrhage events leading to dose interruption occurred in >1 patient in any study period. In the Prior to Coadministration Period, 2 (1.7%) patients had AESI of major hemorrhage (contusion and haematuria, 1 each) that led to dose interruption. Only 1 (0.7%) patient reported haemobilia leading to dose interruption, which occurred in the During Coadministration Period. Similarly, in the After Coadministration Period, only 1 (0.9%) patient had a dose interruption due to major hemorrhage (PT of traumatic haematoma). One patient had a major hemorrhage AESI of contusion leading to dose reduction, which occurred in the Prior to Coadministration Period.

The percentage of patients who had serious AESIs of major hemorrhage was lower in the During Coadministration Period (0.0%) than in the Prior to Coadministration and After Coadministration Periods (3.4% and 1.9%, respectively). The EAIR of major hemorrhage SAEs was 0.25 per 100 person-months, 0.0 per 100 person-months, and 0.09 per 100 person-months, respectively. The only event that occurred in >1 patient by PT in any study period was haematuria (2 (1.7%) patients, 0 (0.0%) patients, and 0 (0.0%) patients, respectively). Other serious AESIs of major hemorrhage by PT occurring in 1 patient were contusion, haemarthrosis, haematoma, and traumatic haematoma.

No AESI of major hemorrhage led to treatment discontinuation or death.

Atrial Fibrillation and Flutter

The percentage of patients with both atrial fibrillation and flutter was higher in the After Coadministration Period (4.7%) than in the Prior to Coadministration and During Coadministration Periods (1.7% and 1.4%, respectively). The EAIR of this AESI in the Prior to Coadministration, During Coadministration, and After Coadministration Periods was 0.13 per 100 person-months, 0.33 per 100 person-months, and 0.23 per 100 person-months, respectively. The percentage of patients in each study period with an AESI by PT of atrial fibrillation was 1.7%, 1.4%, and 2.8%, respectively, while the PT of atrial flutter was reported in 0.0%, 0.0%, and 1.9% of patients, respectively.

Two patients (1 in the Prior to Coadministration Period and 1 in the During Coadministration Period) of the 9 patients total with these AESI had a medical history of atrial fibrillation or flutter.

A higher percentage of patients had Grade ≥3 atrial fibrillation and flutter AESIs in the After Coadministration Period (3.7% (0.18 per 100 person-months)) than in the Prior to and During Coadministration Periods (1.7% (0.13 per 100 person-months) and 1.4% (0.33 per 100 person-months), respectively). All the events of atrial fibrillation were Grade 3, and 2 of the events were ongoing at the time of data cutoff.

One patient in the During the Coadministration Period had Grade 3 atrial fibrillation leading to dose interruption.

A similar percentage of patients had serious AESIs of atrial fibrillation and flutter in the Prior to Coadministration, During Coadministration, and After Coadministration Periods (0.8%, 0.0%, and 1.9%, respectively). The EAIRs of atrial fibrillation and flutter for SAEs were 0.06 per 100 person-months, 0.0 per 100 person-months, and 0.09 per 100 person-months, respectively. By PT, 1 patient had a serious event of atrial fibrillation in the Prior to Coadministration Period, 1 patient had an SAE of atrial fibrillation in the After Coadministration Period, and 1 patient had a serious event of atrial flutter during the After Coadministration Period.

No AESI of atrial fibrillation and flutter led to dose reduction, treatment discontinuation, or death.

Hypertension

The percentage of patients with an AESI of hypertension was lower in the During Coadministration Period compared with the other 2 periods. The percentage of patients with an AESI of hypertension and the EAIRs of these events in the Prior to Coadministration, During Coadministration, and After Coadministration Periods were 12.6% (1.13 per 100 person-months), 2.9% (0.70 per 100 person-months), and 7.5% (0.37 per 100 person-months), respectively. These events consisted mainly of PTs of hypertension, which was reported in 11.8%, 2.9%, and 7.5% of patients, respectively. Additionally, 1 patient had an event of blood pressure increased PT in the Prior to Coadministration Period. The events of hypertension were reported by the investigator as worsening hypertension or aggravated hypertension in 13 of the 26 total patients with PTs of hypertension.

The percentage of patients with AESIs of hypertension ≥Grade 3 followed a similar pattern as all hypertension AESIs; 6.7% of patients in the Prior to Coadministration Period, 0.7% of patients in the During Coadministration Period, and 3.7% of patients in the After Coadministration Period had ≥Grade 3 AESI of hypertension. The EAIRs were 0.56 per 100 person-months, 0.17 per 100 person-months, and 0.18 per 100 person-months, respectively.

One patient had an AESI leading to dose interruption of hypertension in the Prior to Coadministration Period.

One patient in the during the Coadministration Period had a serious AESI of hypertension, with an EAIR of 0.16 per 100 person-months. No AESI of hypertension led to dose reduction, treatment discontinuation, or death.

Second Primary Malignancies

The percentage of patients with at least 1 AESI of second primary malignancies was lower in the During Coadministration Period than in the other 2 periods. The percentage of patients with second primary malignancies and the EAIRs of these events in the Prior to Coadministration, During Coadministration, and After Coadministration Periods were 12.6% (1.05 per 100 person-months), 2.9% (0.72 per 100 person-months), and 12.1% (0.60 per 100 person-months), respectively.

Since de novo tumorigenesis takes an extended period of time, the short duration of coadministration of CYP3A4 inhibitors (median 56.0 days) does not likely reflect the true effect of CYP3A4 inhibitors' potential of risk of second primary malignancies.

The most frequently reported AESI (>2% of patients in any study period) of second primary malignancies by PT were squamous cell carcinoma of skin (5.0%, 0.7%, and 0.9%, respectively) and basal cell carcinoma (4.2%, 0.0%, and 5.6%, respectively). Malignant melanoma occurred in 2 (1.7%) patients in the Prior to Coadministration Period, 0 (0.0%) patients in the During Coadministration Period, and 1 (0.9%) in the After Coadministration Period.

The percentage of patients with AESIs of second primary malignancies ≥Grade 3 was lower in the During Coadministration Period (1.4%) compared with the Prior to Coadministration Period (4.2%) and After Coadministration Period (5.6%). The EAIR of second primary malignancies for AESIs ≥Grade 3 was 0.32 per 100 person-months, 0.33 per 100 person-months, and 0.27 per 100 person-months for the Prior to Coadministration, During Coadministration, and After Coadministration Periods, respectively. The only second primary malignancy PTs ≥Grade 3 that occurred in >1 patient in any study period were basal cell carcinoma (2 (1.7%) patients, 0 (0.0%) patients, and 1 (0.9%) patients, respectively) and squamous cell carcinoma of skin (2 (1.7%) patients, 0 (0.0%) patients, and 1 (0.9%) patients, respectively).

The percentage of patients with at least 1 AESI of second primary malignancies leading to dose interruption was lower in the During Coadministration Period (1.4%) compared with the Prior to Coadministration Period (4.2%) and After Coadministration Period (5.6%). The only events that led to dose interruption in >1 patient of the Prior to Coadministration, During Coadministration, or After Coadministration Period by PT were squamous cell carcinoma of skin (3 (2.5%) patients, 0 (0.0%) patients, and 1 (0.9%) patient, respectively), external ear neoplasm malignant (2 (1.7%) patients, 1 (0.7%) patient, and 0 (0.0%) patients, respectively), and basal cell carcinoma (2 (1.7%) patients, 0 (0.0%) patients, and 1 (0.9%) patient, respectively).

Of the 2 (1.4%) patients with second primary malignancies that were ≥Grade 3 and led to dose interruption during the Coadministration Period, one had sarcomatoid carcinoma of the lung and metastases to central nervous system, both of which were ongoing at the time of data cutoff, and one other patient had external ear neoplasm malignant that was resolved.

No events of second primary malignancies led to dose reduction.

Three (2.8%) patients had an AESI of second primary malignancies that led to treatment discontinuation in the After Coadministration Period with 1 (0.9%) patient who had Grade 3, ongoing chronic myeloid leukemia, 1 (0.9%) patient with Grade 2, ongoing colon cancer, and 1 (0.9%) patient with Grade 5 recurrent squamous cell carcinoma on right periauricular area. No events leading to treatment discontinuation occurred in any other study periods and no events occurred in >1 patient.

The percentages of patients with serious AESI of second primary malignancies in the Prior to Coadministration, During Coadministration, and After Coadministration Periods were 5.0%, 1.4%, and 2.8%, respectively. The EAIRs of second primary malignancies for SAEs were 0.39 per 100 person-months, 0.33 per 100 person-months, and 0.13 per 100 person-months, respectively. The only serious events that occurred in >1 patient by PT in any study period were external ear neoplasm malignant (2 (1.7%) patients, 1 (0.7%) patient, and 0 (0.0%) patients) and squamous cell carcinoma of skin (2 (1.7%) patients, 0 (0.0%) patients, and 0 (0.0%) patients).

Two patients had an AESI of second primary malignancies that led to death, both in the After Coadministration Period. One of these patients had lymphoma transformation that was considered by the investigator to be related to study treatment and was considered by the sponsor as progression of the disease under study. The other patient had skin squamous cell carcinoma recurrent considered to be not related to study treatment by the investigator.

Skin cancer AESI

The percentage of patients with a skin cancer AESI was lower in the During Coadministration Period (0.7%) compared with the Prior Coadministration Period (8.4%) and the After Coadministration Period (8.4%). The percentage of patients with a skin cancer AESI ≥Grade 3, an AESI leading to interruption, or a skin cancer SAE was lower in the During Coadministration Period compared with in the Prior to Coadministration Period and After Coadministration Period. One patient had an AESI (skin squamous cell carcinoma recurrent) leading to treatment discontinuation and leading to death in the After Coadministration Period. No patients had a skin cancer AESI that led to dose reduction. The EAIRs of skin cancers AESIs in the Prior to Coadministration, During Coadministration, and After Coadministration Periods was 0.69 per 100 person-months, 0.17 per 100 person-months, and 0.41 per 100 person-months, respectively; for AESIs ≥Grade 3, it was 0.26 per 100 person-months, 0.00 per 100 person-months, and 0.13 per 100 person-months; and for SAEs, it was 0.26 per 100 person-months, 0.00 per 100 person-months, and 0.04 per 100 person-months.

Tumor Lysis Syndrome

No AESI of tumor lysis syndrome were reported.

Infections

The percentage of patients with at least 1 AESI of infection was lower in the During Coadministration Period compared with the other 2 periods. The percentage of patients with at least 1 AESI of infection was 88.2% in the Prior to Coadministration Period, 34.1% in the During Coadministration Period, and 72.9% in the After Coadministration Period, with EAIRs of 18.08, 16.79, and 9.70 per 100 person-months, respectively.

In the During Coadministration Period, the most frequently reported AESIs (>2% of patients) were pneumonia (6.5%), upper respiratory tract infection (5.8%), lower respiratory tract infection and sinusitis (2.9%, each), and herpes zoster, sepsis, and viral upper respiratory tract infection (2.2%, each).

The most frequently reported AESI (>10% of patients in any study period) of infections by PT in the Prior to Coadministration, During Coadministration, and After Coadministration Periods were upper respiratory tract infection (40.3%, 5.8%, and 25.2%, respectively), urinary tract infection (19.3%, 1.4%, and 13.1%, respectively), pneumonia (16.0%, 6.5%, and 14.0%, respectively), cellulitis (11.8%, 1.4%, and 6.5%, respectively), and lower respiratory tract infection (10.1%, 2.9%, and 10.3%, respectively).

The percentage of patients with at least 1 AESI of infection ≥Grade 3 was lower in the During Coadministration Period (17.4%) compared with the Prior to Coadministration Period (39.5%) and After Coadministration Period (26.2%). In the During Coadministration Period, 7 (5.1%) patients experienced pneumonia, which was the most common ≥Grade 3 infections AESI reported for this period. The EAIR of infections for AESIs ≥Grade 3 was 3.82 per 100 person-months in the Prior to Coadministration Period, 5.83 per 100 person-months in the During Coadministration Period, and 1.45 per 100 person-months in the After Coadministration Period. The most frequently reported ≥Grade 3 AESI (>2% of patients in any study period) of infections by PT in the Prior to Coadministration, During Coadministration, and After Coadministration Periods were pneumonia (10.1%, 5.1%, and 6.5%, respectively), urinary tract infection (5.9%, 0.7%, and 4.7%, respectively), cellulitis (4.2%, 1.4%, and 0.9%, respectively), upper respiratory tract infection (4.2%, 0.0%, and 0.0%, respectively), and skin infection (2.5%, 0.0%, and 0.0%, respectively), and sepsis (0.8%, 2.2%, and 1.9%, respectively).

The percentage of patients with an AESI of infections that led to dose interruption was lower in the During Coadministration Period (8.7%) compared with the Prior to Coadministration Period (27.7%) and the After Coadministration Period (14.0%). The only event that occurred in >5% of patients in any study period was pneumonia (6.7%, 4.3%, and 4.7% in the Prior to Coadministration, During Coadministration, and After Coadministration Period, respectively). Additionally, a lower percentage of patients experienced an AESI of infection that led to dose reduction in the During Coadministration Period (1.4%) and After Coadministration Period (1.9%) compared with the Prior to Coadministration Period (7.6%). The only event occurring in >1 patient that led to dose reduction in the Prior to Coadministration, During Coadministration, and After Coadministration Periods was pneumonia (4 (3.4%) patients, 0 (0.0%) patients, and 1 (0.9%), respectively).

The percentage of patients with an AESI of infection that led to treatment discontinuation in the Prior to Coadministration, During Coadministration, and After Coadministration Periods was 1.7%, 4.3%, and 3.7%, respectively. The only event that occurred in >1 patient was pneumonia (1 (0.8%) patient, 3 (2.2%) patients, and 0 (0.0%) patients, respectively).

A lower percentage of patients had serious AESIs of infection in the During Coadministration Period (18.1%) and After Coadministration Period (21.5%) compared with the Prior to Coadministration Period (36.1%). The EAIR of infection for serious AESIs was 3.31 per 100 person-months, 6.16 per 100 person-months, and 1.15 per 100 person-months for the Prior to Coadministration, During Coadministration, and After Coadministration Periods, respectively. The most frequently reported SAEs (>2% of patients in any study period) of infection by PT were pneumonia (10.1%, 5.1%, and 7.5%, respectively), urinary tract infection (5.0%, 0.0%, and 2.8%, respectively), cellulitis (4.2%, 1.4%, and 0.9%, respectively), influenza (2.5%, 0.0%, and 0.9%, respectively), lower respiratory tract infection (2.5%, 0.0%, and 0.9%, respectively), and sepsis (0.8%, 2.2%, and 1.9%, respectively).

The percentage of patients with an AESI of infections that led to death was slightly higher in the During Coadministration Period (5.1%) compared with the Prior to Coadministration Period (0.8%) and the After Coadministration Period (1.9%). The only event that occurred in >1 patient was pneumonia (1 (0.8%) patients, 2 (1.4%) patients, and 1 (0.9%) patients in the Prior to Coadministration, During Coadministration, and After Coadministration Periods, respectively). One patient receiving a zanubrutinib dose of 320 mg daily died due to a fatal event of COVID-19 pneumonia in the During Coadministration Period, and 1 patient died due to a fatal event of COVID-19 in the After Coadministration Period; both patients had received the moderate CYP3A inhibitor ciprofloxacin. Both events were considered not related to study treatment by the investigator.

It is worth noting that the most common CYP3A inhibitors identified in this analysis were antimicrobials, which were used either as treatment or prophylaxis of infections. Additionally, the treatment duration of the three periods were very short relative to that in the complete studies; therefore, interpretation of EAIRs should be made with caution.

Opportunistic Infection

The percentage of patients with opportunistic infection AESIs was similar in the During Coadministration Period and the After Coadministration Period but higher in the Prior to Coadministration Period. The percentage of patients with an opportunistic infection AESI and the EAIRs of these events in the Prior to Coadministration, During Coadministration, and After Coadministration Periods were 8.4% (0.64 per 100 person-months), 2.9% (0.67 per 100 person-months), and 2.8% (0.13 per 100 person-months), respectively.

The most commonly reported opportunistic infection by PT in the Prior to Coadministration Period was bronchopulmonary aspergillosis (3 (2.5%) patients) followed by meningitis cryptococcal (2 (1.7%) patients).

The percentage of patients with an opportunistic infection AESI ≥Grade 3 was slightly lower in the During Coadministration Period (3 (2.2%) patients) and After Coadministration Period (1 (0.9%) patient) compared with the Prior to Coadministration Period (6 (5.0%) patients). The EAIRs were 0.38 per 100 person-months, 0.50 per 100 person-months, and 0.04 per 100 person-months for the Prior to Coadministration, During Coadministration, and After Coadministration Periods, respectively. In the During Coadministration Period, one patient had Grade 4 meningitis cryptococcal and encephalitis fungal, which both were assessed as related to study treatment; one patient had Grade 3 bronchopulmonary aspergillosis assessed as not related to study treatment; and one patient had Grade 5 *Scedosporium* infection, which was assessed as not related to study treatment.

The percentage of patients with an opportunistic infection AESI leading to dose reduction was 3.4% in the Prior to Coadministration period, 0.7% in the During Coadministration Period, and 0.9% in the After Coadministration Period.

In the Prior to Coadministration Period, the During Coadministration Period, and the After Coadministration Period, a low and similar percentage of patients who experienced an AESI leading to treatment discontinuation (0.8%, 0.7%, and 0.9%, respectively) and SAEs of opportunistic infections (5.0%, 2.2%, and 0.9%, respectively).

The percentage of patients with serious opportunistic AESIs were slightly lower in the During Coadministration Period (2.9%) and After Coadministration Period (2.8%) compared with the Prior to Coadministration Period (8.4%). The EAIRs for opportunistic infection SAEs were 0.38 per 100 person-months, 0.50 per 100 person-months, and 0.04 per 100 person-months for the Prior to Coadministration, During Coadministration, and After Coadministration Periods, respectively.

One patient who received 160 mg BID zanubrutinib had a fatal TEAE of *Scedosporium* infection during the Coadministration Period, and it was assessed by the investigator not to be related to study drug. The event started on Study Day 62 and the patient died on Study Day 190. During this time, the patient received the strong CYP3A inhibitor voriconazole from Study Day 80 to Study Day 108 and Study Day 126 to Study Day 127.

Hepatitis B

Three (2.5%) patients had an AESI of hepatitis B reactivation in the Prior to Coadministration Period, which were ≥Grade 3 for 2 (1.7%) of the patients. These AESIs led to dose interruption for 2 patients and to dose reduction for 1 patient. No AESIs leading to treatment discontinuation, SAEs, or AESIs leading to death were reported.

Cytopenias

Anemia

The percentage of patients with an anemia AESI was lower in the During Coadministration Period compared with the other 2 periods. The percentage of patients with an anemia AESI in the Prior to Coadministration, During Coadministration, and After Coadministration Periods was 12.6%, 7.2%, and 10.3%, respectively. The EAIR of anemia AESIs was 1.07 per 100 person-months, 1.91 per 100 person-months, and 0.53 per 100 person-months, respectively.

The percentage of patients with anemia AESIs ≥Grade 3 was similar in the Prior to Coadministration, During Coadministration, and After Coadministration Periods (6.7%, 6.5%, and 3.7%, respectively). The EAIRs were 0.54 per 100 person-months, 1.70 per 100 person-months, and 0.18 per 100 person-months, respectively.

One patient had an AESI of anemia leading to dose interruption in the During Coadministration Period. One patient had a TEAE of anemia leading to treatment discontinuation in the After Coadministration Period.

Two patients had serious AESIs of anemia: 1 in the Prior to Coadministration Period, and 1 in the After Coadministration Period. The EAIRs were 0.06 per 100 person-months and 0.04 per 100 person-months, respectively.

No patients had an AESI of anemia that led to dose reduction or death.

Neutropenia

The percentage of patients with an AESI of neutropenia was lower in the During Coadministration and After Coadministration Periods compared with the Prior to Coadministration Period. The percentages of patients with an AESI of neutropenia and EAIRs in the Prior to Coadministration, During Coadministration, and After Coadministration Periods were 28.6% (2.72 per 100 person-months), 17.4% (5.43 per 100 person-months), and 16.8% (0.92 per 100 person-months), respectively.

The AESIs of neutropenia reported by PT were neutropenia (17.6%, 8.0%, and 9.3%, respectively), neutrophil count decreased (11.8%, 8.0%, and 7.5%, respectively), febrile neutropenia (1.7%, 2.9%, and 3.7%, respectively), and neutropenic sepsis (0.8%, 0.0%, and 0.0%, respectively).

The incidence of ≥Grade 3 AESIs of neutropenia followed a similar pattern. The percentage of patients with a neutropenia AESI ≥Grade 3 in the Prior to Coadministration, During Coadministration, and After Coadministration Periods was 20.2%, 12.3%, and 20.1%, respectively, with EAIRs of 1.74 per 100 person-months, 3.72 per 100 person-months, and 0.63 per 100 person-months, respectively. These events by PT included neutropenia (12.6%, 6.5%, and 7.5%, respectively), neutrophil count decreased (7.6%, 4.3%, and 3.7%, respectively), febrile neutropenia (1.7%, 2.9%, and 3.7%, respectively), and neutropenic sepsis (0.8%, 0.0%, and 0.0%, respectively).

Neutropenia is an on-target effect of zanubrutinib, and it has not been shown to be associated with higher rate of infections compared to ibrutinib in head-to-head study BGB-3111-302. In this analysis, among the 24 cases of neutropenia during the Coadministration Period, 10 cases were concurrent with an infection (within 14 days of neutropenia). Among the 10 cases of neutropenia with concurrent infections in the During Coadministration Period, 3 concurrent infections were ≥Grade 3, while 4 infections were serious (including 1 Grade 1 event). All 10 concurrent infections resolved except one fatal case. In summary, the majority of the concurrent infections with neutropenia were nonserious, Grade 1 or 2, and were reported as resolved.

The percentage of patients with an AESI of neutropenia that led to treatment interruption was similar in the Prior to Coadministration, During Coadministration, and After Coadministration Periods (7.6%, 7.2%, and 6.5%, respectively). The events that led to dose interruption by PT were neutropenia (5.0%, 3.6%, and 5.6%, respectively), febrile neutropenia (1.7%, 2.2%, and 1.9%, respectively), and neutrophil count decreased (1.7%, 2.2%, and 0.0%, respectively). The percentage of patients with an AESI of neutropenia that led to dose reduction by PT was similar (2.5%, 0.0%, and 1.9%, respectively). These events included neutropenia (1.7%, 0.0%, and 0.9%, respectively), febrile neutropenia (0.8%, 0.0%, and 1.9%, respectively), and neutrophil count decreased (0.8%, 0.0%, and 0.0%, respectively). One patient had an AESI of neutropenia that led to treatment discontinuation in the After Coadministration Period.

A similar percentage of patients had a serious AESI of neutropenia in the Prior to Coadministration, During Coadministration, and After Coadministration Periods (3.4%, 4.3%, and 3.7%, respectively). The EAIRs for serious neutropenia AESIs were 0.26 per 100 person-months, 1.11 per 100 person-months, and 0.18 per 100 person-months, respectively. These events by PT included febrile neutropenia (1.7%, 2.2%, and 2.8%, respectively), neutropenia (1.7%, 1.4%, and 0.9%, respectively), neutrophil count decreased (0.0%, 0.7%, and 0.0%, respectively), and neutropenic sepsis (0.8%, 0%, and 0%, respectively).

No patients experienced an AESI of neutropenia that led to death.

Thrombocytopenia

The percentage of patients with an AESI of thrombocytopenia was similar in the Prior to Coadministration, During Coadministration, and After Coadministration Periods (9.2%, 6.5%, and 8.4%, respectively). The EAIRs were 0.79 per 100 person-months, 1.52 per 100 person-months, and 0.41 per 100 person-months, respectively. Treatment-emergent AEs of thrombocytopenia reported by PT were thrombocytopenia (6.7%, 4.3%, and 3.7%, respectively) and platelet count decreased (3.4%, 2.2%, and 4.7%, respectively).

A similar percentage of patients experienced an AESI of thrombocytopenia Grade 3 in the Prior to Coadministration, During Coadministration, and After Coadministration Periods (3.4%, 3.6%, and 2.8%, respectively), with EAIRs of 0.26 per 100 person-months, 0.83 per 100 person-months, and 0.13 per 100 person-months, respectively. These events by PT included thrombocytopenia (2.5%, 2.2%, and 1.9%, respectively) and platelet count decreased (0.8%, 1.4%, and 0.9%, respectively).

A similar percentage of patients experienced an AESI that led to dose interruption (0.8%, 1.4%, and 0.0%, respectively). One patient had an AESI of thrombocytopenia that led to treatment discontinuation in the During Coadministration Period.

No patients experienced an AESI that led to dose reduction, was a serious AESI, or was an AESI that led to death.

Summary

This report summarizes the assessment of the integrated safety data from 7 single-agent zanubrutinib studies for B-cell malignancies. The analysis included 138 patients who had coadministration of zanubrutinib and strong and moderate CYP3A inhibitors out of 835 patients from the 7 studies. The number of patients experiencing a TEAE and the EAIRs of AESIs did not show any trend for safety concerns across the 3 study periods (Prior to Coadministration, During Coadministration, and After Coadministration Periods).

The median duration of coadministration was approximately 2 months, and the majority of the patients (89.1%) received a full dose of 320 mg zanubrutinib daily during the Coadministration Period.

The EAIRs did not show a clear trend of increase in AESIs during the Coadministration Period. Most of the EAIRs of AESIs were similar across the 3 periods except for cytopenia (including anemia, neutropenia, and thrombocytopenia) and atrial fibrillation and flutter. Only 1 case of thrombocytopenia in the During Coadministration Period led to treatment discontinuation, and no cases of atrial fibrillation and flutter led to treatment discontinuation.

The coadministration of strong and moderate CYP3A inhibitors and zanubrutinib showed a slight increase in the incidence of treatment discontinuation when compared to the Prior to Coadministration Period, and approximately 50% of the TEAEs that led to treatment discontinuation was related to infections, specifically pneumonia. However, the incidences of ≥Grade 3 TEAEs, serious TEAEs, and TEAEs that led to dose interruption or reduction in the During Coadministration Period did not increase compared to the Prior to Coadministration and After Coadministration Periods.

The percentage of patients with a TEAE leading to death was the lowest in the Prior to Coadministration Period and comparable between the During Coadministration Period and After Coadministration Period. The majority of the TEAEs leading to death in the During Coadministration Period were infections, and the CYP3A inhibitors administered for them were mainly antimicrobials. These differences in the percentage of fatal TEAEs between periods may be reflective of the deterioration of the patient's general condition.

Adverse events of special interest are those that are known to be associated with the class of BTK inhibitors. The AESI patterns in this analysis appear to be generally consistent with the known safety profile of zanubrutinib trials. Neutropenia reported during the coadministration of a CYP3A inhibitor and zanubrutinib was not associated with more ≥Grade 3, serious, or fatal concurrent infections. TEAEs leading to death, treatment discontinuation, or dose reduction were generally consistent with the known safety profile of zanubrutinib. Overall, 90% of the patients in the Coadministration Period in this analysis were treated with a 320 mg once daily zanubrutinib dose, prior to the implementation of the dose modification guideline in the current zanubrutinib prescribing information. Combined with the safety results in the current analysis, the current dose modification guidelines in the zanubrutinib label (ie, 80 mg once daily with strong CYP3A inhibitors and 80 mg twice daily with moderate CYP3A inhibitors) are adequate to ensure patient safety. In addition, this safety study surprisingly showed the non-inferior safety profiles at zanubrutinib exposures 2 to 3-fold higher (equivalent to a total daily dose of 640 mg or higher) than therapeutic exposure of zanubrutinib (320 mg total daily dose). Therefore, the overall benefit-risk profile remains favorable when zanubrutinib is concomitantly prescribed with a CYP3A inhibitor.

Example 3

The entire disclosure of NCT03734016 on ClinicalTrials.gov is incorporated herein by reference.

Title of Study: A Phase 3, Randomized Study of Zanubrutinib (BGB-3111) Compared with Ibrutinib in Patients with Relapsed/Refractory Chronic Lymphocytic Leukemia or Small Lymphocytic Lymphoma 1 Study Objectives
  Primary:
    To compare the efficacy of zanubrutinib versus ibrutinib as measured by overall response rate determined by independent central review
  Secondary:
    To compare the efficacy of zanubrutinib versus ibrutinib as measured by:
      Progression-free survival determined by independent central review
      Progression-free survival determined by investigator assessment
      Duration of response as determined by independent central review
      Duration of response as determined by investigator assessment
      Time to treatment failure
      Rate of partial response with lymphocytosis or higher determined by independent central review
      Overall survival
      Patient-reported outcomes
    To compare the safety of zanubrutinib versus ibrutinib
  Exploratory:
    To evaluate the correlation between clinical outcomes (e.g., overall response rate, progression-free survival, duration of response, overall survival, rate of partial response) and the prognostic and predictive biomarkers
    To evaluate the pharmacokinetics of zanubrutinib 2 Study Design
2.1 Summary of Study Design This was a Phase 3, randomized study of zanubrutinib versus ibrutinib in approximately 400 patients with R/R CLL/SLL. Refractory disease was defined as either no objective response to or disease progression within 6 months of the last treatment, and relapsed disease was defined as patients whose disease relapses more than 6 months after the last treatment and subsequently progressed. The primary efficacy endpoint was ORR determined by independent central review. Disease response was assessed per the "modified" 2008 International Workshop on Chronic Lymphocytic Leukemia (IWCLL) guidelines with modification for treatment-related lymphocytosis for patients with CLL, and per Lugano Classification for non-Hodgkin lymphoma (NHL) for patients with SLL. Rate of PR-L or higher was assessed as a secondary efficacy endpoint considering the finding that treatment with BTK inhibitors may lead to lymphocytosis due to redistribution of leukemia cells from lymphoid compartment to blood. In these instances, treatment-related transient progressive lymphocytosis was not a sign of treatment failure or disease progression and has no bearing on treatment outcome.

Patients was randomized in a 1:1 manner to one of the following treatment arms:
  Arm A: Zanubrutinib 160 mg orally twice daily
  Arm B: Ibrutinib 420 mg orally once daily Randomization was stratified by age (<65 years versus ≥65 years), geographic region (China versus non-China), refractory status (yes or no), and del[17p]/TP53 mutation status (present or absent). Patients from China will comprise no more than 20% of the study population.

Treatment with zanubrutinib and ibrutinib was open label. Study treatment must commence within 5 days after randomization/treatment assignment and was continued until disease progression, unacceptable toxicity, treatment consent withdrawal, or study termination. Each cycle consists of 28 days. Based on enrollment prediction, the study duration was approximately 7 years.

2.2 Study Assessments:

Assessments of CLL/SLL status to be performed during the study include disease-related constitutional symptoms, physical examination of lymph nodes, liver, and spleen; laboratory studies; bone marrow examination, genetic alterations in the tumor cells (including del[17p], del[11q], 12q+, and immunoglobulin variable region heavy chain [IGHV] mutation analysis); computed tomography (CT) scan of neck, chest, abdomen, and pelvis with contrast; and patient-reported outcomes (PROs; European quality of life 5-dimensions 5-levels health questionnaire (EQ-5D-5L) and European Organisation for Research and Treatment of Cancer quality of life cancer core questionnaire (EORTC QLQ-C30)).

Imaging of the neck, chest, abdomen, and pelvis and any other disease sites by CT with contrast was performed as indicated in until disease progression, death, lost to follow-up, withdrawal of consent, or end of study, whichever occurs first.

Patients with a potential CR or CRi will undergo a bone marrow examination to confirm CR or CRi, and possibly to determine the presence or absence of minimal residual disease (MRD).

Patients should remain on study treatment until disease progression was confirmed by independent central review.

To measure potential resistance mechanisms for zanubrutinib, a blood sample was obtained from patients receiving zanubrutinib who have progressive disease (PD) confirmed by independent central review.

Assessments of safety will include AEs, SAES, clinical laboratory tests, physical examinations, electrocardiogram (ECG), and vital signs. AEs was graded for severity per National Cancer Institute Common Terminology Criteria for Adverse Events (NCI-CTCAE) v4.03. An independent Data Monitoring Committee (DMC) will periodically monitor safety data.

2.3 Study Schema

Figure 5:
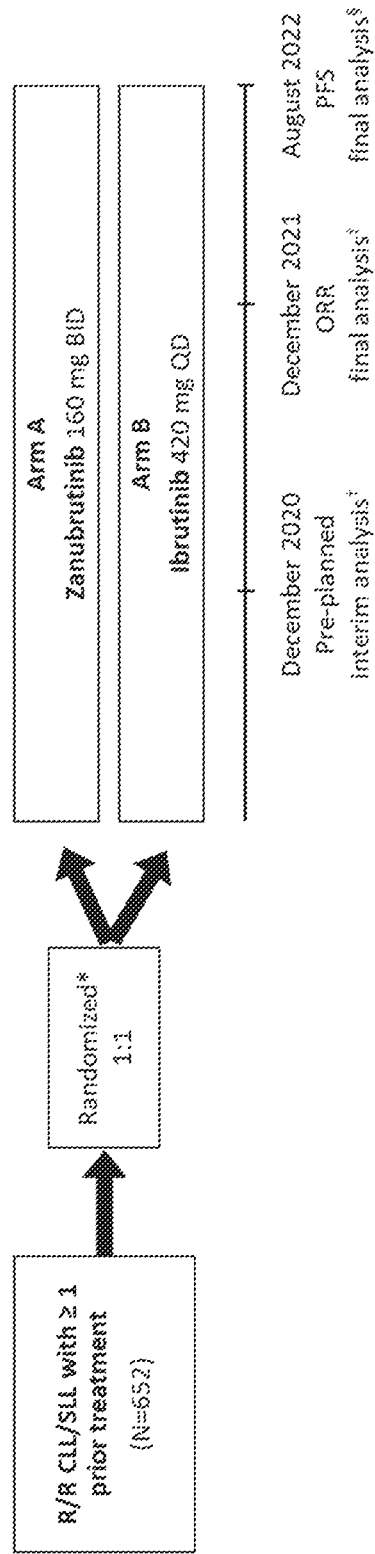
FIG. 5 depicts the Study Schema of Example 2.

FIG. 5 was Study Schema.

ALPINE enrolled 652 patients with relapsed/refractory chronic lymphocytic leukemia or small lymphocytic lymphoma. Patients were randomized 1:1 to receive zanubrutinib 160 mg twice daily or ibrutinib 420 mg once daily until disease progression or unacceptable toxicity.

Randomization was stratified by age (<65 years versus ≥65 years), geographic region (China versus non-China), refractory status (yes or no), and del[17p]/TP53 mutation status (present versus absent).

ORR interim analysis was scheduled approximately 12 months after the enrollment of the first 415 patients.

ORR final analysis was scheduled approximately 12 months after enrollment completion.

PFS final analysis was scheduled when approximately 205 PFS events were observed.

Figure 3:
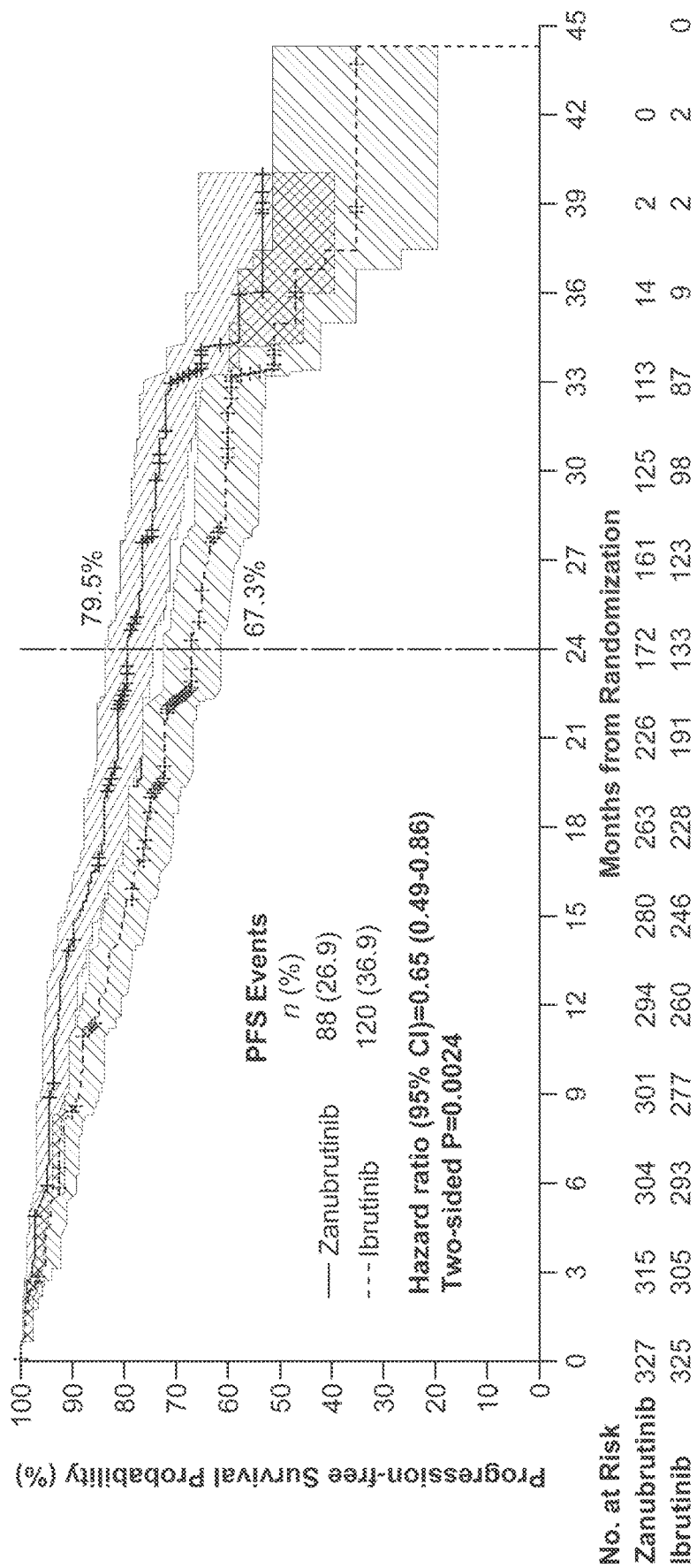
FIG. 3 depicts the Independent-Review Committee Assessment of the Progression-Free Survival in intent-to-treat (ITT) Populations. Noninferiority 1-sided P<0.0001.

In FIG. 3, BID denotes twice daily, CLL denotes chronic lymphocytic leukemia, ORR denotes overall response rate, PFS denotes progression-free survival, QD denotes once daily, R/R denotes relapsed/refractory, and SLL denotes small lymphocytic lymphoma.

2.4 Blinding

Treatment with zanubrutinib and treatment with ibrutinib was open label; however, the assessment of ORR by independent central review (primary endpoint) was blinded.

3 Eligibility Criteria 3.1 Inclusion Criteria

Each patient eligible to participate in this study must meet ALL of the following criteria:
1. Age 18 years or older
2. Confirmed diagnosis of CLL or SLL that meets the IWCLL criteria
3. CLL/SLL requiring treatment as defined by at least 1 of the following criteria:
   a. Evidence of progressive marrow failure as manifested by the development of, or worsening of, anemia and/or thrombocytopenia
   b. Massive (≥6 cm below left costal margin), progressive, or symptomatic splenomegaly
   c. Massive nodes (≥10 cm in longest diameter), or progressive or symptomatic lymphadenopathy
   d. Progressive lymphocytosis with an increase of >50% over a 2-month period or lymphocyte-doubling time of <6 months. Lymphocyte-doubling time may be obtained by linear regression extrapolation of absolute lymphocyte counts obtained at intervals of 2 weeks over an observation period of 2 to 3 months. In patients with initial blood lymphocyte counts of <30×10$^9$/L (30,000/μL), lymphocyte-doubling time should not be used as a single parameter to define treatment indication. In addition, factors contributing to lymphocytosis or lymphadenopathy other than CLL/SLL (e.g., infection) should be excluded.
   e. Autoimmune anemia and/or thrombocytopenia that was poorly responsive to corticosteroids or other standard therapy
   f. Constitutional symptoms, defined as any 1 or more of the following disease-related symptoms or signs:
      i. Unintentional weight loss of >10% within the previous 6 months
      ii. Significant fatigue (ie, inability to work or perform usual activities)
      iii. Fevers >100.5° F. or 38° C. for ≥2 weeks without other evidence of infection
      iv. Night sweats for >1 month without evidence of infection
4. Relapsed or refractory to at least 1 prior systemic therapy for CLL/SLL. A line of therapy was defined as completing at least 2 cycles of treatment of standard regimen according to current guidelines or of an investigational regimen on a clinical trial
5. Measurable disease by CT/magnetic resonance imaging (MRI). Measurable disease was defined as ≥1 lymph node >1.5 cm in longest diameter and measurable in 2 perpendicular diameters
6. Eastern Cooperative Oncology Group (ECOG) performance status of 0, 1, or 2
7. Life expectancy ≥6 months
8. Adequate bone marrow function as defined by:
   a. Absolute neutrophil count (ANC)≥1000/mm$^3$ (growth factor use was allowed), except for patients with bone marrow involvement in which case ANC must be ≥750/mm$^3$
   b. Platelet ≥75,000/mm$^3$ (may be post-transfusion), except for patients with bone marrow involvement by CLL in which case the platelet count must be ≥50,000/mm$^3$
9. Patient must have adequate organ function defined as:
   a. Creatinine clearance ≥30 mL/min (as estimated by the Cockcroft-Gault equation or the Modification of Diet in Renal Disease [MDRD] equation, or as measured by nuclear medicine scan or 24-hour urine collection)
   b. Aspartate aminotransferase/serum glutamic oxaloacetic transaminase, and alanine aminotransferase (ALT)/serum glutamic pyruvic transaminase ≤2.5× upper limit of normal unless due to CLL/SLL
   c. Serum total bilirubin <2.0×upper limit of normal (unless documented Gilbert's syndrome)
10. Female patients of childbearing potential must practice highly effective methods of contraception initiated prior to first dose of study drug, for the duration of the study, and for ≥90 days after the last dose of zanubrutinib or ibrutinib
11. Male patients were eligible if vasectomized or if they agree to the use of barrier contraception with other highly effective methods during the study treatment period and for ≥90 days after the last dose of zanubrutinib or ibrutinib
12. Ability to provide written informed consent and can understand and comply with the requirements of the study.

3.2 Exclusion Criteria

Each patient eligible to participate in this study must NOT meet any of the following exclusion criteria:
1. Known prolymphocytic leukemia or history of, or currently suspected, Richter's transformation (biopsy based on clinical suspicion may be needed to rule out transformation)

2. Clinically significant cardiovascular disease including the following:
   a. Myocardial infarction within 6 months before screening
   b. Unstable angina within 3 months before screening
   c. New York Heart Association class III or IV congestive heart failure
   d. History of clinically significant arrhythmias (e.g., sustained ventricular tachycardia, ventricular fibrillation, Torsades de Pointes)
   e. QTcF >480 milliseconds based on Fridericia's formula
   f. History of Mobitz II second-degree or third-degree heart block without a permanent pacemaker in place
   g. Uncontrolled hypertension as indicated by a minimum of 2 consecutive blood pressure measurements showing systolic blood pressure >170 mmHg and diastolic blood pressure >105 mmHg at screening
3. Prior malignancy within the past 3 years, except for curatively treated basal or squamous cell skin cancer, superficial bladder cancer, or carcinoma in situ of the cervix or breast
4. History of severe bleeding disorder such as hemophilia A, hemophilia B, von Willebrand disease, or history of spontaneous bleeding requiring blood transfusion or other medical intervention
5. History of stroke or intracranial hemorrhage within 180 days before first dose of study drug
6. Severe or debilitating pulmonary disease
7. Unable to swallow capsules or disease significantly affecting gastrointestinal function such as malabsorption syndrome, resection of the stomach or small bowel, bariatric surgery procedures, symptomatic inflammatory bowel disease, or partial or complete bowel obstruction
8. Active fungal, bacterial, and/or viral infection requiring systemic therapy
9. Known central nervous system involvement by leukemia or lymphoma
10. Underlying medical conditions that, in the investigator's opinion, will render the administration of study drug hazardous or obscure the interpretation of toxicity or AEs
11. Known infection with HIV or serologic status reflecting active viral hepatitis B or C infection as follows:
    a. Presence of hepatitis B surface antibody (HBsAb) or hepatitis B core antibody (HBcAb). Patients with presence of HBcAb, but absence of HBsAg, were eligible if hepatitis B virus (HBV) DNA was undetectable (<20 IU), and if they were willing to undergo monthly monitoring for HBV reactivation
    b. Presence of hepatitis C virus (HCV) antibody. Patients with presence of HCV antibody were eligible if HCV RNA was undetectable
12. Moderate or severe hepatic impairment, ie, Child-Pugh class B or C
13. Major surgery within 4 weeks of the first dose of study drug
14. Prior treatment with a BTK inhibitor
15. Last dose of prior therapy for CLL/SLL ≤14 days before randomization, with the following additional exclusion requirements:
    a. Treatment with monoclonal antibody-based therapy within 28 days of first dose of study drug
    b. Treatment with chimeric antigen receptor T-cell therapy within 180 days of first dose of study drug
    c. Treatment with Chinese herbal medicine with anticancer intent within 28 days of first dose of study drug
    d. Chemotherapy or radiation treatment within 21 days of first dose of study drug or hematopoietic stem cell transplantation within 90 days of first dose of study drug
16. Prior steroid use
    For prior corticosteroid use of 10 mg/day or less, regardless of reason or duration of treatment, must stop steroid no later than day prior to first dose.
    For prior corticosteroid use of 10 mg/day or more, regardless of reason or duration of treatment, must stop steroid 4 weeks prior to date of randomization.
17. Toxicity from prior anticancer therapy that has not recovered to ≤Grade 1 (except for alopecia, ANC, and platelet count; for ANC and platelet count, see inclusion criterion 8)
18. Pregnant or lactating women
19. Vaccination with a live vaccine within 35 days prior to the first dose of study drug
20. Ongoing alcohol or drug addiction
21. Hypersensitivity to zanubrutinib, ibrutinib, or any of the other ingredients in either drug
22. Patient requires treatment with warfarin or other vitamin K antagonists
23. Requires ongoing treatment with a strong CYP3A inhibitor or inducer
24. Concurrent participation in another therapeutic clinical trial.

3.3 Pharmacokinetics

Blood was collected to characterize the PK of zanubrutinib.

Sparse PK samples was collected from all patients assigned to Arm A (zanubrutinib) only at the timepoints. The time of study drug administration and actual PK collection time on Cycle 1 Day 1 must be recorded on the eCRF. The actual time each sample was collected was captured to the nearest minute in the eCRF and recorded in the database.

Blood samples (2 mL) for PK analysis was collected into EDTA collection tubes. Details concerning handling of the PK plasma samples, including labeling and shipping instructions, was provided in the laboratory manual for this study.

Samples was shipped to the designated bioanalytical lab for quantification of plasma zanubrutinib concentrations using a validated method.

3.4 Safety Assessments 3.4.1 Cardiac Function

An assessment of left ventricular ejection fraction was performed and documented at Screening and as medically indicated. Note: An echocardiogram, multigated acquisition, and gated heart pool scan were all acceptable.

3.4.2 Physical Examination and Vital Signs

Physical examination, vital signs (sitting blood pressure, heart rate, and body temperature), weight, and review for arrhythmia signs/symptoms (e.g., shortness of breath, dizziness, or fainting) was performed at each study visit during study treatment and at the Safety Follow-up Visit. Height (cm) was determined at Screening only.

A complete physical examination includes an assessment of systems per standard of care at the study site and as clinically indicated by symptoms.

3.4.3 Electrocardiogram

A 12-lead ECG was performed locally in triplicate at screening for all subjects. Subjects should be in the semi-recumbent or supine position.

3.4.4 Concomitant Medications Review

Record any new medications, changes in ongoing medications or procedures, and medications discontinued within 35 days before Cycle 1 Day 1, and on study thereafter.

3.4.5 Adverse Events Review

Record AEs that occurred during Screening on the medical history case report form and in the patient's source document.

Collect non-serious AE information from the time of first dose of study drug through Safety Follow-up. Information on all SAEs (regardless of relatedness) was collected from the time of signing of informed consent through screen failure or Safety Follow-up.

All treatment-related AEs and SAEs was followed until resolution or stabilization. In addition, arrhythmia signs/symptoms was reviewed at every cycle. This will involve the investigators asking subjects for signs and symptoms of ventricular dysfunction (e.g., shortness of breath, dizziness, or fainting) as part of the routine AE monitoring for each cycle.

3.5 Efficacy Assessments

Response was assessed by independent central review and categorized per the "modified" IWCLL criteria with modification for treatment-related lymphocytosis for patients with CLL, and per the Lugano Classification for NHL for patients with SLL using CT-based response criteria. PD assessed by CT for SLL must be confirmed by repeat imaging no sooner than 4 weeks from the first imaging that shows possible progression to rule out pseudo-progression. Patients may continue study treatment while they wait for the confirmatory imaging. Investigators will also assess response locally. The primary endpoint was ORR based on independent central review. In the event of a treatment delay, disease assessments were to continue per the Schedule of Assessments.

3.5.1 Disease-Related Constitutional Symptoms

Disease-related constitutional symptoms based on "modified" IWCLL criteria (unexplained fever of ≥38° C.; unexplained, recurrent drenching night sweats; or unexplained loss of >10% body weight within the previous 6 months) was.

3.5.2 Examination of Liver, Spleen, and Lymph Nodes

Record presence or absence of hepatomegaly, splenomegaly, and/or lymphadenopathy as specified per the Schedule of Assessments. PD assessed by physical examination must be confirmed by a CT scan.

3.5.3 Computed Tomography

All patients must have baseline (within 35 days of randomization) CT scan with intravenous and oral contrast of neck, chest, abdomen, and pelvis and any other disease sites.

A MRI may be used in place of CT only for patients who cannot undergo CT due to contrast allergy. In Germany, an MIII may be used in place of CT in all patients. All efforts was made to ensure that the imaging equipment, contrast agent, and person (investigator or radiologist) performing the evaluation were kept constant throughout a patient's course on study.

CT with contrast of neck, chest, abdomen, and pelvis was performed as specified per the Schedule of Assessments.

All CT scans, and MRIs obtained during the study, was collected and reviewed by a central imaging vendor identified for this trial. De-identified copies of all scans and radiology reports (including those from Screening) must be provided to the sponsor or designee (e.g., central imaging vendor).

3.5.4 Bone Marrow Examination

Bone marrow biopsy was required during the Screening period. Thereafter, bone marrow examination was required for patients with baseline marrow involvement who meet clinical and laboratory criteria for CR or CRi, and need bone marrow examination to confirm CR or CRi (MRD assessment may also be performed on the bone marrow or blood at this time). Patients who were otherwise complete responders, but show bone marrow involvement, should recheck bone marrow as clinically indicated, but at a minimum at least once per year until CR or CRi was confirmed. Patients should also undergo bone marrow biopsy in the setting of progression of cytopenias unrelated to autoimmune cytopenias or study treatment in order to confirm PD. All the bone marrow samples was collected and reviewed by a pathologist from the central pathology laboratory.

4 Statistical Methods and Sample Size Determination

All statistical analyses was performed by the sponsor or designee after the study was completed and the database was locked and released. Data was listed and summarized according to sponsor-agreed reporting standards.

Details of the statistical analyses was included in a separate Statistical Analysis Plan.

4.1 Study Endpoints
4.1.1 Primary Endpoint

The primary endpoint was ORR (PR or higher, defined as CR/CRi+PR+nodular PR) determined by independent central review using the "modified" 2008 IWCLL guidelines with modification for treatment-related lymphocytosis for patients with CLL and per Lugano Classification for non-Hodgkin lymphoma (NHL) for patients with SLL.

4.1.2 Secondary Endpoints

Key Secondary Endpoint:
PFS, defined as the time from randomization to the date of first documentation of disease progression or death, whichever occurs first, determined by independent central review Other Secondary Endpoints:
PFS determined by investigator assessment
Duration of response, defined as the time from the date that response criteria were first met to the date that disease progression was objectively documented or death, whichever occurs first, determined by independent central review
Duration of response by investigator assessment
Time to treatment failure, defined as time from randomization to discontinuation of study drug due to any reason
Rate of PR-L or higher, defined as the proportion of patients who achieve a CR/CRi+PR+nodular PR+PR-L determined by independent central review
Overall survival, defined as the time from randomization to the date of death due to any cause
PROs measured by the EQ-5D-5L and EORTC QLQ-C30 questionnaires
Safety parameters, including AEs, SAES, clinical laboratory tests, physical exams, and vital signs

4.1.3 Exploratory Endpoints

Correlation between clinical outcomes (e.g., ORR, PFS, DOR, OS, rate of PR or higher) and the prognostic and predictive biomarkers
PK parameters

4.2 Statistical Analysis
4.2.1 Randomization Methods

Patients was randomized using the Interactive Response Technology system for this study by permuted block stratified randomization.

The stratified randomization using age (<65 years versus ≥65 years), geographic region (China versus non-China), refractory status (yes or no), and del[17p]/TP53 mutation status (present versus absent) as stratification factors was produced, reviewed, and approved by an independent statistician.

4.2.2 Analysis Sets

The Intent-to-Treat Analysis Set includes all randomized patients. The Intent-to-Treat Analysis Set was the primary analysis set for efficacy analyses.

The Safety Analysis Set includes all patients who received any dose of study drug. Patients was included in the treatment group corresponding to the actual treatment received. The Safety Analysis Set was used for all safety analyses.

The Per-protocol Analysis Set includes patients who received any dose of study drug and had no major protocol deviations. Criteria for exclusion from the Per-protocol Analysis Set was determined and documented before the database lock for the primary analysis. For the primary analysis of non-inferiority testing in ORR by independent central review, the Per-protocol Analysis Set was used as the secondary population.

The PK Analysis Set includes all zanubrutinib-treated patients who have at least 1 post-dose drug concentration.

4.2.3 Subject Disposition

The number of patients screened, randomized, treated, and discontinued from study drug (defined as those who discontinued study drug due to any reason except for PD) was counted. The primary reason for study drug discontinuation was summarized according to the categories recorded in the eCRF. The end-of-study status (alive, death, withdrew consent, or lost to follow-up) at the data cutoff date was summarized as recorded in the eCRF.

4.2.4 Demographics and Other Baseline Characteristics

Demographics and other baseline characteristics was summarized in the Intent-to-Treat Analysis Set using descriptive statistics. Continuous variables include age, weight, vital signs, and time since initial CLL/SLL diagnosis; categorical variables include sex, age group, race, disease stage, ECOG-PS, geographic region, and genetic status including del[17p], del[11q], 12q+, and IGHV mutation analysis.

4.2.5 Prior and Concomitant Therapy

Concomitant medications was assigned an 11-digit code using the World Health Organization Drug Dictionary drug codes. Concomitant medications was further coded to the appropriate Anatomical Therapeutic Chemical code indicating therapeutic classification. Prior and concomitant medications was summarized and listed by drug and drug class in the Clinical Study Report for this protocol. Prior medications was defined as medications that started before the first dose of study drug, whether continuing at or stopped at the first dose of study drug. Concomitant medications was defined as medications that (1) started before the first dose of study drug and were continuing at the time of the first dose of study drug, or (2) started on or after the date of the first dose of study drug up to 30 days after the patient's last dose.

4.2.6 Efficacy Analysis 4.2.6.1 Primary Efficacy Endpoint Analyses

The primary hypothesis testing for the primary endpoint of ORR by independent central review was to demonstrate the non-inferiority of zanubrutinib to ibrutinib. The null and alternative hypotheses for the non-inferiority test were as follows:

H0NI: Response Ratio (zanubrutinib/ibrutinib)≤0.8558
HaNI: Response Ratio (zanubrutinib/ibrutinib)>0.8558

One interim analysis will occur approximately 12 months after 268 patients (67% information fraction) have been randomized. The final analysis will occur approximately 12 months after 400 patients have been randomized.

A Cochran-Mantel-Haenszel test for response ratio adjusting for the 4 randomization stratification factors (age [<65 years versus ≥65 years], geographic region (China versus non-China), refractory status [yes or no], and del [17p]/TP53 status [present versus absent]) was performed for the hypothesis testing. The p-value from the test was compared against the monitoring boundaries for the non-inferiority testing (Table 11) and used for the primary inference. The treatment effect in ORR and its 95% Wald confidence interval (CI) was estimated, and the Clopper-Pearson 95% CIs was calculated for ORR for each treatment group.

If the non-inferiority was demonstrated either at the interim or the final analysis, further testing for the superiority of zanubrutinib to ibrutinib was performed. The null and alternative hypotheses for the superiority test were as follows:

H0 SUP: Response Ratio (zanubrutinib/ibrutinib)≤1
Ha SUP: Response Ratio (zanubrutinib/ibrutinib)>1

The monitoring boundaries for the non-inferiority and superiority tests were based on the O'Brien-Fleming boundary approximated by the Lan-DeMets spending function and were listed in Table 11 and Table 12. The monitoring boundaries was adjusted based on the actual information fraction (number of subjects for ORR) observed up to the data cutoff. Deviation from the scheduled interim analysis will not affect the overall type I error.

TABLE 11

Monitoring Boundaries for the ORR Non-inferiority Testing

| | Number of patients evaluable | Information fraction | Nominal p-value boundary (primary inference) | Response ratio boundary |
|---|---|---|---|---|
| Interim | 268 | 67% | 0.006 | 1.062 |
| Final | 400 | 100% | 0.023 | 0.985 |

Abbreviation: ORR, overall response rate.

TABLE 12

Monitoring Boundaries for the ORR Superiority Testing

| | Number of patients evaluable | Information fraction | Nominal p-value boundary (primary inference) | Response ratio boundary |
|---|---|---|---|---|
| Interim | 268 | 67% | 0.006 | 1.241 |
| Final | 400 | 100% | 0.023 | 1.151 |

Abbreviation: ORR, overall response rate.

Justification of the Non-Inferiority Margin

A non-inferiority margin of 0.8558 in response ratio was derived using the 95% to 95% fixed margin approach (FDA Guidance for Industry Non-Inferiority 2016). In the RESONATE trial, the ibrutinib effect over ofatumumab represented by the ratio of response rate (PR or higher) was 10.43 with a 95% CI of (5.2, 21.0) based on the independent review committee assessment. In the RESONATE2 trial, the ibrutinib effect over chlorambucil represented by the ratio of response rate (PR or higher) was 2.33 with a 95% CI of (1.83, 2.97) based on the independent review committee assessment. In a fixed-effect meta-analysis of the 2 studies using inverse variance weighting, the ibrutinib effect in response rate ratio was estimated as 2.7392 with a 95% CI of (2.1781, 3.4450). Thus, M1 was 2.1781, the lower bound of the 95% CI. Since the effect sizes of ibrutinib were over active controls in both studies (ofatumumab and chlorambucil, respectively), rather than placebos, the choice of M1 was very conservative and results in a narrow margin. Requiring 80% of M1 to be retained (on the log scale) in zanubrutinib to demonstrate non-inferiority generates a non-inferiority margin of 0.8558 (for the response ratio), which was within the clinically acceptable limit.

4.2.6.2 Secondary Efficacy Endpoint Analyses

If the primary objective of demonstrating the non-inferiority of zanubrutinib to ibrutinib in ORR by independent central review was met, the treatment effect of the key secondary efficacy endpoint of PFS by independent central review was tested for non-inferiority under hierarchical testing to control the study-wise type I error.

If non-inferiority was demonstrated for the key secondary efficacy endpoint of PFS by independent central review, further testing of superiority was performed for the endpoint.

Treatment arm comparison for the other secondary efficacy endpoints was descriptive, and no hypothesis testing was performed.

Key Secondary Efficacy Endpoints

Progression-free Survival by Independent Central Review

The non-inferiority of zanubrutinib to ibrutinib for PFS determined by independent central review was tested under the non-inferiority margin of 1.3319 (for the hazard ration [HR] of zanubrutinib/ibrutinib) using a stratified log-rank test based on the 4 randomization stratification factors: age (<65 years versus ≥65 years), geographic region (China versus non-China), refractory status (yes or no), and del [17p]/TP53 mutation status (present versus absent). The null and alternative hypotheses to test the non-inferiority were as below:

H0NI: HR (zanubrutinib/ibrutinib)≥1.3319
HaNI: HR (zanubrutinib/ibrutinib)<1.3319

There were 2 analyses to test the non-inferiority of PFS by independent central review: an interim analysis at the time of the ORR final analysis and a final analysis when 205 events have occurred. Ninety-three (93) PFS events were expected to accrue at the time of the ORR final analysis. Two hundred five (205) PFS events were expected to accrue 65 months after study start. If the p-value from the stratified log-rank test meets the non-inferiority monitoring boundary at either the interim or the final analysis, the non-inferiority of zanubrutinib to ibrutinib in terms of PFS by independent central review was demonstrated. Further testing of superiority in terms of PFS by independent central review was performed in this case. Table 13 and Table 14 include the monitoring boundaries of the PFS non-inferiority and superiority tests at the interim (assuming 93 PFS events) and the final analysis. The monitoring boundaries were based on O'Brien-Fleming boundary approximated by the Lan-DeMets spending function. The monitoring boundaries was adjusted based on the actual information fraction (number of events for PFS) observed up to the data cutoff. Deviation from the scheduled interim analysis did not affect the overall type I error.

TABLE 13

Monitoring Boundaries for the PFS Non-Inferiority Testing

|  | Time (months) | # PFS events | Nominal p-value boundary (primary) | HR boundary |
| --- | --- | --- | --- | --- |
| Interim analysis | 29 | 93 | 0.0009 | 0.6960 |
| Final analysis | 65 | 205 | 0.0247 | 1.0122 |

Abbreviations: HR, hazard ratio; PFS, progression-free survival.

TABLE 14

Monitoring Boundaries for the PFS Superiority Testing

|  | Time (months) | # PFS events | Nominal p-value boundary (primary) | HR boundary |
| --- | --- | --- | --- | --- |
| Interim analysis | 29 | 93 | 0.0009 | 0.5235 |
| Final analysis | 65 | 205 | 0.0247 | 0.7594 |

Abbreviations: HR, hazard ratio; PFS, progression-free survival.

The non-inferiority margin of 1.3319 was derived using the 95%-95% fixed margin method based on a meta-analysis of the RESONATE and RESONATE 2 studies. In the RESONATE2 study, the estimated PFS HR for ibrutinib versus chlorambucil was 0.16 with a 95% CI of (0.09, 0.28). In the updated RESONATE results, the estimated PFS HR for ibrutinib versus ofatumumab was 0.106 with a 95% CI of (0.073, 0.153). In a fixed-effect meta-analysis, the pooled HR was estimated as 0.120 with a 95% CI of (0.088, 0.163). Therefore, the control arm effect (M1) was −0.163 in HR and 1.814 in log HR. Requiring 84.2% of M1 to be retained in zanubritinib, a non-inferiority margin of 1.3319 for the HR (zanubrutinib/ibrutinib) was generated.

The HR for PFS by independent central review and its 95% CI was estimated from a stratified Cox regression model.

The distribution of PFS including median and other quartiles, and PFS rate at selected timepoints, was estimated using the Kaplan-Meier method for each arm.

PFS was calculated as the time from the date of the randomization to the date of the first documentation of disease progression or death due to any cause, regardless of the use of subsequent anticancer therapy prior to the documented PD or death. PFS for the patients without a documented PD or death was censored at the last disease assessment.

Other Secondary Efficacy Endpoints

PFS Determined by Investigator Assessment

The HR for PFS by investigator assessment and its 95% CI was estimated from a stratified Cox regression using the four randomization stratification factors (age [<65 years versus ≥65 years], geographic region (China vs non-China), refractory status [yes or no], and del[17p]/TP53 status [present versus absent]). Kaplan-Meier method was used to estimate the distribution of PFS for each treatment group.

PFS was calculated as the time from the date of randomization to the date of first documentation of disease progression (as assessed by investigator assessment) or death due to any cause, regardless of the use of subsequent anti-cancer therapy prior to documented PD or death. PFS for the patients without a documented PD or death was censored at the last disease assessment.

Duration of Response

The distribution of DOR by independent central review including median and other quartiles, was estimated using the Kaplan-Meier method for each treatment group. There was no treatment arm comparison for DOR. The same analysis was performed for DOR by investigator assessment. The same censoring rule used in the PFS analysis was used for the analysis of DOR.

Time to Treatment Failure

The HR for time to treatment failure and its 95% CI was estimated from a stratified Cox regression using the 4 randomization stratification factors (age [<65 years versus ≥65 years], geographic region (China versus non-China), refractory status [yes or no], and del[17p]/TP53 status [present versus absent]). The Kaplan-Meier method was used to estimate the distribution of time to treatment failure for each treatment group.

Time to treatment failure was calculated as the time from the date of randomization to the date of discontinuation of study treatment due to any cause. Time to treatment failure was censored at the data cutoff for the patients who did not discontinue study treatment.

Rate of PR-L or Higher by Independent Central Review

Rate of response ratio for PR-L or higher by independent central review and its 95% Wald CI was estimated using the Cochran-Mantel-Haenszel method. Clopper-Pearson 95% CI for the rate of response was calculated for each treatment group.

Overall Survival

OS was analyzed using the same methods employed for PFS by investigator assessment.

Patient-Reported Outcomes

The EORTC QLQ-C30 questionnaire was summarized for each assessment timepoint for each treatment group. The percentage of patients with a clinically meaningful change from baseline in "global health status/QOL" and functional domains was summarized as "improved," "stable," or "worsened" and compared between 2 treatment groups. The data may also be analyzed using repeated measure mixed model to account for missing data under the Missing at Random assumption.

Changes in the EQ-5D-5L was summarized for each treatment group.

4.2.6.3 Exploratory Efficacy Analyses

Cox and/or logistic regression models, as well as descriptive comparisons, may be used to explore the association between the prognostic and predictive biomarkers and the clinical outcomes.

4.2.6.4 Sensitivity Analyses

Overall response rate by investigator assessment was analyzed as a sensitivity analysis. The analysis methods in the primary endpoint analysis was repeated in this analysis.

A multiple logistic regression analysis for ORR by independent central review was performed to explore the relationship between the baseline prognostic factors and ORR by independent central review and to estimate the treatment effect adjusted for the imbalances in these factors.

For PFS, alternative censoring rules such as censoring for new anticancer therapy was used as sensitivity analyses. A multiple Cox regression analysis was performed to explore the relationship between the baseline prognostic factors and PFS by independent central review, and to estimate the treatment effect adjusted for the imbalances in these factors.

Subgroup analyses for ORR by independent central review and selected secondary endpoints was performed.

4.2.7 Pharmacokinetics Analyses

A population PK analysis may be performed to include plasma concentrations of zanubrutinib from this trial in an existing model. PK parameters such as apparent systemic clearance and AUC may be derived from the population PK analysis if supported by data.

An exposure-response (efficacy or safety endpoints) analysis may be performed if supported by data. The results from the population PK and exposure-response analyses may be reported separately from the Clinical Study Report.

4.3 Safety Analyses

Safety was assessed by monitoring and recording all AEs graded by NCI-CTCAE v4.03. Laboratory values (CBC, serum chemistry, and coagulation), vital signs, physical exams, and ECG findings will also be used in the safety assessment. Descriptive statistics was used to analyze all safety data by the actual treatment group.

4.3.1 Extent of Exposure

The extent of exposure to the study drug was summarized descriptively as the number of cycles received (number and percentage of patients), duration of exposure (days), cumulative total dose received per patient (mg), dose intensity (mg/day), and relative dose intensity (%).

The number (and percentage) of patients with dose reductions, dose interruption, dose delay, and drug discontinuation was summarized with the respective reasons. The cycles in which dose reduction/interruption occurred was summarized using descriptive statistics. Frequency of dose modifications was summarized by category.

Patient data listings was provided for all dosing records.

4.3.2 Adverse Events

The AE verbatim descriptions (as recorded by the investigator on the eCRF) was classified into standardized medical terminology using Medical Dictionary for Regulatory Activities (MedDRA). AEs was coded to MedDRA (Version 20.0 or higher) lower level term closest to the verbatim term. The linked MedDRA preferred term and primary system organ class will also be captured in the database.

A treatment-emergent AE was defined as an AE that has an onset date on or after the first dose of study drug up to 30 days following the study drug discontinuation or the start of a new anticancer therapy, whichever comes first. After this period, only treatment-related SAEs were to be reported. Only the AEs that were treatment emergent was included in the summary tables. All AEs, treatment emergent or otherwise, was presented in patient data listings.

The incidence of treatment-emergent AEs was reported as the number (and percentage) of patients with treatment-emergent AEs by system organ class and preferred term. A patient was counted only once by the highest severity grade according to CTCAE v4.03 within a system organ class and preferred term, even if the patient experienced more than 1 treatment-emergent AEs within a specific system organ class and preferred term. The number (percentage) of patients with treatment-emergent AEs will also be summarized by the relationship to the study drug.

Treatment-related AEs include those events considered by the investigator to be related to the study drug or with a missing assessment of the causal relationship. SAEs, deaths, treatment-emergent AEs ≥Grade 3, study drug-related treatment-emergent AEs, and treatment-emergent AEs that led to treatment discontinuation, dose reduction, or dose interruption was summarized.

Incidence and time to diarrhea (≥Grade 3), severe bleeding (defined as ≥Grade 3 bleeding of any site or central nervous system bleeding of any grade), and atrial fibrillation (both new onset and exacerbation of existing atrial fibrillation) will also be summarized.

4.3.3 Laboratory Analyses

Selected CBC components and serum chemistry values was evaluated for each laboratory parameter by treatment group. Abnormal laboratory values was flagged and identified as those outside of (above or below) the normal range.

Reference (normal) ranges for laboratory parameters was included in the Clinical Study Report. Descriptive summary statistics (e.g., n, mean, standard deviation, median, minimum, maximum for continuous variables; n [%] for categorical variables) for the laboratory parameters and their changes from baseline was calculated. Laboratory values was summarized by visit and by the worst post-baseline visit.

Laboratory parameters that were graded in NCI-CTCAE (v4.03) was summarized by CTCAE grade. In the summary of laboratory parameters by CTCAE grade, parameters with CTCAE grading in both high and low directions (e.g., calcium, glucose, magnesium, phosphorus, potassium, sodium) was summarized separately.

4.3.4 Vital Signs

Descriptive statistics for the vital sign parameters (systolic and diastolic blood pressure, heart rate, temperature, and weight) and the changes from baseline was presented by visit and treatment group for all visits. Vital signs was listed by patient and visit.

4.3.5 Electrocardiogram

ECG assessments was performed as described. Descriptive statistics for absolute and change from baseline ECG parameters was presented.

4.4 Sample Size Consideration

The sample size calculation was based on the primary efficacy analysis for the primary endpoint of ORR by independent central review. Assuming a response ratio (zanubrutinib arm/ibrutinib arm) of 1.25 (75%/60%), 400 patients will provide more than 99% power to demonstrate the non-inferiority of zanubrutinib to ibrutinib at the non-inferiority margin of 0.8558 (response ratio) and 1-sided alpha level of 0.025 when there was 1 interim analysis at 67% information fraction. Four hundred (400) patients will provide 88% power to demonstrate superiority at the 1-sided alpha level of 0.025 under the alternative hypothesis (response ratio=1.25, 75% versus 60%) with 1 interim analysis. The power for superiority was 70.3% under the alternative hypothesis of a response ratio of 1.2 (72% versus 60%).

Assuming an HR (zanubrutinib arm/ibrutinib arm) of 0.9, 205 events were required to achieve 80% power at a 1-sided alpha of 0.025 to demonstrate the non-inferiority of zanubrutinib to ibrutinib at the non-inferiority margin of 1.3319 (HR) in PFS by independent central review, when 1 interim analysis was expected at 45% (expected number of events at the final ORR analysis) of the target number of events.

If the 400 patients were randomized in a 1:1 ratio to the 2 arms over a 17-month period including a 9-month ramp-up period before reaching the peak enrollment of 33 patients/month with a 0.0017/month hazard rate for drop-out, 205 events were expected to be accumulated in 65 months from study start. A median PFS of 47 months for ibrutinib and an exponential distribution for PFS were also assumed. 4.5 Interim Analysis There was 1 interim analysis for the non-inferiority (and the superiority if the non-inferiority was met) testing of ORR by independent central review. The interim analysis was performed approximately 12 months after the randomization of 268 patients. The monitoring boundaries for the interim and the final analyses for the non-inferiority and superiority tests were based on the O'Brien-Fleming boundary approximated by the Lan-DeMets spending function and were depicted in Table 11 and Table 12.

If the boundary was met for the interim non-inferiority analysis and the DMC recommends stopping the study, the sponsor may stop the study and file the results to the regulatory agencies for approval.

There was 1 interim analysis for the non-inferiority testing of the key secondary efficacy endpoint of PFS by independent central review. The interim analysis for PFS will occur at the time of the ORR final analysis, which was expected to occur at 29 months after study start. Ninety-three (93) PFS events were expected to occur by the interim analysis. The O'Brien-Fleming boundary approximated by the Lan-DeMets spending function was implemented and the nominal p-value boundaries was used for the primary inference in the interim and the final analyses (presented in Table 13 and Table 14).

4.6 Final Analysis

If the primary objective of the ORR non-inferiority was met, the study will continue to follow up for PFS until 205 events were observed, which was estimated to be approximately 65 months from study start. The stopping boundaries for the PFS final analyses were shown in Table 13 and Table 14.

In a randomized, global, phase 3 study, zanubrutinib was compared head-to-head with ibrutinib as treatment for relapsed/refractory chronic lymphocytic leukemia/small lymphocytic lymphoma (CLL/SLL). In predefined interim analyses, zanubrutinib demonstrated superiority over ibrutinib in the primary endpoint, overall response rate. Data from final progression-free survival (PFS) analysis were provided herein.

Methods

Patients (N=652) with relapsed/refractory CLL/SLL who had received ≥1 prior therapy and had measurable disease were randomized 1:1 to receive zanubrutinib or ibrutinib until disease progression or unacceptable toxicity. In this final analysis, the key secondary endpoint, PFS, was tested for noninferiority under hierarchical testing. When PFS noninferiority was demonstrated, superiority of zanubrutinib was assessed and claimed if the 2-sided P-value was <0.04996.

Trial Design

This study was designed to directly compare the efficacy and safety/tolerability of zanubrutinib with ibrutinib in patients with relapsed/refractory CLL; the overall study design is shown in FIG. 5.

Participants

Adults (≥18 years) with a confirmed diagnosis of CLL or SLL that met International Workshop on CLL (iwCLL) criteria and required treatment, who were relapsed after or refractory to at least one prior line of therapy and had measurable disease by imaging, were eligible. Patients who had received prior treatment with a BTK inhibitor or had a history of bleeding disorders, active infections, stroke/intracranial hemorrhage, recent prior malignancies, or major surgery were ineligible.

Randomization, Interventions, and Masking

Enrolled patients were randomized (1:1) to receive zanubrutinib 160 mg twice daily or ibrutinib 420 mg once daily until disease progression or unacceptable toxicity. Study drugs were administered in an open-label fashion due to variations in dosing schedules and suggested dose modifications. Using an interactive web response system, patients were randomized to treatment based on a computer-generated randomization schedule. Randomization was stratified by age, geographic region, refractory status, and del(17p)/TP53' status. Cross-over was not allowed.

Study Outcomes

Investigator-assessed overall response rate, predefined as the proportion of patients achieving complete response or complete response with incomplete bone marrow recovery (CR/CRi), nodular partial response, or partial response (PR), was the primary endpoint. Disease response was assessed per iwCLL 2008 criteria every 3 months for 2 years then every 6 months thereafter, with modification for treatment-related lymphocytosis for patients with CLL and per Lugano Classification for patients with SLL. Key secondary endpoints were PFS assessed by investigator and by a blinded independent review committee and the rate of atrial fibrillation or flutter; overall response rate by independent review committee, overall survival, rate of PR with lymphocytosis (PR-L) or better, and safety parameters were other secondary endpoints. Adverse events of special interest were pre-defined pooled categories of adverse events as defined in the supplement.

Statistical Analysis

In order to provide >90% power to demonstrate noninferiority of zanubrutinib to ibrutinib in overall response rate, a sample size of 600 participants was estimated. Noninferiority of overall response rate between zanubrutinib and ibrutinib was tested at a prespecified overall response rate interim analysis in the first 415 randomized patients as well as at overall response rate final analysis for all randomized patients, approximately 12 months after 600 patients had been randomized. As overall response rate noninferiority and superiority were demonstrated (Table 15), PFS was tested for noninferiority under hierarchical testing when 205 PFS events had occurred. The noninferiority of zanubrutinib to ibrutinib for PFS was tested under the noninferiority margin (hazard ratio) of 1.3319 using a stratified Wald test based on the four randomization stratification factors followed by superiority testing using a stratified log-rank test. Hypothesis testing of PFS was at a 2-sided significance level of 0.04996 after minimal alpha was allocated to PFS at the overall response rate interim analysis and overall response rate final analysis. The statistical analysis plan was developed prior to the predefined first analysis, the overall response rate interim analysis; this predefined plan has not been amended.

TABLE 15

Investigator- and Independent Review Committee-Assessed Best Response Rate in All Patients; Data Cut-Off (ITT Population, N = 652)

| Best Response, n (%) | ITT Population | |
| --- | --- | --- |
| | Zanubrutinib (n = 327) | Ibrutinib (n = 325) |
| Investigator Assessed | | |
| ORR, % (95% CI) | 79.5* (74.7, 83.8) | 71.1 (65.8, 75.9) |
| CR or CRi | 16 (4.9) | 9 (2.8) |
| PR or nPR | 244 (74.6) | 222 (68.3) |
| PR-L | 32 (9.8) | 35 (10.8) |
| SD | 25 (7.6) | 39 (12.0) |
| PD | 1 (0.3) | 6 (1.8) |
| Discontinue prior to first assessment, NA or NE | 9 (2.8) | 14 (4.3) |
| IRC Assessed | | |
| ORR, % (95% CI) | 80.4† (75.7, 84.6) | 72.9 (67.7, 77.7) |
| CR or CRi | 13 (4.0) | 8 (2.5) |
| PR or nPR | 250 (76.5) | 229 (70.5) |
| PR-L | 33 (10.1) | 32 (9.8) |
| SD‡ | 20 (6.1) | 35 (10.8) |
| PD | 3 (0.9) | 7 (2.2) |
| Discontinue prior to first assessment, NA or NE | 8 (2.4) | 14 (4.3) |

*Noninferiority 1-sided P <0.0001, superiority 2-sidedP = 0.0133 (superiority met at ORR IA with data cut-off). Both P-values are descriptive.
†Noninferiority 1-sided P <0.0001, superiority 2-sided P = 0.0264.
‡Includes 2 patients in zanubrutinib arm with response of non-progressive disease.
P-value was calculated for noninferiority via stratified test statistic against a null response ratio of 0.8558 and for superiority via stratified Cochran-Mantel-Haenszel test statistic.
CI denotes confidence interval; CR, complete response; CRi, CR with incomplete bone marrow recovery; IA, interim analysis; IRC, independent review committee; ITT, intent-to-treat; NA, not assessed; NE, not evaluable; nPR, nodular partial response; ORR, overall response rate; PD, progressive disease; PR, partial response; PR-L, partial response with lymphocytosis; SD stable disease.

Efficacy analyses were based on the intent-to-treat (ITT) population, defined as all patients randomized to treatment; safety profile was assessed in the safety population, defined as all patients who received any dose of the study drug. Categorical variables were summarized by the number (percentage) of participants; continuous variables were reported using descriptive statistics. Statistical analyses were performed using SAS version 9.4 (SAS Institute Inc).

Results

With a median follow-up of 29.6 months, zanubrutinib demonstrated superior PFS compared with ibrutinib (HR: 0.65 [95% CI, 0.49-0.86]; P=0.0024) as assessed by investigators; statistical results were identical from independent-review committee assessment. In patients with del(17p)/TP53 mutation, zanubrutinib demonstrated longer PFS than ibrutinib (HR:0.52 [95% CI, 0.30-0.88]); PFS across other major subgroups consistently favored zanubrutinib. Zanubrutinib also demonstrated a higher overall response rate than ibrutinib. Zanubrutinib safety profile was improved over ibrutinib with fewer adverse events leading to treatment discontinuation and fewer cardiac events, including lower rate of cardiac events leading to discontinuation or death.

Patient Disposition and Demographics

Figure 6:
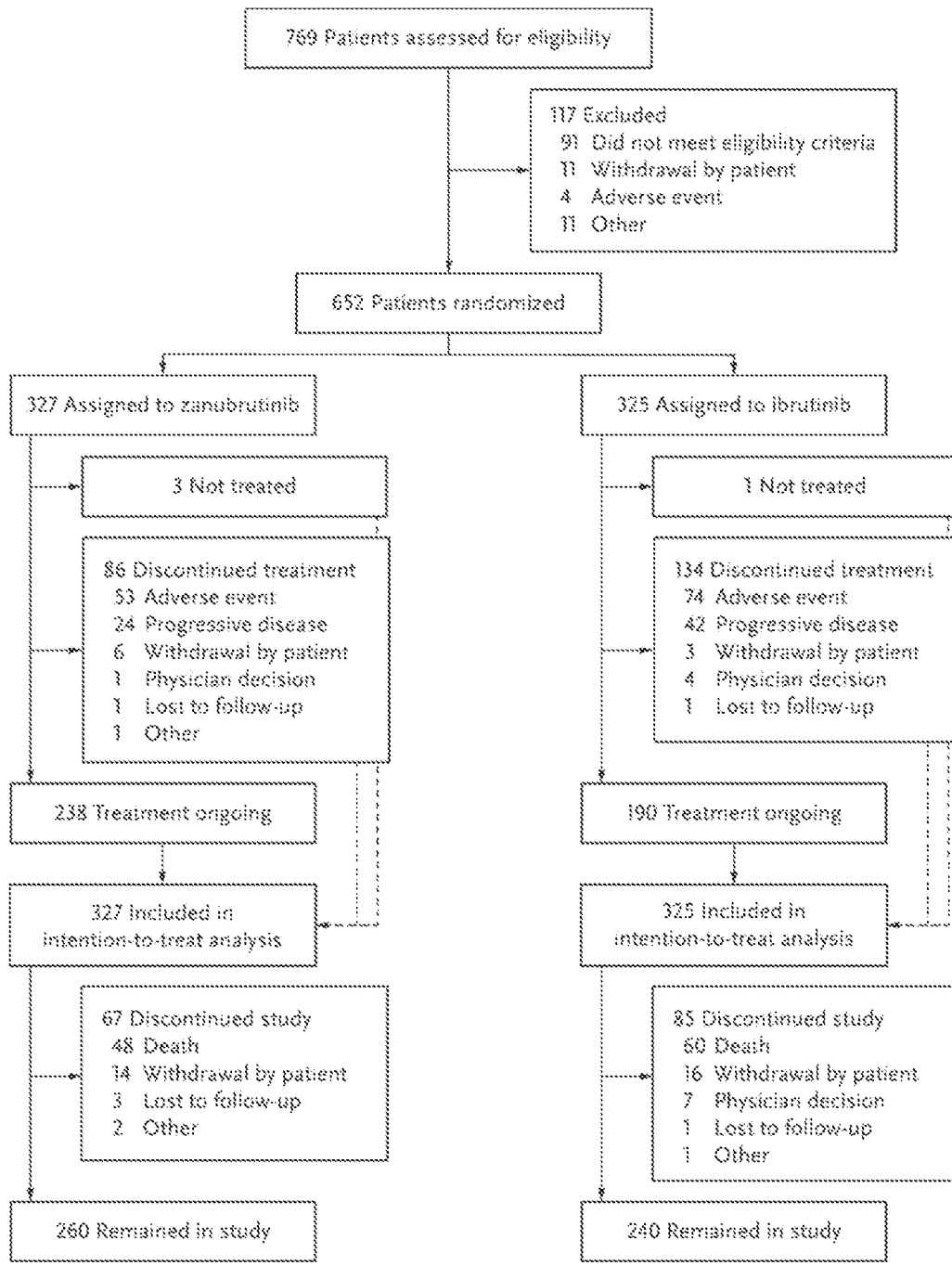
FIG. 6 depicts the Participant Disposition and Study Flow.

Across 15 countries in North America, Europe, and Asia-Pacific, 652 patients were randomized to receive zanubrutinib (n=327) or ibrutinib (n=325) (ITT population; FIG. 6). Demographics and disease characteristics were balanced at baseline, except more female patients received zanubrutinib than ibrutinib (35% vs 29%; Table 25). Median age was 67 years (range, 35-90 years), 81% were white, 14% were Asian; 45% of patients entered the study with bulky disease, 73% with unmutated IGHV status, and 23% had del(17p) and/or TP53 mutations. Median prior line(s) of therapy was one (range, 1-12); 8% of patients had received >3 lines of therapy (Table 25). A total of 80% and 76% of patients on zanubrutinib and ibrutinib, respectively, had previously received chemoimmunotherapy.

Overall, 324 patients in each arm received at least one dose of study treatment. 72.8% (n=238/327) of patients were still receiving zanubrutinib and 58.5% (n=190/325) were still receiving ibrutinib. Across both arms, the most common reasons for treatment discontinuation were adverse events (AEs; zanubrutinib, 16.2% [n=53/327]; ibrutinib, 22.8% [n=74/325]) and progressive disease (zanubrutinib, 7.3% [n=24/327]; ibrutinib, 12.9% [n=42/325]).

Overall Response Rate

Figure 7:
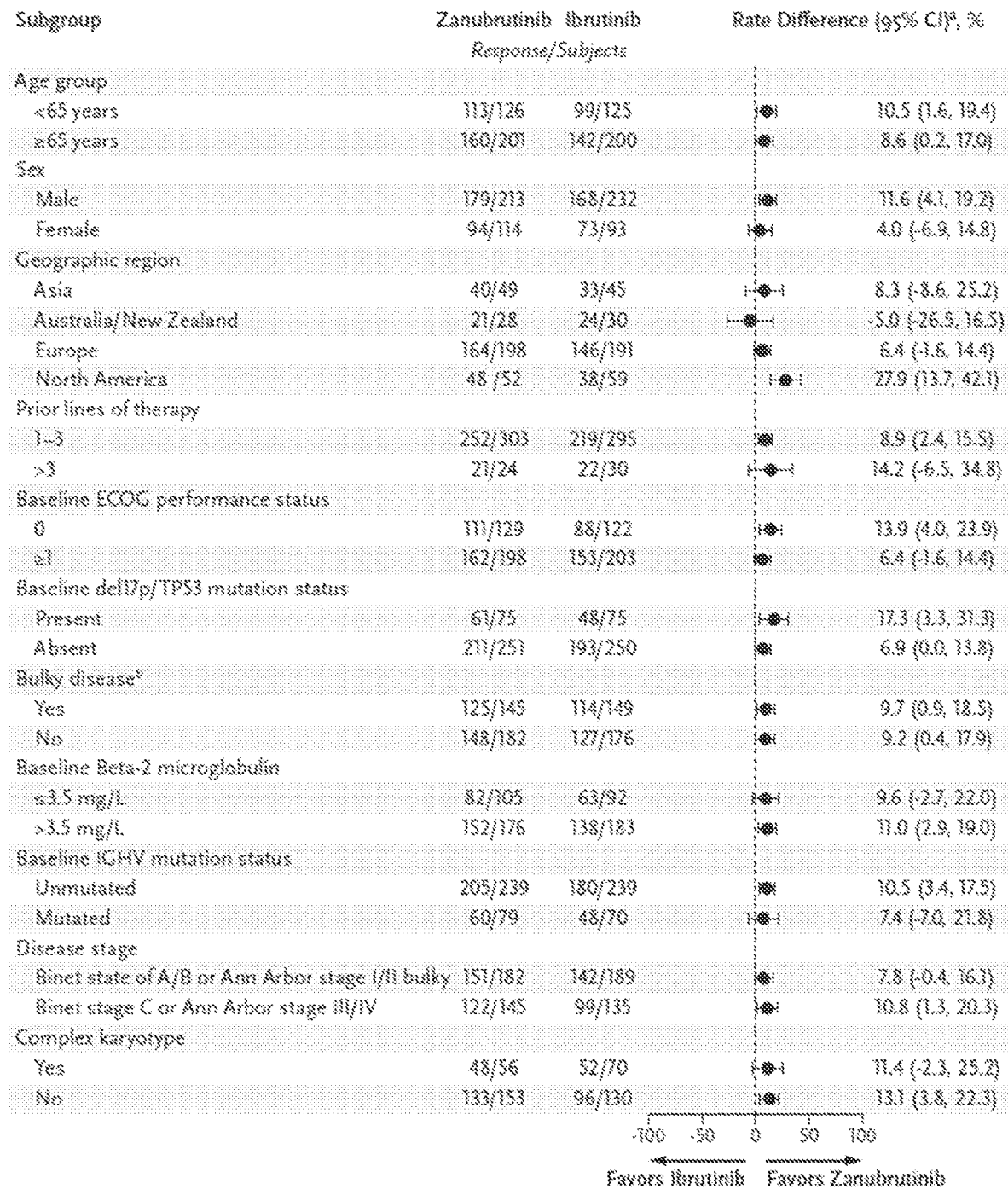
FIG. 7 and FIG. 8 depict subgroup analysis for Investigator and Independent Review Committee (IRC)—Assessed Overall Response Rate (ORR) (ITT Population, N=652), respectively.
Figure 8:
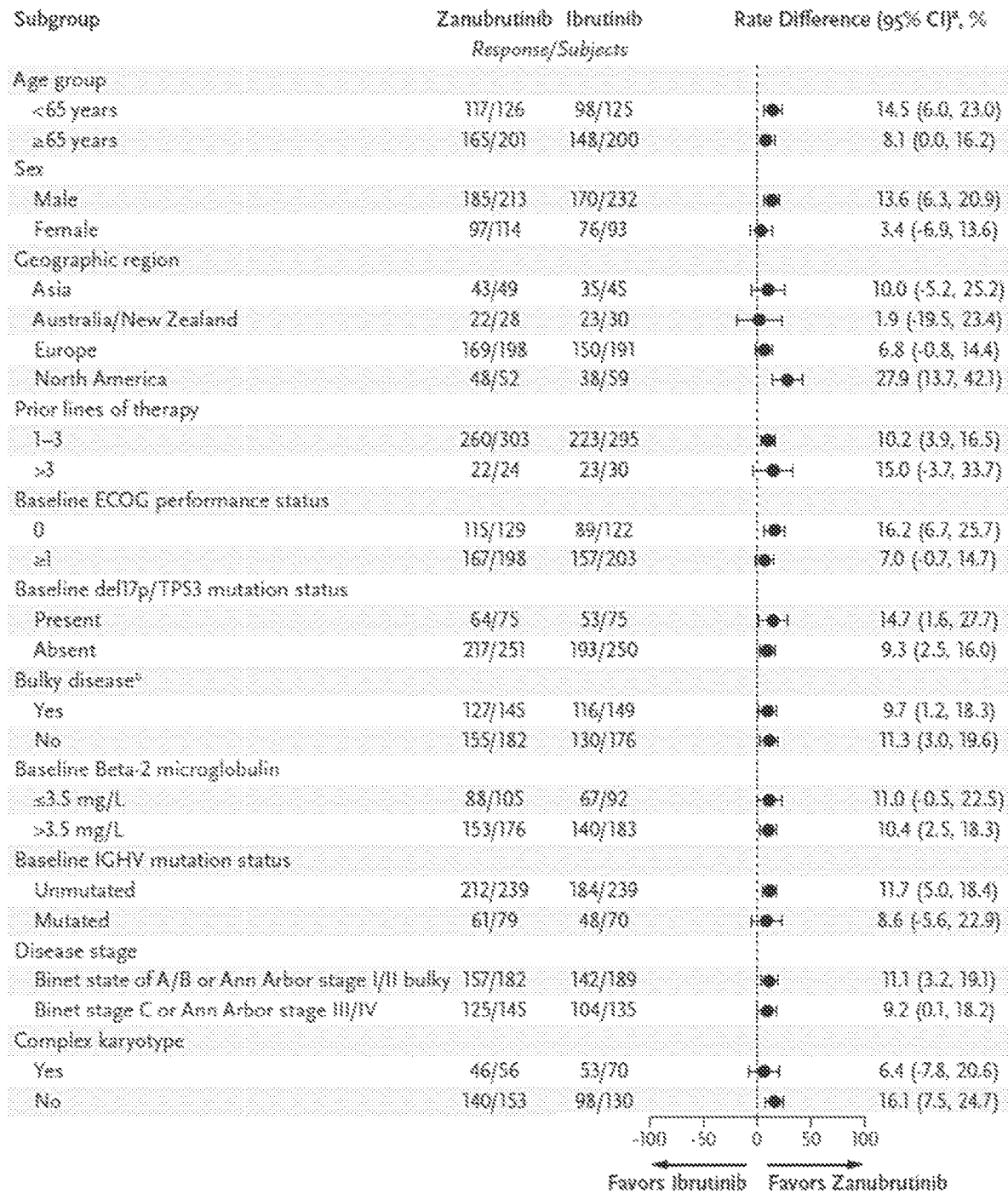

In this final analysis, the overall response rate observed in the ITT population was higher with zanubrutinib compared with ibrutinib by both investigator (83.5% vs 74.2) and independent review committee (86.2% vs 75.7%), respectively (Table 16). A higher proportion of patients with an investigator-assessed rate of partial response with lymphocytosis or better was observed with zanubrutinib (89.9%) compared with patients with ibrutinib (82.5%), which was consistent with the independent review committee assessment. Across prespecified subgroups, overall response rate assessed by both investigator and independent review committee favored zanubrutinib over ibrutinib (FIG. 7 and FIG. 8), including the high-risk del(17p)/TP53$^{mut}$ population (Table 16). The duration of response, by both investigator and independent review committee, was 33.9 months with ibrutinib but had not yet been reached with zanubrutinib (Table 17).

TABLE 16

Investigator- and Independent Review Committee-Assessed Best Response Rate in ITT Population and in Patients With del(17p)/TP53 Mutation

| Best Response, n (%) | ITT Population | | del(17p)/TP53 Mutation | |
|---|---|---|---|---|
| | Zanubrutinib (n = 327) | Ibrutinib (n = 325) | Zanubrutinib (n = 75) | Ibrutinib (n = 75) |
| Investigator Assessed | | | | |
| ORR, % | 83.5 | 74.2 | 81.3 | 64.0 |
| 95% CI | 79.0-87.3 | 69.0-78.8 | 70.7-89.4 | 52.1-74.8 |
| CR or CRi | 23 (7.0) | 16 (4.9) | 5 (6.7) | 3 (4.0) |
| PR or nPR | 250 (76.5) | 225 (69.2) | 56 (74.7) | 45 (60.0) |
| PR-L | 21 (6.4) | 27 (8.3) | 6 (8.0) | 9 (12.0) |
| SD | 23 (7.0) | 37 (11.4) | 5 (6.7) | 13 (17.3) |
| PD | 1 (0.3) | 6 (1.8) | 0 | 2 (2.7) |
| Discontinue prior to first assessment, NA or NE | 9 (2.8) | 14 (4.3) | 3 (4.0) | 3 (4.0) |
| IRC Assessed | | | | |
| ORR, % | 86.2 | 75.7 | 85.3 | 70.7 |
| 95% CI | 82.0-89.8 | 70.7-80.3 | 75.3-92.4 | 59.0-80.6 |
| CR or CRi | 22 (6.7) | 19 (5.8) | 6 (8.0) | 4 (5.3) |
| PR or nPR | 260 (79.5) | 227 (69.8) | 58 (77.3) | 49 (65.3) |
| PR-L | 18 (5.5) | 24 (7.4) | 4 (5.3) | 7 (9.3) |
| SD* | 16 (4.9) | 34 (10.5) | 3 (4.0) | 8 (10.7) |
| PD | 3 (0.9) | 7 (2.2) | 1 (1.3) | 4 (5.3) |
| Discontinue prior to first assessment, NA or NE | 8 (2.4) | 14 (4.3) | 3 (4.0) | 3 (4.0) |

*Includes 2 patients in zanubrutinib arm (1 in del(17p)/TP53 subgroup) with response of non-progressive disease.
Confidence interval widths have not been adjusted for multiplicity and may not be used in place of hypothesis testing.
CI denotes confidence interval; CR, complete response; CRi, CR with incomplete bone marrow recovery; IRC, independent review committee; ITT, intent-to-treat; NA, not assessed; NE, not evaluable; nPR, nodular partial response; ORR, overall response rate; PD, progressive disease; PR, partial response; PR-L, partial response with lymphocytosis; SD stable disease.

TABLE 17

Investigator- and Independent Review Committee-Assessed Duration of Response (N = 652)

| | ITT Population | |
|---|---|---|
| | Zanubrutinib (n = 327) | Ibrutinib (n = 325) |
| Investigator Assessed | | |
| Number of Responders | 273 | 241 |
| Events, n (%) | 53 (19.4) | 62 (25.7) |
| Progressive Disease | 33 (12.1) | 45 (18.7) |
| Death | 20 (7.3) | 17 (7.1) |
| Median Duration of Response, mo (95% CI) | NE (31.3, NE) | 33.9 (33.9, NE) |
| 24-month Event-free Rate, % (95% CI) | 79.5 (73.1-84.6) | 71.3 (63.8-77.5) |
| IRC Assessed | | |
| Number of Responders | 282 | 246 |
| Events, n (%) | 60 (21.3) | 69 (28.0) |
| Progressive Disease | 40 (14.2) | 52 (21.1) |
| Death | 20 (7.1) | 17 (6.9) |
| Median Duration of Response, mo (95% CI) | NE (31.3, NE) | 33.9 (32.2, 41.4) |
| 24-month Event-free Rate, % (95% CI) | 77.4 (71.0-82.5) | 67.8 (60.1-74.3) |

Confidence interval widths have not been adjusted for multiplicity and may not be used in place of hypothesis testing.
CI denotes confidence interval; IRC, independent review committee; mo, months; NE, not estimable.

Progression-Free Survival

Figure 4:
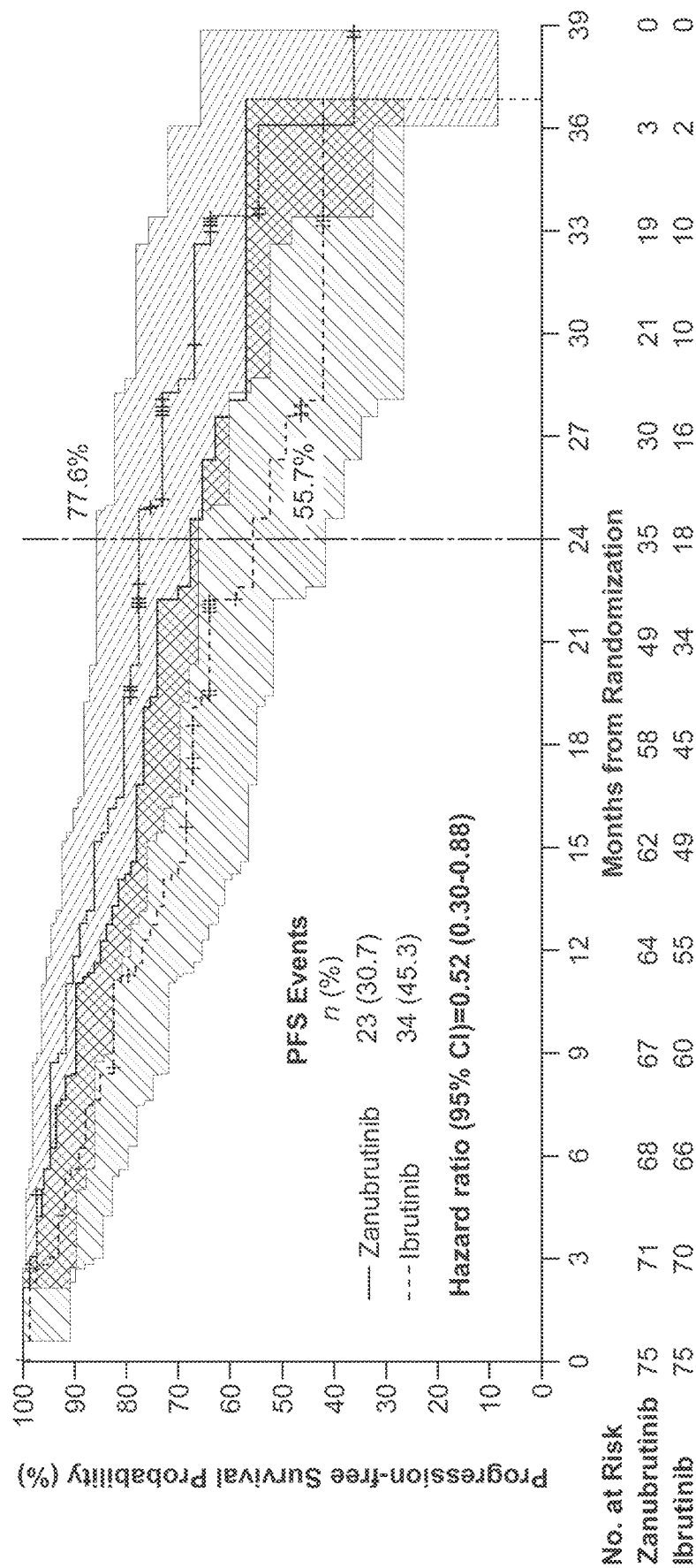
FIG. 4 depicts the Independent-Review Committee Assessment of the Progression-Free Survival in del(17p)/TP53 Mutation Populations.
Figure 9:
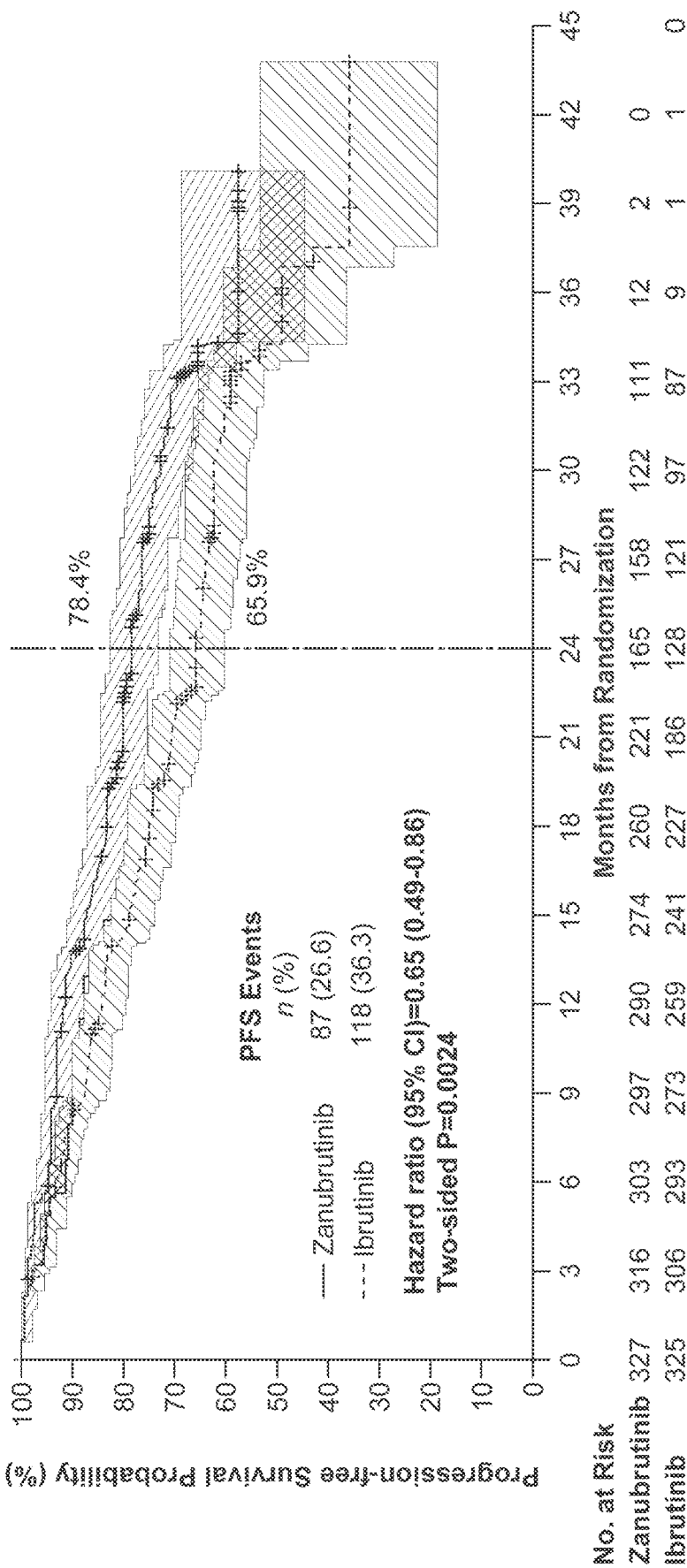
FIG. 9 depicts the Investigator Assessment of the Progression-Free Survival in ITT Populations.

With a median study follow-up of 29.6 months, zanubrutinib demonstrated superiority for investigator-assessed PFS over ibrutinib with a hazard ratio (HR) of 0.65 (95% CI, 0.49-0.86) and 2-sided P-value of 0.0024 (FIG. 9). 87 patients with zanubrutinib and 118 patients with ibrutinib experienced disease progression or death. The most common primary method of disease progression in both treatment arms was increase in lymph nodes (Table 19). Zanubrutinib also met superiority for PFS as assessed by independent review committee with identical statistical results (FIG. 3 and FIG. 4). At 24 months, the investigator-assessed PFS rate was 78.4% (95% CI, 73.3-82.7) with zanubrutinib and 65.9% (95% CI, 60.1-71.1) with ibrutinib. While median PFS was not reached in the zanubrutinib arm, median PFS with ibrutinib was 34.2 months (95% CI, 33.3-NE). Sensitivity analyses were consistent with the primary analyses for both investigator- and independent review committee-assessed PFS (Table 18).

TABLE 18

Sensitivity Analyses for Investigator- and Independent Review Committee-Assessed Progression-Free Survival

| PFS HR (95% CI) | Investigator Assessment | Independent Review Assessment |
|---|---|---|
| Per protocol population (N = 646) | 0.64 (0.48, 0.85) | 0.64 (0.48, 0.85) |
| Alternative Censoring Rules (ITT, N = 652) | 0.65 (0.49, 0.87) | 0.63 (0.48, 0.84) |
| Accounting for Drug Interruption (ITT, N = 652) | 0.71 (0.52, 0.96) | 0.71 (0.53, 0.95) |
| Accounting for Death due to COVID-19 (ITT, N = 652) | 0.62 (0.46, 0.84) | 0.62 (0.45, 0.84) |

Confidence interval widths have not been adjusted for multiplicity and may not be used in place of hypothesis testing. PFS, progression-free survival.

Figure 10:
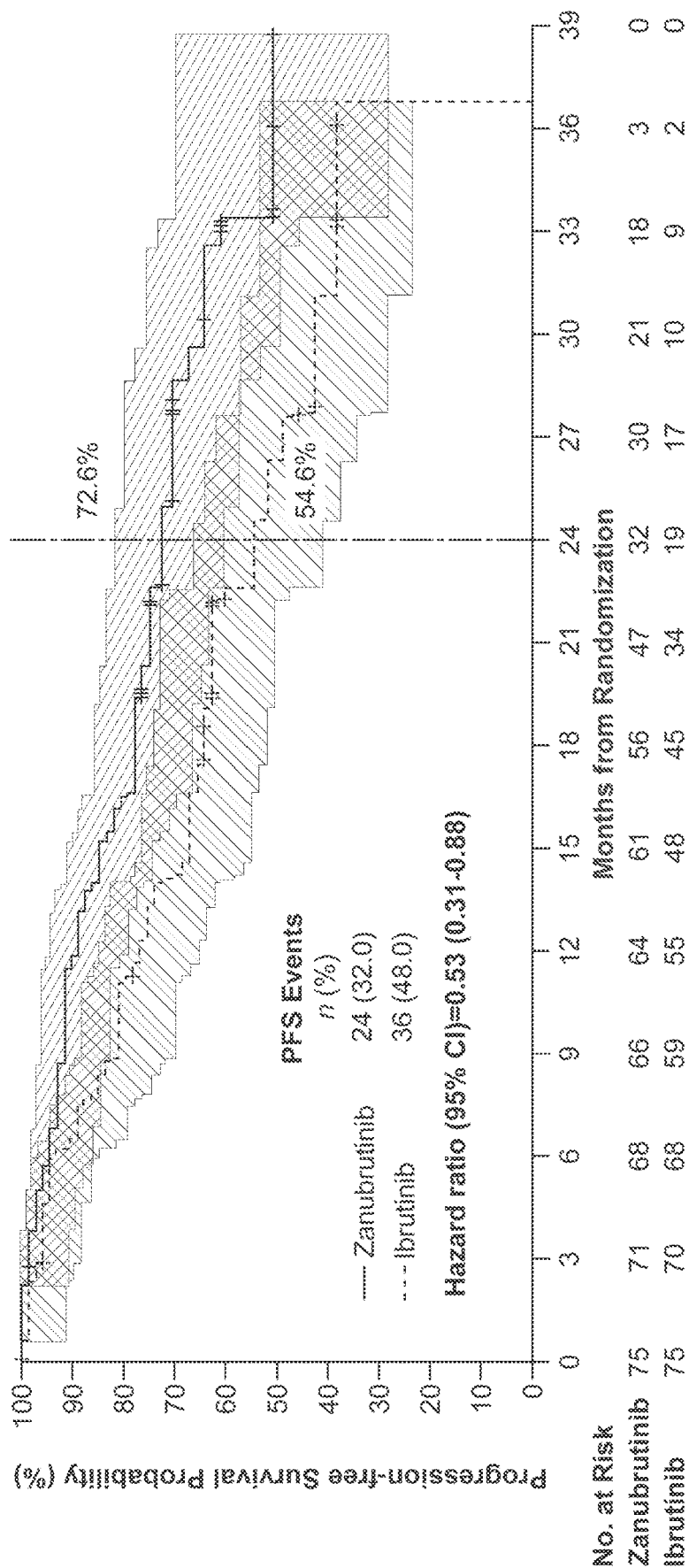
FIG. 10 depicts the Investigator Assessment of the Progression-Free Survival in del(17p)/TP53 Mutation Populations.
Figure 12:
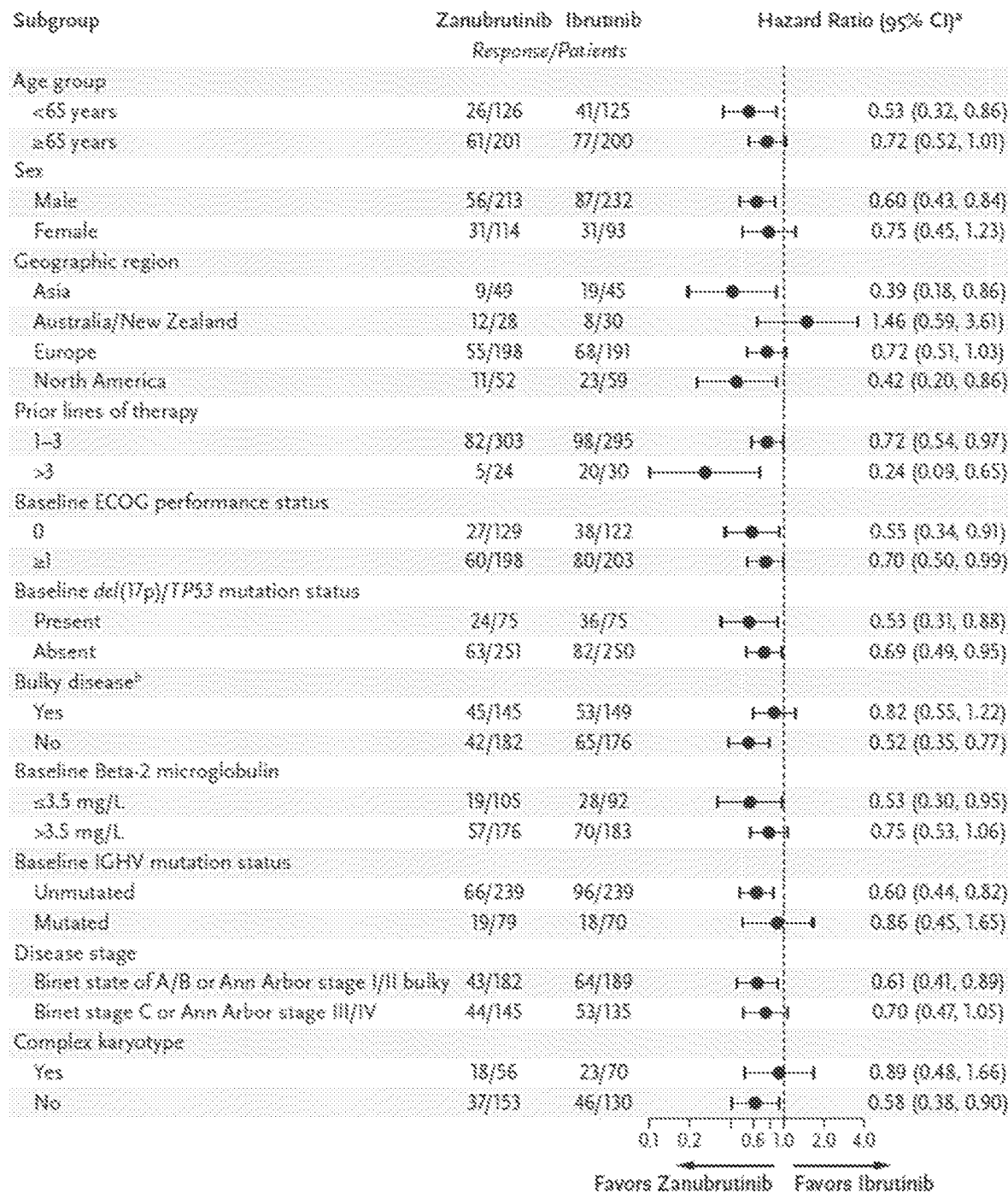
FIG. 12 depicts the subgroup analysis for investigator-assessed progression-free survival (ITT population, N=652). All subgroups, with the exception of complex karyotype were prespecified. Hazard ratio (zanubrutinib over ibrutinib) and 95% CI were unstratified for subgroups. Bulky disease is derived from any target lesion longest diameter ≥5 cm.
Figure 13:
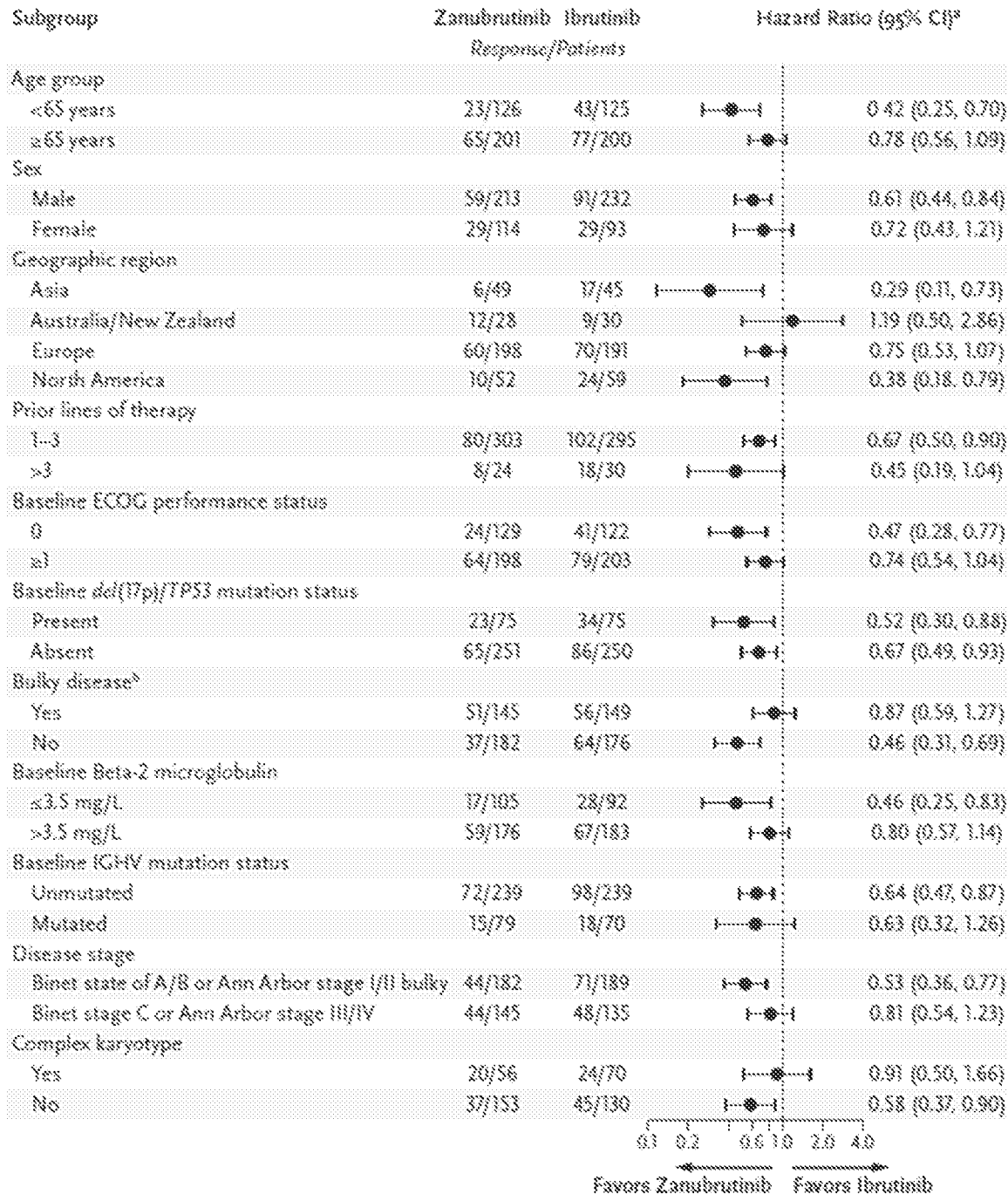
FIG. 13 depicts the subgroup analysis for independent review committee-assessed progression-free survival (ITT population, N=652). All subgroups, with the exception of complex karyotype were prespecified. Hazard ratio (zanubrutinib over ibrutinib) and 95% CI were unstratified for subgroups. Bulky disease is derived from any target lesion longest diameter ≥5 cm.
Figure 14:
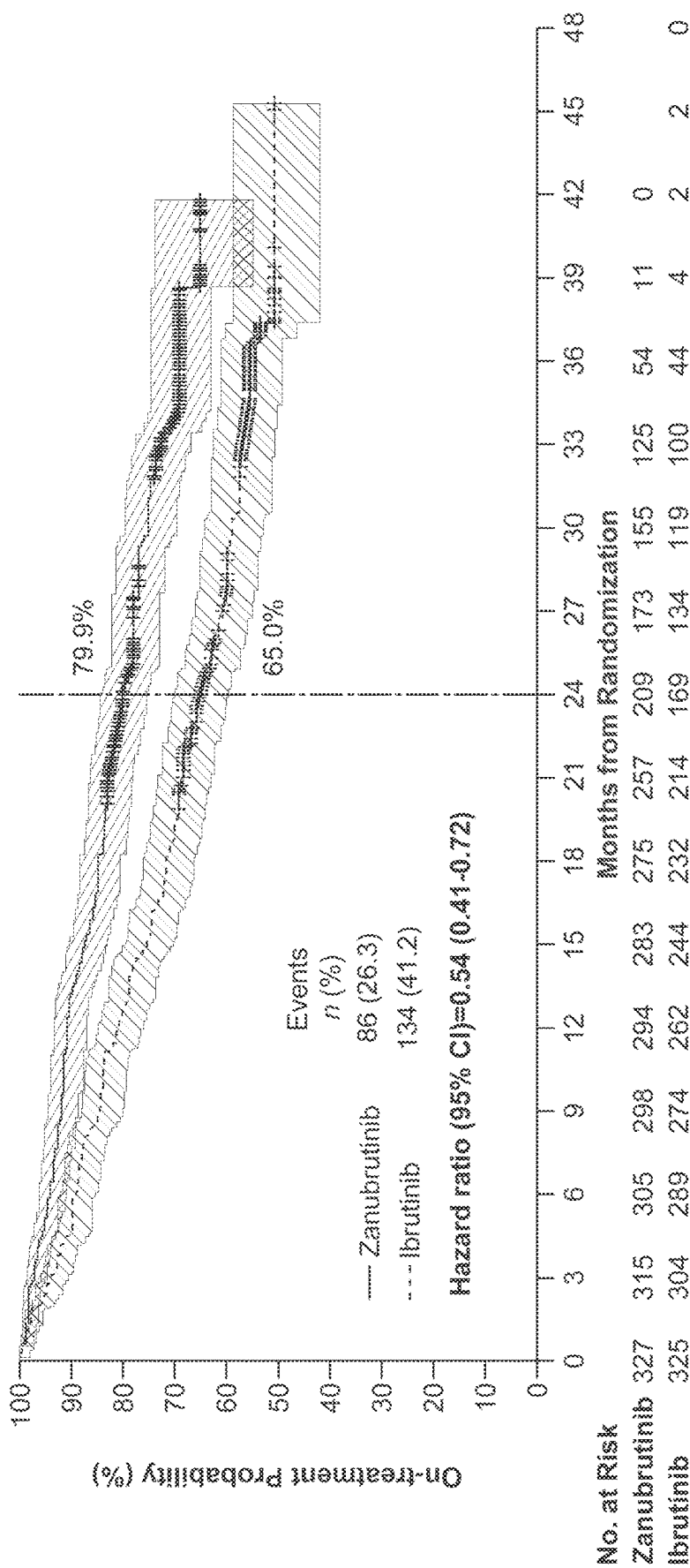
FIG. 14 depicts the time-to-treatment failure.

In a prespecified subgroup of high-risk patients with del(17p)/TP53', longer PFS was demonstrated with zanubrutinib than ibrutinib by both investigator (HR: 0.53 [95% CI, 0.31-0.88]) and independent review committee (HR: 0.52 [95% CI:0.30-0.88]) (FIG. 10 and FIG. 4). Progression-free survival benefit in favor of zanubrutinib was observed in major prespecified subgroups, including age, prior lines of therapy, disease stage, and IGHV mutational status regardless of investigator (FIG. 12) or independent review committee assessment (FIG. 13). Time-to-treatment failure is shown in FIG. 14; at 24 months, the treatment-failure event-free rate was 79.9% (95% CI 75.1-83.9) with zanubrutinib and 65.0% (95% CI 59.5-70.0) with ibrutinib.

TABLE 19

Summary of Progressive Disease by Investigator-Assessment (N = 652)

| | ITT Population | |
| --- | --- | --- |
| | Zanubrutinib (n = 327) | Ibrutinib (n = 325) |
| Patients with Progressive Disease* | 54 (16.5) | 78 (24.0) |
| Primary Method of Detection | | |
| Increase in lymph nodes | 40 (12.2) | 61 (18.8) |
| New enlarged lymph nodes | 3 (0.9) | 6 (1.8) |
| New or increase in splenomegaly | 8 (2.4) | 6 (1.8) |
| New symptomatic disease | 3 (0.9) | 4 (1.2) |
| Decreased in platelet count | 0 | 1 (0.3) |
| Patients with Disease Transformation | 5 (1.5) | 4 (1.2) |

*Isolated lymphocytosis was not a criterion for progressive disease

Overall Survival

Figure 11:
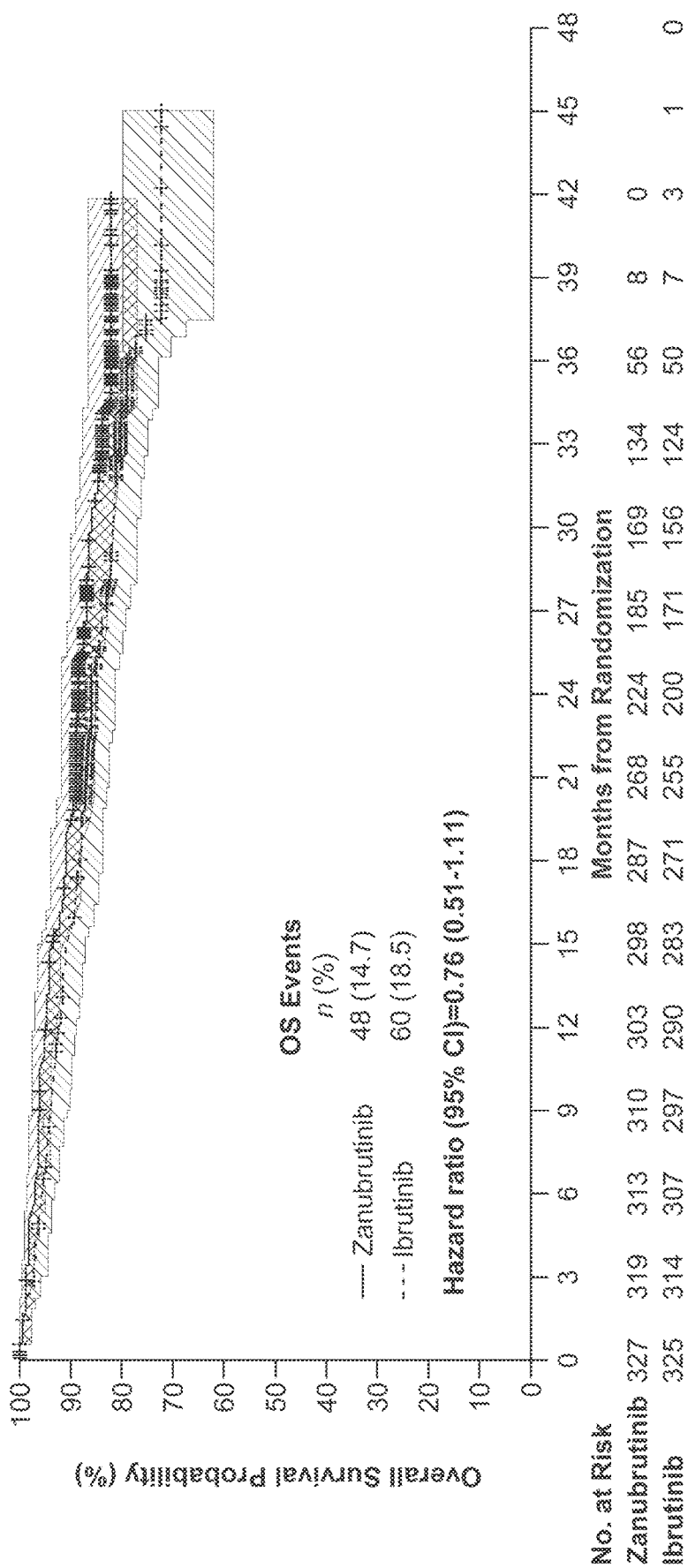
FIG. 11 depicts the overall survival.

As of the final analysis data cut-off, numerically fewer deaths were reported in the zanubrutinib arm (n=48) compared with the ibrutinib arm (n=60). The hazard ratio for overall survival comparing zanubrutinib with ibrutinib was 0.76 (95% CI, 0.51-1.11). See FIG. 11.

Safety and Tolerability Profile

Overall safety data summary is detailed in Table 26; median treatment duration with zanubrutinib was 28.4 months (range, 0.4-41.6) and was 24.3 months (range, 0.1-45.1) with ibrutinib. The treatment-emergent AEs reported in ≥20% of patients with zanubrutinib and ibrutinib were diarrhea (16.0% vs 24.1%), hypertension (21.9% vs 19.8%), neutropenia (22.8% vs 18.2%), COVID-19 (23.1% vs 17.9%), and upper respiratory tract infections (21.0% vs 14.2%), respectively (Table 20). Grade ≥3 AEs occurring in ≥15% of patients were neutropenia (16.0% vs 13.9%) and hypertension (14.8% vs 11.1%) in zanubrutinib and ibrutinib, respectively. Grade 5 treatment-emergent AEs occurred in 33 (10.2%) patients receiving zanubrutinib and 36 (11.1%) receiving ibrutinib; the number of grade 5 AEs related to COVID-19 was 12 (3.7%) in the zanubrutinib arm and 15 (4.6%) in the ibrutinib arm (Table 21).

Figure 15:
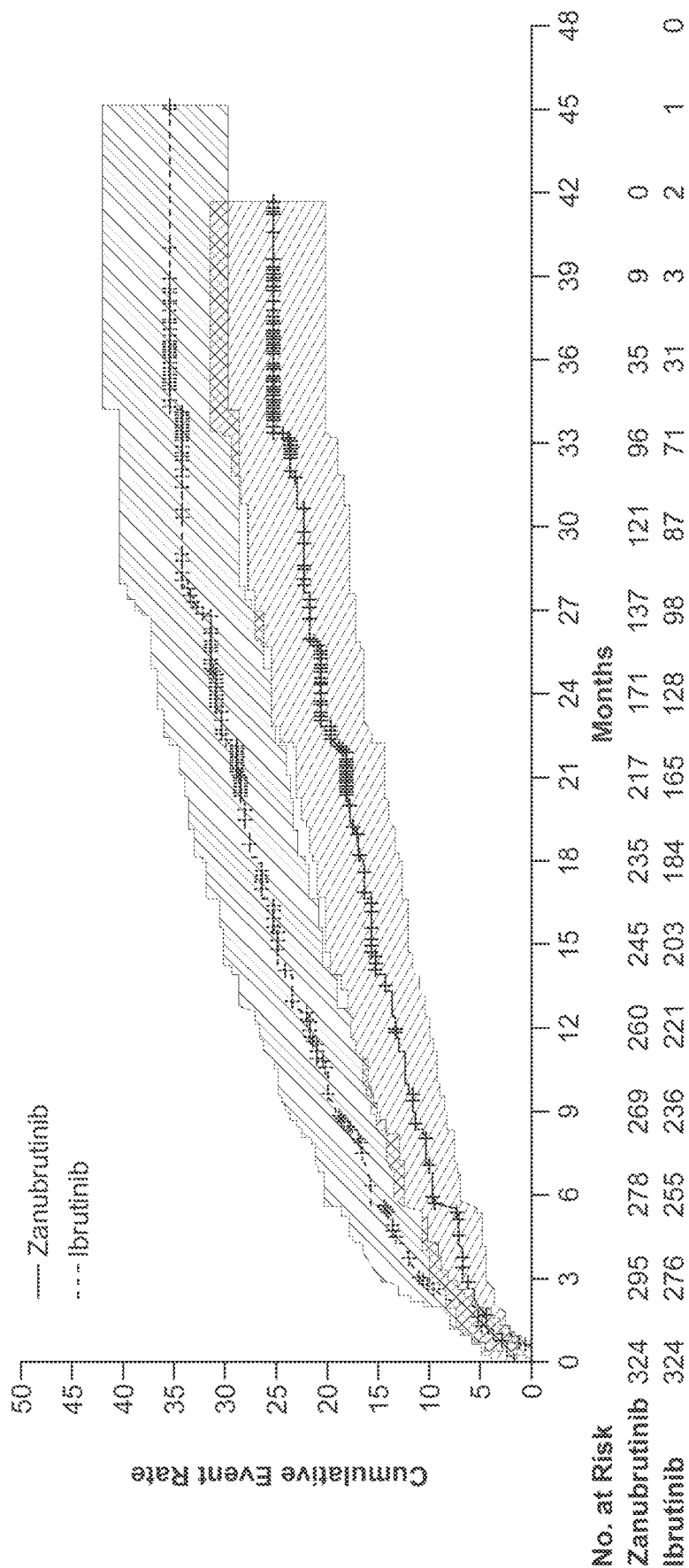
FIG. 15 depicts the Time to Cardiac Disorders and Adverse Events of Special Interest (Safety Population, N=648).

Overall, a lower incidence of cardiac disorders was reported with zanubrutinib (21.3%) versus ibrutinib (29.6%) (FIG. 15; Table 22); cardiac disorders leading to treatment discontinuation occurred in one (0.3%) patient with zanubrutinib and 14 (4.3%) patients with ibrutinib. Six deaths due to cardiac events were reported, all in patients receiving ibrutinib. Of the six patients who died, three died within four months of ibrutinib initiation all with cardiac comorbidities. The other three deaths occurred 2 to 3 years after ibrutinib initiation, one in a patient without any previous cardiac history.

TABLE 20

Most Frequent Treatment-Emergent Adverse Events (>10%) in Either Arm (Safety Population; N = 648)

| TEAE by Preferred Term, n (%) | Zanubrutinib (n = 324) | Ibrutinib (n = 324) |
| --- | --- | --- |
| ≥1 TEAE | 318 (98.1) | 321 (99.1) |
| COVID-19 | 75 (23.1) | 58 (17.9) |
| Neutropenia | 74 (22.8) | 59 (18.2) |
| Hypertension | 71 (21.9) | 64 (19.8) |
| Upper respiratory tract infection | 68 (21.0) | 46 (14.2) |

TABLE 20-continued

Most Frequent Treatment-Emergent Adverse Events (>10%) in Either Arm (Safety Population; N = 648)

| TEAE by Preferred Term, n (%) | Zanubrutinib (n = 324) | Ibrutinib (n = 324) |
| --- | --- | --- |
| Diarrhea | 52 (16.0) | 78 (24.1) |
| Anemia | 49 (15.1) | 51 (15.7) |
| Arthralgia | 47 (14.5) | 53 (16.4) |
| Contusion | 44 (13.6) | 34 (10.5) |
| Cough | 38 (11.7) | 34 (10.5) |
| Pneumonia | 34 (10.5) | 40 (12.3) |
| Rash | 33 (10.2) | 40 (12.3) |
| Fatigue | 31 (9.6) | 43 (13.3) |
| Pyrexia | 27 (8.3) | 33 (10.2) |
| Atrial fibrillation | 15 (4.6) | 40 (12.3) |
| Muscle spasms | 10 (3.1) | 41 (12.7) |

TEAE, treatment-emergent adverse event.

TABLE 21

Summary of COVID-19 Related Treatment Emergent Adverse Events* (Safety Population; N = 648)

| TEAE related to COVID-19, n (%) | Zanubrutinib (n = 324) | Ibrutinib (n = 324) |
| --- | --- | --- |
| Patients with any COVID-19 TEAE* | 93 (28.7) | 70 (21.6) |
| Grade 3 or higher | 40 (12.3) | 28 (8.6) |
| Leading to treatment discontinuation | 12 (3.7) | 16 (4.9) |
| Fatal | 12 (3.7) | 15 (4.6) |

*COVID-19-related TEAE denotes any COVID-19 related preferred terms: COVID-19, COVID-19 pneumonia, post-acute COVID-19 syndrome, suspected COVID-19.

TABLE 22

All Cardiac Adverse Events (Safety Population; N = 648)

| Cardiac Adverse Events | | |
| --- | --- | --- |
| Any event in cardiac disorders SOC | 69 (21.3) | 96 (29.6) |
| Atrial fibrillation | 15 (4.6) | 40 (12.3) |
| Palpitations | 9 (2.8) | 13 (4.0) |
| Atrioventricular block first degree | 5 (1.5) | 3 (0.9) |
| Cardiac failure | 5 (1.5) | 6 (1.9) |
| Sinus bradycardia | 5 (1.5) | 7 (2.2) |
| Angina pectoris | 4 (1.2) | 7 (2.2) |
| Sinus tachycardia | 4 (1.2) | 1 (0.3) |
| Supraventricular extrasystoles | 4 (1.2) | 3 (0.9) |
| Arrhythmia supraventricular | 3 (0.9) | 0 |
| Bundle branch block left | 3 (0.9) | 0 |
| Myocardial ischemia | 3 (0.9) | 1 (0.3) |
| Ventricular extrasystoles | 3 (0.9) | 3 (0.9) |
| Atrial flutter | 2 (0.6) | 3 (0.9) |
| Bundle branch block right | 2 (0.6) | 3 (0.9) |
| Coronary artery disease | 2 (0.6) | 1 (0.3) |
| Supraventricular tachycardia | 2 (0.6) | 1 (0.3) |
| Ventricular arrhythmia | 2 (0.6) | 1 (0.3) |
| Acute coronary syndrome | 1 (0.3) | 0 |
| Acute myocardial infarction | 1 (0.3) | 0 |
| Aortic valve stenosis | 1 (0.3) | 0 |
| Arrhythmia | 1 (0.3) | 2 (0.6) |
| Arteriosclerosis coronary artery | 1 (0.3) | 0 |
| Bradyarrhythmia | 1 (0.3) | 0 |
| Cardiac failure congestive | 1 (0.3) | 2 (0.6) |
| Coronary artery insufficiency | 1 (0.3) | 0 |
| Defect conduction intraventricular | 1 (0.3) | 0 |
| Dilatation atrial | 1 (0.3) | 0 |
| Extrasystoles | 1 (0.3) | 2 (0.6) |
| Left atrial hypertrophy | 1 (0.3) | 0 |
| Left ventricular dysfunction | 1 (0.3) | 0 |
| Left ventricular failure | 1 (0.3) | 0 |
| Mitral valve incompetence | 1 (0.3) | 2 (0.6) |
| Myocardial fibrosis | 1 (0.3) | 0 |
| Myocardial infarction | 1 (0.3) | 3 (0.9) |
| Pericardial effusion | 1 (0.3) | 0 |

TABLE 22-continued

All Cardiac Adverse Events (Safety Population; N = 648)

| | | |
|---|---|---|
| Sinus arrhythmia | 1 (0.3) | 1 (0.3) |
| Sinoatrial block | 1 (0.3) | 0 |
| Tachycardia | 1 (0.3) | 2 (0.6) |
| Ventricular hypokinesia | 1 (0.3) | 0 |
| Bradycardia | 0 | 3 (0.9) |
| Cardiac arrest | 0 | 3 (0.9) |
| Cardiac discomfort | 0 | 3 (0.9) |
| Congestive cardiomyopathy | 0 | 3 (0.9) |
| Ventricular fibrillation | 0 | 2 (0.6) |
| Aortic valve incompetence | 0 | 1 (0.3) |
| Atrial tachycardia | 0 | 1 (0.3) |
| Atrioventricular block | 0 | 1 (0.3) |
| Cardiac disorder | 0 | 1 (0.3) |
| Cardiac failure acute | 0 | 1 (0.3) |
| Cardiac failure chronic | 0 | 1 (0.3) |
| Sinus node dysfunction | 0 | 1 (0.3) |
| Cardiac adverse events leading to treatment discontinuation | | |
| Any TEAE in cardiac disorders SOC | 1 (0.3) | 14 (4.3) |
| Ventricular extrasystoles | 1 (0.3) | 0 |
| Atrial fibrillation | 0 | 5 (1.5) |
| Cardiac arrest | 0 | 2 (0.6) |
| Cardiac failure | 0 | 2 (0.6) |
| Cardiac failure acute | 0 | 1 (0.3) |
| Congestive cardiomyopathy | 0 | 1 (0.3) |
| Myocardial infarction | 0 | 1 (0.3) |
| Palpitations | 0 | 1 (0.3) |
| Ventricular fibrillation | 0 | 1 (0.3) |

SOC based on MedDRA version 24.0 denotes system organ class.

TEAE, Treatment-Emergent Adverse Event.

Figure 16:
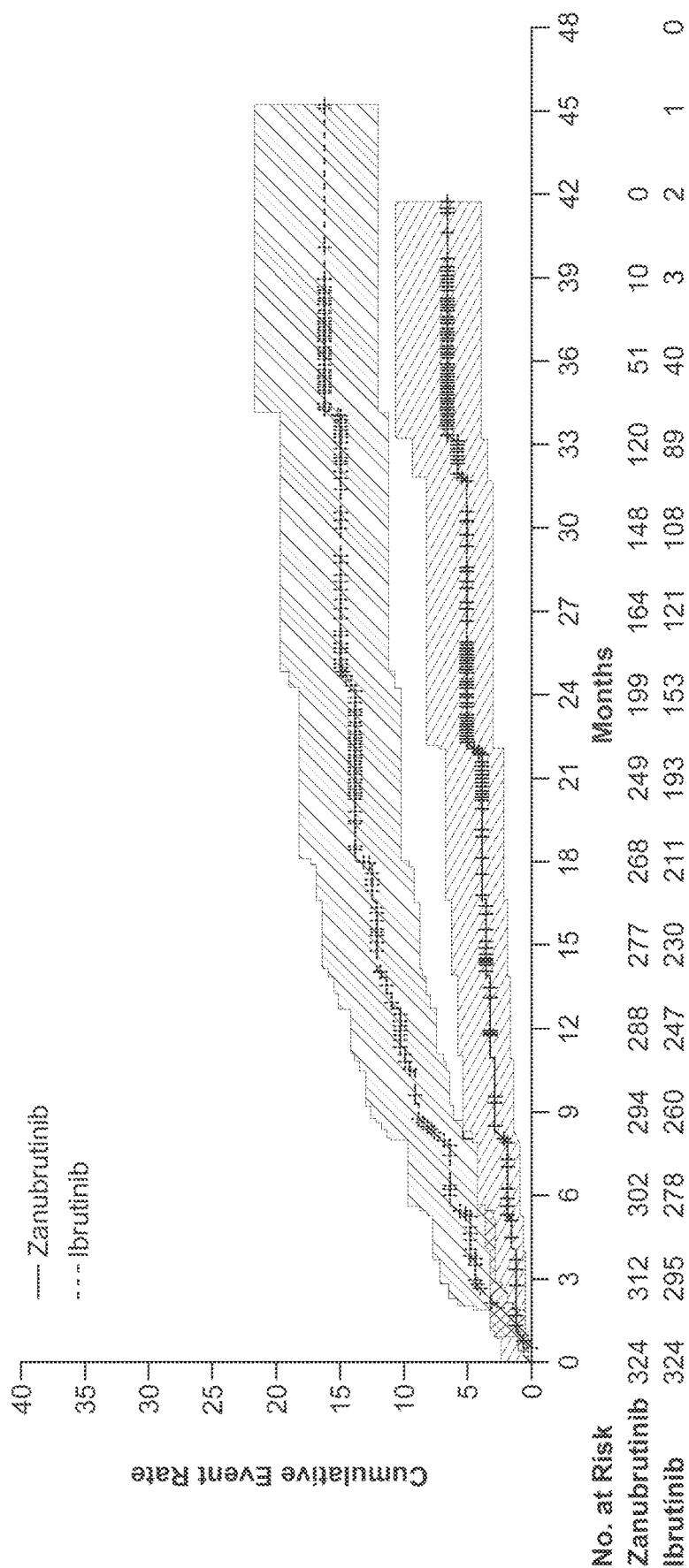
FIG. 16 depicts the Time to Cardiac Disorders and Adverse Events of Special Interest (Safety Population, N=648), i.e., Atrial Fibrillation/Flutter.

Rates of adverse events of special interest are presented in Table 23. The rate of any grade (5.2% [n=17/324] vs 13.3% [n=43/324]) and grade ≥3 (2.5% [n=8/324] vs 4.0% [n=13/324]) atrial fibrillation or flutter was lower with zanubrutinib versus ibrutinib (FIG. 16). Three zanubrutinib- and five ibrutinib-treated patients who had AE of atrial fibrillation or flutter had a medical history of atrial fibrillation/flutter.

Figure 17:
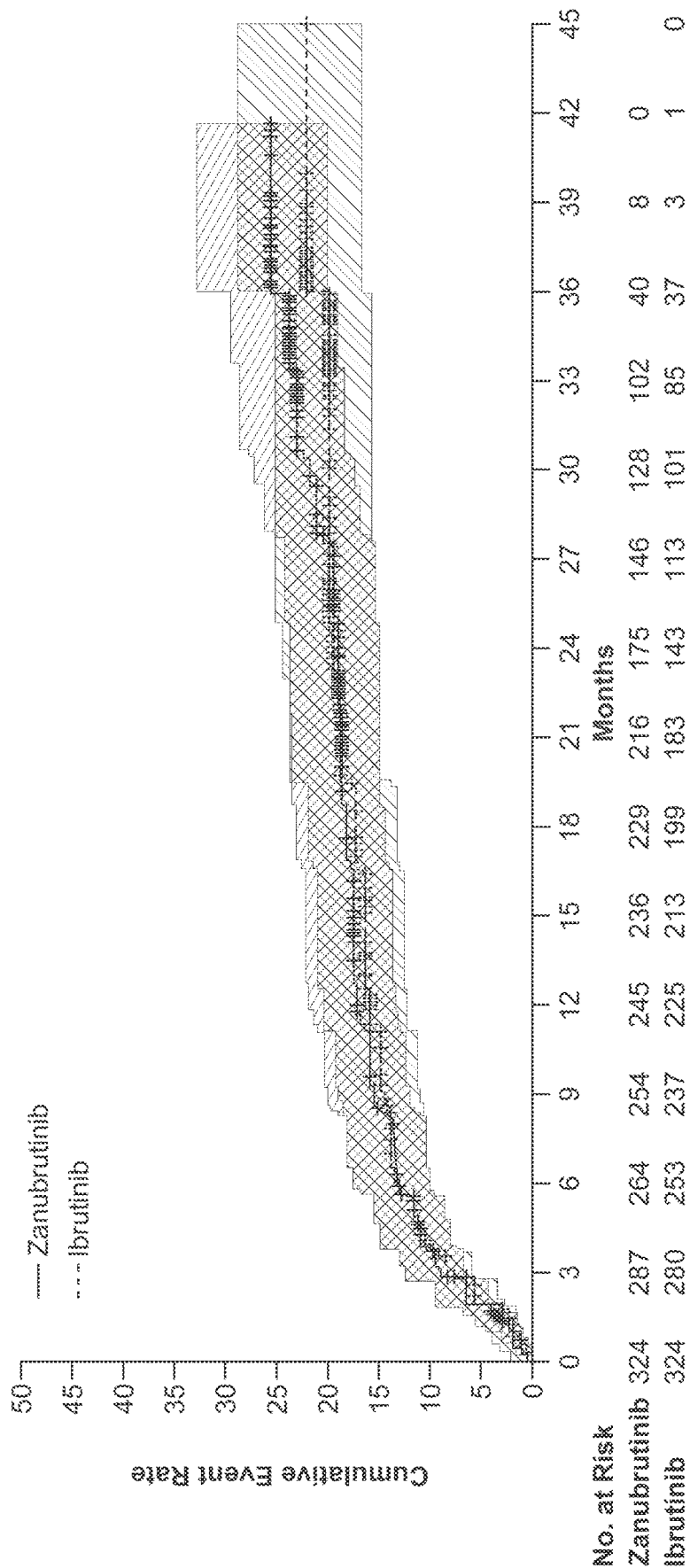
FIG. 17 depicts the Time to Cardiac Disorders and Adverse Events of Special Interest (Safety Population, N=648), i.e., Grade ≥3 Neutropenia.
Figure 18:
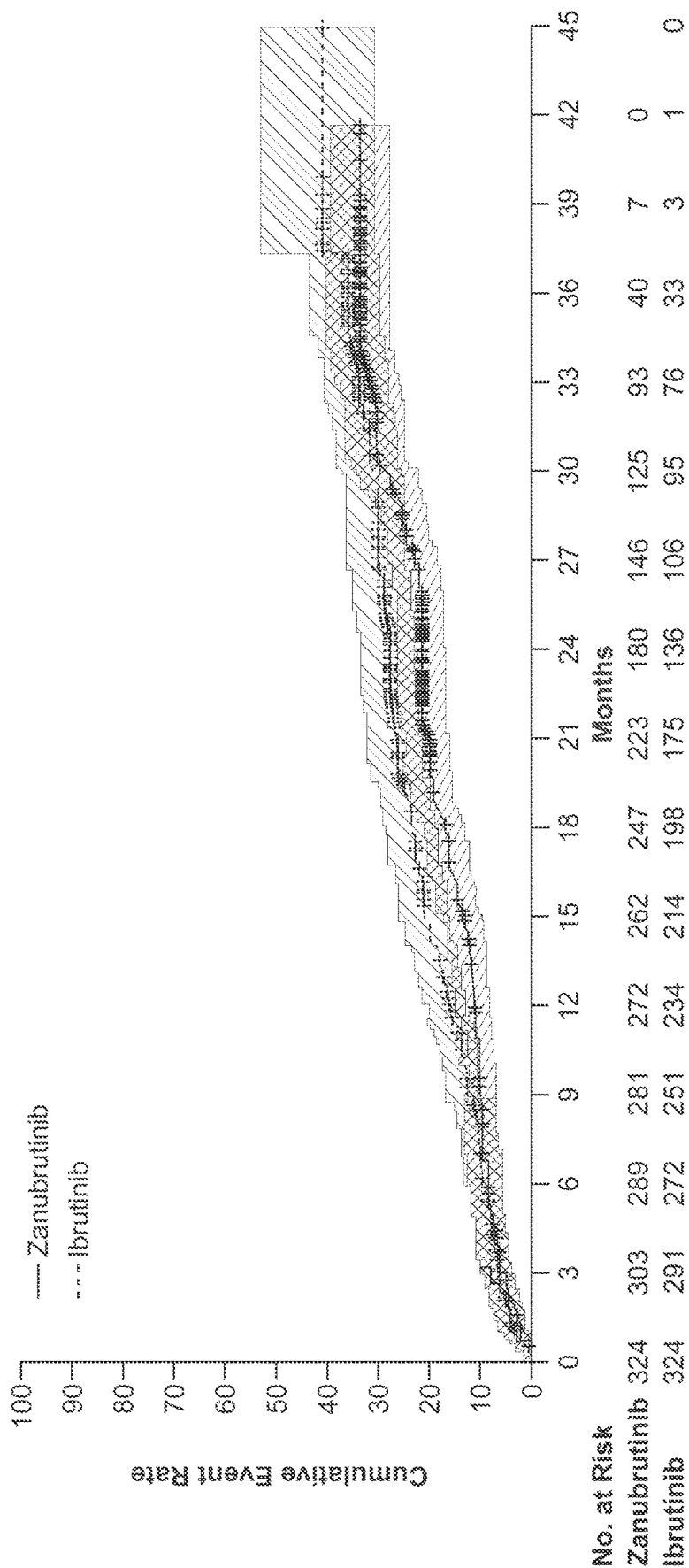
FIG. 18 depicts the Time to Cardiac Disorders and Adverse Events of Special Interest (Safety Population, N=648), i.e., Grade ≥3 Infection.
Figure 19:
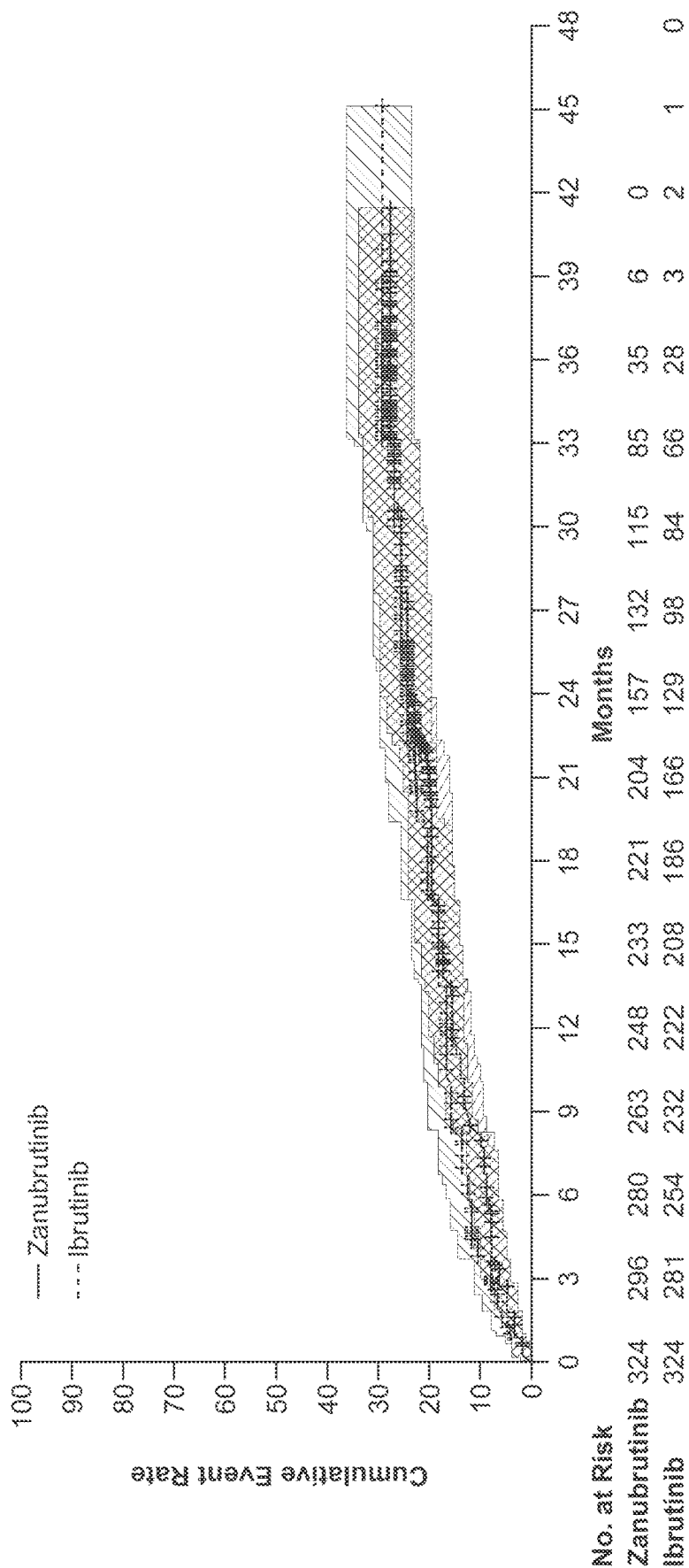
FIG. 19 depicts the Time to Cardiac Disorders and Adverse Events of Special Interest (Safety Population, N=648), i.e., Hypertension.

Neutropenia of any grade was reported at 29.3% in the zanubrutinib arm versus 24.4% in ibrutinib arm; rates of grade ≥3 neutropenia and febrile neutropenia were similar (FIG. 17). Infections of any grade reported in 71.3% and 73.1% and the rates of grade ≥3 infections were 26.5% and 28.1% with zanubrutinib and ibrutinib, respectively (FIG. 18; Table 26). Opportunistic infections of any grade were reported in 7 (2.2%) and 10 (3.1%) patients on zanubrutinib and ibrutinib, respectively (Table 24). Colony-stimulating growth factor was used at a similar rate for patients treated with zanubrutinib versus ibrutinib (15.4% vs 15.7%). Hemorrhagic events, including major hemorrhagic events, occurred with similar frequency in patients on zanubrutinib and ibrutinib (Table 23). Any-grade hypertension was reported in 23.5% and 22.8% (FIG. 19), and grade 3 (no grade ≥4 was reported) in 15.1% and 13.6% of patients receiving zanubrutinib and ibrutinib, respectively.

TABLE 23

Adverse Events of Special Interest* (Safety Population; N = 648)

| | Any Grade | | Grade ≥ 3 | |
|---|---|---|---|---|
| AESI, n (%) | Zanubrutinib (n = 324) | Ibrutinib (n = 324) | Zanu- brutinib (n = 324) | Ibrutinib (n = 324) |
| ≥1 AESI | 294 (90.7) | 300 (92.6) | 186 (57.4) | 184 (56.8) |
| Anemia | 50 (15.4) | 53 (16.4) | 7 (2.2) | 8 (2.5) |
| Atrial fibrillation and flutter | 17 (5.2) | 43 (13.3) | 8 (2.5) | 13 (4.0) |
| Hemorrhage | 137 (42.3) | 134 (41.4) | 11 (3.4) | 12 (3.7) |
| Major hemorrhage | 12 (3.7) | 14 (4.3) | 11 (3.4) | 12 (3.7) |
| Hypertension | 76 (23.5) | 74 (22.8) | 49 (15.1) | 44 (13.6) |
| Infections | 231 (71.3) | 237 (73.1) | 86 (26.5) | 91 (28.1) |
| Opportunistic infection | 7 (2.2) | 10 (3.1) | 5 (1.5) | 5 (1.5) |
| Neutropenia† | 95 (29.3) | 79 (24.4) | 68 (21.0) | 59 (18.2) |
| Secondary primary malignancies | 40 (12.3) | 43 (13.3) | 22 (6.8) | 17 (5.2) |
| Skin cancers | 21 (6.5) | 28 (8.6) | 7 (2.2) | 4 (1.2) |
| Thrombocytopenia | 42 (13.0) | 50 (15.4) | 11 (3.4) | 17 (5.2) |
| Tumor lysis syndrome | 1 (0.3) | 0 | 1 (0.3) | 0 |

*Specific related MedDRA preferred terms were pooled for each AESI category and summarized.
†Febrile neutropenia was reported in 4 (1.2%) vs 3 (0.9%) patients treated with zanubrutinib and ibrutinib, respectively.
AESI, adverse events of special interest.

TABLE 24

Treatment-Emergent Adverse Events of Special Interest Opportunistic Infections. (Safety Population; N = 648)

| | | |
|---|---|---|
| Pneumonia fungal | 2 (0.6) | 2 (0.6) |
| Bronchopulmonary aspergillosis | 2 (0.6) | 1 (0.3) |
| Pneumocystis jirovecii pneumonia | 1 (0.3) | 2 (0.6) |
| Fungal abscess central nervous system | 1 (0.3) | 0 |
| Pneumonia cryptococcal | 1 (0.3) | 0 |
| Herpes ophthalmic | 0 | 2 (0.6) |
| Ophthalmic herpes zoster | 0 | 1 (0.3) |
| Osteomyelitis fungal | 0 | 1 (0.3) |
| Pneumonia legionella | 0 | 1 (0.3) |
| Pulmonary tuberculosis | 0 | 1 (0.3) |

TEAE, treatment-emergent adverse event.

Discussion

In this final PFS analysis, at a median 29.6 months of follow-up, zanubrutinib demonstrated superior PFS to ibrutinib; supporting the superior PFS by investigator assessment are the results by independent review committee assessment and sensitivity analyses including evaluation for the possible impact of disease progression due to study drug interruption. This PFS benefit was observed across all major subgroups, including the high-risk del(17p)/TP53$^{mut}$ population. Zanubrutinib also demonstrated superior overall response rate by both investigator and independent review committee and higher rate of partial response with lymphocytosis or better. This is the first demonstration of improved PFS in a head-to-head study of BTKi monotherapy.

In this study, on the other hand, zanubrutinib demonstrated superior PFS over ibrutinib. zanubrutinib was observed to have improved benefits over ibrutinib in the high-risk del(17p)/TP53$^{mut}$ subgroup, which was not observed in ELEVATE-RR.

As BTKi monotherapy for CLL requires continuous treatment, successful outcomes depend on the ability to deliver complete and sustained occupancy across disease-relevant tissues, long-term tolerability, and low treatment discontinuation rates. Zanubrutinib has demonstrated high (>90%) steady-state BTKI occupancy in peripheral blood mononuclear cells and lymph nodes. In this study, treatment discontinuation, for any reason, was lower with zanubrutinib than ibrutinib, including discontinuation rates due to both AEs and progressive disease.

Ibrutinib is also associated with cardiac toxicities. Deaths due to cardiac disorders or sudden deaths occurred in 1% of 4,896 patients who received ibrutinib across various clinical trials, including in combination regimens. These adverse reactions occurred both in patients with and without preexisting hypertension or cardiac comorbidities. In this study, there were fewer treatment discontinuations due to cardiac disorder events with zanubrutinib (n=1) versus ibrutinib (n=14) and no patient receiving zanubrutinib died due to a cardiac disorder AE, while six patients receiving ibrutinib experienced a fatal cardiac disorder AE.

The significantly lower rate of atrial fibrillation for patients receiving zanubrutinib compared with ibrutinib reported at the final analysis.

While there was a higher rate of neutropenia in patients with zanubrutinib compared with ibrutinib, this did not translate into a higher rate of infection observed in the study. The rate of hypertension was similar between the zanubrutinib and ibrutinib in this analysis.

As is the case with all clinical trials, limitations on the generalizability of these data exist. While the open-label nature of the study could affect investigator assessment of PFS and overall response rate, the independent review committee was blinded to treatment arm and independent review committee-determined PFS and overall response rate rates were similar.

Conclusions: In conclusion, zanubrutinib demonstrated superior efficacy compared with ibrutinib in patients with relapsed/refractory CLL/SLL with no new safety signals. Benefits in both PFS and overall response rate were observed across all major subgroups, including high-risk patients. Furthermore, zanubrutinib had a more favorable safety profile compared with ibrutinib with a lower rate of treatment discontinuation and fewer cardiac disorder events, including fewer deaths. Zanubrutinib, with its favorable risk-benefit profile, has been demonstrated to be a potential new standard of care for BTKi-naïve patients with relapsed/refractory CLL/SLL.

In patients with relapsed/refractory CLL/SLL, zanubrutinib significantly improved PFS compared with ibrutinib and was associated with fewer cardiac adverse events. This is the first demonstration of PFS superiority in a head-to-head comparison of BTK inhibitors for CLL.

TABLE 25

Participant Demographics and Baseline Characteristics (ITT Population, N = 652)

| | | |
|---|---|---|
| Age, median (range), years | 67 (35-90) | 68 (35-89) |
| ≥65 and < 75, n (%) | 127 (38.8) | 131 (40.3) |
| ≥75, n (%) | 74 (22.6) | 69 (21.2) |
| Sex, n (%) | | |
| Male | 213 (65.1) | 232 (71.4) |
| Female | 114 (34.9) | 93 (28.6) |
| ECOG PS ≥ 1, n (%) | 198 (60.6) | 203 (62.5) |

TABLE 25-continued

Participant Demographics and Baseline Characteristics (ITT Population, N = 652)

| | | |
|---|---|---|
| Geographic region, n (%) | | |
| Asia | 49 (15.0) | 45 (13.8) |
| Australia/New Zealand | 28 (8.6) | 30 (9.2) |
| Europe | 198 (60.6) | 191 (58.8) |
| North America | 52 (15.9) | 59 (18.2) |
| del(17p) and/or TP53$^{mut}$, n (%) | 75 (22.9) | 75 (23.1) |
| del(17p) | 45 (13.8) | 50 (15.4) |
| TP53$^{mut}$ and non-del(17p) | 30 (9.2) | 25 (7.7) |
| Missing | 1 (0.3) | 0 |
| del(11q) mutational status, n (%) | | |
| del(11q) | 91 (27.8) | 88 (27.1) |
| Missing | 0 | 1 (0.3) |
| IGHV mutational status, n (%) | | |
| Mutated | 79 (24.2) | 70 (21.5) |
| Unmutated | 239 (73.1) | 239 (73.5) |
| Missing | 9 (2.8) | 16 (4.9) |
| Complex karyotype* | 56 (17.1) | 70 (21.5) |
| Missing | 118 (36.1) | 125 (38.5) |
| Bulky disease (≥5 cm), n (%) | 145 (44.3) | 149 (45.8) |
| Beta-2 microglobulin, n (%) | | |
| ≤3.5 mg/L | 105 (32.1) | 92 (28.3) |
| >3.5 mg/L | 176 (53.8) | 183 (56.3) |
| Missing | 46 (14.1) | 50 (15.4) |
| Lactate dehydrogenase U/L, median (range) | 224 (108, 1828) | 219 (92, 621) |
| Disease stage, n (%) | | |
| Binet stage A/B or Ann Arbor stage I/II | 182 (55.7) | 189 (58.2) |
| Binet stage C or Ann Arbor stage III/IV | 145 (44.3) | 135 (41.5) |
| Missing | 0 | 1 (0.3) |
| Prior lines of systemic therapy, median (range)† | 1 (1-6) | 1 (1-12) |
| 1 prior line, n (%) | 192 (58.7) | 186 (57.2) |
| 2 prior lines, n (%) | 86 (26.3) | 71 (21.8) |
| 3 prior lines, n (%) | 25 (7.6) | 38 (11.7) |
| >3 prior lines, n (%) | 24 (7.3) | 30 (9.2) |
| Anti-CD20 antibody, n (%) | 274 (83.8) | 269 (82.8) |
| Alkylator (excluding bendamustine), n (%) | 274 (83.8) | 258 (79.4) |
| Chemoimmunotherapy, n (%) | 260 (79.5) | 247 (76.0) |
| Purine analogue, n (%) | 178 (54.4) | 169 (52.0) |
| Bendamustine, n (%) | 84 (25.7) | 94 (28.9) |
| PI3K/SYK inhibitor, n (%) | 11 (3.4) | 19 (5.8) |
| BCL2 inhibitor, n (%) | 7 (2.1) | 8 (2.5) |
| IMiD, n (%) | 6 (1.8) | 1 (0.3) |
| Alemtuzumab, n (%) | 2 (0.6) | 1 (0.3) |

*Complex karyotype is defined as having ≥ 3 abnormalities.
†For patients with any prior systemic anticancer therapy, percentages were based on number of patients in the intention-to-treat analysis set.
BCL2 B-cell lymphoma 2, CD20 cluster of differentiation 20, ECOG PS Eastern Cooperative Oncology Group performance status, IGHV immunoglobulin heavy chain variable region, IMiD immunomodulatory drug, PI3K phosphatidylinositol 3-kinase, SYK spleen associated tyrosine kinase.

TABLE 26

Treatment-Emergent Adverse Events Summary (Safety Population, N = 648)

| | | |
|---|---|---|
| ≥1 TEAE | 318 (98.1) | 321 (99.1) |
| Grade ≥ 3 | 218 (67.3) | 228 (70.4) |
| Grade ≥ 3 TEAEs Reported in > 2% of Patients in Either Study Arm | | |
| Neutropenia | 52 (16.0) | 45 (13.9) |
| Hypertension | 48 (14.8) | 36 (11.1) |
| COVID-19 pneumonia | 23 (7.1) | 13 (4.0) |
| COVID-19 | 22 (6.8) | 16 (4.9) |
| Pneumonia | 19 (5.9) | 26 (8.0) |
| Neutrophil count decreased | 17 (5.2) | 14 (4.3) |
| Syncope | 9 (2.8) | 4 (1.2) |
| Thrombocytopenia | 9 (2.8) | 12 (3.7) |

TABLE 26-continued

Treatment-Emergent Adverse Events Summary
(Safety Population, N = 648)

| | | |
|---|---|---|
| Anemia | 7 (2.2) | 8 (2.5) |
| Atrial fibrillation | 6 (1.9) | 12 (3.7) |
| Blood pressure increased | 4 (1.2) | 10 (3.1) |
| Serious AEs | 136 (42.0) | 162 (50.0) |
| AEs leading to dose reduction | 40 (12.3) | 55 (17.0) |
| AEs leading to dose interruption | 162 (50.0) | 184 (56.8) |
| AEs leading to treatment discontinuation | 50 (15.4) | 72 (22.2) |
| AEs leading to death | 33 (10.2) | 36 11.1) |

*All AEs summarized had an onset from the time of first dose of study drug up to 30 days after the last dose of study drug or the day prior to initiation of a new CLL/SLL therapy, whichever occurs first. TEAE treatment-emergent adverse event.

Thus, zanubrutinib (a BTK inhibitor) demonstrated the improved PFS probability compared to other major BTK inhibitors, e.g., ibrutinib and acalabrutinib, based on the head-to-head studies of BTKi monotherapy. Furthermore, zanubrutinib (a BTK inhibitor) significantly improved PFS compared with another major BTK inhibitor, i.e., ibrutinib, and was associated with fewer cardiac adverse events in patients with relapsed/refractory CLL/SLL. This is the first demonstration of PFS superiority of zanubrutinib in a head-to-head comparison of BTK inhibitors for CLL.

The inventors have found that the use of 320 mg BID (a total daily dose of 640 mg) of zanubrutinib on a patient receiving a moderate CYP3A inducer leads to exposure (e.g., AUC or Cmax) similar to that on a patient receiving 160 mg BID of zanubrutinib (a total daily dose of 320 mg). The coadministration of 320 mg BID (a total daily dose of 640 mg) of zanubrutinib with a moderate CYP3A inducer will lead to the similar therapeutic results found in this study, i.e., improved PFS compared with another major BTK inhibitor, i.e., ibrutinib, and fewer cardiac adverse events in patients with relapsed/refractory CLL/SLL.

Example 4

The entire disclosure of NCT04116437 on ClinicalTrials.gov is incorporated herein by reference.

Study Objectives

Primary Objective

To evaluate the safety of zanubrutinib in patients with previously treated chronic lymphocytic leukemia (CLL)/small lymphocytic lymphoma (SLL), Waldenström macroglobulinemia (WM), mantle cell lymphoma (MCL), or marginal zone lymphoma (MZL) intolerant of prior ibrutinib and/or acalabrutinib treatment as defined per protocol, compared with their ibrutinib and/or acalabrutinib intolerance adverse event profile as assessed by the recurrence and the change in severity of adverse events Secondary Objective To evaluate the efficacy of zanubrutinib in patients with previously treated CLL/SLL, WM, MCL, or MZL intolerant of prior ibrutinib and/or acalabrutinib treatment as measured by:

Overall response rate (ORR), investigator assessed
Disease control rate (DCR), investigator assessed
Progression-free survival (PFS), investigator assessed
Health-related quality of life (QoL)

Exploratory Objective

To evaluate improvements in response quality upon transition to zanubrutinib among patients with a previous response or stable disease who received ibrutinib and/or acalabrutinib treatment To evaluate data quality and feasibility of Self-administered Activity and QoL Questionnaire, which was a device-based questionnaire and activity tracker concerning patient activity and QoL Investigational Plan Overall Study Design and Plan: Description This was a Phase 2, multicenter, single-arm, monotherapy study of zanubrutinib in patients with previously treated CLL/SLL, WM, MCL, or MZL who were intolerant to prior ibrutinib treatment only (Cohort 1), or prior acalabrutinib treatment alone or with prior ibrutinib treatment (ie, acalabrutinib ±ibrutinib; Cohort 2) as defined per protocol.

Cohort 1: Intolerant to Ibrutinib Treatment

This study intends to enroll approximately 50 patients in Cohort 1.

Cohort 2: Intolerant to Acalabrutinib±Ibrutinib Treatment

In some cases patients intolerant to acalabrutinib were also intolerant to ibrutinib. This study intends to enroll up to approximately 40 patients (minimum 20) in Cohort 2.

Patients with documented progressive disease during ibrutinib and/or acalabrutinib treatment were excluded.

The primary endpoints were the recurrence and the change in severity of ibrutinib and acalabrutinib intolerance events compared with corresponding treatment-emergent adverse events within each patient. In this document, the term "adverse event" refers to a "treatment-emergent adverse event" unless otherwise stated. Hereafter, the full "treatment-emergent adverse event" was not used.

Overall response was assessed as a secondary endpoint per the 2008 International Workshop on Chronic Lymphocytic Leukemia (iwCLL) guidelines with modification for treatment-related lymphocytosis in patients with CLL; per the Lugano Classification for NHL in patients with SLL, MCL, or MZL; and based on the serum immunoglobulin M (IgM) level and modified sixth International Workshop on Waldenström Macroglobulinemia (IWWM) response criteria in patients with WM. PFS and patient-reported outcomes were assessed as secondary efficacy endpoints.

Patients receive oral zanubrutinib at either 160 mg twice daily or 320 mg once daily on Days 1 to 28 of each 28-day cycle. Investigators in conjunction with patients select the dose regimen to employ; however, once a regimen was chosen, change was not allowed.

Study treatment commences on C1D1 and continues until disease progression, unacceptable toxicity, treatment consent withdrawal, or study termination, whichever occurs first. Approximately 30 days after the date of permanent study drug discontinuation, a safety follow-up visit was required. Patients who permanently discontinue treatment remain in the study and enter long-term follow-up where they were monitored for survival status and subsequent anticancer therapies. All subsequent study visits and assessments were scheduled based on the C1D1 date. Survival status and subsequent therapies for CLL/SLL, WM, MCL, or MZL were assessed approximately every 6 months by either telephone or in-person contact until patient's end of study.

No formal interim analyses were planned for this study. Summaries and analyses of subsets of the study data might be performed on a periodic basis for submission to professional meetings, manuscript preparations, and for internal decision-making, at BeiGene's discretion.

Discussion of the Study Design, Including the Choice of Control Groups

This was a single-arm, monotherapy study without an active control group. The study was designed to evaluate the safety of zanubrutinib monotherapy with respect to the recurrence of adverse events that led to the intolerance of ibrutinib and/or acalabrutinib, and to evaluate the change in severity of recurrent intolerant events in patients with previously treated CLL/SLL, WM, MCL, or MZL. The study enrolls 2 patient cohorts:

Cohort 1: patients who were intolerant only to prior ibrutinib

Cohort 2: patients who were intolerant to prior acalabrutinib only or
  prior acalabrutinib and prior ibrutinib Patients receive oral zanubrutinib at either 160 mg twice daily or 320 mg once daily. At the time of this clinical study report, the 2 chosen dosages have been approved for the following indications in several countries, including the United States and Canada:

Treatment of adult patients with WM

Treatment of adult patients with MCL who have received ≥1 line of prior therapy

Treatment of adult patients with relapsed or refractory MZL who have received ≥1 prior anti-CD20-based therapy Zanubrutinib was also being investigated in other B-cell malignancies and in autoimmune disease.

Disease Assessments

Overall response was assessed by the investigator and was based on the following:

Imaging studies (computed tomography [CT] with/without contrast, positron emission tomography [PET], PET/CT, or magnetic resonance imaging [MIll])

Laboratory assessments (lymphocytes, platelets, hemoglobin, neutrophils, IgM)

Physical findings (enlargement of liver, spleen, lymph nodes)

Bone marrow examination

Disease-related constitutional symptoms

Starting at C4D1, frequency of disease assessments was as follows:

Treatment period: every 3 cycles
Safety follow-up: 30 days after last dose date
Long-term follow-up: every 6 months Imaging scans were reviewed locally as part of the response assessments and response assessments were rendered by the investigator.

All patients were required to undergo a contrast enhanced CT scan at screening.

For patients with screening lymphadenopathy (longest diameter >1.5 cm) and/or organomegaly (spleen >13 cm or liver assessed as enlarged by investigator), on-study CT scans were to be performed at C4D1, C7D1, C10D1, C13D1, C19D1, C25D1, and every 12 cycles thereafter until disease progression, death, lost-to-follow-up, withdrawal of consent, or end of study, whichever occurs first.

For non-WM patients without lymphadenopathy or organomegaly at screening, CT scans were to be performed at C7D1, C13D1, C19D1, C25D1, and every 12 cycles thereafter until disease progression, death, lost-to-follow-up, withdrawal of consent, or end of study, whichever occurs first.

For patients with WM without lymphadenopathy or organomegaly at screening, on-study CT scans were performed at the discretion of the investigator.

Definition of Intolerance

Intolerance was defined as an unacceptable toxicity such that treatment should be discontinued per investigator opinion despite optimal supportive care.

For ibrutinib, an intolerable event was said to occur if any of the following occurred:

≥1 Grade 2 or higher nonhematologic toxicities lasting >7 days (with or without treatment)

≥1 Grade 3 or higher nonhematologic toxicities of any duration

≥1 Grade 3 neutropenia with infection or fever of any duration

Persistent Grade 4 hematologic toxicities leading to therapy cessation per investigator decision due to toxicity (not progression)

For acalabrutinib, an intolerant event was said to occur if any of the following occurred:

≥1 Grade 1 or higher nonhematologic toxicities lasting >7 days (with or without treatment)

≥1 Grade 3 or higher nonhematologic toxicities of any duration

≥1 Grade 3 neutropenia with infection or fever of any duration

Persistent Grade 4 hematologic toxicities leading to therapy cessation per investigator decision due to toxicity (not progression)

≥1 Grade 1 nonhematologic toxicities of any duration with ≥3 recurrent episodes

Inability to use acid-reducing agents or anticoagulants (e.g., proton pump inhibitors, warfarin) due to concurrent acalabrutinib use Intolerance to ibrutinib and/or acalabrutinib may include, but does not require, the need for 1 or more dose reduction and/or treatment interruption.

Selection of Study Population

The inclusion and exclusion criteria described below reflect the most current version of the study protocol.

Inclusion Criteria

For inclusion into the study, patients were required to fulfill all of the following criteria:

Age 18 years or older who received treatment with ibrutinib and/or acalabrutinib for a minimum of 4 weeks prior to enrollment.

Patients must meet disease criteria requiring treatment for their respective disease prior to initiation of ibrutinib or acalabrutinib as follows:

CLL or SLL that met the diagnostic criteria promulgated by iwCLL in patients with a requirement for treatment;

Histologically confirmed diagnosis of MCL based on the World Health Organization 2016 classification of tumors of hematopoietic and lymphoid tissue;

Histologically confirmed diagnosis of MZL requiring treatment, including splenic, nodal, and extranodal subtypes. Gastric MZL must be either *H. pylori* negative or must be *H. pylori*-positive disease that has remained stable, progressed, or relapsed following antibiotic therapy. Patients with a screening immunoelectrophoresis result indicating a monoclonal spike must have a possible diagnosis of WM ruled out; or Clinical and definitive histologic diagnosis of WM meeting at least one criterion for treatment according to consensus panel criteria from the seventh IWWM.

Ibrutinib and acalabrutinib intolerance* was defined as an unacceptable toxicity where, in the opinion of the investigator, treatment should be discontinued in spite of optimal supportive care as a result of one of the following:

For ibrutinib and acalabrutinib intolerance events:

1 or more ≥Grade 2 nonhematologic toxicities for >7 days (with or without treatment);

1 or more ≥Grade 3 nonhematologic toxicity of any duration;

1 or more Grade 3 neutropenia with infection or fever of any duration; or

Grade 4 heme toxicity which persists to the point that the investigator chose to stop therapy due to toxicity NOT progression;

For acalabrutinib intolerance events only:

1 or more ≥Grade 1 nonhematologic toxicities of any duration with ≥3 recurrent episodes; or 1 or more ≥Grade 1 nonhematologic toxicities for >7 days (with or without treatment); or Inability to use acid-reducing agents or anticoagulants (e.g., proton pump inhibitors, warfarin) due to concurrent acalabrutinib use.

*Note: Intolerance to ibrutinib and/or acalabrutinib may include but does not require the need for one or more dose reduction and/or treatment interruption.

Ibrutinib- and/or acalabrutinib-related ≥Grade 2 toxicities must have resolved to ≤Grade 1 or baseline prior to initiating treatment with zanubrutinib. Grade 1 acalabrutinib-related toxicities must have resolved to Grade 0 or baseline prior to initiating treatment with zanubrutinib.

ECOG performance status of 0, 1, or 2.

Absolute neutrophil count ≥1000/mm$^3$ with or without growth factor support and platelet count ≥50,000/mm$^3$ (may be post-transfusion), on or prior to C1D1 of zanubrutinib.

Patient must have adequate kidney and liver function prior to C1D1 of zanubrutinib defined as follows:

Creatinine clearance ≥30 mL/min (as estimated by the Cockcroft-Gault equation or the Modification of Diet in Renal Disease equation, or as measured by nuclear medicine scan or 24-hour urine collection).

Aspartate aminotransferase (AST)/alanine aminotransferase (ALT)≤3.0×upper limit of normal unless due to CLL/SLL, WM, MCL, or MZL.

Serum total bilirubin <2.0×upper limit of normal (unless documented Gilbert's syndrome).

Female patients of childbearing potential must practice highly effective methods of contraception initiated before first dose of study drug, for the duration of the study, and for ≥90 days after the last dose of zanubrutinib.

Male patients were eligible if vasectomized; otherwise, they must agree to the use of barrier contraception combined with other highly effective methods during the study treatment period and for ≥90 days after the last dose of zanubrutinib.

Ability to provide written informed consent and can understand and comply with the requirements of the study.

Exclusion Criteria

Any of the following was regarded as a criterion for exclusion from the study:

Known prolymphocytic leukemia or history of, or currently suspected, Richter's transformation (biopsy based on clinical suspicion may be needed to rule out transformation).

This exclusion criterion was removed as of Protocol Amendment 3.0.

Clinically significant cardiovascular disease including the following:

Myocardial infarction within 6 months before the screening.

Unstable angina within 3 months before the screening.

New York Heart Association class III or IV congestive heart failure.

History of sustained ventricular tachycardia, ventricular fibrillation, and/or Torsades de Pointes.

QT interval corrected by Fridericia's formula >480 milliseconds.

History of Mobitz II second-degree or third-degree heart block without a permanent pacemaker in place.

History of waschemic stroke within 180 days before first dose of zanubrutinib.

History of central nervous system hemorrhage.

Prior malignancy within the past 3 years, except for curatively treated basal or squamous cell skin cancer, superficial bladder cancer, or carcinoma in situ of the cervix or breast. Patients with cancers of low metastatic potential based on a pathologist's opinion may be included in the trial.

History of inherited or acquired hemorrhagic coagulopathy.

Unable to swallow capsules, or disease significantly affecting gastrointestinal function such as malabsorption syndrome, resection of the stomach or small bowel, bariatric surgery procedures, symptomatic inflammatory bowel disease, or partial or complete bowel obstruction.

Active fungal, bacterial, and/or viral infection requiring systemic therapy.

Known central nervous system involvement by leukemia or lymphoma.

Documented progressive disease during ibrutinib and/or acalabrutinib treatment. Note: A disease flare meeting progressive disease criteria while the patient was off ibrutinib and/or acalabrutinib treatment was not considered to be true progressive disease.

Underlying medical conditions that, in the investigator's opinion, will render the administration of study drug hazardous or obscure the interpretation of toxicity or adverse events.

Known infection with human immunodeficiency virus (HIV) or serologic status reflecting active viral hepatitis B (HBV) or viral hepatitis C (HCV) infection as follows:

Patients who were seropositive for hepatitis B surface antigen were ineligible. Patients seropositive for hepatitis B core antibody, but negative for hepatitis B surface antigen were eligible if HBV DNA was undetectable (<20 IU), and if they were willing to undergo monitoring for HBV reactivation while on study.

Presence of HCV antibody. Patients with HCV antibody were eligible if HCV RNA was undetectable.

History of opportunistic infection while on ibrutinib and/or acalabrutinib (e.g., JC virus infection; *Pneumocystis jiroveci* infection).

Major surgery within 4 weeks of the first dose of study drug.

Pregnant or lactating women.

Ongoing alcohol or drug addiction.

Prior exposure to zanubrutinib or hypersensitivity to zanubrutinib formulation excipients.

Concurrent participation in another therapeutic clinical trial.

Have received any anticancer therapy (other than immunotherapy) for CLL/SLL, WM, MCL, and MZL <7 days before any screening assessments were performed or any immunotherapy treatment, taken alone or as part of a chemo-immunotherapy regimen, <4 weeks before any screening assessments were performed.

Requires ongoing need for corticosteroid treatment >10 mg daily of prednisone or equivalent corticosteroid. Note: Systemic corticosteroids must be fully tapered off/discontinued ≥5 days before the first dose of study drug was administered.

Vaccination with a live vaccine ≤35 days before the first dose of study drug. Note: Seasonal vaccines for influenza were generally inactivated vaccines and were allowed. Intranasal vaccines were live vaccines and were not allowed.

Removal of Patients from Therapy or Assessment

Discontinuation from Study Treatment

Any of the following was considered adequate for permanent discontinuation of study drug:

Withdrawal of consent for further study participation.

Pregnancy.

The investigator or sponsor determines it was in the best interest of the patient.

Intercurrent illness that compromises the patient's ability to participate in the study.

Need for prohibited concomitant medication.

Start of alternative anticancer therapy to treat CLL/SLL, WM, MCL, or MZL or start of therapy for secondary malignancy that would interfere with assessment of zanubrutinib safety and efficacy, such as radiotherapy. Patients requiring surgery or hormonal therapy to treat secondary malignancies may continue study treatment.

Study drug interruption >28 days (unless agreed by the investigator and the medical monitor).

Significant, persistent, or recurrent adverse events.

Disease progression.

If possible, patients should remain on study treatment until disease progression was documented.

Patients with evidence of disease progression may continue study drug treatment if they were benefiting from the treatment in the judgment of the investigators, with approval from the medical monitor.

Premature Discontinuation from the Study

Premature discontinuation from the study was permitted under any of the following circumstances:

Patient withdrew consent

Death

Lost to follow-up

Study termination by sponsor

Physician decision

Other (specify)

Treatments

Treatments Administered

Patients in both cohorts receive oral zanubrutinib at either 160 mg twice daily or 320 mg once daily on Days 1 to 28 of each 28-day cycle. Patients/investigators may select either dose regimen; however, they may not switch the dose regimen during the study.

Dose Interruption and Modification

The guidelines below (Table 27) were followed for modification of zanubrutinib dosing for hematologic and nonhematologic toxicities. Laboratory events indicating liver or renal dysfunction were not considered asymptomatic laboratory events and should compel adherence to dose modification guidelines provided below.

TABLE 27

Zanubrutinib Dose Reduction Levels

| Toxicity occurrence | Dose level | Zanubrutinib dose | |
|---|---|---|---|
| First | 0 = starting dose | Restart at 160 mg twice daily | Restart at 320 mg once daily |
| Second | −1 dose level | Restart at 80 mg twice daily | Restart at 160 mg once daily |
| Third | −2 dose level | Restart at 80 mg once daily | |
| Fourth | Discontinue zanubrutinib | Discontinue zanubrutinib | |

Zanubrutinib may be restarted upon resolution of toxicity if interrupted for up to 28 consecutive days, per the investigator's discretion. If, in the investigator's opinion, it was in the patient's best interest to restart treatment after >28 consecutive days of interruption, written approval must be obtained from the medical monitor.

If the investigator determines that a Grade 4 toxicity was possibly related to zanubrutinib, zanubrutinib must be held. After resolving to ≤Grade 1 or baseline, treatment may be restarted at a reduced dose (ie, −1 dose level). If the same toxicity reoccurs at a severity of Grade 4, zanubrutinib must be discontinued.

Selection of Doses in the Study

The total daily dose of zanubrutinib in this study was 320 mg administered orally as either 160 mg twice daily or 320 mg once daily, which were the current United States Food and Drug Administration (FDA)-approved dose regimens for patients with WM, MCL, or relapsed or refractory MZL. The doses selected for the study were based on results from the Phase 1 dose-finding Study BGB-3111-AU-003, which showed numerically comparable efficacy and safety profiles at doses of 320 mg once daily and 160 mg twice daily in patients with various B-cell malignancies. Efficacy demonstrated objective responses at all dose levels in patients with various B-cell malignancies including CLL, MCL, WM, and follicular lymphoma.

Selection and Timing of Dose for Each Patient

Patients receive oral zanubrutinib at either 160 mg twice daily or 320 mg once daily from C1D1 (with no treatment-free periods). Zanubrutinib capsules were administered orally with water in a fed or fasting state at approximately the same time every day. Patients were instructed that if a dose of the study drug was not taken at the scheduled time, and if the time to next dose was ≤8 hours, the patient should skip the dose and return to normal dosing intervals with the next dose thereafter. If a patient vomits after a dose of zanubrutinib, that dose was not to be repeated.

Blinding

This was an open-label study.

Prior and Concomitant Therapy

All medications and herbal supplements taken by or administered to the patient during the study and medications were to be discontinued ≤35 days before C1D1 and ≤30 days after the patient's last dose of zanubrutinib was recorded in the electronic case report form (eCRF), along with indication for use and dates of administration.

Prior medication was defined as any medication started before the first dose date. Concomitant medication was defined as any medication that either started before the first dose of study treatment and were continuing at the time of the first dose of study treatment, or started on or after the date of the first dose of study treatment up to 30 days after the patient's last dose or initiation of a new anticancer therapy, whichever came first.

For the purposes of determining if a medication should be classified as a concomitant medication, the data imputation rules stated in the statistical analysis plan (SAP) were used.

The following treatments were allowed:

COVID-19 vaccination(s).

Blood product transfusions and growth factor support per institutional standards of care.

Intermittent corticosteroids for non-CLL/SLL, WM, MCL, or MZL indications (e.g., to control or prevent infusion reactions, or for short durations [ie, ≤2 weeks of prednisone at a dose of 10 mg/day or equivalent, for example, to control a flare of chronic obstructive pulmonary disease (COPD)]). Chronic systemic corticosteroid use was not permitted, except for adrenal replacement.

Therapy to reduce symptoms per standard of care and institutional guidelines.

Infection prophylaxis per institutional standards of care.

The following treatments were prohibited:

Patients were not permitted to receive other anticancer therapy (including but not restricted to chemotherapy, immunotherapy, corticosteroids for treatment of CLL/SLL, WM, MCL, or MZL, experimental therapy, radiotherapy, and herbal medications) while on treatment in this study. Other anticancer therapies were not permitted until end of study treatment.

Use of live or live-attenuated vaccines was not recommended while receiving treatment with zanubrutinib.

Effects of Cytochrome P450-Inhibiting/Inducing Drugs on Exposure of Zanubrutinib Administration of zanubrutinib with strong/moderate cytochrome P450 (CYP)3A inhibitors or inducers, grapefruit juice, or Seville oranges should be with caution because they may affect the metabolism of zanubrutinib. Patients were encouraged not to administer concurrent strong/moderate CYP3A inhibitors and inducers and consider using alternative agents. If these agents were used, patients were to follow the dose modification table instructions in Table 28. The medical monitor was to be consulted in these situations.

Table 28: Dose Modification for Zanubrutinib when Coadministered with

| Strong/Moderate CYP3A Inhibitors or Inducers | | |
|---|---|---|
| CYP3A | Coadministered Drug | Recommended Use |
| Inhibition | Strong CYP3A inhibitor | 80 mg once daily |
|  | Moderate CYP3A inhibitor | 80 mg twice daily |
| Induction | Strong CYP3A inducer | Avoid concomitant use |
|  | Moderate CYP3A inducer | Avoid concomitant use. |

Abbreviations: CYP, cytochrome P450.

The exemplary moderate CYP3A inducer is rifabutin, bosentan, efavirenz, etravirine, modafinil, or nafcillin.

Effects of Zanubrutinib on Exposure of Other Concomitant Medications

A clinical drug-drug interaction study (Study BGB-3111-108) indicated that zanubrutinib was a mild inducer of CYP3A4 and CYP2C19. Narrow therapeutic index drugs that were metabolized by CYP3A4 (alfentanil, cyclosporine, dihydroergotamine, ergotamine, fentanyl, pimozide, quinidine, sirolimus, and tacrolimus), and CYP2C19 (e.g., S-mephenytoin) should be used with caution, as zanubrutinib may decrease the plasma exposures of these drugs.

Because ethinylestradiol (a key ingredient in a variety of combined oral contraceptives) was partly metabolized by CYP3A4, patients using hormonal contraceptives (e.g., birth control pills or devices) must use a barrier method of contraception (e.g., condoms) as well.

Repeated dosing of zanubrutinib increased exposure of digoxin (P-glycoprotein substrate) with a mean increase of 11% for werea under the plasma concentration-time curve from time 0 to the last measurable concentration ($AUC_{0-t}$) and 34% for maximum observe plasma concentration ($C_{max}$). The coadministration of oral P-glycoprotein substrates with a narrow therapeutic index (e.g., digoxin) were to be used with caution as zanubrutinib may increase their concentrations.

Effect of Hepatic Impairment on the Pharmacokinetics of Zanubrutinib

No dosage modification was recommended in patients with mild to moderate hepatic impairment. Patients with hepatic impairment were monitored for zanubrutinib adverse reactions.

Treatment Compliance

Home administration was detailed in the pharmacy manual. Patients were instructed to take the study drug exactly as prescribed. Diary cards were dispensed for each new cycle onto which the patient was requested to record the date and time of each study drug administration. Patients were requested to bring their patient-completed diary cards, unused medication, and all empty bottles to the study center at each visit. During each visit to the study center, patients were questioned regarding their compliance with study instructions.

The investigator was responsible for zanubrutinib accountability, reconciliation, and record maintenance. In accordance with all applicable regulatory requirements, the investigator or designated study center personnel maintain zanubrutinib drug accountability records throughout the course of the study. They document the amount of zanubrutinib received from BeiGene and the amount supplied and/or administered to and returned by patients, if applicable. Additionally, all dose modifications including the reason(s) were recorded on the appropriate eCRF.

After completion of the study, all unused zanubrutinib were inventoried and packaged for return shipment by designated study center personnel. The inventoried supplies were returned to BeiGene or destroyed onsite, after receiving written approval from BeiGene.

Efficacy and Safety Variables

Efficacy Assessments

Overall response was assessed by the investigator using the 2008 iwCLL criteria with modification for treatment-related lymphocytosis in patients with CLL; the Lugano Classification in patients with SLL, MCL, or MZL; and based on the serum IgM level and modified sixth IWWM response criteria in patients with WM. In the event of a treatment delay, disease assessments were to continue per the Schedule of Assessment and Procedure schedule.

Study Endpoints

Primary Endpoints

The study's primary endpoints were:

Recurrence of ibrutinib and/or acalabrutinib intolerant events while on zanubrutinib Change in severity of recurrent intolerant events Secondary Endpoints The study's secondary endpoints were:

ORR, defined as the proportion of patients achieving a best overall response (BOR) of CR, CRi, nodular partial response, partial response (PR), or partial response with lymphocytosis (PR-L) in patients with CLL; CR or PR in patients with SLL, MCL, or MZL; and CR, very good partial response, PR, or minor response (MR) in patients with WM before initiation of subsequent antineoplastic therapy.

DCR, defined as the proportion of patients who attain a BOR of stable disease or better before initiation of subsequent antineoplastic therapy.

Duration of response (DOR), defined as time from first dose date to date of first documented disease progression or death, whichever occurs first.

PFS, defined as time from first dose date to date of first documented disease progression or death, whichever occurs first.

Time to first response, defined as time from first dose to date of first qualifying response. For example, for a patient who attained a PR-L followed by PR for subsequent assessments, time to first response was the time from first dose to date of first PR-L.

Time to BOR, defined as time from first dose to date of best of overall response. For example, for a patient who attained a PR-L followed by PR at subsequent assessments, time to BOR was the time from first dose to date of first PR.

Health-related QoL as measured by the EQ-5D-5L and EORTC QLQ-C30 questionnaires.

Exploratory Endpoints

The study's exploratory endpoints were:

Improvements in response among patients who previously responded to ibrutinib and/or acalabrutinib upon transition to zanubrutinib Quality of data on QoL and activity while on zanubrutinib (as measured and reported using the Self-administered Activity and QoL Questionnaire Analysis Sets Safety Analysis Set: consists of patients who received at least 1 dose of zanubrutinib.

Efficacy Evaluable Set: consists of patients in the Safety Analysis Set who had a baseline disease assessment and >1 postbaseline disease assessment. Patients who discontinue from the study due to adverse events or death prior to their first scheduled disease assessment were included in this analysis set.

Efficacy Analyses

The primary efficacy analysis set used to summarize efficacy was the Safety Analysis Set. For response endpoints, additional supportive analysis used the Efficacy Evaluable Set.

Analysis of Overall Response and Disease Control

A patient's BOR was the best response recorded throughout the study prior to initiation of any new anticancer therapy and data cutoff. In some cases, the BOR could only be stable disease (e.g., if the patient was in CR at study entry) because patients were not required to progress prior to entering the study.

ORR was the proportion of patients who attained a BOR of:

PR-L or better (CR, CRi, nodular partial response, PR, PR-L) in patients with CLL;

PR or better (CR, PR) in patients with SLL, MCL, and MZL;

MR or better (CR, very good partial response, PR, MR) in patients with WM.

Per the Safety Analysis Set, patients without postbaseline disease assessments were classified as non-responders. ORR was summarized with 95% exact confidence interval. A sensitivity analysis was conducted in patients in the Efficacy Evaluable Set; patients who died or discontinued study prior to their first disease assessment due to adverse events were classified as non-responders.

An additional sensitivity analysis excludes patients with low disease burden at baseline. A patient was said to have low disease burden if all of the following criteria were met:

SLL/MCL/MZL: no splenomegaly, no hepatomegaly, no target lesions

CLL: no splenomegaly, no hepatomegaly, no target lesions, lymphocytes <4×10$^9$/L WM: no splenomegaly, no hepatomegaly, no target lesions, IgM within normal limits DCR was the proportion of patients who attain a BOR of stable disease or better.

Per the Safety Analysis Set, patients without postbaseline disease assessment were considered non-responders. DCR was summarized with 95% exact confidence intervals. A sensitivity analysis of DCR was conducted in patients in the Efficacy Evaluable Set; patients who died or discontinued study prior to their first disease assessment due to adverse events were classified as not achieving disease control. An additional sensitivity analysis of DCR excluded patients with low disease burden, as defined above.

Analysis of Other Response-Related Metrics

DOR, time to first response, and time to best response were summarized among patients in the Safety Analysis Set who achieved a BOR that was better than stable disease.

Analysis of DOR was the same as that for PFS (see Analysis of Progression-Free Survival below).

Analysis of Progression-Free Survival

PFS was defined as the time from the first dose of study treatment to disease progression or death, whichever occurs first.

The PFS distribution and its related metrics such as median PFS and landmark rates were estimated using the Kaplan-Meier method with censoring rules as defined in Table 29.

PFS was analyzed overall, by disease type, and by cohort.

TABLE 29

Censoring Rules For The Analysis of Progression-Free Survival

| Scenario | Event Status | Progression-Free Survival Date |
|---|---|---|
| Progressive disease or death between planned disease assessments | Event | Date of first documented progressive disease or date of death, whichever occurs first |
| Death before first disease assessment | Event | Date of death |
| No postbaseline disease assessments | Censored | Date of first dose |
| New anticancer therapy started prior to progressive disease or death | Censored | Date of last disease assessment prior to initiation of new anticancer therapy |
| Death or progressive disease directly after missing at least 2 consecutive disease assessments | Censored | Date of last disease assessment prior to progressive disease or death |
| Alive and without progressive disease | Censored | Date of last disease assessment |

Health-Related QoL

Responses to the EORTC QLQ-C30 questionnaire were scored to functional, symptom, and global health status scales and summarized for each assessment time point.

Change from baseline of the global health status scale and functional scales were also summarized.

Change of EQ-5D-5L scores of the visual analogue scale from baseline were also summarized descriptively. The activities dimensions (mobility, self-care, pain, anxiety/depression and usual activates) were reported.

EORTC QLQ-C30 and EQ-5D-5L were analyzed overall and by cohort.

Subgroup Analyses

Subgroup analyses of efficacy endpoints were planned for:

cancer type (CLL/SLL, MCL, MZL, WM)

biomarker status such as BTK and PLCγ2 mutations treatment regimen (160 mg bid versus 320 mg once per day)

Safety Analyses

All safety analyses were performed using the Safety Analysis Set. Safety and tolerability were assessed, where applicable, by incidence, severity, and change from baseline for all relevant parameters that include adverse events, laboratory values, vital signs, physical examinations, and electrocardiogram findings.

Extent of Exposure

The following treatment exposure metrics were summarized descriptively:

Duration of study treatment.

Cumulative dose administered.

Actual dose intensity.

Relative dose intensity.

Dose reductions, drug interruptions, and drug withdrawal.

The actual dose intensity was defined as the cumulative dose (mg) taken based on the total daily dose divided by the duration of study treatment (days).

The relative dose intensity was defined as the ratio of the actual dose intensity to the planned dose intensity (320 mg/day) in percentage.

Analysis of Adverse Events

Adverse events were graded per National Cancer Institute Common Terminology Criteria for Adverse Events Version 5.0 (NCI-CTCAE v5.0). The adverse event verbatim descriptions were classified into standardized medical terminology using the Medical Dictionary for Regulatory Activities Version 25.0 (MedDRA v25.0) using the lowest level term closest to the verbatim term. The Preferred Term (PT) and primary System Organ Class (SOC) were also captured.

Adverse events were defined as those that had onset dates that were on or after the date of the first dose of study drug and up to:

30 days after the last dose of study therapy or the initiation of new anticancer therapy, whichever was earlier.

Adverse events (including serious adverse events), ≥Grade 3, treatment-related, or leading to treatment discontinuation) were summarized descriptively.

Adverse events of special interest were defined by the sponsor and summarized by adverse event of special interest category and PT for each of the following groups:

All adverse events of special interest

Grade 3 or higher adverse events of special interest

Serious adverse events of special interest

All deaths and the cause of death summary were classified by deaths within 30 days of last dose of study treatment and deaths more than 30 days after the last dose.

Listings of deaths/fatal adverse events, serious adverse events, and adverse events leading to dose modification or discontinuation of zanubrutinib were also provided.

Analysis of Primary Endpoints: Intolerant Adverse Events

The study's primary endpoint was the recurrence and change in severity of intolerant events (adverse events leading to the intolerance of prior ibrutinib and/or acalabrutinib therapies).

If while on zanubrutinib a patient experienced the same adverse event that led to their intolerance to ibrutinib, the patient was said to experience a recurrence of an ibrutinib intolerant event. If the maximum grade of the recurrent ibrutinib intolerant event was different from the maximum grade experienced on prior ibrutinib, the recurrent ibrutinib intolerant event was said to have a change in severity. Otherwise, the severity was said to be the same. For acalabrutinib intolerant events, recurrence and change in severity were defined similarly.

The number and proportion of the following were summarized:

patients who had a recurrence of any of their BTKi intolerant events, overall and by change in severity patients who had a recurrence of any of their ibrutinib intolerant events, overall and by change in severity patients who had a recurrence of any of their acalabrutinib intolerant events, overall and by change in severity any prior BTKi intolerant events that recurred, overall and by change in severity any prior ibrutinib intolerant events that recurred, overall and by change in severity any prior acalabrutinib intolerant events that recurred, overall and by change in severity In general, a patient reporting multiple events of the same term was counted only once; the maximum toxicity grade was used in determining severity change.

Exploratory Analyses

COVID-19 Related Summaries

To evaluate the pandemic's impact on the study, the following were summarized:

Patients who discontinued study drug or study for reasons related to COVID-19

Patients with important protocol deviations related to COVID-19

Patients diagnosed with COVID-19 infection

Serious adverse events experienced by patients infected with COVID-19

As >20% of patients were infected with COVID-19, the following was also summarized for the infected patients:

Prior and concomitant medications taken to treat COVID-19

Adverse event due to the infection, including the infections themselves

Determination of Sample Size

The study planned to enroll approximately 90 patients; approximately 50 patients in Cohort 1 and approximately 40 (minimum 20) patients in Cohort 2. The sample size calculation was based on the level of precision of the estimated primary endpoint incidences.

Efficacy Conclusions

Most patients in this study obtained clinical benefit from zanubrutinib, despite having been previously treated and discontinued from ibrutinib and/or acalabrutinib due to toxicity. Forty-six of the 68 patients (67.6%) in the Efficacy Evaluable Set showed a BOR that was better than stable disease, with most (45 of 68 patients [66.2%]) having PR as their BOR. Patients with WM had the highest response rate, with 10 of 11 patients (90.9%) having a BOR better than stable disease and 5 of 11 patients (45.5%) having very good partial response. Sixty-five of the 68 patients (95.6%) in the Efficacy Evaluable Set had a BOR of stable disease or better. In patients with WM, 11 of 11 (100%) patients had a BOR of stable disease or better.

At the time of the data cutoff, median DOR was not reached with an estimated probability of responding for at least 12 months of 91.8% (95% CI: 76.7% to 97.3%). In patients with WM, median DOR was also not reached, the estimated probability of responding for at least 12 months was 100% (95% CI: not estimable).

Overall, median PFS was not reached; the estimated event-free rate at 18 months was 80.4% (95% CI: 65.8% to 89.3%). Similarly, in patients with WM, median PFS was also not reached; the estimated event-free rate at 18 months was 100% (95% CI: not estimable).

The median OS follow-up time for all patients was 17.3 months, and patients had 89.3% chance of being alive after 24 months.

Self-reported QoL assessments implied there was no appreciable decrease in health-related QoL over the course of zanubrutinib treatment.

Safety Conclusions

As of the data cutoff, the adverse event profile of zanubrutinib in this study population of patients with CLL/SLL, WM, MCL, or MZL who had been previously treated with, and were intolerant to, ibrutinib or acalabrutinib was generally similar to that observed in completed and other ongoing clinical studies of zanubrutinib.

The incidences of deaths, serious adverse events, and adverse events leading to discontinuation were consistent with the baseline risk of the patient population and with the known safety profile of zanubrutinib. Most of the deaths were due to progressive disease, with just 1 death attributable to an adverse event, which was COVID-19 pneumonia. Aside from serious adverse events related to COVID-19, Atrial fibrillation (2 patients [2.8%]) was the only other serious adverse event that occurred in >1 patient in the study population.

The change from baseline in all parameters of hematology, chemistry, and vital signs were consistent with those observed for zanubrutinib in prior and ongoing studies.

The primary objective of this study was to evaluate the safety of zanubrutinib treatment in patients who had received prior treatment with ibrutinib and/or acalabrutinib and had adverse events that led to intolerance of these BTKis. The safety of zanubrutinib in these patient populations was evaluated by analyzing the recurrence of the reported adverse events associated with intolerance to the prior BTKis. More than half (56.6%) of all patients who were treated with zanubrutinib did not experience any recurrence of their intolerance event(s). Ninety-six of 141 intolerance events (68.1%) did not recur. No intolerance event recurred at a higher severity than the original event. The events that did recur on zanubrutinib were predominantly less severe than the original adverse event associated with the prior BTKi intolerance. Collectively, data from interim analysis suggest that zanubrutinib may have an improved safety profile with respect to these recurrent adverse events associated with ibrutinib and/or acalabrutinib intolerance and provides a viable treatment option for patients intolerant to ibrutinib or acalabrutinib.

Discussion and Overall Conclusions

Discussion

The BTKis ibrutinib and acalabrutinib have demonstrated high efficacy in patients with CLL/SLL, WM, MCL, and MZL, and these patients often undergo long-term treatment to maintain efficacy against their disease. However, long-term treatment was associated with significant toxicities, and high rates of treatment discontinuation due to adverse events have been reported for patients treated with ibrutinib or acalabrutinib.

Data from PK studies, as well as from completed and ongoing clinical studies suggest that zanubrutinib may be an effective treatment for patients who were intolerant to ibrutinib or acalabrutinib. This Phase 2 study was being conducted to evaluate the safety and efficacy of zanubrutinib in patients with CLL/SLL, WM, MCL, or MZL who were intolerant to ibrutinib and/or acalabrutinib. As of the data cutoff date, results from interim analysis of this Phase 2 study suggest that zanubrutinib can be administered after failure of acalabrutinib or ibrutinib due to intolerance.

Patients were enrolled in 1 of 2 cohorts. Patients in Cohort 1 were intolerant to prior ibrutinib treatment, and patients in Cohort 2 were intolerant to prior acalabrutinib treatment alone or with prior ibrutinib treatment (ie, acalabrutinib ±ibrutinib).

There were 33 active sites, of which 21 sites enrolled patients; all sites were located within the United States. The median time from initial diagnosis to first dose of study drug was 51.2 months overall and similar in patients with WM; the time was longer for Cohort 1 than Cohort 2, as expected due to ibrutinib being the only treatment option until acalabrutinib was approved. The median time to BOR was similar across all cohorts at 5.6 months.

Zanubrutinib treatment was generally well-tolerated in patients who had experienced adverse events that led to intolerance and discontinuation of their prior BTKi treatment, with a safety profile consistent with those characterized in completed and ongoing studies of zanubrutinib.

The primary endpoint was the safety of zanubrutinib treatment in patients who had adverse events that led to intolerance of their prior treatment with ibrutinib and/or acalabrutinib BTKis, as assessed by evaluating the recurrence of the reported adverse events associated with intolerance to these prior BTKis. More than half (56.6%) of all patients who were treated with zanubrutinib did not experience any recurrence of their intolerance events. Intolerance adverse events most likely to recur were Diarrhoea, Hemorrhage, and Headache; those least likely to recur were Rash, Hypertension, Arthralgia, Constipation, Muscle spasms, Stomatitis, Atrial fibrillation. The adverse events that did recur on zanubrutinib were predominantly less severe than the original adverse event associated with the prior BTKi intolerance. These data suggest that zanubrutinib may have an improved safety profile with respect to these recurrent adverse events associated with ibrutinib and/or acalabrutinib intolerance.

Most of the zanubrutinib-treated patient population in this study had a best response of PR (45 of 68 patients; 66.2%). Patients with WM had the best response to treatment, with 10 of the 11 patients in the Efficacy Evaluable Set displaying a best response of PR. A subset analysis looking at age, gender, bulky disease, del(17p) status, TP53 mutation, immunoglobulin variable region heavy chain mutation, and dosing regimen showed benefit across all subgroups. Due to the long natural history of these diseases the OS results were not yet available.

The QoL data using the EORTC QLC-C30 and EQ-5D-5L was in line with the tolerability data and showed positive change from baseline, with no significant change in values through Cycle 19, which was consistent with no appreciable loss in QoL during the period that the patients received zanubrutinib treatment.

The effect of COVID-19 on the study was generally limited. There were 20 patients among the 72 patients in the Safety Analysis Set who were affected by COVID-19. This subset of patients affected by COVID-19 had similar level of drug exposure as those in the entire Safety Analysis Set.

Most patients had not experienced a reoccurrence of their previous intolerant adverse event(s) during zanubrutinib treatment. Less than half (44.4%) of all patients treated with zanubrutinib experienced a reoccurrence of their previously intolerant adverse event(s). In addition, the 67.6% ORR and 95.6% DCR for all patients enrolled indicate that the majority of patients who were intolerant to ibrutinib and/or acalabrutinib were able to tolerate and receive clinical benefit in response to zanubrutinib.

Conclusions

The results of this analysis indicate that zanubrutinib provides clinical benefit and presents a viable treatment option for patients who were intolerant to ibrutinib and/or acalabrutinib. The data suggest that most of these patients were unlikely to experience a recurrence of their prior intolerance event and were able to obtain clinical benefit as evidenced by the ORR. In addition, there was no significant decrease in the QoL for these patients while being treated with zanubrutinib.

Additional Analysis

Background

The study aimed to determine whether zanubrutinib would prolong treatment duration by minimising treatment-related toxicities in patients with previously treated B-cell malignancies.

Methods

In this ongoing, phase 2, multicentre, open-label, single-arm study, patients aged ≥18 with previously treated B-cell malignancies who became intolerant of ibrutinib and/or acalabrutinib were administered zanubrutinib 160 mg twice daily or 320 mg once daily per investigator (NCT04116437). Primary endpoint was the recurrence and change in severity of intolerance events per protocol.

Findings 67 patients (36 male, 31 female) who were intolerant of ibrutinib (57; cohort 1) or of acalabrutinib (ten; cohort 2) were enrolled, 63 (94.0%) patients were White. Most intolerance events (81/115 [70.4%] ibrutinib; 15/18 [83.3%] acalabrutinib) did not recur with zanubrutinib. Of the recurring events, 7/34 (20.6%) ibrutinib-intolerance events and 2/3 (66.6%) acalabrutinib-intolerance events recurred at the same severity with zanubrutinib; 27/34 (79.4%) ibrutinib-intolerance events and 1/3 (33.3%) acalabrutinib-intolerance events recurred at a lower severity with zanubrutinib. No events recurred at higher severity. No grade 4 intolerance events recurred. Sixty-four/67 patients experienced ≥1 adverse event (AE) with zanubrutinib; most common AEs include contusion (15/67 [22.4%]), fatigue (14/67 [20.9%]), myalgia (ten/67 [14.9%]), arthralgia (nine/67 [13.4%]), and diarrhoea (nine/67 [13.4%]). Atrial fibrillation occurred in three/67 patients (4.5%; all grade 2). Eight/67 (11.9%) serious AEs occurred. One/67 (1.5%) death occurred due to COVID-19 pneumonia.

Interpretation

Thus, the results demonstrated that zanubrutinib (a BTK inhibitor) is a safe and effective treatment for patients with B-cell malignancies who exhibit intolerance to other major BTK inhibitors, e.g., ibrutinib and/or acalabrutinib.

Provided herein are safety and efficacy outcomes of the phase 2 study of zanubrutinib monotherapy in patients with B-cell malignancies who discontinued ibrutinib and/or acalabrutinib treatment due to intolerance.

Methods

Study Design and Participants

This ongoing, phase 2, multicentre, open-label, single-arm study evaluates the safety and efficacy of zanubrutinib in patients with B-cell malignancies who exhibited intolerance of ibrutinib and/or acalabrutinib.

The study design comprised two cohorts. Cohort 1 included 57 patients intolerant of only ibrutinib. Cohort 2 included ten patients intolerant of acalabrutinib. Zanubrutinib was administered as either 160 mg twice daily (bid) or 320 mg once daily (qd) on a 28-day cycle; dosing schedule was decided in collaboration between patients and investigators. Patients were not allowed to switch schedule during the study. Before zanubrutinib monotherapy was initiated, all grade ≥2 intolerance events must have had resolved to grade 1 or better; all grade 1 intolerance events must have had fully resolved.

The patient population comprised adults aged ≥18 years with a confirmed diagnosis of CLL, small lymphocytic lymphoma (SLL), MCL, MZL, or WM who were intolerant of ibrutinib and/or acalabrutinib. Patients were required to have had one treatment prior to the initial ibrutinib and/or acalabrutinib treatment and must have had ≥1 protocol-specified toxicity that defined ibrutinib and/or acalabrutinib intolerance (Protocol). Patients' sex was self-reported. Patients who had documented progressive disease (PD) during ibrutinib and/or acalabrutinib treatment were excluded. Pregnant or lactating female patients were excluded. Ibrutinib and acalabrutinib intolerance was investigator-assessed and defined as unacceptable toxicity that mandated treatment discontinuation. Ibrutinib intolerance was defined as grade ≥2 non-haematologic toxicity lasting >7 days regardless of intervention, grade ≥3 non-haematologic toxicity of any duration, grade 3 neutropenia with infection or fever, or grade 4 haematologic toxicity leading to an investigator-assessed decision to stop therapy. Intolerance of acalabrutinib was further defined as any-grade non-haematological toxicity lasting for either 7 days or recurring three times, or the inability to use acid-reducing agents or anticoagulants due to concurrent acalabrutinib. Patients must have had an Eastern Cooperative Oncology Group performance status of 0, 1, or 2. All patients must have practiced highly effective methods of contraception during the study treatment period and for ≥90 days after the last dose of zanubrutinib.

This study was conducted in accordance with the declaration of Helsinki and the International Conference on Harmonisation Guidelines for Good Clinical Practice. Written informed consent was obtained from each patient and Institutional Review Board approval was obtained at each study site.

Procedures

Zanubrutinib capsules were taken orally with water and with or without food. Imaging and laboratory assessments at study entry were considered baseline for response assessment; patients were not required to meet criteria for initiation of treatment at study entry. Response was assessed according to the modified International Workshop on CLL (iwCLL) criteria for patients with CLL; Lugano classification for patients with SLL, MCL, or MZL; and modified $6^{th}$ International Workshop on WM for patients with WM, with the assessments occurring every 3 cycles after starting zanubrutinib. Bone marrow biopsy was required for confirmation of a complete response (CR).

Disease status was assessed by computed tomography or positron emission tomography/computed tomography, physical examination, and laboratory tests. Radiographic disease assessment was performed at baseline, every three cycles for the first 12 cycles, every six cycles for the next 12 cycles, and every 12 cycles thereafter. For patients with CLL/SLL, MCL, or MZL with neither lymphadenopathy nor organomegaly at screening, imaging started at cycle seven, then every six cycles until after cycle 25, and then every 12 cycles thereafter. For patients with WM with neither lymphadenopathy nor organomegaly at screening, on-study imaging was not required.

AEs and prior AEs for ibrutinib and acalabrutinib were evaluated and graded according to the Common Terminology Criteria for Adverse Events (CTCAE) version 5.0. In patients with CLL, treatment-emergent cytopenias were graded per iwCLL criteria. Prior ibrutinib- and acalabrutinib-intolerant AEs were recorded at study entry. An intolerant AE was considered to have recurred if the same Medical Dictionary for Regulatory Activities (MedDRA) preferred term, independent of grade, occurred while on zanubrutinib therapy.

Patients' peripheral blood was collected before treatment and at or after the time of disease progression. DNA was isolated from peripheral blood mononuclear cells or plasma, and the mutational status of BTK and PLCG2 genes was assessed using a targeted next-generation sequencing 106-gene HEME panel (Predicine, Hayward, Calif.).

Kinase selectivity of zanubrutinib, ibrutinib, acalabrutinib, and acalabrutinib's major metabolite, M27, was assessed by Reaction Biology Corp (Malvern, Pa., USA) at their respective 100× $IC_{50}$ (BTK) concentrations ($IC_{50}$ of zanubrutinib: 0.71±0.09 nM, ibrutinib: 0.32±0.09 nM, acalabrutinib: 24±9.2 nM, and M27: 63±28 nM).

Outcomes

The primary endpoint was to determine the recurrence and change in severity of ibrutinib and/or acalabrutinib-intolerance events based on investigator-assessed AEs. Secondary endpoints included investigator-assessed overall response rate (ORR), defined as partial response (PR) with lymphocytosis (PR-L) or better in patients with CLL, PR or better in patients with SLL, MCL, or MZL, and minor response or better in patients with WM; disease control rate (DCR), defined as SD or better; duration of response (DOR), defined as time from initial response to disease progression or death; and progression-free survival (PFS), defined as time from first dose of zanubrutinib to disease progression or death. An exploratory analysis was performed retrospectively to examine the molecular resistance to BTKi. Additional secondary and exploratory endpoints of patient-reported outcomes and quality of life data will be reported in a separate publication.

Statistical Analysis

Descriptive statistics were used to summarise baseline characteristics, disposition, safety (including recurrence of prior BTKi-intolerance events), ORR, DCR, and drug exposure. PFS, DOR, and safety were assessed in all patients treated with >1 dose of zanubrutinib. ORR and DCR were assessed in efficacy-evaluable patients (patients with >90 days of study duration). Sensitivity analysis excluding patients with low disease burden at study entry was also performed. Confidence intervals for rates of recurrent intolerant events, ORR, and DCR were calculated based on an exact method. PFS and DOR were summarised by the Kaplan-Meier method. At the time of data cutoff, patients were censored if there were no documented disease progression or death, had no post-baseline disease assessment, initiated non-study anti-cancer therapy prior to progression, or progressed or died after >1 missed disease assessments. The investigator determined whether a patient was assessable for disease. The planned sample size was maximum 90 (minimum 70) patients, calculated based on precision of the rate of recurrence of intolerant events. No formal interim analysis was planned. All statistical analyses were conducted using SAS version 9.4. This study is registered with ClinicalTrials.gov (NCT04116437), the entire content of which is incorporated herein by reference.

Results

Figure 20:
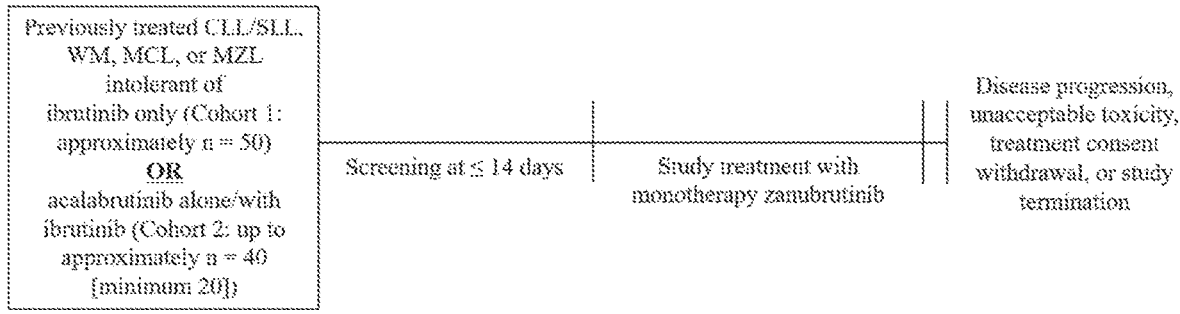
FIG. 20 depicts the Study Schema of Example 3. Abbreviations: CLL, chronic lymphocytic leukemia; MCL, mantle cell lymphoma; MZL, marginal zone lymphoma; SLL, small lymphocytic lymphoma; WM, Waldenström macroglobulinemia.

This study enrolled 67 patients in 20 centres across the US as of the data cutoff and aims to enrol up to 90 patients by study completion. Fifty-seven patients (44 CLL/SLL, nine WM, two MCL, two MZL) intolerant of ibrutinib were enrolled in cohort 1, and ten patients (six CLL/SLL, two WM, one MCL, one MZL) intolerant of acalabrutinib only (four) or to acalabrutinib and ibrutinib (six) were enrolled in cohort 2 (FIG. 20). Sixty-four patients were included in the efficacy and safety analyses. Thirty-six/67 (53.7%) patients were men 31/67 (46.3%) were women, and 63/67 (94.0) were White. The median age was 71.0 years (range, 49-91) in cohort 1 and 73.5 years (range, 65-83) in cohort 2. At study entry, most (45/67 [67.2%]) patients had low-risk disease, defined as Binet A or B, Ann Arbor stage I or II, or WM International Staging System low-risk. Nine/67 (13.4%) patients entered the study with baseline disease parameters that precluded them from any responses other than SD, CR, or PD. Patients in cohorts 1 and 2 received a median of one prior regimen (range, 1-12) and 2.5 prior regimens (range, 1-5), respectively. Median cumulative duration of ibrutinib treatment for cohort 1 was 10.6 months (range, 1.1-73.7) and acalabrutinib treatment for cohort 2 was 3.3 months (range, 0.5-26.9). Fifty-six/57 (98.2%) patients from cohort 1 and all ten patients from cohort 2 received ibrutinib or acalabrutinib, respectively, as their most recent prior treatment. Median duration from the end of last BTKi treatment to zanubrutinib initiation was 1.0 month (range, 0.5-34.8) for cohort 1 and 1.5 months (range, 0.5-10.0) for cohort 2. The median duration of zanubrutinib treatment was 11.6 months (range, 0.6-20.3) in cohort 1 and 9.8 months (range, 0.5-12.0) in cohort 2.

Sixty-two patients reported 115 ibrutinib-intolerance events (1 grade 1, 72 grade 2, 38 grade 3, and four grade 4) and ten patients reported 18 acalabrutinib-intolerance events (14 grade 2, and four grade 3, respectively). Two patients reported the same intolerance event on ibrutinib and acalabrutinib. Median number of intolerance events per patient was two (range, 1-5) for both cohorts. The most common ibrutinib-intolerance events reported were fatigue (13/62 [20.9%]), hypertension (11/62 [17.7%]), arthralgia (ten/62 [16.1%]), rash (ten/62 [16.1%]), and atrial fibrillation (ten/62 [16.1%]); grades 2, 3, and 4 events were reported by 31/62 (50.0%), 28/62 (45.1%), and three/62 (4.8%) patients, respectively. The most common grade ≥3 ibrutinib-intolerance events were atrial fibrillation (seven/62 [11.3%]), hypertension (six/62 [9.7%]), and fatigue (four/62 [6.5%]). Among the ten patients who reported acalabrutinib-intolerance events, the most common events were arthralgia (four/10 [40.0%]) and myalgia (three/10 [30.0%]); grades 2 and 3 events were reported by seven/10 (70.0%) and three/10 (30.0%) patients, respectively. The most common grade 3 acalabrutinib-intolerance events were abdominal pain, arthralgia, insomnia, and myalgia (one/10 [10.0%] each). The median follow-up time was 12.0 months (interquartile range [IQR] defined as Q1-Q3, 8.2-15.6 months), 12.3 months (IQR, 8.3-16.3) for cohort 1, and 10.4 months (IQR, 2.3-12.0) for cohort 2.

Figure 21:
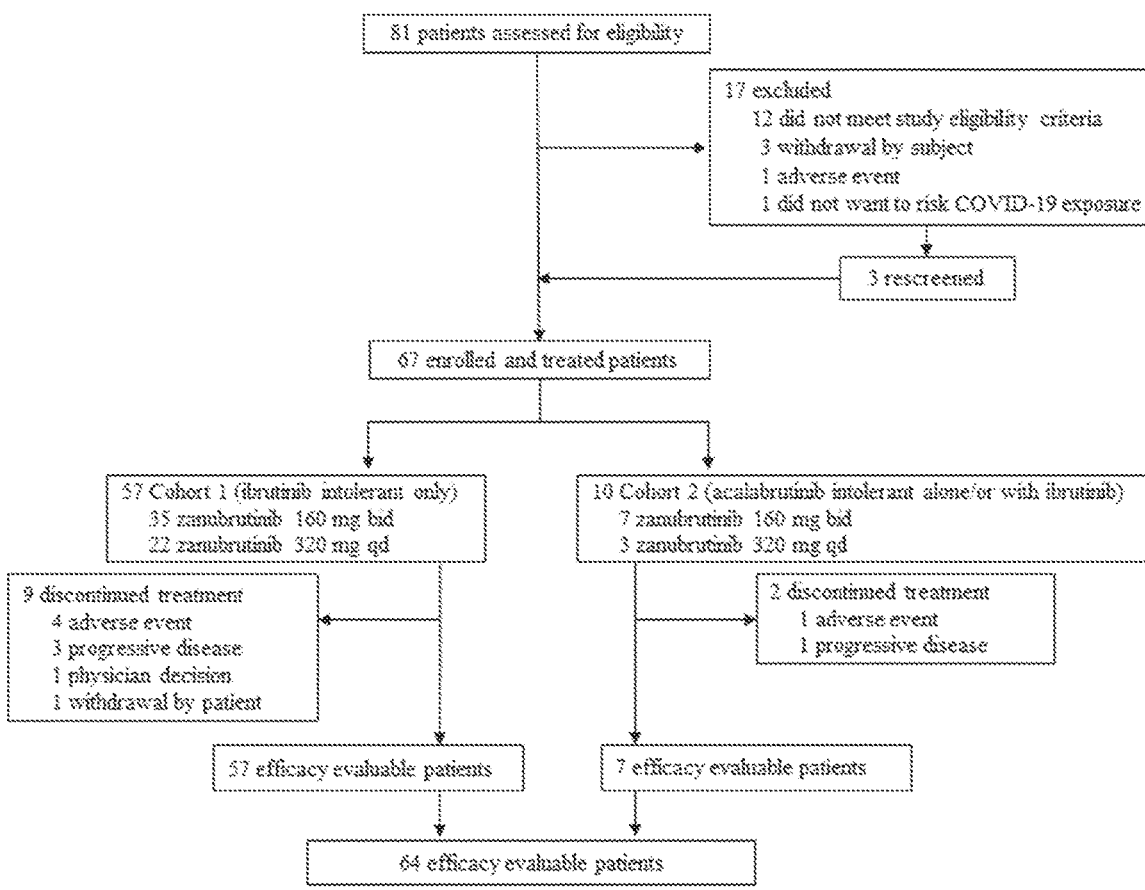
FIG. 21 depicts the Study CONSORT diagram of Example 3. Abbreviations: bid: twice daily. qd: once daily. COVID-19: coronavirus disease 2019.
Figure 22:
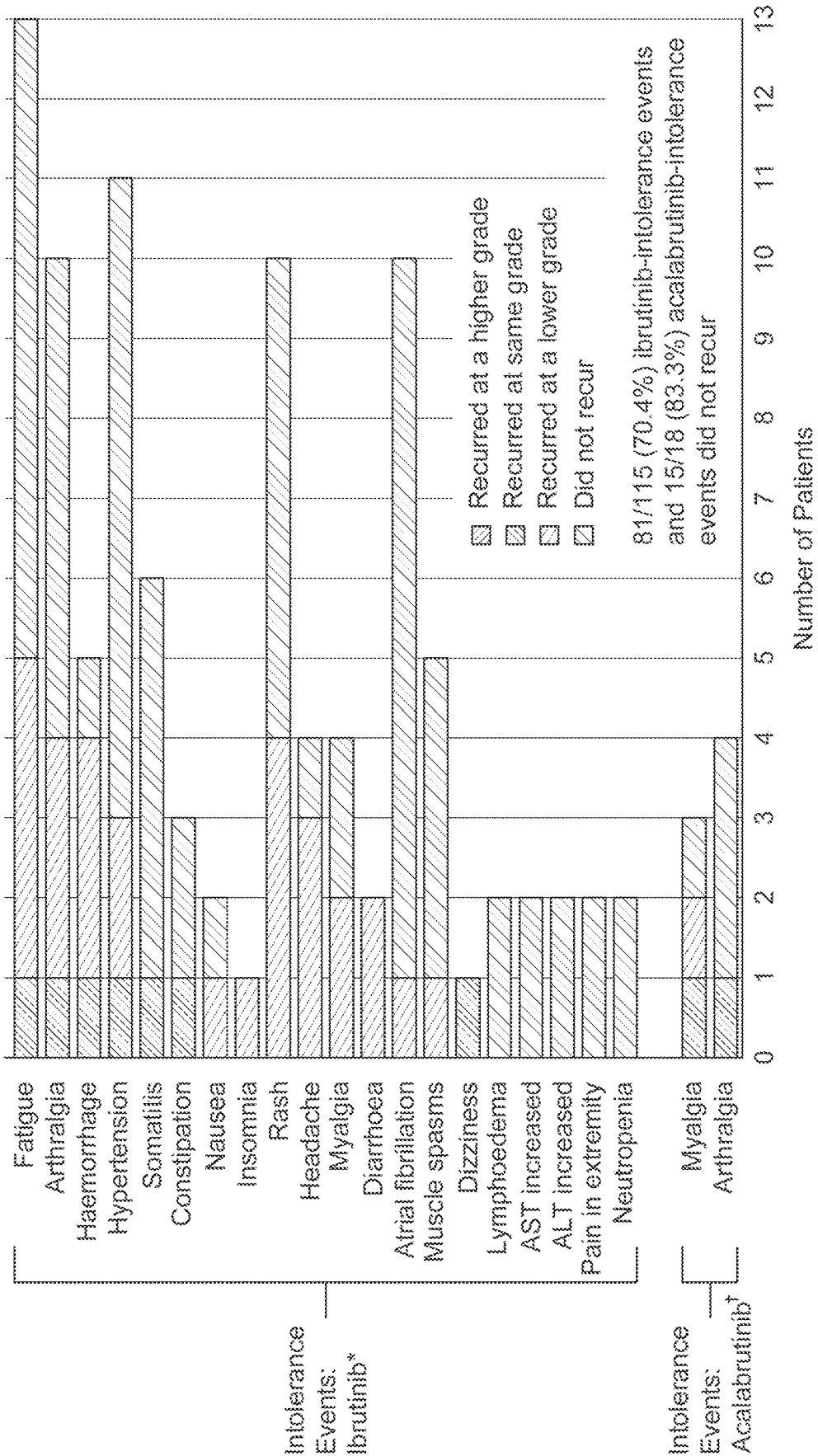
FIG. 22 depicts the recurrence and change in severity of ibrutinib- and acalabrutinib-intolerance events on zanubrutinib. *Eighteen additional ibrutinib-related intolerance events (arthritis, bone pain, bronchitis, embolism, irregular heart rate, malaise, pericardial effusion, pleural effusion, pneumonia, psoriasis, pyrexia, sinusitis, subcutaneous abscess, supraventricular tachycardia, transaminases increased, ventricular extrasystoles, vertigo, and vomiting) occurred in one patient and did not recur on zanubrutinib (data not shown). †Eleven additional acalabrutinib-related intolerance events (abdominal pain, asthenia, atrial fibrillation, dyspepsia, fatigue, groin pain, headache, insomnia, malaise, pain in extremity, and rash) occurred in one patient and did not recur on zanubrutinib (data not shown). ALT=alanine aminotransferase. AST=aspartate aminotransferase.

Of the 62 patients previously treated with ibrutinib (in either cohort 1 or cohort 2), 37/62 (59.7%) did not experience a recurrence of their ibrutinib-intolerance event, accounting for 81/115 (70.4%) ibrutinib-intolerance events not recurring (FIG. 21). The most common ibrutinib-intolerance events that recurred were fatigue, arthralgia, rash, and haemorrhage. Of those 34 events that recurred, 27 (79.4%) recurred at a lower severity. No ibrutinib-intolerance event recurred at a higher severity. Of the 38 grade 3 ibrutinib-intolerance events, only 13 (34.2%) recurred: 12 (92.3%) recurred at a lower severity and one (7.7%) recurred at the same severity. None of the four grade 4 ibrutinib-intolerance events recurred. The median time to first recurrence was 61 days (range, 1-384). Of the 25 patients with a recurrent ibrutinib-intolerance event, only six (24.0%) discontinued zanubrutinib treatment (three due to another AE, two PD, one by investigator's decision). No recurrent ibrutinib-intolerance-event resulted in treatment discontinuation.

Most acalabrutinib-intolerance events did not recur while on zanubrutinib (FIG. 21). Seven/10 (70.0%) patients with acalabrutinib intolerance did not experience a recurrence of their intolerance events, accounting for 15/18 (83.3%) acalabrutinib-intolerance events not recurring. Acalabrutinib-intolerance events that recurred were myalgia (two/18 [11.1%]) and arthralgia (one/18 [5.6%]). Of the three recurring acalabrutinib-intolerance events, one (33.3%; myalgia) event recurred at a lower severity, and two (66.7%) recurred at the same severity. The time to first recurrence was 12, 32, and 94 days after starting zanubrutinib. No acalabrutinib-intolerance events recurred at a higher severity. Two (66.7%) of the three patients in cohort 2 that experienced an acalabrutinib-intolerance event recurrence discontinued zanubrutinib treatment (one myalgia, one PD). Only one (25.0%) of the four grade 3 acalabrutinib-intolerance events recurred, but at a lower severity.

To investigate the selectivity of zanubrutinib for BTK, a kinome profiling study was performed. Zanubrutinib, ibrutinib, acalabrutinib, and M27 (a metabolite of acalabrutinib) were profiled against a panel of 370 kinases at the compounds' respective 100× $IC_{50}$ (BTK) concentrations. Zanubrutinib inhibited seven off-target kinases whereas ibrutinib, acalabrutinib, and M27 inhibited 17, 15, and 23 kinases, respectively.

Sixty-four/67 (95.5%) patients experienced ≥1 AE while on zanubrutinib. The most common AEs were contusion (15/67 [22.4%]), fatigue (14/67 [20.9%]), myalgia (ten/67 [14.9%]), arthralgia (9/67 [13.4%]), and diarrhoea (nine/67 [13.4%]). Twenty/67 (29.9%) patients had grade ≥3 Aes, the most common were neutropenia or neutrophil count decreased (eight/67 [11.9%]) and syncope (two/67 [3.0%]). Eight/67 (11.9%) patients experienced serious Aes (SAES): anaemia, atrial fibrillation, bronchitis, COVID-19, COVID-19 pneumonia, febrile neutropenia, *salmonella* gastroenteritis, transfusion reaction, trigeminal nerve disorder, and urinary tract infection (one/67 [1.5%], each).

Six/64 (9.0%) patients required dose reductions. Nine/57 (15.8%) patients discontinued zanubrutinib treatment in cohort 1, four/57 (7.0%) due to AEs (penile haemorrhage, COVID-19 pneumonia, alanine aminotransferase and aspartate aminotransferase increase, and autoimmune haemolytic anaemia; none of these were recurrences of ibrutinib intolerant events). Two/10 (20.0%) patients discontinued treatment in cohort 2, one patient due to AE (myalgia; FIG. 20). One/67 death (1.5%) was recorded, in cohort 1 due to COVID-19 pneumonia.

Atrial fibrillation occurred in three/67 patients (4.5%; grade 2), two of whom had a history of atrial fibrillation. Two of the three atrial fibrillation AEs were treated with anti-arrhythmics. One patient had atrial fibrillation as an incidental finding upon hospitalisation for grade 3 trigeminal nerve disorder related to shingles. The investigator elected to hold zanubrutinib, but not institute anti-arrhythmics. Seven patients had a history of atrial fibrillation or atrial flutter and did not have a recurrence of their atrial fibrillation or atrial flutter event while on zanubrutinib.

Bleeding events occurred in 25 patients (19 grade 1; six grade 2). Events that occurred in >1 patient were contusion (15/67 [22.4%]), epistaxis (five/67 [7.5%]), and petechiae (five/67 [7.5%]). There was no central nervous system bleeding.

Hypertension occurred in eight/67 (11.9%) patients (seven grade 2; one grade 3), four had a history of controlled hypertension. Median time to onset of the first hypertensive event was 105 (range, 1-253) days after starting zanubrutinib.

Among the 64 efficacy-evaluable patients, DCR was 93.8% (95% CI: 84.8, 98.3) and ORR was 64.1% (95% CI: 51.1, 75.7), with 19/64 (29.7%) patients achieving a best overall response (BOR) of SD and two/64 (3.1%) patients with BOR of PD (Table 32). The median time to first response (better than SD) was 3.0 months (range, 2.6-11.1). The median DOR was not reached; the 12-month event-free DOR rate was 95.0% (95% CI: 69.5, 99.3). Similarly, median PFS was not reached; the 18-month event-free PFS rate was 83.8% (95% CI: 62.6-93.6). When the eight patients who were ineligible for PR due to low baseline disease burden were excluded, ORR was 73.2% (95% CI: 59.7, 84.2). In this study, 42/67 (62.7%) patients received 160 mg bid zanubrutinib and 25/67 (37.3%) patients received 320 mg qd zanubrutinib. In the 160 mg bid and 320 mg qd groups, DCR was 95.0% (38; 95% CI: 83.1-99.4) and 91.7% (22; 95% CI: 73.0-99.0), and ORR was 70.0% (28; 95% CI: 53.5-83.4) and 54.2% (13; 95% CI: 32.8-74.5), respectively.

Five patients (four CLL/SLL, one MCL) progressed while on treatment. Mutational analysis confirmed three of the four patients with CLL/SLL had BTKi resistance mutations in BTK and/or PLCG2 at disease progression. One of these three patients had a clinically significant BTK C481S clone before starting treatment; this patient's BOR was PD. One patient with CLL/SLL did not have any detectable BTK or PLCG2 mutations at progression; this patient progressed due to the detection of new lesions. However, the patient continued zanubrutinib treatment beyond progression and subsequently achieved a PR. The patient with MCL did not have BTK or PLCG2 mutation at progression but had a CCND1-IGH fusion mutation.

Five (7.5%) patients had no response assessments: three patients did not reach the first response assessment before data cut-off occurred, one patient withdrew from the study, and one patient died from COVID-19 pneumonia before reaching the first response assessment.

Proportions of patients with ≥1 AE were 95.2% and 96% in the 160 mg bid and 320 mg qd groups, respectively. In the 160 mg bid group, 12/42 (28.6%) patients experienced a grade ≥3 AE, and an SAE was reported in four/42 (9.5%) patients. In the 320 mg qd group, eight/25 (32.0%) patients experienced a grade ≥3 AE, and four/25 (16.0%) patients reported an SAE. Treatment discontinuation due to AEs was lower, but not significantly different, in patients on zanubrutinib 160 mg bid (two/42 [4.8%]) than in those on 320 mg qd (three/25 [12.0%]). More patients developed neutropenia on the 160 mg bid dose than the 320 mg qd dose (eight/42 [19.0%] vs two/25 [8.0%], respectively).

Discussion

Here, the first study demonstrated evaluate recurrence of ibrutinib and acalabrutinib intolerances in patients with CLL, SLL, WM, MCL, and MZL. The toxicities leading to intolerance to ibrutinib and/or acalabrutinib were consistent with the known safety profiles of the drugs and had a low recurrence during treatment with zanubrutinib. The results demonstrated that zanubrutinib was an effective option for patients with previously treated CLL or other B-cell malignancies who were intolerant of ibrutinib or acalabrutinib, with a generally manageable safety profile and a low discontinuation rate that is consistent with prior studies of zanubrutinib. Designed to maximise BTK occupancy and minimise off-target inhibition, zanubrutinib may be a potential treatment option for patients who are intolerant of other BTKis.

The rate of zanubrutinib discontinuation due to AEs was low (<10%) regardless of the BTKi of which the patient was initially intolerant. Only one recurrence of a prior intolerance event (myalgia) led to zanubrutinib discontinuation in this study. One patient who discontinued ibrutinib due to a haemorrhagic event (haemorrhagic cyst) discontinued zanubrutinib due to a different haemorrhagic event (penile haemorrhage) and as such was not counted as a recurrence.

Similarly, two patients experienced an ibrutinib intolerance event of rash, and an on-study AE of rash macular or fungal skin infection, which may have been recurrences; however, as the preferred term was incongruent, they were not counted as recurrences. Although the definition used for recurrence in this study was very specific, the main conclusions would be upheld even if a more liberal definition of recurrence were used. Most AEs that led to ibrutinib (81/115 [70.4%]) and/or acalabrutinib (15/18 [83.3%]) intolerance did not recur with zanubrutinib. Twenty-seven (79.4%) of 34 ibrutinib and one (33.0%) of three acalabrutinib-intolerance event of any grade recurred at a lower severity. No events recurred at a higher severity.

In clinical trials, the most common adverse events reported with ibrutinib were diarrhoea (42/85 [49%]), upper respiratory tract infection (28/85 [33%]), fatigue (27/85 [32%]), and cough (26/85 [31%]). The most common grade ≥3 AEs with ibrutinib were neutropenia (13/85 [15%]) and pneumonia (10/85 [12%]). Grade ≥3 infections typically occurred early in the course of treatment. In a long-term follow-up study of patients treated with ibrutinib, the most common grade ≥3 AEs were hypertension (27/132 [20%]), pneumonia (27/132 [20%]), neutropenia (19/132 [14%]), thrombocytopenia (11/132 [8%]), atrial fibrillation (8/132 [6%]), diarrhoea (8/132 [6%]), sepsis (6/132 [5%]) and fatigue (7/132 [5%]). These AEs led to treatment discontinuation in 17/132 (13%) of patients. Non-relapsed discontinuations due to AEs accounted for 58% of treatment discontinuations. A similar safety profile was observed with the two approved dosing regimens, zanubrutinib 160 mg bid and 320 mg qd, which aligns with the similar plasma exposure reported for both doses in patients with MCL.

Acalabrutinib, a second generation BTK inhibitor, demonstrated an improved safety profile compared with that of ibrutinib in a phase 3 study in patients with relapsed/refractory CLL: the rates of any-grade arthralgia (42/266 [15.8%] vs 60/263 [22.8%]), hypertension (23/266 [8.6%] vs 60/263 [22.8%]), and atrial fibrillation (24/266 [9.0%] vs 41/263 [15.6%]) were lower with acalabrutinib versus ibrutinib, respectively. However, patients experienced significantly more headaches (92/266 [34.6%] vs 53/263 [20.2%]), cough (77/266 [28.9%] vs 56/263 [21.3%]), and grade ≥3 fatigue (9/266 [3.4%] vs 0/263 [0%]). The rates of grade ≥3 infections were similar (82/266 [30.8%] vs 79/263 [30.0%]) with acalabrutinib versus ibrutinib, respectively.

In this study, AEs that occurred with zanubrutinib tended to be low-grade and manageable, and few led to treatment discontinuation or interruption.

BTKis impair cell proliferation, migration, and activation of NK-κB in B-cell malignancies. The prolonged exposure to BTKi during continuous therapy increases the likelihood for developing BTKi-related AEs. A retrospective analysis of four studies of ibrutinib in patients with CLL found that patients who discontinued ibrutinib therapy for non-relapse reasons had a poor prognosis, with a median survival of 8 days after treatment discontinuation (95% CI: 0-56). Many patients withdrew from the studies due to infections; 16 of the 28 patients with infections died the same day they discontinued treatment, whereas only two remained alive at their respective last follow-up on days 63 and 176. Additionally, a BTK/PLCG2 resistant mutation analysis of 5 patients suggested that BTKi sensitivity remains an important factor in selection of BTKi therapy. Patients who progressed early had BTKi-resistant mutations (e.g., BTK C481S, PLCG2 R665W and L845F) present at screening or at the time of disease progression, suggesting that zanubrutinib may not be effective in patients who have typical resistance mutations. Of note, one patient with low levels of BTK C481S mutation (variant allele fraction=0.89%) and an uncommon PLCG2 mutation (N868K) at the start of zanubrutinib treatment remained on the study.

In this study population, the ORR of 64.1% and DCR of 93.8% are from patients that were neither required to have an indication for treatment nor lymphadenopathy (ie, lymph nodes >1.5 cm in the longest diameter) at study entry; eight patients entered the study with only non-target lesions or mild anaemia. In this study, results must be interpreted with the understanding that most efficacy-evaluable patients (45/67 [67.2%]) had low disease burden at study entry; further studies are needed to evaluate zanubrutinib in patients with a high disease burden.

Tables

TABLE 30

Baseline characteristics of all treated patients

| Characteristics | Cohort 1 (n = 57) | Cohort 2 (n = 10) | Total (n = 67) |
|---|---|---|---|
| Indication, n (%) | | | |
| CLL | 38 (66.7) | 5 (50.0) | 43 (64.2) |
| WM | 9 (15.8) | 2 (20.0) | 11 (16.4) |
| SLL | 6 (10.5) | 1 (10.0) | 7 (10.4) |
| MCL | 2 (3.5) | 1 (10.0) | 3 (4.5) |
| MZL | 2 (3.5) | 1 (10.0) | 3 (4.5) |
| Age, median (IQR), year | 71.0 (65-79) | 73.5 (70-76) | 71.0 (66-78) |
| Sex, n (%) | | | |
| Male | 30 (52.6) | 6 (60.0) | 36 (53.7) |
| Female | 27 (47.4) | 4 (40.0) | 31 (46.3) |
| Ethnicity, n (%) | | | |
| White | 54 (94.7) | 9 (90.0) | 63 (94.0) |
| Multiple | 0 (0.0) | 1 (10.0) | 1 (1.5) |
| Not Reported or Unknown | 3 (5.3) | 0 (0.0) | 3 (4.5) |
| ECOG PS 0, n (%) | 33 (57.9) | 4 (40.0) | 37 (55.2) |
| No. of prior therapy regimens, median (IQR) | 1.0 (1-3) | 2.5 (2-3) | 1.0 (1-3) |
| Time on prior BTKi, median (IQR), months | 10.6 (5.6-28.9)* | 3.3 (1.4-10.1)† | N/A |

TABLE 30-continued

Baseline characteristics of all treated patients

| Characteristics | Cohort 1 (n = 57) | Cohort 2 (n = 10) | Total (n = 67) |
|---|---|---|---|
| Baseline cytopenias, n (%) | | | |
| ANC ≤ 1.5 × 10$^9$/L | 4 (7.0) | 0 (0.0) | 4 (6.0) |
| Haemoglobin ≤ 11.0 g/dL | 7 (12.3) | 3 (30.0) | 10 (14.9) |
| Platelets ≤ 100 × 10$^9$/L | 7 (12.3) | 0 (0.0) | 7 (10.4) |
| Bulky disease, n (%) | | | |
| LDi < 5 cm | 33 (57.9) | 8 (80.0) | 41 (61.2) |
| LDi ≥ 5 cm | 8 (14.0) | 1 (10.0) | 9 (13.4) |
| No measurable disease | 16 (28.1) | 1 (10.0) | 17 (25.4) |
| Disease staging, n (%) | | | |
| Binet Staging (CLL) | | | |
| Stage A | 13 (22.8) | 1 (10.0) | 14 (20.9) |
| Stage B | 20 (35.1) | 4 (40.9) | 24 (35.8) |
| Stage C | 5 (8.8) | 0 (0.0) | 5 (7.5) |
| Ann Arbor Stage (SLL/MCL/MZL) | | | |
| Stage I | 2 (3.5) | 1 (10.0) | 3 (4.5) |
| Stage II | 2 (3.5) | 0 (0.0) | 2 (3.0) |
| Stage III | 5 (8.8) | 0 (0.0) | 5 (7.5) |
| Stage IV | 1 (1.8) | 2 (20.0) | 3 (4.5) |
| WM International Staging System (WM) | | | |
| Low-risk group | 2 (3.5) | 0 (0.0) | 2 (3.0) |
| Intermediate-risk group | 3 (5.3) | 1 (10.0) | 4 (6.0) |
| High-risk group | 0 (0.0) | 0 (0.0) | 0 (0.0) |
| Unknown | 4 (7.0) | 1 (10.0) | 5 (7.5) |
| Genomic status, n (%) | | | |
| CLL/SLL | | | |
| del(11q) | 8 (18.2) | 1 (16.7) | 9 (18.0) |
| del(17p) | 4 (9.1) | 1 (16.7) | 5 (10.0) |
| del(13q) nullisomy | 5 (11.4) | 1 (16.7) | 6 (12.0) |
| TP53 mutation | 11 (25.0) | 0 (0.0) | 11 (22.0) |
| Unmutated IGHV | 8 (18.2) | 2 (33.3) | 10 (20.0) |
| WM | | | |
| MYD88 mutation | 2 (22.2) | 0 (0.0) | 2 (18.2) |
| CXCR4 mutation | 1 (11.1) | 0 (0.0) | 1 (9.1) |
| MZL | | | |
| t(11;18) | 0 (0.0) | 0 (0.0) | 0 (0.0) |
| BIRC3 mutation | 0 (0.0) | 0 (0.0) | 0 (0.0) |

*Ibrutinib.
†Acalabrutinb.
ANC = absolute neutrophil count. BIRC3 = Baculoviral IAP Repeat Containing 3. BTKi = Bruton tyrosine kinase inhibitor. CLL = chronic lymphocytic leukaemia. CXCR4 = C-X-C chemokine receptor type 4. ECOG PS = Eastern Cooperative Oncology Group performance status. IGHV = immunoglobulin heavy chain. IQR = interquartile range. LDi = longest diameter. MCL = mantle cell lymphoma. MYD88 = myeloid differentiation primary response 88. MZL = marginal zone lymphoma. N/A = not applicable. SLL = small lymphocytic lymphoma. TP53 = tumour protein 53. WM = Waldenström macroglobulinemia.

TABLE 31

Most common AEs (≥5% any grade) during zanubrutinib treatment

| AE, n (%) | Grade 1 | Grade 2 | Grade 3 | Grade 4 | Total |
|---|---|---|---|---|---|
| Contusion | 12 (17.9) | 3 (4.5) | 0 (0.0) | 0 (0.0) | 15 (22.4) |
| Fatigue | 8 (11.9) | 6 (9.0) | 0 (0.0) | 0 (0.0) | 14 (20.9) |
| Myalgia | 8 (11.9) | 2 (3.0) | 0 (0.0) | 0 (0.0) | 10 (14.9) |
| Arthralgia | 4 (6.0) | 5 (7.5) | 0 (0.0) | 0 (0.0) | 9 (13.4) |
| Diarrhoea | 6 (9.0) | 2 (3.0) | 1 (1.5) | 0 (0.0) | 9 (13.4) |
| Hypertension | 0 (0.0) | 7 (10.4) | 1 (1.5) | 0 (0.0) | 8 (11.9) |
| Dizziness | 3 (4.5) | 4 (6.0) | 0 (0.0) | 0 (0.0) | 7 (10.4) |
| Nausea | 6 (9.0) | 1 (1.5) | 0 (0.0) | 0 (0.0) | 7 (10.4) |
| Pain in extremity | 3 (4.5) | 3 (4.5) | 0 (0.0) | 0 (0.0) | 6 (9.0) |
| Cough | 4 (6.0) | 1 (1.5) | 0 (0.0) | 0 (0.0) | 5 (7.5) |
| Epistaxis | 4 (6.0) | 1 (1.5) | 0 (0.0) | 0 (0.0) | 5 (7.5) |
| Insomnia | 3 (4.5) | 2 (3.0) | 0 (0.0) | 0 (0.0) | 5 (7.5) |

TABLE 31-continued

Most common AEs (≥5% any grade) during zanubrutinib treatment

| AE, n (%) | Grade 1 | Grade 2 | Grade 3 | Grade 4 | Total |
|---|---|---|---|---|---|
| Muscle spasms | 4 (6.0) | 1 (1.5) | 0 (0.0) | 0 (0.0) | 5 (7.5) |
| Neutropenia | 0 (0.0) | 0 (0.0) | 5 (7.5) | 0 (0.0) | 5 (7.5) |
| Neutrophil count decrease | 0 (0.0) | 2 (3.0) | 2 (3.0) | 1 (1.5) | 5 (7.5) |
| Petechiae | 5 (7.5) | 0 (0.0) | 0 (0.0) | 0 (0.0) | 5 (7.5) |
| Rash | 5 (7.5) | 0 (0.0) | 0 (0.0) | 0 (0.0) | 5 (7.5) |
| Urinary tract infection | 1 (1.5) | 4 (6.0) | 0 (0.0) | 0 (0.0) | 5 (7.5) |
| Back pain | 2 (3.0) | 2 (3.0) | 0 (0.0) | 0 (0.0) | 4 (6.0) |
| Bronchitis | 0 (0.0) | 3 (4.5) | 1 (1.5) | 0 (0.0) | 4 (6.0) |
| COVID-19 | 0 (0.0) | 3 (4.5) | 1 (1.5) | 0 (0.0) | 4 (6.0) |
| Cellulitis | 0 (0.0) | 3 (4.5) | 1 (1.5) | 0 (0.0) | 4 (6.0) |
| Constipation | 3 (4.5) | 1 (1.5) | 0 (0.0) | 0 (0.0) | 4 (6.0) |
| Headache | 4 (6.0) | 0 (0.0) | 0 (0.0) | 0 (0.0) | 4 (6.0) |
| Pruritus | 3 (4.5) | 1 (1.5) | 0 (0.0) | 0 (0.0) | 4 (6.0) |
| Seborrheic keratosis | 3 (4.5) | 1 (1.5) | 0 (0.0) | 0 (0.0) | 4 (6.0) |
| Skin laceration | 2 (3.0) | 2 (3.0) | 0 (0.0) | 0 (0.0) | 4 (6.0) |
| Upper respiratory tract infection | 3 (4.5) | 1 (1.5) | 0 (0.0) | 0 (0.0) | 4 (6.0) |

AE = adverse event, COVID-19 = coronavirus disease 2019.

TABLE 32

Investigator-assessed responses in patients with >90-day study duration*

| Response | Cohort 1 (prior ibrutinib) (n = 57) | Cohort 2 (prior acalabrutinib ± ibrutinib) (n = 7) | Total (n = 64) |
|---|---|---|---|
| DCR (SD or better), n (%, 95% CI) | 54 (94.7, 85.4-98.9) | 6 (85.7, 42.1-99.6) | 60 (93.8, 84.8-98.3) |
| ORR (better than SD), n (%, 95% CI) | 36 (63.2, 49.3-75.6) | 5 (71.4, 29.0-96.3) | 41 (64.1, 51.1-75.7) |
| BOR rate, n (%) | | | |
| PR-L or better† | 36 (63.2) | 5 (71.4) | 41 (64.1) |
| SD | 18 (31.6) | 1 (14.3) | 19 (29.7) |
| PD | 1 (1.8) | 1 (14.3) | 2 (3.1) |
| Not done | 2 (3.5) ‡ | 0 (0) | 2 (3.1) |
| Months to BOR,§ median (range) | 5.5 (2.6-11.3) | 7.9 (2.9-11.1) | 5.6 (2.6-11.3) |
| Months to first OR, median (range) | 2.92 (2.6-11.1) | 3.02 (2.7-11.1) | 2.96 (2.6-11.1) |

*Investigator-assessed responses disaggregated by sex are listed in Supplementary Table 31.
†PR-L or better includes minor response (WM only), partial response with lymphocytosis (CLL only), partial response, nodular partial response (CLL only) and very good partial response (WM only).
‡ One patient withdrew from study before first assessment timepoint due to syncope; one patient died from COVID-19 pneumonia before first response assessment.
§In patients who responded. BOR = best overall response. BTKi = Bruton tyrosine kinase inhibitor. CI = confidence interval. CLL = chronic lymphocytic leukaemia. DCR = disease control rate. OR = overall response. ORR = overall response rate. PD = progressive disease. PR = partial response. PR-L = partial response with lymphocytosis. SD = stable disease. WM = Waldenström macroglobulinemia.

Thus, the results demonstrated that zanubrutinib (a BTK inhibitor) is a safe and effective treatment for patients with B-cell malignancies who exhibit intolerance to other major BTK inhibitors, e.g., ibrutinib and acalabrutinib.

The inventors have found that the use of 320 mg BID (total daily dose of 640 mg) of zanubrutinib on a patient receiving a moderate CYP3A inducer leads to exposure (e.g., AUC or Cmax) similar to that on a patient receiving 160 mg BID (a total daily dose of 320 mg) of zanubrutinib. The coadministration of 320 mg BID of zanubrutinib with a moderate CYP3A inducer will be a safe and effective treatment for patients with B-cell malignancies who exhibit intolerance to other major BTK inhibitors, e.g., ibrutinib and acalabrutinib.

A number of references have been cited, the disclosures of which were incorporated herein by reference in their entirety.

What is claimed is:

1. A method of treating or delaying progression of a B-cell proliferative disorder in a patient receiving a moderate CYP3A inducer, the method comprising
concomitantly administering to the patient zanubrutinib, or a pharmaceutically acceptable salt thereof, at a total daily dose of about 640 mg, and the moderate CYP3A inducer,
wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

2. The method of claim 1, wherein zanubrutinib is administered at a dose of about 320 mg twice a day.

3. The method of claim 1, wherein the B-cell proliferative disorder is chronic lymphocytic leukemia (CLL).

4. The method of claim 1, wherein the B-cell proliferative disorder is small lymphocytic lymphoma (SLL).

5. The method of claim 1, wherein the B-cell proliferative disorder is Waldenström macroglobulinemia (WM).

6. The method of claim 1, wherein the B-cell proliferative disorder is mantle cell lymphoma (MCL).

7. The method of claim 1, wherein the B-cell proliferative disorder is marginal zone lymphoma (MZL).

8. The method of claim 1, wherein the moderate CYP3A inducer is rifabutin, bosentan, efavirenz, etravirine, modafinil, phenobarbital or nafcillin.

9. The method of claim 1, wherein the administration prolongs the progression-free survival (PFS) time of the patient as compared to the PFS time of a comparable patient orally administered with ibrutinib at a dose of 420 mg once daily.

10. The method of claim 1, wherein the administration causes lower rate of atrial fibrillation or flutter as compared to the rate of atrial fibrillation or flutter of a comparable patient orally administered with ibrutinib at a dose of 420 mg once daily.

11. A method of treating or delaying progression of a B-cell proliferative disorder in a patient, the method comprising
  determining whether the patient is being treated with a moderate CYP3A inducer; and
  if the patient is being treated with a moderate CYP3A inducer, concomitantly administering to the patient zanubrutinib, or a pharmaceutically acceptable salt thereof, at a total daily dose of about 640 mg; and the moderate CYP3A inducer,
  wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

12. The method of claim 11, wherein zanubrutinib is administered at a dose of about 320 mg twice a day.

13. The method of claim 11, wherein the B-cell proliferative disorder is chronic lymphocytic leukemia (CLL).

14. The method of claim 11, wherein the B-cell proliferative disorder is small lymphocytic lymphoma (SLL).

15. The method of claim 11, wherein the B-cell proliferative disorder is Waldenström macroglobulinemia (WM).

16. The method of claim 11, wherein the B-cell proliferative disorder is mantle cell lymphoma (MCL).

17. The method of claim 11, wherein the B-cell proliferative disorder is marginal zone lymphoma (MZL).

18. The method of claim 11, wherein the moderate CYP3A inducer is rifabutin, bosentan, efavirenz, etravirine, modafinil, phenobarbital or nafcillin.

19. The method of claim 11, wherein the administration prolongs the progression-free survival (PFS) time of the patient as compared to the PFS time of a comparable patient orally administered with ibrutinib at a dose of 420 mg once daily.

20. The method of claim 11, wherein the administration causes lower rate of atrial fibrillation or flutter as compared to the rate of atrial fibrillation or flutter of a comparable patient orally administered with ibrutinib at a dose of 420 mg once daily.

21. A method of treating or delaying progression of a B-cell proliferative disorder in a patient receiving a moderate CYP3A inducer, the method comprising
  assessing the patient as to whether administration of the moderate CYP3A inducer can be avoided; and
  if the administration of the moderate CYP3A inducer cannot be avoided, concomitantly administering to the patient zanubrutinib, or a pharmaceutically acceptable salt thereof, at a total daily dose of about 640 mg, and the moderate CYP3A inducer,
  wherein the B-cell proliferative disorder is chronic lymphocytic leukemia (CLL), small lymphocytic lymphoma (SLL), Waldenström macroglobulinemia (WM), mantle cell lymphoma (MCL), marginal zone lymphoma (MZL), or follicular lymphoma (FL).

22. The method of claim 21, wherein zanubrutinib is administered at a dose of about 320 mg twice a day.

23. The method of claim 21, wherein the B-cell proliferative disorder is chronic lymphocytic leukemia (CLL).

24. The method of claim 21, wherein the B-cell proliferative disorder is small lymphocytic lymphoma (SLL).

25. The method of claim 21, wherein the B-cell proliferative disorder is Waldenström macroglobulinemia (WM).

26. The method of claim 21, wherein the B-cell proliferative disorder is mantle cell lymphoma (MCL).

27. The method of claim 21, wherein the B-cell proliferative disorder is marginal zone lymphoma (MZL).

28. The method of claim 21, wherein the moderate CYP3A inducer is rifabutin, bosentan, efavirenz, etravirine, modafinil, phenobarbital or nafcillin.

29. The method of claim 21, wherein the administration prolongs the progression-free survival (PFS) time of the patient as compared to the PFS time of a comparable patient orally administered with ibrutinib at a dose of 420 mg once daily.

30. The method of claim 21, wherein the administration causes lower rate of atrial fibrillation or flutter as compared to the rate of atrial fibrillation or flutter of a comparable patient orally administered with ibrutinib at a dose of 420 mg once daily.

\* \* \* \* \*

UNITED STATES PATENT AND TRADEMARK OFFICE
CERTIFICATE OF CORRECTION

PATENT NO. : 11,786,531 B1
APPLICATION NO. : 18/098938
DATED : October 17, 2023
INVENTOR(S) : Jason Paik et al.

It is certified that error appears in the above-identified patent and that said Letters Patent is hereby corrected as shown below:

On the Title Page

Item (72) Inventors:

Jason Paik, please replace "Cambridge, MA" with --San Mateo, CA-- (US)
Ying Ou, please replace "Cambridge, MA" with --Palo Alto, CA-- (US);
Please add --Motohisa Takai, Albany, CA (US)--

Signed and Sealed this
Fourteenth Day of May, 2024

Katherine Kelly Vidal
*Director of the United States Patent and Trademark Office*